(12) United States Patent
Igawa et al.

(10) Patent No.: US 11,046,784 B2
(45) Date of Patent: Jun. 29, 2021

(54) METHODS FOR CONTROLLING BLOOD PHARMACOKINETICS OF ANTIBODIES

(75) Inventors: Tomoyuki Igawa, Shizuoka (JP);
Hiroyuki Tsunoda, Shizuoka (JP);
Tatsuhiko Tachibana, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/295,039

(22) PCT Filed: Mar. 30, 2007

(86) PCT No.: PCT/JP2007/057036
§ 371 (c)(1),
(2), (4) Date: Jan. 20, 2009

(87) PCT Pub. No.: WO2007/114319
PCT Pub. Date: Oct. 11, 2007

(65) Prior Publication Data
US 2009/0324589 A1  Dec. 31, 2009

(30) Foreign Application Priority Data
Mar. 31, 2006 (JP) .................. 2006-097796

(51) Int. Cl.
*C07H 21/04* (2006.01)
*C07K 16/40* (2006.01)

(52) U.S. Cl.
CPC .......... *C07K 16/40* (2013.01); *C07K 2317/24* (2013.01); *C07K 2317/31* (2013.01); *C07K 2317/56* (2013.01)

(58) Field of Classification Search
None
See application file for complete search history.

(56) References Cited

U.S. PATENT DOCUMENTS

| | | |
|---|---|---|
| 4,208,479 A | 6/1980 | Maggio et al. |
| 4,444,878 A | 4/1984 | Paulus |
| 4,474,893 A | 10/1984 | Reading |
| 5,126,250 A | 6/1992 | McDonough et al. |
| 5,322,678 A | 6/1994 | Morgan et al. |
| 5,455,030 A | 10/1995 | Ladner et al. |
| 5,468,634 A | 11/1995 | Liu |
| 5,496,549 A | 3/1996 | Yamazaki et al. |
| 5,591,828 A | 1/1997 | Bosslet et al. |
| 5,639,641 A | 6/1997 | Pedersen et al. |
| 5,670,373 A | 9/1997 | Kishimoto |
| 5,744,446 A | 4/1998 | Lollar et al. |
| 5,795,965 A | 8/1998 | Tsuchiya et al. |
| 5,817,790 A | 10/1998 | Tsuchiya et al. |
| 5,827,733 A | 10/1998 | Lee et al. |
| 5,859,205 A | 1/1999 | Adair et al. |
| 5,945,311 A | 8/1999 | Lindhofer et al. |
| 5,990,286 A | 11/1999 | Khawli et al. |
| 5,994,524 A | 11/1999 | Matsushima et al. |
| 6,005,091 A | 12/1999 | Blackburn et al. |
| 6,010,902 A | 1/2000 | Ledbetter et al. |
| 6,018,032 A | 1/2000 | Koike et al. |
| 6,024,956 A | 2/2000 | Matsushima et al. |
| 6,074,642 A | 6/2000 | Wang et al. |
| 6,096,506 A | 8/2000 | Lee et al. |
| 6,126,980 A | 10/2000 | Smith et al. |
| 6,129,914 A | 10/2000 | Weiner et al. |
| 6,165,745 A | 12/2000 | Ward et al. |
| 6,245,894 B1 | 6/2001 | Matsushima et al. |
| 6,309,636 B1 | 10/2001 | do Couto et al. |
| 6,329,511 B1 | 12/2001 | Vasquez et al. |
| 6,355,245 B1 | 3/2002 | Evans et al. |
| 6,485,943 B2 | 11/2002 | Stevens et al. |
| 6,677,436 B1 | 1/2004 | Sato et al. |
| 6,723,319 B1 | 4/2004 | Ito et al. |
| 6,737,056 B1 | 5/2004 | Presta |
| 6,821,505 B2 | 11/2004 | Ward |
| 6,884,879 B1 | 4/2005 | Baca et al. |
| 6,913,747 B1 | 7/2005 | Co et al. |
| 7,018,632 B2 | 3/2006 | Lindhofer et al. |
| 7,033,590 B1 | 4/2006 | Scheiflinger et al. |
| 7,052,873 B2 | 5/2006 | Tsuchiya |
| 7,122,637 B2 | 10/2006 | Presta |
| 7,217,797 B2 | 5/2007 | Hinton et al. |
| 7,247,302 B1 | 7/2007 | Rosok et al. |
| 7,261,893 B2 | 8/2007 | Geertruida et al. |
| 7,276,585 B2 * | 10/2007 | Lazar et al. ............... 530/387.1 |
| 7,282,568 B2 | 10/2007 | Teeling et al. |
| 7,320,789 B2 | 1/2008 | Aghajanian et al. |
| 7,371,826 B2 | 5/2008 | Presta |
| 7,432,356 B2 | 10/2008 | Fung et al. |
| 7,479,543 B2 | 1/2009 | Tsuchiya et al. |
| 7,482,440 B2 | 1/2009 | Maeda et al. |
| 7,538,196 B2 | 5/2009 | Jung |
| 7,632,499 B2 | 12/2009 | Davies et al. |

(Continued)

FOREIGN PATENT DOCUMENTS

| | | |
|---|---|---|
| AR | 068564 | 11/2009 |
| AU | 2007/255753 | 12/2007 |

(Continued)

OTHER PUBLICATIONS

Ghetie et al. (Nature Biotechnology, vol. 15, Jul. 1997).*

(Continued)

*Primary Examiner* — Meera Natarajan
(74) *Attorney, Agent, or Firm* — Fish & Richardson P.C.

(57) ABSTRACT

The present inventors discovered that the half-life in blood of an IgG antibody which is a polypeptide comprising an FcRn-binding domain can be controlled by controlling the surface charge through modification of residues exposed on the surface among residues in the variable regions of the IgG antibody. Antibodies whose half-life in blood had been controlled by the methods of the present invention were confirmed to actually retain the original activity. The methods of the present invention are widely applicable to polypeptides comprising an FcRn-binding domain, such as IgG antibodies, which are recycled via the FcRn salvage pathway regardless of the type of target antigen.

50 Claims, 8 Drawing Sheets
Specification includes a Sequence Listing.

(56) References Cited

U.S. PATENT DOCUMENTS

| | | |
|---|---|---|
| 7,670,600 B2 | 3/2010 | Dall'Acqua et al. |
| 7,732,149 B2 | 6/2010 | Kojima et al. |
| 7,785,792 B2 | 8/2010 | Presta |
| 7,807,159 B2 | 10/2010 | Chin et al. |
| 7,888,486 B2 | 2/2011 | Walsh et al. |
| 8,030,461 B2 | 10/2011 | Kojima |
| 8,062,635 B2 | 11/2011 | Hattori et al. |
| 8,147,829 B2 | 4/2012 | Hariharan et al. |
| 8,188,231 B2 | 5/2012 | Lazar et al. |
| 8,217,147 B2 | 7/2012 | Stavenhagen et al. |
| 8,323,962 B2 | 12/2012 | Dall'Acqua et al. |
| 8,329,867 B2 | 12/2012 | Lazar et al. |
| 8,337,841 B2 | 12/2012 | Kojima |
| 8,367,805 B2 | 2/2013 | Chamberlain et al. |
| 8,415,459 B2 | 4/2013 | La Vallie et al. |
| 8,562,991 B2 | 10/2013 | Igawa et al. |
| 8,568,726 B2 | 10/2013 | Beaumont et al. |
| 8,575,317 B2 | 11/2013 | Kuramochi et al. |
| 8,592,562 B2 | 11/2013 | Kannan et al. |
| 8,604,174 B2 | 12/2013 | Babcook et al. |
| 8,637,641 B2 | 1/2014 | Dahiyat et al. |
| 8,753,629 B2 | 6/2014 | Lazar et al. |
| 8,802,820 B2 | 8/2014 | Chamberlain et al. |
| 9,029,515 B2 | 5/2015 | Pons et al. |
| 9,051,373 B2 | 6/2015 | Lazar et al. |
| 9,079,949 B1 | 7/2015 | Andrien et al. |
| 9,096,651 B2 | 8/2015 | Igawa et al. |
| 9,228,017 B2 | 1/2016 | Igawa et al. |
| 9,334,331 B2 | 5/2016 | Igawa et al. |
| 9,340,615 B2 | 5/2016 | Maeda et al. |
| 9,399,680 B2 | 7/2016 | Kuramochi et al. |
| 9,527,926 B2 | 12/2016 | Ho et al. |
| 9,556,279 B2 | 1/2017 | Niwa et al. |
| 9,605,061 B2 | 3/2017 | Lazar et al. |
| 9,637,557 B2 | 5/2017 | Scheer et al. |
| 9,670,269 B2 | 6/2017 | Igawa et al. |
| 9,688,762 B2 | 6/2017 | Igawa et al. |
| 9,765,135 B2 | 9/2017 | Ruike et al. |
| 9,828,429 B2 | 11/2017 | Igawa et al. |
| 9,969,800 B2 | 5/2018 | Igawa et al. |
| 9,975,966 B2 | 5/2018 | Igawa et al. |
| 10,000,560 B2 | 6/2018 | Ruike et al. |
| 10,011,858 B2 | 7/2018 | Igawa et al. |
| 10,023,630 B2 | 7/2018 | Ruike et al. |
| 10,024,867 B2 | 7/2018 | Igawa |
| 10,066,018 B2 | 9/2018 | Igawa et al. |
| 10,150,808 B2 | 12/2018 | Kuramochi et al. |
| 10,253,091 B2 | 4/2019 | Igawa et al. |
| 10,253,100 B2 | 4/2019 | Igawa et al. |
| 10,385,122 B2 | 8/2019 | Ruike et al. |
| 10,435,458 B2 | 10/2019 | Kuramochi et al. |
| 10,450,381 B2 | 10/2019 | Igawa et al. |
| 10,519,229 B2 | 12/2019 | Igawa et al. |
| 10,618,965 B2 | 4/2020 | Igawa et al. |
| 10,662,245 B2 | 5/2020 | Igawa et al. |
| 1,073,811 A1 | 8/2020 | Ruike et al. |
| 10,738,111 B2 | 8/2020 | Ruike et al. |
| 10,774,148 B2 | 9/2020 | Kakehi et al. |
| 2001/0001663 A1 | 5/2001 | Kishimoto et al. |
| 2002/0062010 A1 | 5/2002 | Arathoon et al. |
| 2002/0082396 A1 | 6/2002 | Matsushima et al. |
| 2002/0098193 A1 | 7/2002 | Ward |
| 2002/0137897 A1 | 9/2002 | Stevens et al. |
| 2002/0142374 A1 | 10/2002 | Gallo et al. |
| 2002/0147326 A1 | 10/2002 | Chaiklin et al. |
| 2002/0164339 A1 | 11/2002 | Do et al. |
| 2002/0164668 A1 | 11/2002 | Durham et al. |
| 2002/0187150 A1 | 12/2002 | Mihara et al. |
| 2003/0125520 A1 | 7/2003 | Maeda et al. |
| 2003/0190311 A1 | 10/2003 | Dall'Acqua et al. |
| 2003/0207346 A1 | 11/2003 | Arathoon et al. |
| 2003/0215838 A1 | 11/2003 | Sprecher et al. |
| 2003/0219441 A1 | 11/2003 | Thorpe et al. |
| 2003/0224397 A1* | 12/2003 | Lowman ............... C07K 16/00 435/6.13 |
| 2003/0224487 A1 | 12/2003 | Sprecher et al. |
| 2004/0071706 A1 | 4/2004 | Ito et al. |
| 2004/0081651 A1 | 4/2004 | Karpusas et al. |
| 2004/0110226 A1 | 6/2004 | Lazar et al. |
| 2004/0223970 A1 | 11/2004 | Afar et al. |
| 2004/0236080 A1 | 11/2004 | Aburatani et al. |
| 2005/0095243 A1 | 5/2005 | Chan et al. |
| 2005/0130224 A1 | 6/2005 | Saito et al. |
| 2005/0142133 A1 | 6/2005 | Lazar et al. |
| 2005/0142635 A1 | 6/2005 | Tsuchiya et al. |
| 2005/0191293 A1 | 9/2005 | Deshpande et al. |
| 2005/0244403 A1 | 11/2005 | Lazar et al. |
| 2005/0261229 A1 | 11/2005 | Gillies |
| 2005/0266425 A1 | 12/2005 | Zauderer et al. |
| 2006/0019342 A1 | 1/2006 | Dall Acqua et al. |
| 2006/0024298 A1 | 2/2006 | Lazar et al. |
| 2006/0057149 A1 | 3/2006 | Johnson et al. |
| 2006/0063228 A1 | 3/2006 | Kasaian et al. |
| 2006/0074225 A1 | 4/2006 | Chamberlain |
| 2006/0121022 A1 | 6/2006 | Koga et al. |
| 2006/0134709 A1 | 6/2006 | Stavenhagen et al. |
| 2006/0134805 A1 | 6/2006 | Berg et al. |
| 2006/0141456 A1 | 6/2006 | Edwards et al. |
| 2006/0160184 A1 | 7/2006 | Hoogenboom et al. |
| 2006/0182743 A1 | 8/2006 | Bilsborough |
| 2006/0194280 A1 | 8/2006 | Dillon et al. |
| 2006/0194291 A1 | 8/2006 | Behrens et al. |
| 2006/0198840 A1 | 9/2006 | Dall'Acqua et al. |
| 2006/0204493 A1 | 9/2006 | Huang et al. |
| 2006/0275282 A1 | 12/2006 | Moore et al. |
| 2006/0292147 A1 | 12/2006 | Yoshizaki et al. |
| 2007/0003546 A1 | 1/2007 | Lazar et al. |
| 2007/0009523 A1 | 1/2007 | Presta |
| 2007/0036785 A1 | 2/2007 | Kishimoto et al. |
| 2007/0041978 A1 | 2/2007 | Hattori et al. |
| 2007/0054354 A1 | 3/2007 | Humphreys et al. |
| 2007/0059312 A1 | 3/2007 | Baca et al. |
| 2007/0110757 A1 | 5/2007 | Wei et al. |
| 2007/0134234 A1 | 6/2007 | Smith et al. |
| 2007/0148163 A1 | 6/2007 | Takahashi et al. |
| 2007/0148164 A1 | 6/2007 | Farrington et al. |
| 2007/0160611 A1 | 7/2007 | Yao et al. |
| 2007/0190056 A1 | 8/2007 | Kambadur et al. |
| 2007/0212357 A1 | 9/2007 | Pons et al. |
| 2007/0224174 A1 | 9/2007 | Kang et al. |
| 2007/0224188 A1 | 9/2007 | Allan et al. |
| 2007/0237767 A1 | 10/2007 | Lazar et al. |
| 2007/0253951 A1 | 11/2007 | Ng et al. |
| 2007/0280945 A1 | 12/2007 | Stevens et al. |
| 2008/0063635 A1 | 3/2008 | Takahashi et al. |
| 2008/0075712 A1 | 3/2008 | Hattori et al. |
| 2008/0089892 A1 | 4/2008 | Allan et al. |
| 2008/0125579 A1 | 5/2008 | Owens et al. |
| 2008/0166756 A1 | 7/2008 | Tsuchiya et al. |
| 2008/0219971 A1 | 9/2008 | Smith et al. |
| 2008/0274506 A1 | 11/2008 | Presta |
| 2009/0053240 A1 | 2/2009 | Lazar et al. |
| 2009/0117097 A1 | 5/2009 | Igawa et al. |
| 2009/0136485 A1 | 5/2009 | Chu et al. |
| 2009/0202556 A1 | 8/2009 | Ohta et al. |
| 2009/0208416 A1 | 8/2009 | Moretta et al. |
| 2009/0221803 A1 | 9/2009 | Dall'Acqua et al. |
| 2009/0263392 A1 | 10/2009 | Igawa et al. |
| 2009/0291076 A1 | 11/2009 | Morichika et al. |
| 2010/0003254 A1 | 1/2010 | Hattori et al. |
| 2010/0004429 A1 | 1/2010 | Kai et al. |
| 2010/0008907 A1 | 1/2010 | Nishimoto et al. |
| 2010/0015133 A1 | 1/2010 | Igawa et al. |
| 2010/0055092 A1 | 3/2010 | Hasegawa et al. |
| 2010/0098710 A1 | 4/2010 | Hariharan et al. |
| 2010/0098730 A1 | 4/2010 | Lowman et al. |
| 2010/0099147 A1 | 4/2010 | Hariharan et al. |
| 2010/0129365 A1 | 5/2010 | Kim et al. |
| 2010/0166748 A1 | 7/2010 | Guild et al. |
| 2010/0216187 A1 | 8/2010 | Lasters et al. |
| 2010/0239577 A1 | 9/2010 | Igawa et al. |
| 2010/0247523 A1 | 9/2010 | Kano et al. |
| 2010/0285030 A1 | 11/2010 | Bowdish et al. |
| 2010/0286374 A1 | 11/2010 | Kannan et al. |

(56) References Cited

U.S. PATENT DOCUMENTS

| | | |
|---|---|---|
| 2010/0291072 A1 | 11/2010 | Lowman et al. |
| 2010/0297697 A1 | 11/2010 | Ambrosius et al. |
| 2010/0298542 A1 | 11/2010 | Igawa et al. |
| 2010/0310556 A1 | 12/2010 | Higuchi et al. |
| 2010/0316636 A1 | 12/2010 | Radin et al. |
| 2010/0331527 A1 | 12/2010 | Davis et al. |
| 2011/0002931 A1 | 1/2011 | Tamburini |
| 2011/0044984 A1 | 2/2011 | Kittazawa et al. |
| 2011/0059093 A1 | 3/2011 | Bohrmann et al. |
| 2011/0076275 A1 | 3/2011 | Igawa et al. |
| 2011/0098450 A1 | 4/2011 | Igawa et al. |
| 2011/0105724 A1 | 5/2011 | Clegg et al. |
| 2011/0111406 A1 | 5/2011 | Igawa et al. |
| 2011/0129459 A1 | 6/2011 | Kuramochi et al. |
| 2011/0135662 A1 | 6/2011 | Finney et al. |
| 2011/0229459 A1 | 9/2011 | Kuramochi et al. |
| 2011/0229489 A1 | 9/2011 | Pons et al. |
| 2011/0236374 A1 | 9/2011 | Shitara et al. |
| 2011/0245473 A1 | 10/2011 | Igawa et al. |
| 2011/0287009 A1 | 11/2011 | Scheer et al. |
| 2011/0311454 A1 | 12/2011 | Dall'Acqua et al. |
| 2012/0009188 A1 | 1/2012 | Behrens et al. |
| 2012/0010387 A1 | 1/2012 | Niwa et al. |
| 2012/0028304 A1 | 2/2012 | Dahiyat et al. |
| 2012/0065379 A1 | 3/2012 | Igawa et al. |
| 2012/0071634 A1 | 3/2012 | Igawa et al. |
| 2012/0121587 A1 | 5/2012 | Maeda et al. |
| 2012/0149876 A1 | 6/2012 | Von Kreudenstein |
| 2012/0189639 A1 | 7/2012 | Schebye et al. |
| 2012/0237517 A1 | 9/2012 | Hattori et al. |
| 2012/0238729 A1 | 9/2012 | Kuramochi et al. |
| 2012/0253016 A1 | 10/2012 | Igawa et al. |
| 2012/0301460 A1 | 11/2012 | Bao et al. |
| 2012/0301488 A1 | 11/2012 | Zhang et al. |
| 2013/0011866 A1 | 1/2013 | Igawa et al. |
| 2013/0018174 A1 | 1/2013 | Igawa et al. |
| 2013/0022624 A1 | 1/2013 | Weaver et al. |
| 2013/0030156 A1 | 1/2013 | Apostolou et al. |
| 2013/0039913 A1 | 2/2013 | Labrijn et al. |
| 2013/0052196 A1 | 2/2013 | Apostolou et al. |
| 2013/0064836 A1 | 3/2013 | Diefenbach-Streiber et al. |
| 2013/0085074 A1 | 4/2013 | Walker et al. |
| 2013/0085199 A1 | 4/2013 | Tamori et al. |
| 2013/0101581 A1 | 4/2013 | Kuramochi et al. |
| 2013/0115208 A1 | 5/2013 | Ho et al. |
| 2013/0131319 A1 | 5/2013 | Igawa et al. |
| 2013/0195849 A1 | 8/2013 | Spreter et al. |
| 2013/0209457 A1 | 8/2013 | Lazar et al. |
| 2013/0209489 A1 | 8/2013 | Han et al. |
| 2013/0247236 A1 | 9/2013 | McWhirter et al. |
| 2013/0302315 A1 | 11/2013 | Lazar et al. |
| 2013/0302399 A1 | 11/2013 | Feldhaus et al. |
| 2013/0303396 A1 | 11/2013 | Igawa et al. |
| 2013/0317203 A1 | 11/2013 | Igawa et al. |
| 2013/0330345 A1 | 12/2013 | Igawa et al. |
| 2013/0336963 A1 | 12/2013 | Igawa et al. |
| 2014/0037632 A1 | 2/2014 | Igawa et al. |
| 2014/0039165 A1 | 2/2014 | Kuramochi et al. |
| 2014/0051833 A1 | 2/2014 | Fischer et al. |
| 2014/0056878 A1 | 2/2014 | McConnell et al. |
| 2014/0105889 A1 | 4/2014 | Igawa et al. |
| 2014/0112883 A1 | 4/2014 | Ponath et al. |
| 2014/0112914 A1 | 4/2014 | Nezu et al. |
| 2014/0127209 A1 | 5/2014 | Grabstein et al. |
| 2014/0227292 A1 | 8/2014 | Flanagan et al. |
| 2014/0234340 A1 | 8/2014 | Igawa et al. |
| 2014/0249297 A1 | 9/2014 | Lazar et al. |
| 2014/0255398 A1 | 9/2014 | Igawa et al. |
| 2014/0271459 A1 | 9/2014 | Dutzar et al. |
| 2014/0294833 A1 | 10/2014 | Desjarlais et al. |
| 2014/0303356 A1 | 10/2014 | Gramer et al. |
| 2014/0335089 A1 | 11/2014 | Igawa et al. |
| 2014/0363426 A1 | 12/2014 | Moore et al. |
| 2014/0363428 A1 | 12/2014 | Igawa et al. |
| 2014/0370018 A1 | 12/2014 | Igawa et al. |
| 2014/0377253 A1 | 12/2014 | Harding et al. |
| 2015/0050269 A1 | 2/2015 | Igawa et al. |
| 2015/0056182 A1 | 2/2015 | Igawa et al. |
| 2015/0079088 A1 | 3/2015 | Lowman et al. |
| 2015/0118184 A1 | 4/2015 | Kawai |
| 2015/0166654 A1 | 6/2015 | Igawa et al. |
| 2015/0166666 A1 | 6/2015 | Igawa et al. |
| 2015/0175704 A1 | 6/2015 | Kuramochi et al. |
| 2015/0239966 A1 | 8/2015 | Baciu et al. |
| 2015/0247849 A1 | 9/2015 | Tamburini |
| 2015/0274809 A1 | 10/2015 | Igawa et al. |
| 2015/0284465 A1 | 10/2015 | Igawa et al. |
| 2015/0299305 A1 | 10/2015 | Andrien, et al. |
| 2015/0315278 A1 | 11/2015 | Igawa et al. |
| 2015/0353630 A1 | 12/2015 | Igawa et al. |
| 2016/0068592 A1 | 3/2016 | Chung |
| 2016/0159915 A1 | 6/2016 | Igawa et al. |
| 2016/0176954 A1 | 6/2016 | Ruike et al. |
| 2016/0200807 A1 | 7/2016 | Ruike et al. |
| 2016/0222129 A1 | 8/2016 | Igawa et al. |
| 2016/0229908 A1 | 8/2016 | Igawa et al. |
| 2016/0229915 A1 | 8/2016 | Igawa et al. |
| 2016/0244526 A1 | 8/2016 | Igawa et al. |
| 2017/0022270 A1 | 1/2017 | Igawa et al. |
| 2017/0022287 A1 | 1/2017 | Igawa et al. |
| 2017/0022293 A1 | 1/2017 | Igawa et al. |
| 2017/0145111 A1 | 5/2017 | Hattori et al. |
| 2017/0181987 A1 | 6/2017 | Camilla et al. |
| 2017/0267783 A1 | 9/2017 | Nezu et al. |
| 2017/0275332 A1 | 9/2017 | Igawa et al. |
| 2018/0016327 A1 | 1/2018 | Murata et al. |
| 2018/0142027 A1 | 5/2018 | Igawa et al. |
| 2018/0148509 A1 | 5/2018 | Kakehi et al. |
| 2018/0162902 A1 | 6/2018 | Igawa et al. |
| 2018/0244800 A1 | 8/2018 | Hattori et al. |
| 2019/0062368 A1 | 2/2019 | Igawa et al. |
| 2019/0085085 A1 | 3/2019 | Igawa et al. |
| 2019/0112390 A1 | 4/2019 | Hattori et al. |
| 2019/0185557 A1 | 6/2019 | Igawa et al. |
| 2019/0211081 A1 | 7/2019 | Igawa et al. |
| 2019/0233525 A1 | 8/2019 | Igawa et al. |
| 2019/0315884 A1 | 10/2019 | Igawa et al. |
| 2019/0330268 A1 | 10/2019 | Tanaka et al. |
| 2019/0352334 A1 | 11/2019 | Igawa et al. |
| 2019/0359728 A1 | 11/2019 | Hattori et al. |
| 2020/0002429 A1 | 1/2020 | Kuramochi et al. |
| 2020/0172610 A1 | 6/2020 | Igawa et al. |
| 2020/0199241 A1 | 6/2020 | Igawa et al. |
| 2020/0207805 A1 | 7/2020 | Igawa et al. |
| 2020/0231688 A1 | 7/2020 | Igawa et al. |
| 2020/0277402 A1 | 9/2020 | Hattori et al. |

FOREIGN PATENT DOCUMENTS

| | | |
|---|---|---|
| AU | 2008332271 | 6/2009 |
| AU | 2009290162 | 4/2010 |
| AU | 2011/244851 | 11/2011 |
| AU | 2015/227424 | 10/2015 |
| BR | PI0821145-0 | 6/2015 |
| BR | PI0821110-8 | 7/2015 |
| CA | 1 332 367 | 10/1994 |
| CA | 2 203 182 | 5/1996 |
| CA | 2 019 559 | 1/2002 |
| CA | 2 443 294 | 10/2002 |
| CA | 2 523 577 | 11/2004 |
| CA | 2 531 482 | 1/2005 |
| CA | 2 549 467 | 7/2005 |
| CA | 2 560 953 | 9/2005 |
| CA | 2 603 264 | 10/2006 |
| CA | 2 625 773 | 4/2007 |
| CA | 2 626 688 | 4/2007 |
| CA | 2 647 846 | 10/2007 |
| CA | 2 648 644 | 10/2007 |
| CA | 2 700 394 | 4/2009 |
| CA | 2 700 498 | 4/2009 |
| CA | 2 700 986 | 4/2009 |
| CA | 2 708 065 | 6/2009 |
| CA | 2 708 532 | 6/2009 |
| CA | 2 721 052 | 10/2009 |

(56) References Cited

FOREIGN PATENT DOCUMENTS

| | | |
|---|---|---|
| CA | 2 819 530 | 6/2012 |
| CA | 2 831 770 | 10/2012 |
| CA | 2 899 589 | 8/2014 |
| CN | 1763097 | 4/2006 |
| CN | 101098890 | 1/2008 |
| CN | 101198698 | 6/2008 |
| CN | 101282992 | 10/2008 |
| CN | 1012777976 | 10/2008 |
| CN | 101479381 | 7/2009 |
| CN | 101511871 | 8/2009 |
| CN | 101849006 | 9/2010 |
| CN | 102946906 | 10/2011 |
| CN | 102271703 | 12/2011 |
| CN | 102471378 | 5/2012 |
| CN | 102597005 | 7/2012 |
| CN | 102844332 | 12/2012 |
| CN | 102782131 | 1/2013 |
| CN | 103097415 | 5/2013 |
| CN | 103221426 | 7/2013 |
| CN | 103328632 | 9/2013 |
| CN | 103429737 | 12/2013 |
| CN | 103476793 | 12/2013 |
| CN | 103492565 | 1/2014 |
| CN | 103833852 | 6/2014 |
| CN | 104302169 | 1/2015 |
| CN | 106459189 | 2/2017 |
| CN | 101874042 | 9/2018 |
| CO | 07124506 | 11/2007 |
| CO | 11080753 | 6/2011 |
| CO | 13047993 | 11/2013 |
| CO | 15075851 | 4/2015 |
| EA | 009026 | 10/2007 |
| EA | 2008/01027 | 10/2008 |
| EA | 2011/00300 | 12/2011 |
| EP | 0 361 902 | 4/1990 |
| EP | 0 369 566 | 5/1990 |
| EP | 0 329 185 | 4/1994 |
| EP | 0 628 639 A | 12/1994 |
| EP | 0 637 593 | 2/1995 |
| EP | 0 404 097 | 9/1996 |
| EP | 0 770 628 | 5/1997 |
| EP | 0 783 893 | 7/1997 |
| EP | 0 791 359 | 8/1997 |
| EP | 0 811 691 | 12/1997 |
| EP | 0 983 767 | 3/2000 |
| EP | 1 004 315 | 5/2000 |
| EP | 1 069 185 | 1/2001 |
| EP | 1 074 268 | 2/2001 |
| EP | 1 188 830 | 3/2002 |
| EP | 1 220 923 | 7/2002 |
| EP | 1 327 681 | 7/2003 |
| EP | 1 334 731 | 8/2003 |
| EP | 1 374 900 | 1/2004 |
| EP | 1 382 969 | 1/2004 |
| EP | 1510943 A1 | 3/2005 |
| EP | 0 979 281 | 7/2005 |
| EP | 1 605 058 | 12/2005 |
| EP | 1 690 550 | 8/2006 |
| EP | 1 693 448 | 8/2006 |
| EP | 0 770 628 | 9/2006 |
| EP | 1 701 979 | 9/2006 |
| EP | 1 707 215 | 10/2006 |
| EP | 1 728 801 | 12/2006 |
| EP | 1 733 740 | 12/2006 |
| EP | 1 773 391 | 4/2007 |
| EP | 1 847 602 | 10/2007 |
| EP | 1 870 458 | 12/2007 |
| EP | 1 870 459 | 12/2007 |
| EP | 1 876 236 | 1/2008 |
| EP | 1 900 814 | 3/2008 |
| EP | 1 941 907 | 7/2008 |
| EP | 1 941 908 | 7/2008 |
| EP | 1 967 207 | 9/2008 |
| EP | 1 967 209 | 9/2008 |
| EP | 1 990 060 | 11/2008 |
| EP | 2 006 381 | 12/2008 |
| EP | 2 009 101 | 12/2008 |
| EP | 2 031 064 | 3/2009 |
| EP | 1 505 148 | 4/2009 |
| EP | 2 047 863 | 4/2009 |
| EP | 2 107 115 | 10/2009 |
| EP | 2 123 302 | 11/2009 |
| EP | 2 174 667 | 4/2010 |
| EP | 2 194 066 | 6/2010 |
| EP | 2 196 220 | 6/2010 |
| EP | 2 196 541 | 6/2010 |
| EP | 2 202 245 | 6/2010 |
| EP | 2 206 775 | 7/2010 |
| EP | 2 228 392 | 9/2010 |
| EP | 2 236 604 | 10/2010 |
| EP | 2 241 332 | 10/2010 |
| EP | 2 275 443 | 1/2011 |
| EP | 2 305 306 | 4/2011 |
| EP | 2 314 618 | 4/2011 |
| EP | 2 330 193 | 6/2011 |
| EP | 1 688 488 | 8/2011 |
| EP | 2 354 161 | 8/2011 |
| EP | 2 366 713 | 9/2011 |
| EP | 2 409 991 | 1/2012 |
| EP | 2 431 393 | 3/2012 |
| EP | 2 471 813 A | 7/2012 |
| EP | 2 238 985 | 8/2012 |
| EP | 2 522 724 | 11/2012 |
| EP | 2 526 963 A | 11/2012 |
| EP | 2 543 727 | 1/2013 |
| EP | 2 578 233 | 4/2013 |
| EP | 2 644 698 | 10/2013 |
| EP | 2 647 706 | 10/2013 |
| EP | 2 647 707 | 10/2013 |
| EP | 2 679 681 | 1/2014 |
| EP | 2 698 431 | 2/2014 |
| EP | 1 509 770 B | 7/2014 |
| EP | 2 762 493 A | 8/2014 |
| EP | 2 762 564 | 8/2014 |
| EP | 2 853 898 | 4/2015 |
| EP | 2 889 377 | 7/2015 |
| EP | 2 905 290 | 8/2015 |
| EP | 2 914 634 | 9/2015 |
| EP | 2 940 043 | 11/2015 |
| EP | 2 975 055 | 1/2016 |
| EP | 3 199 628 A | 8/2017 |
| EP | 3 240 804 | 11/2017 |
| EP | 3 263 132 A | 1/2018 |
| JP | H01-144991 | 6/1989 |
| JP | 2-028200 | 1/1990 |
| JP | H02-501112 | 4/1990 |
| JP | 02-145187 | 6/1990 |
| JP | 2-163096 | 6/1990 |
| JP | H02-163085 | 6/1990 |
| JP | H03-500644 | 2/1991 |
| JP | 05-184383 | 7/1993 |
| JP | 05-199894 | 8/1993 |
| JP | 05-203652 | 8/1993 |
| JP | 05-213775 | 8/1993 |
| JP | 05-304992 | 11/1993 |
| JP | 07-67688 | 3/1995 |
| JP | 08-500979 | 2/1996 |
| JP | H08-217799 | 8/1996 |
| JP | 8-510555 | 11/1996 |
| JP | 09-506001 | 6/1997 |
| JP | 10-165184 | 6/1998 |
| JP | 10-511085 | 10/1998 |
| JP | 11-500915 | 1/1999 |
| JP | 11-500916 | 1/1999 |
| JP | 11-071288 | 3/1999 |
| JP | 11-506310 | 6/1999 |
| JP | 3032287 | 4/2000 |
| JP | 2001-523971 | 11/2001 |
| JP | 2002-514406 | 5/2002 |
| JP | 2002-518041 | 6/2002 |
| JP | 2003-055398 | 2/2003 |
| JP | 2003-509049 | 3/2003 |
| JP | 2003-512019 | 4/2003 |
| JP | 2004-86862 | 3/2004 |

(56) References Cited

FOREIGN PATENT DOCUMENTS

| | | |
|---|---|---|
| JP | 2004-511426 | 4/2004 |
| JP | 2005-501514 | 1/2005 |
| JP | 2005-101105 | 3/2005 |
| JP | 2005-532805 | 11/2005 |
| JP | 2005-535341 | 11/2005 |
| JP | 2005-378266 | 12/2005 |
| JP | 2005/537009 | 12/2005 |
| JP | 2006-517525 | 7/2006 |
| JP | 2006-519583 | 8/2006 |
| JP | 3865418 | 1/2007 |
| JP | 2007-532139 | 11/2007 |
| JP | 2008-510466 | 4/2008 |
| JP | 2008-512995 | 5/2008 |
| JP | 2008-519860 | 6/2008 |
| JP | 2008-523140 | 7/2008 |
| JP | 2008-538920 | 11/2008 |
| JP | 2009-500458 | 1/2009 |
| JP | 2009-541352 | 11/2009 |
| JP | 2010-505436 | 2/2010 |
| JP | 2010-079667 | 3/2010 |
| JP | 2010-521194 | 6/2010 |
| JP | 2010-522701 | 7/2010 |
| JP | 2010-250830 | 11/2010 |
| JP | 2011-504096 | 2/2011 |
| JP | 2011-507963 | 3/2011 |
| JP | 2011-508604 | 3/2011 |
| JP | 2011-184418 | 9/2011 |
| JP | 2011-529700 | 12/2011 |
| JP | 2012-504970 | 3/2012 |
| JP | 2012-505833 | 3/2012 |
| JP | 2012-082201 | 4/2012 |
| JP | 2012-510281 | 5/2012 |
| JP | 2012-512641 | 6/2012 |
| JP | 2012-522527 | 9/2012 |
| JP | 2012-531418 | 12/2012 |
| JP | 2012-531439 | 12/2012 |
| JP | 5144499 | 2/2013 |
| JP | 2013-515509 | 5/2013 |
| JP | 2013-518131 | 5/2013 |
| JP | 2013-518606 | 5/2013 |
| JP | 2013-521772 | 6/2013 |
| JP | 2013-529084 | 7/2013 |
| JP | 2013-529190 | 7/2013 |
| JP | 2013-165716 | 8/2013 |
| JP | 2013-531486 | 8/2013 |
| JP | 2015-510764 | 9/2013 |
| JP | 2013-537425 | 10/2013 |
| JP | 2013-541594 | 11/2013 |
| JP | 5334319 | 11/2013 |
| JP | 2014-055145 | 3/2014 |
| JP | 5484060 | 5/2014 |
| JP | 2014-528906 | 10/2014 |
| JP | 2014-257647 | 12/2014 |
| JP | 2015-510769 | 4/2015 |
| JP | 5717624 | 5/2015 |
| JP | 2015-130883 | 7/2015 |
| JP | 5787446 | 9/2015 |
| JP | 2016-026190 | 2/2016 |
| JP | 2016-69329 | 5/2016 |
| JP | 6088703 | 3/2017 |
| JP | 2017-509312 | 4/2017 |
| JP | 2017-113013 | 6/2017 |
| JP | 6175590 | 8/2017 |
| JP | 2018-123125 | 8/2018 |
| JP | 2018-141025 | 9/2018 |
| JP | 6534615 | 6/2019 |
| KR | 2006/0010765 | 2/2006 |
| KR | 2007/0035482 | 3/2007 |
| KR | 2009/0107091 | 10/2009 |
| KR | 2010/0056467 | 5/2010 |
| KR | 2010/0074221 | 7/2010 |
| KR | 2010/0097721 | 9/2010 |
| KR | 2012-0035192 | 4/2012 |
| KR | 2012/0123055 | 11/2012 |
| KR | 2013/0102113 | 9/2013 |
| KR | 2013/0102640 | 9/2013 |
| KR | 2013/0130765 | 12/2013 |
| KR | 2014/0005864 | 1/2014 |
| KR | 2017/0092449 | 8/2017 |
| NO | 20062087 | 7/2006 |
| RU | 94028282 | 7/1996 |
| RU | 2195960 | 1/2003 |
| RU | 2232773 | 7/2004 |
| RU | 2266298 | 12/2005 |
| RU | 2006/104842 | 8/2007 |
| RU | 2339696 | 11/2008 |
| RU | 2007/121679 | 12/2008 |
| RU | 2367667 | 9/2009 |
| RU | 2008/128133 | 1/2010 |
| RU | 2399381 | 9/2010 |
| RU | 2009/112723 | 10/2010 |
| RU | 2422460 | 6/2011 |
| RU | 2009/149451 | 7/2011 |
| RU | 2445975 | 3/2012 |
| RU | 2010/150931 | 6/2012 |
| RU | 2477137 | 3/2013 |
| RU | 2012/112067 | 10/2013 |
| SG | 183867 | 10/2012 |
| SG | 112017701119 R | 3/2017 |
| TW | 416960 | 1/2001 |
| TW | 2007/14313 | 4/2007 |
| TW | 2007/22517 | 6/2007 |
| TW | 200810778 | 3/2008 |
| TW | 200932266 | 8/2009 |
| TW | 2010/00127 | 1/2010 |
| TW | 2012/06466 | 2/2012 |
| TW | 2012/49872 | 12/2012 |
| TW | 2013/02219 | 1/2013 |
| TW | I452135 | 9/2014 |
| TW | I452136 | 9/2014 |
| TW | 2016/19193 | 6/2016 |
| TW | 2016/42902 | 12/2016 |
| TW | 2016/43190 | 12/2016 |
| TW | 2017/12032 | 4/2017 |
| WO | WO 88/04692 | 6/1988 |
| WO | WO 89/01343 | 2/1989 |
| WO | WO 91/01335 | 2/1991 |
| WO | WO 1991/008770 | 6/1991 |
| WO | WO 1991/013631 | 9/1991 |
| WO | WO 92/19759 | 11/1992 |
| WO | WO 1993/011161 | 6/1993 |
| WO | WO 1994/005690 | 3/1994 |
| WO | WO 94/10354 | 5/1994 |
| WO | WO 94/12215 | 6/1994 |
| WO | WO 94/13804 | 6/1994 |
| WO | WO 1994/021681 | 9/1994 |
| WO | WO 95/01571 | 1/1995 |
| WO | WO 95/02187 | 1/1995 |
| WO | WO 95/014710 | 6/1995 |
| WO | WO 1995/029697 | 11/1995 |
| WO | WO 95/33844 | 12/1995 |
| WO | WO 96/01653 | 1/1996 |
| WO | WO 1996/002576 | 2/1996 |
| WO | WO 96/07754 | 3/1996 |
| WO | WO 96/11020 | 4/1996 |
| WO | WO 96/12503 | 5/1996 |
| WO | WO 1996/016673 | 6/1996 |
| WO | WO 96/23071 | 8/1996 |
| WO | WO 96/27011 | 9/1996 |
| WO | WO 1996/026964 | 9/1996 |
| WO | WO 97/09351 | 3/1997 |
| WO | WO 97/10354 | 3/1997 |
| WO | WO 97/34631 | 9/1997 |
| WO | WO 98/03546 | 1/1998 |
| WO | WO 98/05787 | 2/1998 |
| WO | WO 98/42377 | 10/1998 |
| WO | WO 98/50431 | 11/1998 |
| WO | WO 99/03495 | 1/1999 |
| WO | WO 99/08707 | 2/1999 |
| WO | WO 1999/010494 | 3/1999 |
| WO | WO 99/018212 | 4/1999 |
| WO | WO 99/47170 | 9/1999 |
| WO | WO 99/51642 | 10/1999 |
| WO | WO 99/51743 | 10/1999 |

(56) References Cited

FOREIGN PATENT DOCUMENTS

| | | |
|---|---|---|
| WO | WO 99/58572 | 11/1999 |
| WO | WO 1999/067359 | 12/1999 |
| WO | WO 00/34317 | 6/2000 |
| WO | WO 00/42072 | 7/2000 |
| WO | WO 00/75314 | 12/2000 |
| WO | WO 01/19992 | 3/2001 |
| WO | WO 01/30854 | 5/2001 |
| WO | WO 01/82899 | 11/2001 |
| WO | WO 01/90192 | 11/2001 |
| WO | WO 02/06838 | 1/2002 |
| WO | WO 2002/009641 | 2/2002 |
| WO | WO 02/30463 | 4/2002 |
| WO | WO 02/30985 | 4/2002 |
| WO | WO 02/33073 | 4/2002 |
| WO | WO 2002/030985 | 4/2002 |
| WO | WO 02/34292 | 5/2002 |
| WO | WO 02/060919 | 8/2002 |
| WO | WO 02/072605 | 9/2002 |
| WO | WO 02/080969 | 10/2002 |
| WO | WO 03/000883 | 1/2003 |
| WO | WO 2003/015819 | 2/2003 |
| WO | WO 03/020949 | 3/2003 |
| WO | WO 03/027248 | 4/2003 |
| WO | WO 2003/035835 | 5/2003 |
| WO | WO 2003/042231 | 5/2003 |
| WO | WO 03/057881 | 7/2003 |
| WO | WO 03/060090 | 7/2003 |
| WO | WO 03/074679 | 9/2003 |
| WO | WO 2003/087163 | 10/2003 |
| WO | WO 2003/091424 | 11/2003 |
| WO | WO 03/105757 | 12/2003 |
| WO | WO 2004/007553 | 1/2004 |
| WO | WO 2004/008147 | 1/2004 |
| WO | WO 2004/009618 | 1/2004 |
| WO | WO 2004/016740 | 2/2004 |
| WO | WO 2004/020579 | 3/2004 |
| WO | WO 2004/024890 | 3/2004 |
| WO | WO 2004/029207 | 4/2004 |
| WO | WO 2004/035752 | 4/2004 |
| WO | WO 2004/037861 | 5/2004 |
| WO | WO 2004/058797 | 7/2004 |
| WO | WO 2004/060919 | 7/2004 |
| WO | WO 2004/065611 | 8/2004 |
| WO | WO 2004/068931 | 8/2004 |
| WO | WO 2004/085476 | 10/2004 |
| WO | WO 2004/091543 | 10/2004 |
| WO | WO 2004/092219 | 10/2004 |
| WO | WO 2004/096273 | 11/2004 |
| WO | WO 2004/097041 | 11/2004 |
| WO | WO 2004/099249 | 11/2004 |
| WO | WO 2004/108157 | 12/2004 |
| WO | WO 2004/111233 | 12/2004 |
| WO | WO 2004/113387 | 12/2004 |
| WO | WO 2005/000900 | 1/2005 |
| WO | WO 2005/005604 | 1/2005 |
| WO | WO 2005/020936 | 3/2005 |
| WO | WO 2005/025615 | 3/2005 |
| WO | WO 2005/035753 | 4/2005 |
| WO | WO 2005/035754 | 4/2005 |
| WO | WO 2005/035756 | 4/2005 |
| WO | WO 2005/037315 | 4/2005 |
| WO | WO 2005/037867 | 4/2005 |
| WO | WO 2005/047307 | 5/2005 |
| WO | WO 2005/047327 | 5/2005 |
| WO | WO 2005/056606 | 6/2005 |
| WO | WO 2005/056759 | 6/2005 |
| WO | WO 2005/059106 | 6/2005 |
| WO | WO 2005/061000 | 7/2005 |
| WO | WO 2005/062916 | 7/2005 |
| WO | WO 2005/066204 | 7/2005 |
| WO | WO 2005/067620 | 7/2005 |
| WO | WO 2005/070963 | 8/2005 |
| WO | WO 2005/074607 | 8/2005 |
| WO | WO 2005/077981 | 8/2005 |
| WO | WO 2005/080429 | 9/2005 |
| WO | WO 2005/090405 | 9/2005 |
| WO | WO 2005/092925 | 10/2005 |
| WO | WO 2005/094446 | 10/2005 |
| WO | WO 2005/112564 | 12/2005 |
| WO | WO 2005/115452 | 12/2005 |
| WO | WO 2005/121180 | 12/2005 |
| WO | WO 2005/123126 | 12/2005 |
| WO | WO 2005/123780 | 12/2005 |
| WO | WO 2006/004663 | 1/2006 |
| WO | WO 2006/019447 | 2/2006 |
| WO | WO 2006/020114 | 2/2006 |
| WO | WO 2006/023144 | 3/2006 |
| WO | WO 2006/023403 | 3/2006 |
| WO | WO 2006/029879 | 3/2006 |
| WO | WO 2006/030200 | 3/2006 |
| WO | WO 2006/030220 | 3/2006 |
| WO | WO 2006/031370 | 3/2006 |
| WO | WO 2006/033386 | 3/2006 |
| WO | WO 2006/047340 | 5/2006 |
| WO | WO 2006/047350 | 5/2006 |
| WO | WO 2006/050166 | 5/2006 |
| WO | WO 2006/050491 | 5/2006 |
| WO | WO 2006/053301 | 5/2006 |
| WO | WO 2006/065208 | 6/2006 |
| WO | WO 2006/067913 | 6/2006 |
| WO | WO 2006/070286 | 7/2006 |
| WO | WO 2006/071877 | 7/2006 |
| WO | WO 2006/075668 | 7/2006 |
| WO | WO 2006/083182 | 8/2006 |
| WO | WO 2006/083183 | 8/2006 |
| WO | WO 2006/085967 | 8/2006 |
| WO | WO 2006/088855 | 8/2006 |
| WO | WO 2006/102095 | 9/2006 |
| WO | WO 2006/105338 | 10/2006 |
| WO | WO 2006/106903 | 10/2006 |
| WO | WO 2006/106905 | 10/2006 |
| WO | WO 2006/109592 | 10/2006 |
| WO | WO 2006/113643 | 10/2006 |
| WO | WO 2006/113767 | 10/2006 |
| WO | WO 2006/116260 | 11/2006 |
| WO | WO 2006/116269 | 11/2006 |
| WO | WO 2006/118959 | 11/2006 |
| WO | WO 2006/119062 | 11/2006 |
| WO | WO 2006/119115 | 11/2006 |
| WO | WO 2006/121852 | 11/2006 |
| WO | WO 2006/130834 | 12/2006 |
| WO | WO 2007/001422 | 1/2007 |
| WO | WO 2007/008943 | 1/2007 |
| WO | WO 2007/009065 | 1/2007 |
| WO | WO 2007/021841 | 2/2007 |
| WO | WO 2007/024249 | 3/2007 |
| WO | WO 2007/024535 | 3/2007 |
| WO | WO 2007/041635 | 4/2007 |
| WO | WO 2007/043641 | 4/2007 |
| WO | WO 2007/044411 | 4/2007 |
| WO | WO 2007/044616 | 4/2007 |
| WO | WO 2007/046489 | 4/2007 |
| WO | WO 2007/047112 | 4/2007 |
| WO | WO 2007/058194 | 5/2007 |
| WO | WO 2007/060411 | 5/2007 |
| WO | WO 2007/061029 | 5/2007 |
| WO | WO 2005/068411 | 6/2007 |
| WO | WO 2007/074880 | 7/2007 |
| WO | WO 2007/084253 | 7/2007 |
| WO | WO 2007/086490 | 8/2007 |
| WO | WO 2007/092772 | 8/2007 |
| WO | WO 2007/103134 | 9/2007 |
| WO | WO 2007/103549 | 9/2007 |
| WO | WO 2007/106585 | 9/2007 |
| WO | WO 2007/108559 | 9/2007 |
| WO | WO 2007/108756 | 9/2007 |
| WO | WO 2007/114319 | 10/2007 |
| WO | WO 2007/114325 | 10/2007 |
| WO | WO 2007/133816 | 11/2007 |
| WO | WO 2007/137984 | 12/2007 |
| WO | WO 2007/142325 | 12/2007 |
| WO | WO 2007/143168 | 12/2007 |
| WO | WO 2007/147901 | 12/2007 |
| WO | WO 2007/150015 | 12/2007 |

(56) References Cited

FOREIGN PATENT DOCUMENTS

| | | |
|---|---|---|
| WO | WO 2007/150016 | 12/2007 |
| WO | WO 2008/022152 | 2/2008 |
| WO | WO 2008/030706 | 3/2008 |
| WO | WO 2008/031056 | 3/2008 |
| WO | WO 2008/036688 | 3/2008 |
| WO | WO 2008/043822 | 4/2008 |
| WO | WO 2008/069889 | 6/2008 |
| WO | WO 2008/090901 | 7/2008 |
| WO | WO 2008/090960 | 7/2008 |
| WO | WO 2008/091798 | 7/2008 |
| WO | WO 2008/091954 | 7/2008 |
| WO | WO 2008/092117 | 7/2008 |
| WO | WO 2008/098115 | 8/2008 |
| WO | WO 2008/103432 | 8/2008 |
| WO | WO 2008/113834 | 9/2008 |
| WO | WO 2008/118970 | 10/2008 |
| WO | WO 2008/119353 | 10/2008 |
| WO | WO 2008/121160 | 10/2008 |
| WO | WO 2008/130969 | 10/2008 |
| WO | WO 2008/132453 | 11/2008 |
| WO | WO 2008/143954 | 11/2008 |
| WO | WO 2008/145141 | 12/2008 |
| WO | WO 2008/145142 | 12/2008 |
| WO | WO 2008/150494 | 12/2008 |
| WO | WO 2009/000098 | 12/2008 |
| WO | WO 2009/000099 | 12/2008 |
| WO | WO 2009/012394 | 1/2009 |
| WO | WO 2009/014263 | 1/2009 |
| WO | WO 2009/026117 | 2/2009 |
| WO | WO 2009/032145 | 3/2009 |
| WO | WO 2009/032782 | 3/2009 |
| WO | WO 2009/036209 | 3/2009 |
| WO | WO 2009/084659 | 3/2009 |
| WO | WO 2009/041062 | 4/2009 |
| WO | WO 2009/041613 | 4/2009 |
| WO | WO 2009/041621 | 4/2009 |
| WO | WO 2009/041643 | 4/2009 |
| WO | WO 2009/041734 | 4/2009 |
| WO | WO 2009/044774 | 4/2009 |
| WO | WO 2009/052439 | 4/2009 |
| WO | WO 2009/053358 | 4/2009 |
| WO | WO 2009/053368 | 4/2009 |
| WO | WO 2009/058346 | 5/2009 |
| WO | WO 2009/058492 | 5/2009 |
| WO | WO 2009/063965 | 5/2009 |
| WO | WO 2009/072598 | 6/2009 |
| WO | WO 2009/072604 | 6/2009 |
| WO | WO 2009/079649 | 6/2009 |
| WO | WO 2009/086320 | 7/2009 |
| WO | WO 2009/089004 | 7/2009 |
| WO | WO 2009/089846 | 7/2009 |
| WO | WO 2009/095235 | 8/2009 |
| WO | WO 2009/100309 | 8/2009 |
| WO | WO 2009/125825 | 10/2009 |
| WO | WO 2009/137880 | 11/2009 |
| WO | WO 2009/139822 | 11/2009 |
| WO | WO 2009/148148 | 12/2009 |
| WO | WO 2010/015608 | 2/2010 |
| WO | WO 2010/033736 | 3/2010 |
| WO | WO 2010/035769 | 4/2010 |
| WO | WO 2010/042904 | 4/2010 |
| WO | WO 2010/045193 | 4/2010 |
| WO | WO 2010/054403 | 5/2010 |
| WO | WO 2010/058860 | 5/2010 |
| WO | WO 2010/063746 | 6/2010 |
| WO | WO 2010/064090 | 6/2010 |
| WO | WO 2010/064456 | 6/2010 |
| WO | WO 2010/064697 | 6/2010 |
| WO | WO 2010/065078 | 6/2010 |
| WO | WO 2010/070094 | 6/2010 |
| WO | WO 2010/081173 | 7/2010 |
| WO | WO 2010/085682 | 7/2010 |
| WO | WO 2010/106180 | 9/2010 |
| WO | WO 2010/106812 | 9/2010 |
| WO | WO 2010/107109 | 9/2010 |
| WO | WO 2010/107110 | 9/2010 |
| WO | WO 2010/115589 | 10/2010 |
| WO | WO 2010/129304 | 11/2010 |
| WO | WO 2010/131733 | 11/2010 |
| WO | WO 2010/151338 | 12/2010 |
| WO | WO 2010/151526 | 12/2010 |
| WO | WO 2010/151792 | 12/2010 |
| WO | WO 2011/021009 | 2/2011 |
| WO | WO 2011/090088 | 2/2011 |
| WO | WO 2011/025964 | 3/2011 |
| WO | WO 2011/037158 | 3/2011 |
| WO | WO 2011/043643 | 4/2011 |
| WO | WO 2011/078332 | 6/2011 |
| WO | WO 2011/090754 | 7/2011 |
| WO | WO 2011/090762 | 7/2011 |
| WO | WO 2011/091177 | 7/2011 |
| WO | WO 2011/091181 | 7/2011 |
| WO | WO 2011/094593 | 8/2011 |
| WO | WO 2011/100271 | 8/2011 |
| WO | WO 2011/108502 | 9/2011 |
| WO | WO 2011/108714 | 9/2011 |
| WO | WO 2011/109338 | 9/2011 |
| WO | WO 2011/111007 | 9/2011 |
| WO | WO 2011/122011 | 10/2011 |
| WO | WO 2011/125674 | 10/2011 |
| WO | WO 2011/131746 | 10/2011 |
| WO | WO 2011/133886 | 10/2011 |
| WO | WO 2011/137362 | 11/2011 |
| WO | WO 2011/143545 | 11/2011 |
| WO | WO 2011/149046 | 12/2011 |
| WO | WO 2011/150008 | 12/2011 |
| WO | WO 2011/151432 | 12/2011 |
| WO | WO 2012/016227 | 2/2012 |
| WO | WO 2012/020096 | 2/2012 |
| WO | WO 2012/024242 | 2/2012 |
| WO | WO 2012/033953 | 3/2012 |
| WO | WO 2012/064627 | 5/2012 |
| WO | WO 2012/067176 | 5/2012 |
| WO | WO 2012/073985 | 6/2012 |
| WO | WO 2012/073992 | 6/2012 |
| WO | WO 2012/088247 | 6/2012 |
| WO | WO 2012/093704 | 7/2012 |
| WO | WO 2012/115241 | 8/2012 |
| WO | WO 2012/132067 | 10/2012 |
| WO | WO 2012/133782 | 10/2012 |
| WO | WO 2012/145238 | 10/2012 |
| WO | WO 2012/177653 | 12/2012 |
| WO | WO 2013/004842 | 1/2013 |
| WO | WO 2013/012733 | 1/2013 |
| WO | WO 2013/046704 | 4/2013 |
| WO | WO 2013/046722 | 4/2013 |
| WO | WO 2013/047748 | 4/2013 |
| WO | WO 2013/047752 | 4/2013 |
| WO | WO 2013/060867 | 5/2013 |
| WO | WO 2013/065708 | 5/2013 |
| WO | WO 2013/081143 | 6/2013 |
| WO | WO 2013/124450 | 8/2013 |
| WO | WO 2013/125667 | 8/2013 |
| WO | WO 2013/131866 | 9/2013 |
| WO | WO 2013/136186 | 9/2013 |
| WO | WO 2013/138680 | 9/2013 |
| WO | WO 2013/149111 | 10/2013 |
| WO | WO 2013/152001 | 10/2013 |
| WO | WO 2013/157954 | 10/2013 |
| WO | WO 2013/158856 | 10/2013 |
| WO | WO 2013/166099 | 11/2013 |
| WO | WO 2013/181543 | 12/2013 |
| WO | WO 2013/186719 | 12/2013 |
| WO | WO 2014/006217 | 1/2014 |
| WO | WO 2014/028354 | 2/2014 |
| WO | WO 2014/030728 | 2/2014 |
| WO | WO 2014/043344 | 3/2014 |
| WO | WO 2014/047500 | 3/2014 |
| WO | WO 2011/044368 | 4/2014 |
| WO | WO 2014/051433 | 4/2014 |
| WO | WO 2014/054804 | 4/2014 |
| WO | WO 2014/067011 | 5/2014 |
| WO | WO 2014/074532 | 5/2014 |
| WO | WO 2014/100689 | 6/2014 |

(56) References Cited

FOREIGN PATENT DOCUMENTS

| | | |
|---|---|---|
| WO | WO 2014/114651 | 7/2014 |
| WO | WO 2014/119969 | 8/2014 |
| WO | WO 2014/144903 | 9/2014 |
| WO | WO 2014/145159 | 9/2014 |
| WO | WO 2014/145806 | 9/2014 |
| WO | WO 2014/160958 | 10/2014 |
| WO | WO 2014/163101 | 10/2014 |
| WO | WO 2014/182676 | 11/2014 |
| WO | WO 2014/184384 | 11/2014 |
| WO | WO 2014/190441 | 12/2014 |
| WO | WO 2015/022658 | 2/2015 |
| WO | WO 2015/023972 | 2/2015 |
| WO | WO 2005/023193 | 3/2015 |
| WO | WO 2015/046467 | 4/2015 |
| WO | WO 2015/046554 | 4/2015 |
| WO | WO 2015/063339 | 5/2015 |
| WO | WO 2015/111008 | 7/2015 |
| WO | WO 2015/127134 | 8/2015 |
| WO | WO 2015/134894 | 9/2015 |
| WO | WO 2015/156268 | 10/2015 |
| WO | WO 2015/162590 | 10/2015 |
| WO | WO 2015/174439 | 11/2015 |
| WO | WO 2015/194233 | 12/2015 |
| WO | WO 2016/000813 | 1/2016 |
| WO | WO 2016/136933 | 1/2016 |
| WO | WO 2016/047722 | 3/2016 |
| WO | WO 2016/073853 | 5/2016 |
| WO | WO 2016/073879 | 5/2016 |
| WO | WO 2016/073906 | 5/2016 |
| WO | WO 2016/092439 | 6/2016 |
| WO | WO 2016/098356 | 6/2016 |
| WO | WO 2016/098357 | 6/2016 |
| WO | WO 2016/117346 | 7/2016 |
| WO | WO 2016/125495 | 8/2016 |
| WO | WO 2016/136933 | 9/2016 |
| WO | WO 2016/159213 | 10/2016 |
| WO | WO 2016/160756 | 10/2016 |
| WO | WO 2016/166014 | 10/2016 |
| WO | WO 2016/168613 | 10/2016 |
| WO | WO 2016/171202 | 10/2016 |
| WO | WO 2016/178980 | 11/2016 |
| WO | WO 2016/209956 | 12/2016 |
| WO | WO 2017/046994 | 3/2017 |
| WO | WO 2017/049011 | 3/2017 |
| WO | WO 2017/064615 | 4/2017 |
| WO | WO 2017/104779 | 6/2017 |
| WO | WO 2017/104783 | 6/2017 |
| WO | WO 2017/110981 | 6/2017 |
| WO | WO 2017/115773 | 7/2017 |
| WO | WO 2017/120523 | 7/2017 |
| WO | WO 2017/123636 | 7/2017 |
| WO | WO 2017/129585 | 8/2017 |
| WO | WO 2017/159287 | 9/2017 |
| WO | WO 2017/188356 | 11/2017 |
| WO | WO 2017/217524 | 12/2017 |
| WO | WO 2017/217525 | 12/2017 |
| WO | WO 2017/218592 | 12/2017 |
| WO | WO 2018/025982 | 2/2018 |
| WO | WO 2018/143266 | 8/2018 |
| WO | WO 2018/169993 | 9/2018 |
| WO | WO 2018/181870 | 10/2018 |
| WO | WO 2019/084438 | 5/2019 |
| WO | WO 2019/112984 | 6/2019 |
| WO | WO 2020/027279 | 2/2020 |

OTHER PUBLICATIONS

Del Rio et al. (Ann. Ny. Acad. Sci, vol. 799, pp. 61-64, 1996).*
Onda et al. (Cancer Research, 61, Jul. 1, 2001, pp. 5070-5077).*
Lin et al. (J. Pharmacol Exp Therapeutics 1999; 288:371-78).*
Li et al. (Immunology, 116(4):487-98, Dec. 2005). (Year: 2005).*
Verhoeyen et al. (Immunology 78:364-370, 1993). (Year: 1993).*
Bartelds et al., "Clinical response to adalimumab: relationship to anti-adalimumab antibodies and serum adalimumab concentrations in rheumatoid arthritis," Ann Rheum. Dis., 66:921-926 (2007).
Bender et al., "Immunogenicity, efficacy and adverse events of adalimumab in RA patients," Rheumatol. Int., 27:269-274 (2007).
Blazar, "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," J. Immunol., 157:3250-59 (1996).
Chirino et al., "Minimizing the immunogenicity of protein therapeutics," Drug Discov. Today., 9:82-90 (2004).
Deng et al., "An Agonist Murine Monoclonal Antibody to the Human c-Mpl Receptor Stimulates Megakaryocytopoiesis," Blood, 92:1981-88 (1998).
Dillon et al., "Structural and functional characterization of disulfide isoforms of the human IgG2 subclass," J. Biol. Chem., 283:16206-15 (2008).
Gessner et al., "The IgG Fc receptor family," Ann. Hematol., 76:231-248 (1998).
Hanson et al., "Catalytic antibodies and their applications," Curr. Opin. Biotechnol., 16:631-636 (2005).
Hwang et al., "Use of human germline genes in a CDR homology-based approach to antibody humanization," Methods, 36:35-42 (2005).
Ito et al., "The His-probe method: effects of histidine residues introduced into the complementarity-determining regions of antibodies on antigen-antibody interactions at different pH values," FEBS Lett., 309:85-88 (1992).
Johnson et al., "Cation exchange-HPLC and mass spectrometry reveal C-terminal amidation of an IgG1 heavy chain," Anal. Biochem., 360:75-83 (2007).
Jones et al., "Identification and removal of a promiscuous CD4+ T cell epitope from the C1 domain of factor VIII," Thromb. Haemost., 3:991-1000 (2005).
Lund et al., "Expression and characterization of truncated forms of humanized L243 IgG1. Architectural features can influence synthesis of its oligosaccharide chains and affect superoxide production triggered through human Fcgamma receptor I," Eur. J. Biochem., 267:7246-57 (2000).
Maini et al., "Double-blind randomized controlled clinical trial of the interleukin-6 receptor antagonist, tocilizumab, in European patients with rheumatoid arthritis who had an incomplete response to methotrexate," Arthritis Rheum., 54:2817-29 (2006).
Nishimoto et al., "Humanized anti-interleukin-6 receptor antibody treatment of multicentric Castleman disease," Blood, 106:2627-32 (2005).
Nishimoto et al., "Interleukin 6: from bench to bedside," Nat. Clin. Pract. Rheumatol., 2:619-626 (2006).
Ohsugi et al., Pharm. Stage, 7:13-18 (2007) (English translation included).
Rajpal et al., "A general method for greatly improving the affinity of antibodies by using combinatorial libraries," Proc. Natl. Acad. Sci. U.S.A., 102:8466-71 (2005).
Rathanaswami et al., "Demonstration of an in vivo generated sub-picomolar affinity fully human monoclonal antibody to interleukin-8," Biochem. Biophys. Res. Commun., 334:1004-13 (2005).
Rothe et al., "Ribosome display for improved biotherapeutic molecules," Expert Opin. Biol. Ther., 6:177-187 (2006).
Salfeld et al., "Isotype selection in antibody engineering," Nat. Biotechnol., 25:1369-72 (2007).
Sato et al., "Reshaping a human antibody to inhibit the interleukin 6-dependent tumor cell growth," Cancer Res., 53:851-856 (1993).
Schmidt et al., Human Physiology, Moscow, 2:431-436 (1996), and English translation: Schmidt et al., "Hemostatis and Coagulation," Human Physiology, R.F. Schmidt, G. Thews (Eds.), Second, Completely Revised Edition, 418-423 [translated by Marguerite A. Biederman-Thorson], Springer-Verlag, 1989.
Schmidt et al., Human Physiology, Moscow, 3:764 (1996), and English translation: Schmidt et al., "Enzymes of the pancreatic juice," Human Physiology, R.F. Schmidt, G. Thews (Eds.), Second, Completely Revised Edition, 716 [translated by Marguerite A. Biederman-Thorson], Springer-Verlag, 1989.

(56) References Cited

OTHER PUBLICATIONS

Shire et al., "Challenges in the development of high protein concentration formulations," J. Pharm. Sci., 93:1390-1402 (2004).
Strand et al., "Biologic therapies in rheumatology: lessons learned, future directions," Nat. Rev. Drug Discov., 6:75-92 (2007).
Van Walle et al., Immunogenicity screening in protein drug development, Expert Opin. Biol. Ther., 7:405-418 (2007).
Wu et al., "Development of motavizumab, an ultra-potent antibody for the prevention of respiratory syncytial virus infection in the upper and lower respiratory tract," J. Mol. Biol., 368:652-665 (2007).
International Search Report for App. Ser. No. PCT/JP2008/067534, dated Oct. 21, 2008, 4 pages.
International Preliminary Report on Patentability for App. Ser. No. PCT/JP2008/067534, dated Apr. 7, 2010, 7 pages.
International Search Report for App. Ser. No. PCT/JP2009/057309, dated Jul. 7, 2009, 8 pages.
International Preliminary Report on Patentability for App. Ser. No. PCT/JP2009/057309, dated Nov. 30, 2010, 7 pages.
International Search Report for App. Ser. No. PCT/JP2009/066590, dated Oct. 20, 2009, 2 pages.
International Preliminary Report on Patentability for App. Ser. No. PCT/JP2008/067499, dated Apr. 7, 2010, 6 pages.
European Search Report for App. Ser. No. 07 74 0494, dated Sep. 3, 2009, 3 pages.
Fish & Richardson P.C., Amendment and Response to Restriction Requirement dated Nov. 18, 2009 in U.S. Appl. No. 10/575,905, filed Apr. 16, 2010, 12 pages.
Fish & Richardson P.C., Amendment in Reply to Action dated Jun. 23, 2010 in U.S. Appl. No. 10/575,905, filed Dec. 22, 2010, 10 pages.
Fish & Richardson P.C., Amendment in Reply to Action dated Jun. 23, 2010 in U.S. Appl. No. 10/575,193, filed Dec. 22, 2010, 13 pages.
USPTO Restriction Requirement in U.S. Appl. No. 12/295,075, dated Feb. 22, 2011, 9 pages.
USPTO Final Office Action in U.S. Appl. No. 10/575,905, dated Feb. 24, 2011, 7 pages.
USPTO Notice of Allowance in U.S. Appl. No. 10/575,193, dated Mar. 18, 2011, 11 pages.
USPTO Restriction Requirement in U.S. Appl. No. 11/910,836, dated Mar. 18, 2011, 7 pages.
Panka et al., "Variable region framework differences result in decreased or increased affinity of variant anti-digoxin antibodies," *Proc. Natl. Acad. Sci. U.S.A.*, 85(9):3080-4 (1988).
Calbiochem® Buffers, "A guide for the preparation and use of buffers in biological systems," by Chandra Mohan, Ph.D., Copyright© 2003 EMD Biosciences, Inc., an Affiliate of Merck KGaA, Darmstadt, Germany, 37 pages.
Chamow et al., "A humanized, bispecific immunoadhesin-antibody that retargets CD3+ effectors to kill HIV-1-infected cells," *J. Immunol.*, 153(9):4268-80 (1994).
European Search Report for Application No. EP 07 74 0474, dated Mar. 16, 2009, 6 pages.
Ghetie et al., "Multiple roles for the major histocompatibility complex class I-related receptor FcRn," Annu. Rev. Immunol., 18:739-766 (2000).
Martin et al., "Crystal structure at 2.8 A of an FcRn/heterodimeric Fc complex: mechanism of pH-dependent binding," Mol. Cell., 7:867-877 (2001).
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276:6591-6604 (2000).
Marvin et al., "Redesigning an antibody fragment for faster association with its antigen," Biochemistry, 42:7077-83 (2003).
Sal-Man et al., "Arginine mutations within a transmembrane domain of Tar, an *Escherichia coli* aspartate receptor, can drive homodimer dissociation and heterodimer association in vivo," Biochem. J., 385:29-36 (2005).

Shaul, "Exploring the charge space of protein-protein association: a proteomic study," Proteins, 60:341-352 (2005).
Adams et al., "Humanization of a recombinant monoclonal antibody to produce a therapeutic HER dimerization inhibitor, pertuzumab," Cancer Immunol. Immunother., 55:717-727 (2006).
Binz et al., "Engineering novel binding proteins from nonimmunoglobulin domains," Nature Biotechnol., 23:1257-68 (2005).
Comper and Glasgow, "Charge selectivity in kidney ultrafiltration," Kidney Int., 47:1242-51 (1995).
Couto et al., "Anti-BA46 Monoclonal Antibody Mc3: Humanization Using a Novel Positional Consensus and in Vivo and in Vitro Characterization," Cancer Res., 55:1717-22 (1995).
Deen et al., "Structural determinants of glomerular permeability," Am. J. Physiol. Renal. Physiol., 281:F579-F596 (2001).
del Rio et al., "An Engineered Penicillin Acylase with Altered Surface Charge Is More Stable in Alkaline pH," Ann. NY Acad. Sci., 799:61-64 (1996).
Ewert et al., "Stability improvement of antibodies for extracellular and intracellular applications: CDR grafting to stable frameworks and structure-based framework engineering," Methods, 34:184-199 (2004).
Ghetie and Ward, "FcRn: the MHC class I-related receptor that is more than an IgG transporter," Immunol. Today, 18:592-598 (1997).
Ghetie et al., "Increasing the serum persistence of an IgG fragment by random mutagenesis," Nature Biotechnol., 15:637-640 (1997).
Gobburu et al., "Pharmacokinetics/Dynamics of 5c8, a Monoclonal Antibody to CD154 (CD40 Ligand) Suppression of an Immune Response in Monkeys," J. Pharmacol. Exp. Ther., 286:925-930 (1998).
Goode et al., "The glomerular basement membrane charge-selectivity barrier: an oversimplified concept?" Nephrol. Dial. Transplant., 11:1714-16 (1996).
Graves et al., "Molecular Modeling and Preclinical Evaluation of the Humanized NR-LU-13 Antibody," Clin. Cancer Res., 5:899-908 (1999).
He et al., "Humanization and Pharmacokinetics of a Monoclonal Antibody with Specificity for Both E- and P-Selectin," J. Immunol., 160:1029-35 (1998).
Hinton et al., "An Engineered Human IgG1 Antibody with Longer Serum Half-Life," J. Immunol., 176:346-356 (2006)
Kashmiri et al., "Generation, Characterization, and in Vivo Studies of Humanized Anticarcinoma Antibody CC49," Hybridoma, 14:461-473 (1995).
Khawli et al., "Improved Tumor Localization and Radioimaging with Chemically Modified Monoclonal Antibodies," Cancer Biother. Radiopharm., 11:203-215 (1996).
Kim et al., "Antibody Engineering for the Development of Therapeutic Antibodies," Mol. Cells, 20:17-29 (2005).
Kim et al., "Chemical Modification to Reduce Renal Uptake of Disulfide-Bonded Variable Region Fragment of Anti-Tac Monoclonal Antibody Labeled with $^{99m}$Tc," Bioconjugate Chem., 10:447-453 (1999).
Kim et al., "Lowering of pI by acylation improves the renal uptake of $^{99m}$Tc-labeled anti-Tac dsFv: effect of different acylating reagents," Nucl. Med. Biol., 29:795-801 (2002).
Kobayashi et al., "The Pharmacokinetic Characteristics of Glycolated Humanized Anti-Tac Fabs Are Determined by Their Isoelectric Points," Cancer Res., 59:422-430 (1999).
Lobo et al., "Antibody Pharmacokinetics and Pharmacodynamics," J. Pharm. Sci., 93:2645-68 (2004).
Pavlinkova et al., "Charge-Modified Single Chain Antibody Constructs of Monoclonal Antibody CC49: Generation, Characterization, Pharmacokinetics, and Biodistribution Analysis," Nucl. Med. Biol., 26:27-34 (1999).
Pavlou and Belsey, "The therapeutic antibodies market to 2008," Eur. J. Pharm. Biopharm., 59:389-396 (2005).
Poduslo and Curran, "Polyamine Modification Increases the Permeability of Proteins at the Blood-Nerve and Blood-Brain Barriers," J. Neurochem., 66:1599-1609 (1996).
Rajpal et al., "A general method for greatly improving the affinity of antibodies by using combinational libraries," Proc. Natl. Acad. Sci. USA, 102:8466-71 (2005).

(56) References Cited

OTHER PUBLICATIONS

Reichert et al., "Monoclonal antibody successes in the clinic," Nature Biotechnol., 23:1073-78 (2005).
Schaeffer et al., "The Rat Glomerular Filtration Barrier Does Not Show Negative Charge Selectivity," Microcirculation, 9:329-342 (2002).
ten Kate et al., "Effect of isoelectric point on biodistribution and inflammation: imaging with indium-111-labelled IgG," Eur. J. Nucl. Med., 17:305-309 (1990).
Tsurushita et al., "Design of humanized antibodies: From anti-Tac to Zenapax," Methods, 36:69-83 (2005).
Yamasaki et al., "Pharmacokinetic Analysis of in Vivo Disposition of Succinylated Proteins Targeted to Liver Nonparenchymal Cells via Scavenger Receptors: Importance of Molecular Size and Negative Charge Density for in Vivo Recognition by Receptors," J. Pharmacol. Exp. Ther., 301:467-477 (2002).
Yang et al., "Tailoring structure-function and pharmacokinetic properties of single-chain Fv proteins by site-specific PEGylation," Protein Eng., 16:761-770 (2003).
Zuckier et al., "Chimeric Human-Mouse IgG Antibodies with Shuffled Constant Region Exons Demonstrate that Multiple Domains Contribute to in Vivo Half-Life," Cancer Res., 58:3905-08 (1998).
U.S. Appl. No. 12/295,075, filed Apr. 20, 2009, Igawa et al.
Branden and Tooze, "Recognition of Foreign Molecules by the Immune System," *Introduction to Protein Structure*, 2d Ed., Garland Publishing, pp. 299-323 (1999).
Carter, "Bispecific human IgG by design," J Immunol. Meth., 248:7-15 (2001).
Gupta and Suresh, "Affinity chromatography and co-chromatography of bispecific monoclonal antibody immunoconjugates," *J Biochem. Biophys. Methods*, 51:203-216 (2002).
Kreutz et al., "Efficient bispecific monoclonal antibody purification using gradient thiophilic affinity chromatography," J Chromatogr. B, 714:161-170 (1998).
Lindhofer et al., "Preferential Species-Restricted Heavy/Light Chain Pairing in Rat/Mouse Quadromas," *J Immunol.*, 155:219-225 (1995).
Manzke et al., "Single-step purification of bispecific monoclonal antibodies for immunotherapeutic use by hydrophobic interaction chromatography," J Immunol. Meth., 208:65-73 (1997).
Marvin and Zhu "Recombinant approaches to IgG-like bispecific antibodies," Acta. Pharmacol. Sin., 26:649-658 (2005).
Merchant et al., "An efficient route to human bispecific IgG," Nat. Biotechnol., 16:677-681 (1998).
Segal et al., "Bispecific antibodies in cancer therapy," Curr. Opin. Immunol., 11:558-562 (1999).
Tarditi et al., "Selective high-performance liquid chromatographic purification of bispecific monoclonal antibodies," J. Chromatogr., 599:13-20 (1992).
International Preliminary Report on Patentability for App. Ser. No. PCT/JP2007/057058, dated Oct. 21, 2008, 11 pages.
Japanese Patent Office, International Search Report App. Ser. No. PCT/JP2007/057058, dated May 7, 2001, 2 pages.
International Preliminary Report on Patentability for App. Ser. No. PCT/JP2007/057036, dated Oct. 21, 2008, 6 pages.
Japanese Patent Office, International Search Report for App. Ser. No. PCT/JP2007/057036, dated May 1, 2007, 2 pages.
Gelderman et al., "The inhibitory effect of CD46, CD55, and CD59 on complement activation after immunotherapeutic treatment of cervical carcinoma cells with monoclonal antibodies or bispecific monoclonal antibodies," Lab Invest., 82(4):483-93 (2002).
Bilsborough, "IL-31 is associated with cutaneous lymphocyte antigen-positive skin homing T cells in patients with atopic dermatitis," J. Allergy Clin. Immunol., 117(2):418-25 (2006).
Dillon et al., "Interleukin 31, a cytokine produced by activated T cells, induces dermatitis in mice," Nat. Immunol., 5(7):752-760 (2004).
Diveu et al., "GPL, a novel cytokine receptor related to GP130 and leukemia inhibitory factor receptor," *J. Biol. Chem.*, 278(50):49850-49859 (2003).

Hanes et al., "Picomolar affinity antibodies from a fully synthetic naive library selected and evolved by ribosome display," Nat. Biotechnol., 18(12):1287-1292 (2000).
Neis et al., "Enhanced expression levels of IL-31 correlate with IL-4 and IL-13 in atopic and allergic contact dermatitis," J. Allergy Clin. Immunol., 118(4):930-937 (2006).
Raap et al., "Correlation of IL-31 serum levels with severity of atopic dermatitis," *J Allergy Clin. Immunol.*, 122(2):421-423 (2008).
Sonkoly et al., "IL-31: a new link between T cells and pruritus in atopic skin inflammation," J. Allergy Clin. Immunol., 117:411-417 (2006).
Tan et al., "Engineering the isoelectric point of a renal cell carcinoma targeting antibody greatly enhances scFv solubility," Immunotechnology, 4(2):107-114 (1998).
Yagi et al., "Interleukin-31 stimulates production of inflammatory mediators from human colonic subepithelial myofibroblasts," Int. J. Mol. Med., 19(6):941-946 (2007).
Algonomics—Tripole® applications [online] [retrieved on Feb. 29, 2012]. Retrieved from the Internet: http://web.archive.org/web20090221052902/http://www.algonomics.com/proteinengineering/tripole_applications.php, 2 pages (Feb. 21, 2009).
Almagro et al., "Humanization of antibodies," *Front Biosci.*, 13:1619-33 (2008).
Armour et al., "Recombinant human IgG molecules lacking Fcgamma receptor I binding and monocyte triggering activities," Eur. J. Immunol., 29(8):2613-24 (1999).
Chau et al., "HuM291(Nuvion), a humanized Fc receptor-nonbinding antibody against CD3, anergizes peripheral blood T cells as partial agonist of the T cell receptor," Transplantation., 71(7):941-50 (2001).
Chen et al., "Generation and analysis of random point mutations in an antibody CDR2 sequence: many mutated antibodies lose their ability to bind antigen," J. Exp. Med., 176(3):855-66 (1992).
Chen et al., "Defective secretion of an immunoglobulin caused by mutations in the heavy chain complementarity determining region 2," J Exp. Med., 180(2):577-86 (1994).
Chu et al., "Accumulation of succinimide in a recombinant monoclonal antibody in mildly acidic buffers under elevated temperatures," Pharm. Res., 24(6):1145-56 (2007).
Cole et al., "Human IgG2 variants of chimeric anti-CD3 are nonmitogenic to T cells," J. Immunol., 159(7):3613-21 (1997).
Cordoba et al., "Non-enzymatic hinge region fragmentation of antibodies in solution," J. Chromatogr. B. Analyt. Technol. Biomed. Life Sci., 818(2):115-21 (2005).
Damschroder et al., "Framework shuffling of antibodies to reduce immunogenicity and manipulate functional and biophysical properties," Mol. Immunol., 44(11):3049-60 (2007).
De Groot et al., "De-immunization of therapeutic proteins by T-cell epitope modification," Dev. Biol. (Basel), 122:171-94 (2005).
Fujii, "Antibody affinity maturation by random mutagenesis," Methods Mol. Biol., 248:345-59 (2004).
Gerstner et al., "Sequence plasticity in the antigen-binding site of a therapeutic anti-HER2 antibody," *J. Mol. Biol.*, 321(5):851-62 (2002).
Guyre et al., "Increased potency of Fc-receptor-targeted antigens," Cancer Immunol. Immunother., 45(3-4):146-8 (1997).
Hinton et al., "Engineered human IgG antibodies with longer serum half-lives in primates," J. Biol. Chem., 279(8):6213-6 (2004).
Katayose et al., "MUC1-specific targeting immunotherapy with bispecific antibodies: inhibition of xenografted human bile duct carcinoma growth," Cancer Res., 56(18):4205-12 (1996).
Komissarov et al., "Site-specific mutagenesis of a recombinant anti-single-stranded DNA Fab. Role of heavy chain complementarity-determining region 3 residues in antigen interaction," *J Biol. Chem.*, 272(43):26864-70 (1997).
Leong et al., "Adapting pharmacokinetic properties of a humanized anti-interleukin-8 antibody for therapeutic applications using site-specific pegylation," Cytokine, 16(3):106-19 (2001).
Liu et al., "Heterogeneity of monoclonal antibodies," *J. Pharm. Sci.*, 97(7):2426-47 (2008).
Nesterova et al., "Glypican-3 as a novel target for an antibody-drug conjugate," AACR Abstract No. 656, Los Angeles, CA (Apr. 4-18, 2007).

(56) References Cited

OTHER PUBLICATIONS

Ono et al., "The humanized anti-HM1.24 antibody effectively kills multiple myeloma cells by human effector cell-mediated cytotoxicity," *Mol. Immunol.*, 36(6):387-95 (1999).
Pardridge et al., "Enhanced endocytosis in cultured human breast carcinoma cells and in vivo biodistribution in rats of a humanized monoclonal antibody after cationization of the protein," *J. Pharmacol. Exp. Ther.*, 286(1):548-54 (1998).
Pons et al., "Energetic analysis of an antigen/antibody interface: alanine scanning mutagenesis and double mutant cycles on the HyHEL-10/lysozyme interaction," *Protein Sci.*, 8(5):958-68 (1999).
Presta, "Engineering of therapeutic antibodies to minimize immunogenicity and optimize function," *Adv. Drug Deliv. Rev.*, 58(5-6):640-56 (2006).
Reddy et al., "Elimination of Fc receptor-dependent effector functions of a modified IgG4 monoclonal antibody to human CD4," *J. Immunol.*, 164(4):1925-33 (2000).
Reichert et al., "Development trends for monoclonal antibody cancer therapeutics," *Nat. Rev. Drug Discov.*, 6(5):349-56 (2007).
Schmitz et al., "Phage display: a molecular tool for the generation of antibodies—a review," *Placenta.*, 21 Suppl A:S106-12 (2000).
Teeling et al., "The biological activity of human CD20 monoclonal antibodies is linked to unique epitopes on CD20," *J. Immunol.*, 177(1):362-71 (2006).
Vaisitti et al., "Cationization of monoclonal antibodies: another step towards the "magic bullet"?," *J. Biol. Regul. Homeost. Agents.*, 19(3-4):105-12 (2005).
Vajdos et al., "Comprehensive functional maps of the antigen-binding site of an anti-ErbB2 antibody obtained with shotgun scanning mutagenesis," *J. Mol. Biol.*, 320(2):415-28 (2002).
Wiens et al., "Somatic mutation in VH complementarity-determining region 2 and framework region 2: differential effects on antigen binding and Ig secretion," *J Immunol.*, 159(3):1293-302 (1997).
Wiens et al., "Mutation of a single conserved residue in VH complementarity-determining region 2 results in a severe Ig secretion defect," *J. Immunol.*, 167(4):2179-86 (2001).
Xiang et al., "Study of B72.3 combining sites by molecular modeling and site-directed mutagenesis," *Protein Eng.*, 13(5):339-44 (2000).
Zwick et al., "The long third complementarity-determining region of the heavy chain is important in the activity of the broadly neutralizing anti-human immunodeficiency virus type 1 antibody 2F5," *J. Virol.*, 78(6):3155-61 (2004).
USPTO Notice of Allowance in U.S. Appl. No. 12/680,087, dated Feb. 24, 2012, 5 pages.
USPTO Notice of Allowance in U.S. Appl. No. 10/575,193, dated Jul. 13, 2011, 8 pages.
International Preliminary Report on Patentability for App. No. PCT/JP2009/066590, dated May 10, 2011, 6 pages.
International Preliminary Report on Patentability for App. No. PCT/JP2009/070376, dated Jul. 5, 2011, 11 pages.
Fish & Richardson P.C., Response to Restriction Requirement dated Feb. 22, 2011 in U.S. Appl. No. 12/295,075, filed Aug. 18, 2011, 2 pages.
USPTO Non-Final Office Action in U.S. Appl. No. 12/295,075, dated Nov. 4, 2011, 14 pages.
Fish & Richardson P.C., Response to Restriction Requirement dated Mar. 18, 2011 in U.S. Appl. No. 11/910,836, filed Sep. 6, 2011, 1 page.
USPTO Non-Final Office Action in U.S. Appl. No. 11/910,836, dated Sep. 30, 2011, 21 pages.
USPTO Non-Final Office Action U.S. Appl. No. 12/680,087, dated Oct. 27, 2011, 6 pages.
USPTO Restriction Requirement in U.S. Appl. No. 12/936,587, dated Dec. 6, 2011, 7 pages.
Dall'Acqua et al., "Antibody humanization by framework shuffling," *Methods*, 36(1):43-60 (2005).
Sinha et al., "Electrostatics in protein binding and function," *Curr. Protein Pept. Sci.*, 3(6):601-14 (2002).
Tsuchiya, Credit Suisse Seminar, "Therapeutic Antibody," at Fuji-Gotemba Laboratories, p. 21 (2006).
Fish & Richardson P.C., Response to Restriction Requirement dated Jun. 9, 2011 in U.S. Appl. No. 11/910,128, filed Dec. 2, 2011, 1 page.
Fish & Richardson P.C., Amendment and Reply to Action dated Oct. 27, 2011 in U.S. Appl. No. 12/680,087, filed Jan. 26, 2012, 6 pages.
Fish & Richardson P.C., Amendment in U.S. Appl. No. 10/575,193, filed Jun. 17, 2011, 15 pages.
USPTO Restriction Requirement in U.S. Appl. No. 11/910,128, dated Jun. 9, 2011, 10 pages.
U.S. Appl. No. 13/518,861, filed Jun. 22, 2013, Igawa et al.
U.S. Appl. No. 13/595,139, filed Aug. 27, 2012, Igawa et al.
U.S. Appl. No. 13/582,073, filed Aug. 31, 2012, Kuramochi et al.
U.S. Appl. No. 13/637,415, filed Sep. 26, 2012, Igawa et al.
USPTO Non-Final Office Action in U.S. Appl. No. 12/679,922, dated Jan. 3, 2013, 25 pages.
International Search Report for App. Ser. No. PCT/JP2011/001888, dated Nov. 2, 2011, 7 pages.
Fay et al., "The size of human factor VIII heterodimers and the effects produced by thrombin," *Biochim Biophys Acta.*, 871(3):268-78 (1986).
Helfrich et al., "A rapid and versatile method for harnessing scFv antibody fragments with various biological effector functions," *J. Immunol. Methods*, 237(1-2):131-45 (2000).
Hombach et al., "A CD16/CD30 bispecific monoclonal antibody induces lysis of Hodgkin's cells by unstimulated natural killer cells in vitro and in vivo," *Int J Cancer*, 55:830-6 (1993).
Hoyer, "The factor VIII complex: structure and function," *Blood*, 58(1):1-13 (1981).
Jain et al., "Engineering antibodies for clinical applications," *Trends Biotechnol.*, 25(7):307-16 (2007).
Janeway et al., "Structure of the Antibody Molecule and Immunoglobulin Genes," *Immunobiology, 3$^{rd}$ Edition*, Garland Press, 3:1-3:11 (1997).
Kerschbaumer et al., "An antibody specific for coagulation factor IX enhances the activity of the intrinsic factor X-activating complex," *J. Biol. Chem.*, 279(39):40445-50 (2004).
Kufer et al., "A revival of bispecific antibodies," *Trends Biotechnol.*, 22(5):238-44 (2004).
Miyazaki et al., "Generation of bispecific IgG, which mimics the cofactor function of blood coagulation factor VIII," *Seikagaku*, Poster sessions (2P-B-161) (2006).
Paul, William ed., *Fundamental Immunology, 3$^{rd}$ edition*, p. 242 (1993).
Portolano et al., "Lack of Promiscuity in Autoantigen-Specific H and L Chain Combinations as Revealed by Human H and L Chain "Roulette"," *J. Immunol.*, 150(3):880-887 (1993).
Roguska et al., "Humanization of murine monoclonal antibodies through variable domain resurfacing," *Proc Natl Acad Sci U.S.A.*, 91:969-73 (1994).
Saito et al., "Factor VIII Mimetic Antibody: (1) Establishment and Characterization of Anti-factor IX/anti-factor X Bispecific Antibodies," *2005 International Society of Thrombosis and Haemostasis*, vol. 3, Issue Supplement sl, p. #OR160.
Saito et al., "Establishment of Factor VIII Mimetic Antibodies and Their In Vitro Activities in Hemophilia A," *2006 National Hemophilia Foundation Symposia*.
Shima et al., "Factor VIII Mimetic Antibody: (2) In Vitro Assessment of Cofactor Activity in Hemophilia A," *2005 International Society of Thrombosis and Haemostasis*, vol. 3, Issue Supplement sl, p. #P0038.
Shima, M., "Bispecific antibodies to coagulation factors IXa and X mimic the function of factor VIII," *2006 World Federation of Haemophilia* (Haemophilia, 12(Suppl. 2):98 (2006)).
Shirahata, Minna ni yakudatsu ketsuyubyo no. kiso to rinsho. Iyaku (Medicine and Drug) Journal Co., Ltd., 280-9 (2009) (including English translation).
Soeda et al., "Factor VIII Taitei Kotai (1) Ko FIXa/FX bispecific Kotai no Sakusei oyobi characterization," Rinsho Ketsueki, 46(8):728 (2005) (including English translation).

(56) References Cited

OTHER PUBLICATIONS

Soeda et al., "Phage library-ho ni yori Sakusei shita Ko-FIXa/Ko-FX bispecific Kotai no FVIII Taitei Sayo," *Jpn J Thromb Hemost.*, 16(5):526 (2005) (including English translation).

Staerz et al., "Hybrid hybridoma producing a bispecific monoclonal antibody that can focus effector T-cell activity," *Proc Natl Acad Sci U.S.A.*, 83:1453-7 (1986).

Vehar et al., "Structure of human factor VIII," *Nature*, 312(5992):337-42 (1984).

Wood et al., "Expression of active human factor VIII from recombinant DNA clones," *Nature*, 312(5992):330-7 (1984).

International Search Report for App. Ser. No. PCT/JP2011/076486, dated Dec. 27, 2011, 4 pages.

Amersham Biosciences, "Affinity Chromatography: Principles and Methods," Edition AD, pp. 16-18, 137 (2002).

Zhu et al., "MHC class I-related neonatal Fc receptor for IgG is functionally expressed in monocytes, intestinal macrophages, and dendritic cells," *J. Immunol.*, 166(5):3266-76 (2001).

Fish & Richardson P.C., Amendment in Reply to Action dated Jul. 19, 2012 in U.S. Appl. No. 12/295,075, filed Jan. 17, 2013, 113 pages.

Fish & Richardson P.C., Response to Restriction Requirement dated Jul. 27, 2012 and Preliminary Amendment in U.S. Appl. No. 13/434,643, filed Jan. 24, 2013, 10 pages.

Fish & Richardson P.C., Response to Restriction Requirement dated Dec. 18, 2012 in U.S. Appl. No. 13/320,317, filed Jan. 18, 2013, 3 pages.

Presta et al., "Molecular engineering and design of therapeutic antibodies," *Curr. Opin. Immunol.*, 20(4):460-70 (2008).

U.S. Appl. No. 12/680,087, filed Jan. 3, 2011.

U.S. Appl. No. 12/680,112, filed Jun. 23, 2010.

Abe et al., "Purification of monoclonal antibodies with light-chain heterogeneity produced by mouse hybridomas raised with NS-1 myelomas: application of hydrophobic interaction high-performance liquid chromatography," *J. Biochem. Biophys. Methods*, 27:215-227 (1993).

Amersham Biosciences, "Protein Purification Handbook," Edition AC, 98 pages (2001).

Kranenborg et al., "Development and characterization of anti-renal cell carcinoma x antichelate bispecific monoclonal antibodies for two-phase targeting of renal cell carcinoma," *Cancer Res.*, 55:5864s-5867s (1995).

Lansdorp et al., "Purification and analysis of bispecific tetrameric antibody complexes," *Mol. Immunol.*, 27:659-666 (1990).

Morimoto et al., "Single-step purification of F(ab')2 fragments of mouse monoclonal antibodies (immunoglobulins G1) by hydrophobic interaction high performance liquid chromatography using TSKgel Phenyl-5PW," *J. Biochem. Biophys. Methods*, 24:107-117 (1992).

Suresh et al., "Bispecific monoclonal antibodies from hybrid hybridomas," Methods Enzymol., 121:210-228 (1986).

Warnaar et al., "Purification of bispecific F(ab')2 from murine trinoma OC/TR with specificity for CD3 and ovarian cancer," *Hybridoma*, 13:519-526 (1994).

USPTO Non Final Office Action in U.S. Appl. No. 12/680,112, dated Feb. 4, 2013, 9 pages.

USPTO Non-Final Office Action U.S. Appl. No. 12/680,082, dated Feb. 14, 2013, 12 pages.

USPTO Non-Final Office Action in U.S. Appl. No. 13/434,643, dated Feb. 12, 2013, 17 pages.

Dahlback, "Blood coagulation," *Lancet*, 355(9215):1627-32 (2000).

Fay et al., "Chapter 2B Nonenzymatic cofactors: factor VIII," *Comprehensive Biochemistry*, 13:35-37 (1986).

Hu et al., "Development and characterization of a novel fusion protein composed of a human lgG1 heavy chain constant region and a single-chain fragment variable antibody against Venezuelan equine encephalitis virus," *J Biochem.*, 133(1):59-66 (2003).

Sampei et al., "Identification and multidimensional optimization of an asymmetric bispecific lgG antibody mimicking the function of factor VIII cofactor activity," *PLoS One*, 2013;8(2):e57479. doi: 10.1371/journal.pone.0057479. Epub Feb. 28, 2013.

Zuo et al., "An efficient route to the production of an IgG-like bispecific antibody," *Protein Eng.*, 13(5):361-7 (2000).

Krauss et al., "Impact of antibody framework residue VH-71 on the stability of a humanised anti-MUC1 scFv and derived immunoenzyme," *Br. J. Cancer*, 90:1863-70 (2004).

Marks et al., "By-passing immunization: building high affinity human antibodies by chain shuffling," *Biotechnology (N.Y.)*, 10(7):779-83 (1992).

Roitt et al., *Immunology, M., Mir*, 110, 150, 537-9 (2000) (with English translations).

Singer et al., Genes & Genomes (Russian translation from English) 1:63 (1998) (with English translation).

Yang et al., "CDR walking mutagenesis for the affinity maturation of a potent human anti-HIV-1 antibody into the picomolar range," *J. Mol. Biol.*, 254(3):392-403 (1995).

USPTO Restriction Requirement in U.S. Appl. No. 13/257,145, dated Mar. 20, 2013, 11 pages.

USPTO Restriction Requirement in U.S. Appl. No. 13/524,528, dated Mar. 21, 2013, 7 pages.

Amigorena et al., "Cytoplasmic domain heterogeneity and functions of IgG Fc receptors in B lymphocytes," *Science*, 256(5065):1808-12 (1992).

Amigorena et al., "Fc gamma RII expression in resting and activated B lymphocytes," *Eur J Immunol.*, (8):1379-85 (1989).

Armour et al., "Differential binding to human FcgammaRIIa and FcgammaRIIb receptors by human IgG wildtype and mutant antibodies," *Mol Immunol.*, 40(9):585-93 (2003).

Blank et al., Decreased transcription of the human FCGR2B gene mediated by the -343 G/C promoter polymorphism and association with systemic lupus erythematosus. *Hum Genet.*, 117(2-3):220-7 (2005).

Boruchov et al., "Activating and inhibitory IgG Fc receptors on human DCs mediate opposing functions," *J Clin Invest.*, 115(10):2914-23 (2005).

Boumpas et al., "A short course of BG9588 (anti-CD40 ligand antibody) improves serologic activity and decreases hematuria in patients with proliferative lupus glomerulonephritis," *Arthritis Rheum.*, 48(3):719-27 (2003).

Bruhns et al., Specificity and affinity of human Fcgamma receptors and their polymorphic variants for human IgG subclasses, *Blood*, 113(16):3716-25 (2009).

Cemerski et al., "Suppression of mast cell degranulation through a dual-targeting tandem IgE-IgG Fc domain biologic engineered to bind with high affinity to FcγRIIb," *Immunol Lett.*, 143(1):34-43 (2012).

Chen et al., "Association of a transmembrane polymorphism of Fcgamma receptor IIb (FCGR2B) with systemic lupus erythematosus in Taiwanese patients," *Arthritis Rheum.*, 54(12):3908-17 (2006).

Chu et al., "Inhibition of B cell receptor-mediated activation of primary human B cells by coengagement of CD19 and FcgammaRIIb with Fc-engineered antibodies," *Mol Immunol.*, 45(15):3926-33 (2008).

Chu et al., "Reduction of total IgE by targeted coengagement of IgE B-cell receptor and FcγRIIb with Fc-engineered antibody," *J Allergy Clin Immunol.*, 129(4):1102-15 (2012).

Chuntharapai et al., "Isotype-dependent inhibition of tumor growth in vivo by monoclonal antibodies to death receptor 4," *J Immunol.*, 166(8):4891-8 (2001).

Clark, "IgG effector mechanisms," *Chem Immunol.*, 65:88-110 (1997).

Dall'Acqua et al., "Properties of human IgG1s engineered for enhanced binding to the neonatal Fc receptor (FcRn)," *J Biol Chem.*, 281(33):23514-24 (2006).

Datta-Mannan et al., "Monoclonal antibody clearance. Impact of modulating the interaction of IgG with the neonatal Fc receptor," *J Biol Chem.*, Jan. 19, 2007;282(3):1709-17. Epub Nov. 29, 2006.

Dhodapkar et al., "Selective blockade of inhibitory Fcgamma receptor enables human dendritic cell maturation with IL-12p70 production and immunity to antibody-coated tumor cells," *Proc Natl Acad Sci USA*, 102(8):2910-5 (2005).

(56) References Cited

OTHER PUBLICATIONS

Duffau et al., "Platelet CD154 potentiates interferon-alpha secretion by plasmacytoid dendritic cells in systemic lupus erythematosus," *Sci Transl Med.*, 2(47):47ra63 (2010).
Floto et al., "Loss of function of a lupus-associated FcgammaRIIb polymorphism through exclusion from lipid rafts," *Nat Med.*, 11(10):1056-8 (2005).
Fournier et al., "Activation of human peripheral IgM+ B cells is transiently inhibited by BCR-independent aggregation of Fc gammaRIIB," *J Immunol.*, 181(8):5350-9 (2008).
Greenwood et al., "Structural motifs involved in human IgG antibody effector functions," *Eur J Immunol.*, 23(5):1098-104 (1993).
Heyman, "Feedback regulation by IgG antibodies," *Immunol Lett.*, 88(2):157-61 (2003).
Jefferis et al., "Interaction sites on human IgG-Fc for FcgammaR: current Models," *Immunol Lett.*, 82(1-2):57-65 (2002).
Kohrt et al., "Stimulation of natural killer cells with a CD137-specific antibody enhances trastuzumab efficacy in xenotransplant models of breast cancer," *J Clin Invest.*, 122(3):1066-75 (2012).
Li et al., "CD72 down-modulates BCR-induced signal transduction and diminishes survival in primary mature B lymphocytes," *J Immunol.*, 176(9):5321-8 (2006).
Li et al., "Inhibitory Fcγ receptor engagement drives adjuvant and anti-tumor activities of agonistic CD40 antibodies," *Science*, 333(6045):1030-4 (2011).
Liang et al., "Immunity against a therapeutic xenoprotein/Fc construct delivered by gene transfer is reduced through binding to the inhibitory receptor FcγRIIb," *J Gene Med.*, 13(9):470-7 (2011)
Mackay et al., "Selective dysregulation of the FcgammaIIB receptor on memory B cells in SLE," *J Exp Med.*, 203(9):2157-64 (2006).
Manger et al., "Fcgamma receptor IIa polymorphism in Caucasian patients with systemic lupus erythematosus: association with clinical symptoms," *Arthritis Rheum.*, 41(7):1181-9 (1998).
Meyer et al., "Bevacizumab immune complexes activate platelets and induce thrombosis in FCGR2A transgenic mice," *J Thromb Haemost.*, Jan. 2009;7(1):171-81. Epub Oct. 30, 2008.
Mi et al., "Targeting the neonatal fc receptor for antigen delivery using engineered fc fragments," *J Immunol.*, 181(11):7550-61 (2008).
Morgan et al., "The N-terminal end of the CH2 domain of chimeric human IgG1 anti-HLA-DR is necessary for Clq, Fc gamma RI and Fc gamma RIII binding," *Immunology.*, 86(2):319-24 (1995).
Muta et al., "A 13-amino-acid motif in the cytoplasmic domain of Fc gamma RIIB modulates B-cell receptor signaling," *Nature*, 368(6466):70-3 (1994).
Nakamura et al., "Fcgamma receptor IIB-deficient mice develop Goodpasture's syndrome upon immunization with type IV collagen: a novel murine model for autoimmune glomerular basement membrane disease," *J Exp Med.*, 191(5):899-906 (2000).
Nicholas et al., "Regulation of the immune response. I. Reduction in ability of specific antibody to inhibit long-lasting IgG immunological priming after removal of the Fc fragment," *J Exp Med.*, 129(6):1183-201 (1969).
Niebecker et al., "Safety of therapeutic monoclonal antibodies," *Curr Drug Saf.*, 5(4):275-86 (2010).
Nimmerjahn et al., "Fcgamma receptors as regulators of immune responses," *Nat Rev Immunol.*, 8(1):34-47 (2008).
Olferiev et al., "The role of activating protein 1 in the transcriptional regulation of the human FCGR2B promoter mediated by the -343 G -> C polymorphism associated with systemic lupus erythematosus," *J Biol Chem.*, 282(3):1738-46 (2007).
Paul, "Structure and function of immunoglobulins," Fundamental Immunology, Third Edition, 292-295 (1993).
Qiao et al., "Dependence of antibody-mediated presentation of antigen on FcRn," *Proc Natl Acad Sci USA*, 105(27):9337-42 (2008).
Radaev et al., "The role of Fc glycosylation and the binding of peptide inhibitors," *J Biol Chem.*, 276(19):16478-83 (2001).
Ravetch et al., "Immune inhibitory receptors," *Science*, 290(5489):84-9 (2000).

Richards et al., "Optimization of antibody binding to FcgammaRIIa enhances macrophage phagocytosis of tumor cells," *Mol Cancer Ther.*, 7(8):2517-27 (2008).
Robles-Carrillo et al., "Anti-CD40L immune complexes potently activate platelets in vitro and cause thrombosis in FCGR2A transgenic mice," *J Immunol.*, 185(3):1577-83 (2010).
Salmon et al., "Fc gamma RIIA alleles are heritable risk factors for lupus nephritis in African Americans," *J Clin Invest.*, 97(5):1348-54 (1996).
Scappaticci et al., "Arterial thromboembolic events in patients with metastatic carcinoma treated with chemotherapy and bevacizumab," *J Natl Cancer Inst.*, 100(2):156 (2008).
Smith et al., "FcgammaRIIB in autoimmunity and infection: evolutionary and therapeutic implications," *Nat Rev Immunol.*, May;10(5):328-43 (2010).
Su et al., Expression profile of FcgammaRIIb on leukocytes and its dysregulation in systemic lupus erythematosus, *J Immunol.*, 178(5):3272-80 (2007).
Veri et al., "Therapeutic control of B cell activation via recruitment of Fcgamma receptor IIb (CD32B) inhibitory function with a novel bispecific antibody scaffold," *Arthritis Rheum.*, 62(7):1933-43 (2010).
Veri et al., "Monoclonal antibodies capable of discriminating the human inhibitory Fcgamma-receptor IIb (CD32B) from the activating Fcgamma-receptor IIA (CD32A): biochemical, biological and functional characterization," *Immunology*, 121(3):392-404 (2007).
Warmerdam et al., Molecular basis for a polymorphism of human Fc gamma receptor II (CD32), *J Exp Med.*, 172(1):19-25 (1990).
Wernersson et al., "IgG-mediated enhancement of antibody responses is low in Fc receptor gamma chain-deficient mice and increased in Fc gamma RII-deficient mice," *J Immunol.*, 163(2):618-22 (1999).
Wilson et al., "An Fcγ receptor-dependent mechanism drives antibody-mediated target-receptor signaling in cancer cells," *Cancer Cell*, 19(1):101-13 (2011).
Xu et al., "Fc gamma Rs modulate cytotoxicity of anti-Fas antibodies: implications for agonistic antibody-based therapeutics," *J Immunol.*, 171(2):562-8 (2003).
Yuasa et al., "Deletion of fcgamma receptor IIB renders H-2(b) mice susceptible to collagen-induced arthritis," *J Exp Med.*, 189(1):187-94 (1999).
Zhang et al., "Effective therapy for a murine model of human anaplastic large-cell lymphoma with the anti-CD30 monoclonal antibody, HeFi-1,does not require activating Fc receptors," *Blood*, 108(2):705-10 (2006).
Scappaticci et al., "Arterial thromboembolic events in patients with metastatic carcinoma treated with chemotherapy and bevacizumab," *J Natl Cancer Inst.*, 99(16):1232-9 (2007).
Fish & Richardson P.C., Response to Restriction Requirement dated Dec. 13, 2012 in U.S. Appl. No. 12/809,138, filed Apr. 5, 2013, 2 pages.
Allen et al., "Interchain disulfide bonding in human IgG2 antibodies probed by site-directed mutagenesis," *Biochemistry*, 48(17):3755-66 (2009).
Gussow et al., "Humanization of monoclonal antibodies," *Methods Enzymol.*, 203:99-121 (1991).
Hamilton, "Molecular engineering: applications to the clinical laboratory," *Clin. Chem.*, 39(9):1988-97 (1993).
Mariuzza et al., "The structural basis of antigen-antibody recognition," *Annu. Rev. Biophys. Chem.*, 16:139-59 (1987).
Mihara et al., "Tocilizumab inhibits signal transduction mediated by both mIL-6R and sIL-6R, but not by the receptors of other members of IL-6 cytokine family," *Int. Immunopharmacol.*, 5(12):1731-40 (2005).
Suzuki et al., "Importance of neonatal FcR in regulating the serum half-life of therapeutic proteins containing the Fc domain of human IgG1: a comparative study of the affinity of monoclonal antibodies and Fc-fusion proteins to human neonatal FcR," *J. Immunol.*, 184(4):1968-76 (2010).
Winkler et al., "Changing the antigen binding specificity by single point mutations of an anti-p24 (HIV-1) antibody," *J. Immunol.*, 165:4505-14 (2000).
Zalevsky et al., "Enhanced antibody half-life improves in vivo activity," *Nat. Biotechnol.*, 28(2):157-9 (2010).

(56) References Cited

OTHER PUBLICATIONS

USPTO Notice of Allowance in U.S. Appl. No. 12/680,087, dated Apr. 15, 2013, 9 pages.
Fish & Richardson P.C., Amendment in Reply to Office Action dated Oct. 18, 2012 in U.S. Appl. No. 12/745,781, filed Apr. 17, 2013, 23 pages.
Fish & Richardson P.C., Response to Restriction Requirement dated Dec. 6, 2012 in U.S. Appl. No. 13/497,269, filed May 1, 2013, 2 pages.
USPTO Non-Final Office Action in U.S. Appl. No. 13/320,317, dated Dec. Apr. 25, 2013, 25 pages.
Fish & Richardson P.C., Preliminary Amendment and Response to Restriction Requirement dated Mar. 20, 2013 in U.S. Appl. No. 13/257,145, filed Apr. 22, 2013, 7 pages.
International Search Report for App. Ser. No. PCT/JP2012/075083, dated Oct. 23, 2012, 2 pages.
International Preliminary Report on Patentability for App. Ser. No. PCT/JP2012/075083, dated Apr. 1, 2014, 8 pages.
International Preliminary Report on Patentability for App. Ser. No. PCT/JP2012/058603, dated Oct. 8, 2013, 11 pages.
International Search Report for App. Ser. No. PCT/JP2012/058603, dated May 29, 2012, 2 pages.
Fish & Richardson P.C., Amendment in Reply to Office Action dated Feb. 12, 2013 in U.S. Appl. No. 13/434,643, filed May 13, 2013, 18 pages.
USPTO Final Office Action in U.S. Appl. No. 12/745,781, dated May 21, 2013, 16 pages.
Lindsay, "Chapter 4: Determination of the Kinetics and Mechanism of tg-FIX Activation by Factor XIa," 49-75 (2004).
Manz et al., Bioanalytical Chemistry, World Scientific Publishing Co., p. 7 (2003).
Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (2001).
Smans et al., "Bispecific antibody-mediated lysis of primary cultures of ovarian carcinoma cells using multiple target antigens," Int. J. Cancer, 83:270-277 (1999).
USPTO Non-Final Office Action in U.S. Appl. No. 12/295,075, dated Jun. 7, 2013, 17 pages.
Igawa et al., "Antibody optimization technologies for developing next generation antibody therapeutics," Bio Industry, 28(7):15-21 (2011) (with English translation).
Ishii et al., "FcRn, a critical regulator of antibody pharmacokinetics," Folia Phamacol. Jpn., 136(5):280-284 (2010) (with English translation).
Sims et al., "HMGB1 and RAGE in inflammation and cancer," Annu Rev Immunol., 28:367-88 (2010).
Wang et al., "HMG-1 as a late mediator of endotoxin lethality in mice," Science, 285(5425):248-51 (1999).
Tsubaki et al., "C-terminal modification of monoclonal antibody drugs: amidated species as a general product-related substance," Int J Biol Macromol., 52:139-47. doi: 10.1016/j.ijbiomac.2012.09.016. Epub Sep. 25, 2012.
Fish & Richardson P.C., Amendment in Reply to Action dated Jan. 3, 2013 in U.S. Appl. No. 12/679,922, filed Jul. 2, 2013, 18 pages.
USPTO Final Office Action in U.S. Appl. No. 13/434,643, dated Jul. 11, 2013, 19 pages.
USPTO Non-Final Office Action in U.S. Appl. No. 13/257,145, dated Jul. 2, 2013, 20 pages.
International Preliminary Report on Patentability for App. Ser. No. PCT/JP2011/076486, dated Jun. 12, 2013, 9 pages.
Baker et al., "Conversion of a T cell antagonist into an agonist by repairing a defect in the TCR/peptide/MHC interface: implications for TCR signaling," Immunity, 13:475-484 (2000).
Bowie et al., "Deciphering the message in protein sequences: tolerance to amino acid substitutions," Science, 247:1306-1310 (1990).

Ju et al., "Conversion of the interleukin 1 receptor antagonist into an agonist by site-specific mutagenesis," Proc. Natl. Acad. Sci. U.S.A., 88:2658-2662 (1991).
Pakula et al., "Genetic Analysis of Protein Stability and Function," Annu. Rev. Genet., 23:289-310 (1989).
Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
USPTO Final Office Action in U.S. Appl. No. 12/679,922, dated Aug. 2, 2013, 12 pages.
USPTO Notice of Allowance in U.S. Appl. No. 12/680,087, dated Aug. 2, 2013, 8 pages.
Fish & Richardson P.C., Amendment in Reply to Non-Final Office Action dated Feb. 14, 2013 in U.S. Appl. No. 12/680,082, filed Aug. 12, 2013, 17 pages.
USPTO Non-Final Office Action in U.S. Appl. No. 13/497,269, dated Aug. 15, 2013, 13 pages.
Allen et al., "Novel mechanism for gonadotropin-releasing hormone neuronal migration involving Gas6/Ark signaling to p38 mitogen-activated protein kinase," Mol. Cell. Biol., 22(2):599-613 (2002).
Bellosta et al., "Signaling through the ARK tyrosine kinase receptor protects from apoptosis in the absence of growth stimulation," Oncogene., 15(20):2387-97 (1997).
Budagian et al., "A promiscuous liaison between IL-15 receptor and Axl receptor tyrosine kinase in cell death control," EMBO J., 24(24):4260-70 (2005).
Chien et al., "Significant structural and functional change of an antigen-binding site by a distant amino acid substitution: proposal of a structural mechanism," Proc. Natl. Acad. Sci. U.S.A., 86(14):5532-6 (1989).
Chung et al., "Expression of the proto-oncogene Axl in renal cell carcinoma," DNA Cell Biol., 22(8):533-40 (2003).
Craven et al., "Receptor tyrosine kinases expressed in metastatic colon cancer," Int. J. Cancer, 60(6):791-7 (1995).
Davies et al., "Affinity improvement of single antibody VH domains: residues in all three hypervariable regions affect antigen binding," Immunotechnology, 2(3):169-79 (1996).
De Pascalis et al., "Grafting of "abbreviated" complementarity-determining regions containing specificity-determining residues essential for ligand contact to engineer a less immunogenic humanized monoclonal antibody," J. Immunol., 169(6):3076-84 (2002).
Fridell et al., "GAS6 induces Axl-mediated chemotaxis of vascular smooth muscle cells," J. Biol. Chem., 273(12):7123-6 (1998).
Goruppi et al., "Requirement of phosphatidylinositol 3-kinase-dependent pathway and Src for Gas6-Axl mitogenic and survival activities in NiH 3T3 fibroblasts," Mol. Cell Biol., 17(8):4442-53 (1997).
Hafizi et al., "Interaction of Axl receptor tyrosine kinase with C1-TEN, a novel C1 domain-containing protein with homology to tensin," Biochem. Biophys. Res. Commun., 299(5):793-800 (2002).
Hafizi et al., "Signalling and functional diversity within the Axl subfamily of receptor tyrosine kinases," Cytokine Growth Factor Rev., 17(4):295-304 (2006).
Holland et al., "Multiple roles for the receptor tyrosine kinase axl in tumor formation," Cancer Res., 65(20):9294-303.
Holt et al., "Domain antibodies: proteins for therapy," Trends Biotechnol., 21(11):484-90 (2003).
Igawa et al., "Engineering the variable region of therapeutic IgG antibodies," MAbs, 3(3):243-52 (2011).
Igawa et al., "Reduced elimination of IgG antibodies by engineering the variable region," Protein Eng. Des. Sel., 23(5):385-92 (2010).
Igawa et al., "Antibody recycling by engineered pH-dependent antigen binding improves the duration of antigen neutralization," Nat. Biotechnol., 28(11):1203-7 (2010).
Ito et al., "Expression of receptor-type tyrosine kinase, Axl, and its ligand, Gas6, in pediatric thyroid carcinomas around Chernobyl," Thyroid., 12(11):971-5 (2002).
Kurfis et al., "Role of Arg182 in the second extracellular loop of angiotensin II receptor AT2 in ligand binding," Biochem. Biophys. Res. Commun., 263:816-819 (1999).

(56) References Cited

OTHER PUBLICATIONS

Levin et al., "Optimizing the affinity and specificity of proteins with molecular display," *Mol Biosyst.*, 2(1):49-57 (2006) (Epub Nov. 8, 2005).
Maeda et al., "pH-dependent receptor/ligand dissociation as a determining factor for intracellular sorting of ligands for epidermal growth factor receptors in rat hepatocytes," *J Control Release*, 82(1):71-82 (2002).
Martinez et al., "Disulfide connectivity of human immunoglobulin G2 structural isoforms," *Biochemistry*, 47(28):7496-7508 (2008).
Maxfield et al., "Endocytic recycling," *Nat. Rev. Mol. Cell Biol.*, 5(2):121-32 (2004).
Maynard et al., "Antibody engineering," *Annu. Rev. Biomed. Eng.*, 2:339-76 (2000).
McCloskey et al., "GAS6 mediates adhesion of cells expressing the receptor tyrosine kinase Axl," *J. Biol. Chem.*, 272(37):23285-91 (1997).
Meric et al., "Expression profile of tyrosine kinases in breast cancer," *Clin. Cancer Res.*, 8(2):361-7 (2002).
Murtaugh et al., "A combinatorial histidine scanning library approach to engineer highly pH-dependent protein switches," *Protein Sci.*, 20(9):1619-31 doi:10.1002/pro 696 (2011).
Nakano et al., "Vascular smooth muscle cell-derived, Gla-containing growth-potentiating factor for Ca(2+)-mobilizing growth factors," *J. Biol. Chem.*, 270(11):5702-5 (1995).
Nakano et al., "Prevention of growth arrest-induced cell death of vascular smooth muscle cells by a product of growth arrest-specific gene, gas6," *FEBS Lett.*, 387(1):78-80 (1996).
Neubauer et al., "Expression of axl, a transforming receptor tyrosine kinase, in normal and malignant hematopoiesis," *Blood*, 84(6):1931-41 (1994).
O'Bryan et al., "axl, a transforming gene isolated from primary human myeloid leukemia cells, encodes a novel receptor tyrosine kinase," *Mol. Cell Biol.*, 11(10):5016-31 (1991).
Pavlaki et al., "Matrix metalloproteinase inhibitors (MMPIs): the beginning of phase I or the termination of phase III clinical trials," *Cancer Metastasis Rev.*, 22(2-3):177-203 (2003).
Pini et al., "Design and use of a phage display library. Human antibodies with subnanomolar affinity against a marker of angiogenesis eluted from a two-dimensional gel," *J. Biol. Chem.*, 273(34):21769-76 (1998).
Queen et al., "A humanized antibody that binds to the interleukin 2 receptor," *Proc. Natl. Acad. Sci. USA.*, 86(24):10029-10033 (1989).
Raffen et al., "Reengineering immunoglobulin domain interactions by introduction of charged residues," *Protein Eng.*,11:303-309 (1998).
R&D Systems (R&D Systems, Anti-human IL-31 RA Antibody, Catalog #AF2769, Oct. 2008).
Rudikoff et al., "Single amino acid substitution altering antigen-binding specificity," *Proc. Natl. Acad. Sci. U.S.A.*, 79(6):1979-83 (1982).
Sainaghi et al., "Gas6 induces proliferation in prostate carcinoma cell lines expressing the Axl receptor," *J. Cell. Physiol.*, 204(1):36-44 (2005).
Sawabu et al., "Growth arrest-specific gene 6 and Axl signaling enhances gastric cancer cell survival via Akt pathway," *Mol. Carcinog.*, 46(2):155-64 (2007).
Shieh et al., "Expression of axl in lung adenocarcinoma and correlation with tumor progression," *Neoplasia.*, 7(12):1058-64 (2005).
Stenhoff et al., "Vitamin K-dependent Gas6 activates ERK kinase and stimulates growth of cardiac fibroblasts," *Biochem. Biophys. Res. Commun.*, 319(3):871-8 (2004).
Sun et al., "Coexpression of Gas6/Axl in human ovarian cancers," *Oncology*, 66(6):450-7 (2004).
Vajkoczy et al., "Dominant-negative inhibition of the Axl receptor tyrosine kinase suppresses brain tumor cell growth and invasion and prolongs survival," *Proc. Natl. Acad. Sci. U.S.A.*, 103(15):5799-804 (2006).

Varnum et al., "Axl receptor tyrosine kinase stimulated by the vitamin K-dependent protein encoded by growth-arrest-specific gene 6," *Nature*, 373(6515):623-6 (1995).
Wang et al., "Polyethylene Glycol-modified Chimeric Toxin Composed of Transforming Growth Factor alpha and *Pseudomonas* Exotoxin," *Cancer. Res.*, 53:4588-4594 (1993).
Wu et al., "Humanization of a murine monoclonal antibody by simultaneous optimization of framework and CDR residues," *J. Mol. Biol.*, 294(1):151-62 (1999).
Wypych et al., "Human IgG2 antibodies display disulfide-mediated structural isoforms," *J. Biol. Chem.*, 283(23):16194-16205 (2008).
Yamagata et al., "Synaptic adhesion molecules," *Curr. Opin. Cell Biol.*, 15(5):621-32 (2003).
Fish & Richardson P.C., Third Preliminary Amendment and Response to Restriction Requirement dated Dec. 6, 2011 in U.S. Appl. No. 12/936,587, filed Jun. 5, 2012, 7 pages.
USPTO Restriction Requirement in U.S. Appl. No. 12/936,587, dated Jun. 25, 2012, 5 pages.
European Search Report for App. Ser. No. EP 09 72 9337, dated Nov. 3, 2011, 3 pages.
Fish & Richardson P.C., Amendment in Reply to Action dated Nov. 4, 2011 in U.S. Appl. No. 12/295,075, filed May 3, 2012, 12 pages.
USPTO Non-Final Office Action in U.S. Appl. No. 11/910,128, dated Apr. 25, 2012, 21 pages.
USPTO Notice of Allowance in U.S. Appl. No. 12/680,087, dated Jun. 25, 2012, 11 pages.
International Preliminary Report on Patentability for App. Ser. No. PCT/JP2010/058166, dated Dec. 16, 2011, 15 pages.
USPTO Restriction Requirement in U.S. Appl. No. 12/680,082, dated Jun. 6, 2012, 12 pages.
Fish & Richardson P.C., Fourth Preliminary Amendment and Response to Restriction Requirement dated Jun. 6, 2012 in U.S. Appl. No. 12/680,082, filed Jun. 29, 2012, 13 pages.
International Search Report for App. Ser. No. PCT/JP2010/066490, dated Nov. 9, 2010, 5 pages.
International Preliminary Report on Patentability for App. Ser. No. PCT/JP2010/066490, dated Apr. 11, 2012, 6 pages.
USPTO Final Office Action in U.S. Appl. No. 12/295,075, dated Jul. 19, 2012, 12 pages.
Fish & Richardson P.C., Response to Species Election Requirement dated Jun. 25, 2012 in U.S. Appl. No. 12/936,587, filed Jul. 25, 2012, 1 page.
USPTO Restriction Requirement in U.S. Appl. No. 13/434,643, dated Jul. 27, 2012, 6 pages.
USPTO Restriction Requirement in U.S. Appl. No. 12/745,781, dated Jul. 30, 2012, 9 pages.
USPTO Restriction Requirement in U.S. Appl. No. 12/680,112, dated Oct. 7, 2011, 6 pages.
Fish & Richardson P.C., Amendment and Response to Species Election Requirement dated Oct. 7, 2011 in U.S. Appl. No. 12/680,112, filed Dec. 6, 2011, 15 pages.
USPTO Non Final Office Action in U.S. Appl. No. 12/680,112, dated Feb. 29, 2012, 8 pages.
Fish & Richardson P.C., Amendment in Reply to Action of Feb. 29, 2012 in U.S. Appl. No. 12/680,112, filed Aug. 27, 2012, 12 pages.
USPTO Restriction Requirement in U.S. Appl. No. 12/745,781, dated Sep. 4, 2012, 10 pages.
Aslan et al., "Engineering a novel, stable dimeric streptavidin with lower isoelectric point," *J. Biotechnol.*, 128(2):213-25 (2007).
Atwell et al., "Stable heterodimers from remodeling the domain interface of a homodimer using a phage display library," *J. Mol. Biol.*, 270:26-35 (1997).
Baerga-Ortiz et al., "Two different proteins that compete for binding to thrombin have opposite kinetic and thermodynamic profiles," *Protein Sci.*, 13(1):166-76 (2004).
Gunasekaran et al., "Enhancing antibody Fc heterodimer formation through electrostatic steering effects: applications to bispecific molecules and monovalent IgG," *J Biol. Chem.*, 285(25):19637-46 (2010).
Marti et al., "Inverse electrostatic effect: electrostatic repulsion in the unfolded state stabilizes a leucine zipper," *Biochemistry*, 43(39):12436-47 (2004).

(56) References Cited

OTHER PUBLICATIONS

Ridgway et al., "'Knobs-into-holes' engineering of antibody $C_H3$ domains for heavy chain heterodimerization," Protein Eng., 9:617-621 (1996).
USPTO Notice of Allowance in U.S. Appl. No. 12/809,138, dated Aug. 23, 2013, 9 pages.
Stephen L. Rawlings, Uspto Final Office Action in U.S. Appl. No. 11/910,128, dated Sep. 10, 2013, 12 pages.
Padlan et al., "Structure of an antibody-antigen complex: crystal structure of the HyHEL-10 Fab-lysozyme complex," Proc. Natl. Acad. Sci. USA, 86:5938-5942 (1989).
Fish & Richardson P.C., Reply to Restriction Requirement dated Mar. 21, 2013 in U.S. Appl. No. 13/524,528, filed Sep. 13, 2013, 1 page.
USPTO Non-Final Office Action in U.S. Appl. No. 13/524,528, dated Sep. 30, 2013, 9 pages.
Burges et al., "Effective relief of malignant ascites in patients with advanced ovarian cancer by a trifunctional anti-EpCAM x anti-CD3 antibody: a phase I/II study," Clin. Cancer Res., 13(13):3899-905 (2007).
Dall'Acqua et al., "Modulation of the effector functions of a human IgG1 through engineering of its hinge region," J Immunol., 177(2):1129-38 (2006).
Elliott et al., "Activation of the erythropoietin (EPO) receptor by bivalent anti-EPO receptor antibodies," J. Biol. Chem., 271(40):24691-7 (1996).
Kai et al., "Switching constant domains enhances agonist activities of antibodies to a thrombopoietin receptor," Nat. Biotechnol., 26(2):209-11 (2008).
Kim et al., "Mapping the site on human IgG for binding of the MHC class I-related receptor, FcRn," Eur. J. Immunol., 29(9):2819-25 (1999).
Kobayashi et al., "A monoclonal antibody specific for a distinct region of hen egg-white lysozyme," Mol. Immunol., 19:619-30 (1982).
Morell et al., "Metabolic properties of IgG subclasses in man," J. Clin. Invest., 49(4):673-80 (1970).
Ruf et al., "Pharmacokinetics and in vivo stability of intraperitoneally administered therapeutic antibody catumaxomab," J. Clin. Oncol., 26 (May 20 suppl) (2008), abstr 14006.
USPTO Restriction Requirement in U.S. Appl. No. 12/679,922, dated Oct. 2, 2012, 9 pages.
USPTO Restriction Requirement in U.S. Appl. No. 12/680,082, dated Sep. 14, 2012, 6 pages.
Fish & Richardson P.C., Response to Restriction Requirement dated Sep. 4, 2012 in U.S. Appl. No. 12/745,781, filed Sep. 21, 2012, 176 pages.
USPTO Restriction Requirement in U.S. Appl. No. 12/680,112, dated Sep. 19, 2012, 6 pages.
Fish & Richardson P.C., Amendment in Reply to Office Action dated May 21, 2013 in U.S. Appl. No. 12/745,781, filed Oct. 18, 2013, 13 pages.
USPTO Restriction Requirement in U.S. Appl. No. 13/257,112, dated Oct. 15, 2013, 10 pages.
Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell. Biol., 111:2129-2138 (1990).
Lazar et al., "Transforming growth factor alpha: mutation of aspartic acid 47 and leucine 48 results in different biological activities," Mol. Cell. Biol., 8:1247-1252 (1988).
Ohno et al., "Antigen-binding specificities of antibodies are primarily determined by seven residues of VH," Proc. Natl. Acad. Sci. U.S.A., 82(9):2945-9 (1985).
Ozhegov et al., Tolkovyi Slovar Russkogo iazyka: 2004, p. 292 (with an English translation of the corresponding part only).
Padlan et al., "Identification of specificity-determining residues in antibodies," FASEB J., 9:133-139 (1995).
R&D Systems (R&D Systems, Biotinylated Anti-human IL-31 RA Antibody, Catalog #BAF2769, Nov. 2005), 1 page.

Fish & Richardson P.C., Amendment and Reply to Restriction Requirement dated Sep. 19, 2012 in U.S. Appl. No. 12/680,112, filed Oct. 17, 2012, 13 pages.
USPTO Non-Final Office Action in U.S. Appl. No. 12/745,781, dated Oct. 18, 2012, 21 pages.
Fish & Richardson P.C., Response to Restriction Requirement dated Oct. 2, 2012 in U.S. Appl. No. 12/679,922, filed Nov. 1, 2012, 2 pages.
Fish & Richardson P.C., Amendment in Reply to Office Action dated Apr. 25, 2012 in U.S. Appl. No. 11/910,128, filed Oct. 25, 2012, 32 pages.
International Preliminary Report on Patentability for App. No. PCT/JP2010/073361, dated Aug. 14, 2012, 7 pages.
USPTO Non-Final Office Action in U.S. Appl. No. 12/936,587, dated Nov. 7, 2012, 13 pages.
Fish & Richardson P.C., Amendment and Response to Election Requirement dated Sep. 14, 2012 in U.S. Appl. No. 12/680,082, filed Nov. 8, 2012, 14 pages.
Bayry et al., "Immuno affinity purification of foot and mouth disease virus type specific antibodies using recombinant protein adsorbed to polystyrene wells," J. Virol. Methods, 81:21-30 (1999).
Fish & Richardson P.C., Supplemental Amendment in U.S. Appl. No. 11/910,128, filed Nov. 14, 2012, 20 pages.
James L. Rogers, USPTO Non-Final Office Action in U.S. Appl. No. 13/595,139, dated Nov. 14, 2012, 10 pages.
Brown et al., "Tolerance of single, but not multiple, amino acid replacements in antibody $V_H$ CDR2: a means of minimizing B cell wastage from somatic hypermutation?," J. Immunol., 156(9):3285-91 (1996).
Dall'Acqua et al., "Increasing the affinity of a human IgG1 for the neonatal Fc receptor: biological consequences," J. Immunol., 169(9):5171-80 (2002).
Jefferis et al., "Recognition sites on human IgG for Fc gamma receptors: the role of glycosylation," Immunol. Lett., 44(2-3):111-7 (1995).
Lay et al., "Sulfasalazine suppresses drug resistance and invasiveness of lung adenocarcinoma cells expressing AXL," Cancer Res., 67(8):3878-87 (2007).
MacCallum et al., "Antibody-antigen interactions: contact analysis and binding site topography," J. Mol. Biol., 262:732-45 (1996).
Sarmay et al., "Mapping and comparison of the interaction sites on the Fc region of IgG responsible for triggering antibody dependent cellular cytotoxicity (ADCC) through different types of human Fc gamma receptor," Mol. Immunol., 29(5):633-9 (1992).
Yeung et al., "Engineering human IgG1 affinity to human neonatal Fc receptor: impact of affinity improvement on pharmacokinetics in primates," J. Immunol., 182(12):7663-71 (2009).
USPTO Non-Final Office Action in U.S. Appl. No. 12/679,922, dated Dec. 10, 2012, 22 pages.
USPTO Notice of Allowance in U.S. Appl. No. 12/680,087, dated Nov. 26, 2012, 7 pages.
International Search Report for App. Ser. No. PCT/JP2011/055101, dated May 10, 2011, 4 pages.
International Preliminary Report on Patentability for App. Ser. No. PCT/JP2011/055101, dated Oct. 2, 2012, 6 pages.
USPTO Restriction Requirement in U.S. Appl. No. 13/497,269, dated Dec. 6, 2012, 9 pages.
USPTO Restriction Requirement in U.S. Appl. No. 12/809,138, dated Dec. 13, 2012, 8 pages.
USPTO Restriction Requirement in U.S. Appl. No. 13/320,317, dated Dec. 18, 2012, 13 pages.
U.S. Appl. No. 14/007,947, filed Sep. 26, 2013, Igawa et al.
U.S. Appl. No. 14/047,316, filed Oct. 7, 2013, Kuramochi et al.
U.S. Appl. No. 13/959,489, filed Aug. 5, 2013, Igawa et al.
U.S. Appl. No. 13/885,421, filed Aug. 30, 2013, Igawa et al.
U.S. Appl. No. 14/019,117, filed Sep. 5, 2013, Igawa et al.
U.S. Appl. No. 14/019,712, filed Sep. 6, 2013, Igawa et al.
Dumont et al., "Monomeric Fc fusions: impact on pharmacokinetic and biological activity of protein therapeutics," BioDrugs., 20(3):151-60 (2006).
Jendeberg et al., "Engineering of Fc(1) and Fc(3) from human immunoglobulin G to analyse subclass specificity for staphylococcal protein A," J. Immunol. Methods., 201(1):25-34 (1997).

(56) References Cited

OTHER PUBLICATIONS

Van Loghem et al., "Staphylococcal protein A and human IgG subclasses and allotypes," *Scand. J. Immunol.*, 15(3):275-8 (1982).
Jackman et al., "Development of a two-part strategy to identify a therapeutic human bispecific antibody that inhibits IgE receptor signaling," *J Biol Chem.*, Jul. 2, 2010;285(27): 20850-9. doi: 10.1074/jbc.M110.113910. Epub May 5, 2010.
Spiess et al., "Bispecific antibodies with natural architecture produced by co-culture of bacteria expressing two distinct half-antibodies," *Nat Biotechnol.*, Aug. 2013; 31(8):753-8. doi: 10.1038/nbt.2621. Epub Jul. 7, 2013.
Lin et al., "Preclinical pharmacokinetics, interspecies scaling, and tissue distribution of a humanized monoclonal antibody against vascular endothelial growth factor," *J Pharmacol Exp Ther.*, 288(1):371-8 (1999).
Bendig, "Humanization of rodent monoclonal antibodies by CDR grafting," *METHODS: A Comparison to Methods in Enzymology*, 8:83-93 (1995).
Casset et al., "A peptide mimetic of an anti-CD4 monoclonal antibody by rational design," *Biochem Biophys Res Commun.*, Jul. 18, 2003;307:198-205.
Figini et al., "In vitro assembly of repertoires of antibody chains on the surface of phage by renaturation," *J Mol Biol.*, May 27, 1994;239(1):68-78.
Vaughan et al., "Human antibodies with sub-nanomolar affinities isolated from a large non-immunized phage display library," *Nat Biotechnol.*, Mar. 1996;14(3):309-14.
Wally et al., "Identification of a novel substitution in the constant region of a gene coding for an amyloidogenic kappal light chain," *Biochim Biophys Acta.*, May 31, 1999;1454(1):49-56.
Alley et al., "Antibody-drug conjugates: targeted drug delivery for cancer," *Curr Opin Chem Biol.*, Aug. 2010;14(4):529-37. doi: 10.1016/j.cbpa.2010.06.170. Epub Jul. 17, 2010.
Baeuerle et al., "BiTE: Teaching antibodies to engage T-cells for cancer therapy," *Curr Opin Mol Ther.*, 11(1):22-30 (2009).
Clark, "An alignment of IgG sequences from Human, Mouse and Rat," Part II Immunoglobulin lectures (v4), pp. 5(i)-(ii) [retrieved on Jul. 25, 2014]. Retrieved from the Internet: http://www.path.cam.ac.uk/~mrc7/lecturenotes/handout1a.pdf.
Davda et al., "Properties of a general PK/PD model of antibody-ligand interactions for therapeutic antibodies that bind to soluble endogenous targets," *MAbs*, Sep.-Oct. 2010;2(5):576-88. doi: 10.4161/mabs.2.5.12833. Epub Sep. 1, 2010.
De Bono et al., "ING-1, a monoclonal antibody targeting Ep-CAM in patients with advanced adenocarcinomas," *Clin Cancer Res.*, 10(22):7555-65 (2004).
Deng et al., "Pharmacokinetics of humanized monoclonal anti-tumor necrosis factor-{alpha} antibody and its neonatal Fc receptor variants in mice and cynomolgus monkeys," *Drug Metab Dispos.*, Apr. 2010;38(4):600-5. doi: 10.1124/dmd.109.031310. Epub Jan. 13, 2010.
Desjarlais et al., "Optimizing engagement of the immune system by anti-tumor antibodies: an engineer's perspective," *Drug Discov Today*, Nov. 2007;12(21-22):898-910. Epub Oct. 22, 2007.
Haringman et al., "A randomized controlled trial with an anti-CCL2 (anti-monocyte chemotactic protein 1) monoclonal antibody in patients with rheumatoid arthritis," *Arthritis Rheum.*, 54(8):2387-92 (2006).
Juszczak et al., "Ipilimumab: a novel immunomodulating therapy causing autoimmune hypophysitis: a case report and review," *Eur J Endocrinol.*, Jul. 2012;167(1):1-5. doi: 10.1530/EJE-12-0167. Epub Apr. 10, 2012.
Lewis et al., "Differential responses of human tumor cell lines to anti-p185HER2 monoclonal antibodies," *Cancer Immunol Immunother.*, 37(4):255-63 (1993).
Lutterbuese et al., "T cell-engaging BiTE antibodies specific for EGFR potently eliminate KRAS- and BRAF-mutated colorectal cancer cells," *Proc Natl Acad Sci USA.*, Jul. 13, 2010;107(28):12605-10. doi: 10.1073/pnas.1000976107. Epub Jun. 28, 2010.

Martin et al., "Preclinical safety and immune-modulatng effects of therapeutic monoclonal antibodies to interleukin-6 and tumor necrosis factor-α in cynomolgus macaques," *J Immunotoxicol.*, Jul. 1, 2004;1(3):131-9. doi:10.1080/15476910490894904.
Nam et al., "Current evidence for the management of rheumatoid arthritis with biological disease-modifying antirheumatic drugs: a systematic literature review informing the EULAR recommendations for the management of RA," *Ann Rheum Dis.*, Jun. 2010;69(6):976-86. doi: 10.1136/ard.2009.126573. Epub May 6, 2010.
Nishimoto et al., "Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease," *Blood*, Nov. 15, 2008;112(10):3959-64. doi: 10.1182/blood-2008-05-155846. Epub Sep. 10, 2008.
Petkova et al., "Enhanced half-life of genetically engineered human IgG1 antibodies in a humanized FcRn mouse model: potential application in humorally mediated autoimmune disease," *Int Immunol.*, Dec. 2006;18(12):1759-69. Epub Oct. 31, 2006.
Riechelmann et al., "Phase I trial with the CD44v6-targeting immunoconjugate bivatuzumab mertansine in head and neck squamous cell carcinoma," *Oral Oncol.*, Sep. 2008;44(9):823-9. doi: 10.1016/j.oraloncology.2007.10.009. Epub Jan. 18, 2008.
Reverberi et al., "Factors affecting the antigen-antibody reaction," *Blood Transfus.*, Nov. 2007;5(4):227-40. doi: 10.2450/2007.0047-07.
Roopenian et al., "FcRn: the neonatal Fc receptor comes of age," *Nat Rev Immunol.*, Sep. 2007;7(9):715-25. Epub Aug. 17, 2007.
Satoh et al., "Non-fucosylated therapeutic antibodies as next-generation therapeutic antibodies," *Expert Opin Biol Ther.*, 6(11):1161-73 (2006).
Schuster et al., "Signaling of human ciliary neurotrophic factor (CNTF) revisited. The interleukin-6 receptor can serve as an alpha-receptor for CTNF," *J Biol Chem.*, Mar. 14, 2003;278(11):9528-35.
Sebba et al., "Tocilizumab: the first interleukin-6-receptor inhibitor," *Am J Health Syst Pharm.*, Aug. 1, 2008;65(15):1413-8. doi: 10.2146/ajhp070449.
Seda et al., "B-cell receptor signalling and its crosstalk with other pathways in normal and malignant cells," *Eur J Haematol.*, Aug. 1, 2014. doi: 10.1111/ejh.12427.
Takeuchi et al., "The Japanese experience with biologic therapies for rheumatoid arthritis," *Nat Rev Rheumatol.*, Nov. 2010;6(11):644-52. doi: 10.1038/nrrheum.2010.154. Epub Sep. 28, 2010.
Takkinen et al., "Affinity and Specificity Maturation by CDR Walking," Antibody Engineering, Springer Lab Manuals, pp. 540-545 (2001).
Trinh et al., "Ipilimumab in the treatment of melanoma," *Expert Opin Biol Ther.*, Jun. 2012;12(6):773-82. doi: 10.1517/14712598.2012.675325. Epub Apr. 14, 2012.
Vaccaro et al., "Engineering the Fc region of immunoglobulin G to modulate in vivo antibody levels," *Nat Biotechnol.*, 23(10):1283-8 (2005).
Weiner et al., "Monoclonal antibodies: versatile platforms for cancer immunotherapy," *Nat Rev Immunol.*, May 2010;10(5):317-27. doi: 10.1038/nri2744.
Xiao et al., "Pharmacokinetics of anti-hepcidin monoclonal antibody Ab 12B9m and hepcidin in cynomolgus monkeys," *AAPS J.*, Dec. 2010;12(4):646-57. doi: 10.1208/s12248-010-9222-0. Epub Aug. 25, 2010.
Zheng et al., "Translational pharmacokinetics and pharmacodynamics of an FcRn-variant anti-CD4 monoclonal antibody from preclinical model to phase I study," *Clin Pharmacol Ther.*, Feb. 2011;89(2):283-90. doi: 10.1038/clpt.2010.311. Epub Dec. 29, 2010.
International Search Report for App. Ser. No. PCT/JP2012/006218, dated Mar. 26, 2013, 11 pages.
Medesan et al., "Delineation of the amino acid residues involved in transcytosis and catabolism of mouse IgG1," *J Immunol.*, Mar. 1, 1997;158(5):2211-7.
Pan et al., "Blocking neuropilin-1 function has an additive effect with anti-VEGF to inhibit tumor growth," *Cancer Cell*, Jan. 2007;11(1):53-67.
Singer et al., Genes & Genomes, 1998;1:63-64.
Singer et al., Genes & Genomes, 1991;67-69.

(56) References Cited

OTHER PUBLICATIONS

Kabat et al., Sequence of Proteins of Immunological Interest, 5th Edition 1991, p. 690 and p. 693.
Chappel et al., "Identification of a secondary Fc gamma RI binding site within a genetically engineered human IgG antibody," *J Biol Chem.*, Nov. 25, 1993;268(33):25124-31.
Chappel et al., "Identification of the Fc gamma receptor class I binding site in human IgG through the use of recombinant IgG1/IgG2 hybrid and point-mutated antibodies," *Proc Natl Acad Sci U S A.*, Oct. 15, 1991;88(20):9036-40.
Reist et al., "Human IgG2 constant region enhances in vivo stability of anti-tenascin antibody 81C6 compared with its murine parent," *Clin Cancer Res.*, Oct. 1998;4(10):2495-502.
McPhee et al., "Engineering human immunodeficiency virus 1 protease heterodimers as macromolecular inhibitors of viral maturation," *Proc Natl Acad Sci U S A.*, Oct. 15, 1996; 93(21):11477-81.
Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," *Biochemistry*, Jun. 30, 1987;26(13):4131-8.
Allard et al., "Antigen binding properties of highly purified bispecific antibodies," *Mol Immunol.*, Oct. 1992;29(10):1219-27.
Bowen, Haemophilia A and haemophilia B: molecular insights, Mol Pathol., Feb. 2002;55(1):1-18.
Brandstetter et al., "X-ray structure of clotting factor IXa: active site and module structure related to Xase activity and hemophilia B," Proc Natl Acad Sci U S A, Oct. 10, 1995;92(21):9796-800.
Fay, "Activation of factor VIII and mechanisms of cofactor action," Blood Rev., Mar. 2004;18(1):1-15.
Gonzales et al., "Minimizing the immunogenicity of antibodies for clinical application," Tumour Biol., Jan.-Feb. 2005;26(1):31-43.
Haagen et al., "Unprimed CD4+ and CD8+ T cells can be rapidly activated by a CD3×CD19 bispecific antibody to proliferate and become cytotoxic," Cancer Immunol Immunother., Dec. 1994;39(6):391-6.
IMGT Scientific charts depicting the correspondence between Eu and Kabat numberings for the human IgG constant region, created May 17, 2001 and last updated Aug. 13, 2014.
Iwahashi et al., "CDR substitutions of a humanized monoclonal antibody (CC49): contributions of individual CDRs to antigen binding and immunogenicity," Mol Immunol Oct.-Nov. 1999;36(15-16):1071-91.
Jirholt et al., "Exploiting sequence space: shuffling in vivo formed complementarity determining regions into a master framework," Gene., Jul. 30, 1998;215(2):471-6.
Lloyd et al., "The production of a bispecific anti-CEA, anti-hapten (4-amino-phthalate) hybrid-hybridoma," *J Natl Med Assoc.*, Oct. 1991;83(10):901-4.
Patton et al., "An acid dissociation bridging ELISA for detection of antibodies directed against therapeutic proteins in the presence of antigen," J Immunol Methods, Sep. 2005;304(1-2):189-95.
Schmidt et al., "Structure-function relationships in factor IX and factor IXa," Trends Cardiovasc Med., Jan. 2003;13(1):39-45.
Tamura et al., "Structural correlates of an anticarcinoma antibody: identification of specificity-determining residues (SDRs) and development of a minimally immunogenic antibody variant by retention of SDRs only," J Immunol., Feb. 1, 2000;164(3):1432-41.
Notice of Opposition against EP 1 876 236, dated May 20, 2015, in the name of Chugai Seiyaku Kabushiki Kaisha brought by Novo Nordisk A/S, 23 pages.
Notice of Opposition against EP 1 876 236, dated May 22, 2015, in the name of Chugai Seiyaku Kabushiki Kaisha brought by Baxalta Innovations GmbH, 37 pages.
Igawa et al., "VH/VL interface engineering to promote selective expression and inhibit conformational isomerization of thrombopoietin receptor agonist single-chain diabody," *Protein Eng Des Sel.*, Aug. 2010;23(8):667-77. doi: 10.1093/protein/gzq034. Epub Jun. 24, 2010.
Kenanova et al., "Tailoring the pharmacokinetics and positron emission tomography imaging properties of anti-carcinoembryonic antigen single-chain Fv-Fc antibody fragments," *Cancer Res.*, Jan. 15, 2005;65(2):622-31.
Lebégue et al., "Production and characterization of hybrid monoclonal antibodies with IgG1/IgG3 double isotype," *C R Acad Sci III.*, 1990;310(9):377-82.
Michaelsen et al., "A mutant human IgG molecule with only one C1q binding site can activate complement and induce lysis of target cells," *Eur J Immunol.*, Jan. 2006;36(1):129-38.
O'Shea et al., "Peptide 'Velcro': design of a heterodimeric coiled coil," *Curr Biol.*, Oct. 1, 1993;3(10):658-67.
Batra et al., "Pharmacokinetics and biodistribution of genetically engineered antibodies," *Curr Opin Biotechnol.*, Dec. 2002;13(6):603-8.
Borrebaeck et al., "Antibody evolution beyond Nature," *Nat Biotechnol.*, Dec. 2002;20(12):1189-90.
Wang et al., "Conserved amino acid networks involved in antibody variable domain interactions," *Proteins*, Jul. 2009;76(1):99-114. doi: 10.1002/prot.22319.
Griffin et al., "Analysis of heavy and light chain sequences of conventional camelid antibodies from Camelus dromedarius and Camelus bactrianus species," *J Immunol Methods*, Mar. 2014;405:35-46. doi: 10.1016/j.jim.2014.01.003. Epub Jan. 18, 2014.
Hamers-Casterman et al., "Naturally occurring antibodies devoid of light chains," *Nature*, Jun. 3, 1993;363(6428):446-8.
Male et al., "Antibodies" *Immunology*, 7th Edition (2006), published by Elsevier Ltd., pp. 59-86.
Roitt et al., *Immunology, M., Mir*, 5th Edition (2000), pp. 97-13.
Gramer et al., "Production of stable bispecific IgG1 by controlled Fab-arm exchange: scalability from bench to large-scale manufacturing by application of standard approaches," *MAbs.*, Nov.-Dec. 2013;5(6):962-73. doi: 10.4161/mabs.26233. Epub Aug. 22, 2013.
Klein et al., "Progress in overcoming the chain association issue in bispecific heterodimeric IgG antibodies," *MAbs.*, Nov.-Dec. 2012;4(6):653-63. doi: 10.4161/mabs.21379. Epub Aug. 27, 2012.
Labrijn et al., "Efficient generation of stable bispecific IgG1 by controlled Fab-arm exchange," *Pro Natl Acad Sci U S A.*, Mar. 26, 2013;110(13):5145-50. doi: 10.1073/pnas.1220145110. Epub Mar. 11, 2013.
Labrijn et al., "Species-specific determinants in the IgG CH3 domain enable Fab-arm exchange by affecting the noncovalent CH3-CH3 interaction strength," *J Immunol.*, Sep. 15, 2011;187(6):3238-46. doi: 10.4049/jimmunol.1003336. Epub Aug. 12, 2011.
Rispens et al., "Dynamics of inter-heavy chain interactions in human immunoglobulin G (IgG) subclasses studied by kinetic Fab arm exchange," *J Biol Chem.*, Feb. 28, 2014;289(9):6098-109. doi: 10.1074/jbc.M113.541813. Epub Jan. 14, 2014.
Schaefer et al., "Immunoglobulin domain crossover as a generic approach for the production of bispecific IgG antibodies," *Proc Natl Acad Sci U S A.*, Jul. 5, 2011;108(27):11187-92. doi: 10.1073/pnas.1019002108. Epub Jun. 20, 2011.
Schuurman et al., "Normal human immunoglobulin G4 is bispecific: it has two different antigen-combining sites," *Immunology*, Aug. 1999;97(4):693-8.
Schuurman et al., "The inter-heavy chain disulfide bonds of IgG4 are in equilibrium with intra-chain disulfide bonds," *Mol Immunol.*, Jan. 2001;38(1):1-8.
Van Der Neut Kolfschoten et al., "Anti-inflammatory activity of human IgG4 antibodies by dynamic Fab arm exchange," *Science*, Sep. 14, 2007;317(5844):1554-7.
U.S. Appl. No. 15/210,360, filed Jul. 14, 2016, Igawa et al.
U.S. Appl. No. 15/210,353, filed Jul. 14, 2016, Igawa et al.
U.S. Appl. No. 15/263,617, filed Sep. 13, 2016, Igawa et al.
[No Author Listed] "Hemophilia and von Willebrand's disease: 2. Management. Association of Hemophilia Clinic Directors of Canada," CMAJ., 153(2):147-157, Jul. 15, 1995.
Arndt et al., "Factors influencing the dimer to monomer transition of an antibody single-chain Fv fragment," Biochemistry, 37(37):12918-12926, Sep. 15, 1998.
Asselta et al., "Factor V deficiency," Semin Thromb Hemost., 35(4):382-389, Jun. 2009.

(56) References Cited

OTHER PUBLICATIONS

Bajaj et al., "A monoclonal antibody to factor IX that inhibits the factor VIII: Ca potentiation of factor X activation," J Biol Chem., 260(21):11574-11580, Sep. 25, 1985.
Bebbington et al., "High-level expression of a recombinant antibody from myeloma cells using a glutamine synthetase gene as an amplifiable selectable marker," Biotechnology (N Y)., 10(2):169-175, Feb. 1992.
Berglund et al., "The epitope space of the human proteome," Protein Sci., 17(4):606-13, Apr. 2008.
Beringhelli et al., "pH and ionic strength dependence of protein (un)folding and ligand binding to bovine beta-lactoglobulins A and B," Biochemistry, 41(51):15415-22, Dec. 24, 2002.
Bessos et al., "The characterization of a panel of monoclonal antibodies to human coagulation factor IX," Thromb Res., 40(6):863-867, Dec. 15, 1985.
Bian et al., "Discovery of promiscuous HLA-II-restricted T cell epitopes with TEPITOPE," Methods, 34(4):468-475, Dec. 2004.
Bolton-Maggs et al., "Haemophilias A and B," Lancet, 361(9371):1801-1809, May 24, 2003.
Bogdanovich et al., "Functional improvement of dystrophic muscle by myostatin blockade," Nature, 420(6914):418-421, Nov. 28, 2002.
Bos et al., "Enhanced transfection of a bacterial plasmid into hybridoma cells by electroporation: application for the selection of hybrid hybridoma (quadroma) cell lines," Hybridoma, 11(1):41-51, Feb. 1992.
Brennan et al., "Preparation of bispecific antibodies by chemical recombination of monoclonal immunoglobulin G1 fragments," Science, 229(4708):81-83, Jul. 5, 1985.
Brinkman et al., "Phospholipid-binding domain of factor VIII is involved in endothelial cell-mediated activation of factor X by factor IXa," Arterioscler Thromb Vasc Biol., 22(3):511-516, Mar. 1, 2002.
Burmeister et al., "Crystal structure of the complex of rat neonatal Fc receptor with Fc," Nature, 372(6504):379-83, Nov. 24, 1994.
Chatellier et al., "Functional mapping of conserved residues located at the VL and VH domain interface of a Fab," J Mol Biol., 264(1):1-6, Nov. 22, 1996.
Chen et al., "Selection and analysis of an optimized anti-VEGF antibody: crystal structure of an affinity-matured Fab in complex with antigen," J Mol Biol., 293(4):865-81, Nov. 5, 1999.
Chugai Seiyaku Kabushiki Kaisha's letter dated Jun. 12, 2013, regarding oral proceedings scheduled on Jun. 26, 2013, in App. Ser. No. EP 06 73 0769.4-1412.
Clynes et al., "Fc receptors are required in passive and active immunity to melanoma," Proc Natl Acad Sci U.S.A., 95(2):652-656, Jan. 20, 1998.
Clynes et al., "Inhibitory Fc receptors modulate in vivo cytotoxicity against tumor targets," Nat Med., 6(4):443-446, Apr. 2000.
Davie et al., "The coagulation cascade: initiation, maintenance, and regulation," Biochemistry, 30(43):10363-10370, Oct. 29, 1991.
Davies et al., "Antibody VH domains as small recognition units," Biotechnology (N Y)., 13(5):475-479, May 1995.
De Groot et al., "Reducing risk, improving outcomes: bioengineering less immunogenic protein therapeutics," Clin Immunol., May 2009;131(2):189-201, Epub Mar. 6, 2009.
Desai et al., "Fc gamma receptor IIB on dendritic cells enforces peripheral tolerance by inhibiting effector T cell responses," J Immunol., 178(10):6217-6226, May 15, 2007.
Dhiman et al., "Gene expression microarrays: a 21st century tool for directed vaccine design," Vaccine, 20(1-2):22-30, Oct. 12, 2001.
Dmytrijuk et al., "FDA report: eculizumab (Soliris) for the treatment of patients with paroxysmal nocturnal hemoglobinuria," Oncologist, 13(9):993-1000, Sep. 10, 2008.
Epstein, "Non-randomness of amino-acid changes in the evolution of homologous proteins," Nature, 215(5099):355-9, Jul. 22, 1967.
Fillipovich, Biochemical basis of human life, VLADOS, 2005:49-50 (with English translation).

Francois et al., "Construction of a bispecific antibody reacting with the alpha- and beta-chains of the human IL-2 receptor. High affinity cross-linking and high anti-proliferative efficiency," J. Immunol., 150(10):4610-4619, May 15, 1993.
Genbank Accession No. AAC26541, "anti BoNT/A Hc scFv antibody, partial [synthetic construct]," Aug 1, 2001, 3 pages.
Grosse-Hovest et al., "A recombinant bispecific single-chain antibody induces targeted, supra-agonistic CD28-stimulation and tumor cell killing," Eur J Immunol., 33(5):1334-1340, May 2003.
Hammerling et al., "Use of hybrid antibody with anti-gamma-G and anti-ferritin specificities in locating cell surface antigens by electron microscopy," J Exp Med., 128(6):1461-1473, Dec. 1, 1968.
Haviland et al., "Complete cDNA sequence of human complement pro-C5. Evidence of truncated transcripts derived from a single copy gene," J Immunol., 146(1):362-368, Jan. 1, 1991.
Hoad et al., "Characterisation of monoclonal antibodies to human factor X/Xa. Initial observations with a quantitative ELISA procedure," J Immunol Methods., 136(2):269-278, Feb. 15, 1991.
Holash et al., "VEGF-Trap: a VEGF blocker with potent antitumor effects," Proc Natl Acad Sci U.S.A., 99(17):11393-11398, Aug. 20, 2002.
Holm et al., "Functional mapping and single chain construction of the anti-cytokeratin 8 monoclonal antibody TS1," Mol Immunol., 44(6):1075-84, Feb. 2007.
Holers, "The spectrum of complement alternative pathway-mediated diseases," Immunol Rev., 223:300-316, Jun. 2008.
Holliger et al., "Diabodies : small bivalent and bispecific antibody fragments," Proc Natl Acad Sci U S A., 90(14):6444-6448, Jul. 15, 1993.
Hoodless et al., "Mechanism and function of signaling by the TGF beta superfamily," Curr Top Microbiol Immunol., 228:235-72, 1998.
Hsia et al., "Treatment of acquired factor X inhibitor by plasma exchange with concomitant intravenous immunoglobulin and corticosteroids," Am J Hematol., 83(4):318-320, Apr. 2008.
Huse et al., "Generation of a large combinatorial library of the immunoglobulin repertoire in phage lambda," Science, 246(4935):1275-1281, Dec. 8, 1989.
Johnson et al., "Kabat database and its applications: 30 years after the first variability plot," Nucleic Acids Res., 28(1):214-218, Jan. 1, 2000.
Jung et al., "The importance of framework residues H6, H7 and H10 in antibody heavy chains: experimental evidence for a new structural subclassification of antibody V(H) domains," J Mol. Biol., 309(3):701-716, Jun. 8, 2001.
Kamei et al., "Quantitative methods for developing Fc mutants with extended half-lives," Biotechnol Bioeng., 92(6):748-760, Dec. 20, 2005.
Kang et al., "Linkage of recognition and replication functions by assembling combinatorial antibody Fab libraries along phage surfaces," Proc Natl Acad Sci U S A., 88(10):4363-4366, May 15, 1991.
Karpovsky et al., "Production of target-specific effector cells using hetero-cross-linked aggregates containing anti-target cell and anti-Fc gamma receptor antibodies," J Exp Med., 160(6):1686-1701, Dec. 1, 1984.
Khalifa et al., "Effects on interaction kinetics of mutations at the VH-VL interface of Fabs depend on the structural context," J Mol Recognit., 13(3):127-139, May-Jun. 2000.
Kim et al., "Mammalian type I interferon receptors consists of two subunits: IFNaR1 and IFNaR2," Gene, 196(1-2):279-286, Sep. 1, 1997.
Kingsley et al., "The TGF-beta superfamily: new members, new receptors, and new genetic tests of function in different organisms," Genes Dev., 8(2):133-46, Jan. 1994.
Kipriyanov et al., "Bispecific tandem diabody for tumor therapy with improved antigen binding and pharmacokinetics," J Mol Biol., 293(1):41-56, Oct. 15, 1999.
Kipriyanov et al., "Effect of domain order on the activity of bacterially produced bispecific single-chain Fv antibodies," J Mol Biol., 330(1):99-111, Jun. 27, 2003.
Kontermann, "Recombinant bispecific antibodies for cancer therapy," Acta Pharmacol Sin., 26(1):1-9, Jan. 2005.

(56) References Cited

OTHER PUBLICATIONS

Korn et al., "Recombinant bispecific antibodies for the targeting of adenoviruses to CEA-expressing tumour cells: a comparative analysis of bacterially expressed single-chain diabody and tandem scFv," J Gene Med., 6(6):642-651, Jun. 2004.

Kroesen et al., "Phase I study of intravenously applied bispecific antibody in renal cell cancer patients receiving subcutaneous interleukin 2," Br J Cancer., 70(4):652-661, Oct. 1994.

Kumar et al., "The second PDZ domain of INAD is a type I domain involved in binding to eye protein kinase C. Mutational analysis and naturally occurring variants," J Biol Chem., 276(27):24971-24977, Epub May 7, 2001.

Kurokawa et al., "Enhanced fibrinolysis by a bispecific monoclonal antibody reactive to fibrin and tissue plasminogen activator," Bio/Technology, 7:1163-1167, Nov. 1989.

Lapan et al., "Interaction of the A1 subunit of factor VIIIa and the serine protease domain of factor X identified by zero-length crosslinking," Thromb Haemost., 80(3):418-422, Sep. 1998.

Lazar et al., "Engineered antibody Fc variants with enhanced effector function," Proc Natl Acad Sci U S A., 103(11):4005-4010, Epub Mar. 6, 2006.

Le Doussal et al., "Bispecific monoclonal antibody-mediated targeting of an indium-111-labeled DTPA dimer to primary colorectal tumors: pharmacokinetics, biodistribution, scintigraphy and immune response," J Nucl Med., 34(10):1662-1671, Oct. 1993.

Le Gall et al., "Effect of linker sequences between the antibody variable domains on the formation, stability and biological activity of a bispecific tandem diabody," Protein Eng Des Sel., 17(4):357-366, Epub May 4, 2004.

Lee et al., "Genetic analysis of the role of proteolysis in the activation of latent myostatin," PLoS One, 3(2):e1628, Feb. 20, 2008.

Lee et al., "Regulation of myostatin activity and muscle growth," Proc Natl Acad Sci U S A., 98(16):9306-9311, Jul. 31, 2001.

Lenting et al., "The life cycle of coagulation factor VIII in view of its structure and function," Blood, 92(11):3983-3996, Dec. 1, 1998.

Li et al., "Apoptotic and antitumor activity of death receptor antibodies require inhibitory Fcγ receptor engagement," Proc Natl Acad Sci U S A., Jul. 3, 2012;109(27):10966-10971, Epub Jun. 20, 2012.

Link et al., "Production and characterization of a bispecific IgG capable of inducing T-cell-mediated lysis of malignant B cells," Blood, 81(12):3343-3349, Jun. 15, 1993.

Liu et al., "Functional interactions between arginine-133 and aspartate-88 in the human reduced folate carrier: evidence for a charge-pair association," Biochem J., 358(Pt 2):511-516, Sep. 1, 2001.

Lofqvist et al., "Haemophilia prophylaxis in young patients—a long-term follow-up," J Intern Med., 241(5):395-400, May 1997.

Lu et al., "Di-diabody: a novel tetravalent bispecific antibody molecule by design," J Immunol Methods., 279(1-2):219-232, Aug. 2003.

Lu et al., "Fab-scFv fusion protein: an efficient approach to production of bispecific antibody fragments," J Immunol Methods., 267(2):213-226, Sep. 15, 2002.

Luttrell et al., "Reaction coupling of chelation and antigen binding in the calcium ion-dependent antibody binding of cyclic AMP," J Biol Chem., 266(32):21626-30, Nov. 15, 1991.

Maity et al., "Equilibrium unfolding of dimeric and engineered monomeric forms of lambda Cro (F58W) repressor and the effect of added salts: evidence for the formation of folded monomer induced by sodium perchlorate," Arch Biochem Biophys, 434(1):93-107, Feb. 1, 2005.

Malbec et al., "Antibodies against growth factor receptors can inhibit the proliferation of transformed cells via a cis-interaction with inhibitory FcR," Immunol Lett., 143(1):28-33, Mar. 30, 2012.

Massino et al., "Quantitative analysis of the products of IgG chain recombination in hybrid hybridomas based on affinity chromatography and radioimmunoassay," J Immunol Methods., 201(1):57-66, Feb. 14, 1997.

McCafferty et al., "Phage antibodies: filamentous phage displaying antibody variable domains," Nature, 348(6301):552-554, Dec. 6, 1990.

McCroskery et al., "Improved muscle healing through enhanced regeneration and reduced fibrosis in myostatin-null mice," J Cell Sci., 118(Pt 15):3531-3541, Aug. 1, 2005.

McPherron et al., "Regulation of skeletal muscle mass in mice by a new TGF-beta superfamily member," Nature, 387(6628):83-90, May 1, 1997.

McPherron et al., "Double muscling in cattle due to mutations in the myostatin gene," Proc Natl Acad Sci U S A., 94(23):12457-12461, Nov. 11, 1997.

Menegatti et al., "Factor X deficiency," Semin Thromb Hemost., 35(4):407-415, Jun. 2009.

Mertens et al., "Factor VIII-factor IX interactions: molecular sites involved in enzyme-cofactor complex assembly," Thromb Haemost., 82(2):209-217, Aug. 1999.

Milstein et al., "Hybrid hybridomas and their use in immunohistochemistry," Nature, 305(5934):537-540, Oct. 6-12, 1983.

Mollnes et al., "Identification of a human C5 beta-chain epitope exposed in the native complement component but concealed in the SCSb-9 complex," Scand J Immunol., 28(3):307-312, Sep. 1988.

Narhi et al, "Asn to Lys mutations at three sites which are N-glycosylated in the mammalian protein decrease the aggregation of Escherichia coli-derived erythropoietin," Protein Eng., 14(2):135-140, Feb. 2001.

National Haemophilia Foundation (NHF) Medical and Scientific Advisory Council (MASAC) Recommendations Concerning Prophylaxis, Medical Bulletin. #193, 1994.

Nemoto et al., "Overexpression of protein tyrosine kinases in human esophageal cancer," Pathobiology., 65(4):195-203, 1997.

Nieba et al., "Disrupting the hydrophobic patches at the antibody variable/constant domain interface: improved in vivo folding and physical characterization of an engineered scFv fragment," Protein Eng., 10(4):435-444, Apr. 1997.

Nilsson et al., "Induction of split tolerance and clinical cure in high-responding hemophiliacs with factor IX antibodies," Proc Natl Acad Sci U S A., 83(23):9169-9173, Dec. 1986.

Nilsson et al., "Twenty-five years' experience of prophylactic treatment in severe haemophilia A and B," J Intern Med., 232(1):25-32, Jul. 1992.

Nishimura et al., "Genetic variants in C5 and poor response to eculizumab," N Engl J Med., 370(7):632-639, Feb. 13, 2014.

Nitta et al., "Preliminary trial of specific targeting therapy against malignant glioma," Lancet., 335(8686):368-371, Feb. 17, 1990.

Nohaile et al., "Altering dimerization specificity by changes in surface electrostatics," Proc Natl Acad Sci U S A. Mar. 13, 2001;98(6):3109-3114. Epub Feb. 27, 2001.

Okubo, "The production and characterization of four monoclonal antibodies to human factor X," J Nara Med Ass., 38(1):20-28, Jan. 8, 1987.

Piper et al., "Interferon therapy in primary care," Prim Care Update Ob Gyns., 8(4):163-169, Jul. 2001.

Pokkuluri et al., "A domain flip as a result of a single amino-acid substitution," Structure, 6(8):1067-1073, Aug. 15, 1998.

Price et al., "Tissue factor and tissue factor pathway inhibitor," Anaesthesia, 59(5):483-492, May 2004.

Rader et al., "A phage display approach for rapid antibody humanization: designed combinatorial V gene libraries," Proc Natl Acad Sci U S A. 95(15):8910-8915, Jul. 21, 1998.

Ruef et al., "A bispecific antifibrin-antiplatelet urokinase conjugate (BAAUC) induces enhanced clot lysis and inhibits platelet aggregation," Thromb Haemost., 82(1):109-114, Jul. 1999.

Russo et al., "The CXCL8/IL-8 chemokine family and its receptors in inflammatory diseases," Expert Rev Clin Immunol., May 10, 2014(5):593-619, Epub Mar. 29, 2914.

Sato et al., "Properties of two VEGF receptors, Flt-1 and KDR, in signal transduction," Ann N Y Acad Sci., 902:201-205; discussion 205-207, May 2000.

Segal et al., "Introduction: bispecific antibodies," J Immunol Methods., 248(1-2):1-6, Feb. 1, 2001.

(56) References Cited

OTHER PUBLICATIONS

Shalaby et al., "Development of humanized bispecific antibodies reactive with cytotoxic lymphocytes and tumor cells overexpressing the HER2 protooncogene," J Exp Med., 175(1):217-225, Jan. 1, 1992.
Shima, "Factor VIII Mimetic Antibody: (2) In Vitro Assessment of Cofactor Activity in Hemophilia A," Rinsho Ketsueki, 46(8):777(#WS-36-5), Aug. 30, 2005 (English translation).
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem., Jan. 31, 2003;278(5):3466-73.
Stickney et al., "Bifunctional antibody: a binary radiopharmaceutical delivery system for imaging colorectal carcinoma," Cancer Res., 51(24):6650-6655, Dec. 15, 1991.
Suresh et al., "Advantages of bispecific hybridomas in one-step immunocytochemistry and immunoassays," Proc Natl Acad Sci U S A., 83(20):7989-7993, Oct. 1986.
Szlama et al., "Latent myostatin has significant activity and this activity is controlled more efficiently by WFIKKN1 than by WFIKKN2," FEBS J., Aug. 2013;280(16):3822-39. doi: 10.1111/febs.12377. Epub Jul. 5, 2013.
Taki, The Journal of Japanese Society on Thrombosis and Hemostasis. 13(1):109-113, Feb. 2, 2002.
Tan et al., "Contributions of a highly conserved VH/VL hydrogen bonding interaction to scFv folding stability and refolding efficiency," Biophys J., 75(3):1473-1482, Sep. 1998.
Thies et al., "The alternatively folded state of the antibody C(H)3 domain," J Mol Biol., 309(5):1077-1085, Jun. 22, 2001.
Vargas-Madrazo et al., "An improved model of association for VH-VL immunoglobulin domains asymmetries between VH and VL in the packing of some interface residues," J Mol Recognit., 16(3):113-120, May-Jun. 2003.
Wagner et al., "Loss of myostatin attenuates severity of muscular dystrophy in mdx mice," Ann Neurol., 52(6):832-836, Dec. 2002.
Weiner et al., "A human tumor xenograft model of therapy with a bispecific monoclonal antibody targeting c-erbB-2 and CD16," Cancer Res., 53(1):94-100, Jan. 1, 1993.
Weiner et al., "The role of T cell activation in anti-CD3 x antitumor bispecific antibody therapy," J Immunol., 152(5):2385-2392, Mar. 1, 1994.
Wenink et al., "The inhibitory Fc gamma IIb, receptor dampens TLR4-mediated immune responses and is selectively up-regulated on dendritic cells from rheumatoid arthritis patients with quiescent disease," J Immunol., Oct. 1, 2009;183(7):4509-20, Epub Sep. 4, 2009.
Whittemore et al., "Inhibition of myostatin in adult mice increases skeletal muscle mass and strength," Biochem Biophys Res Commun., 300(4):965-971, Jan. 24, 2003.
Worn et al., "Stability engineering of antibody single-chain Fv fragments," J Mol Biol., 305(5):989-1010, Feb. 2, 2001.
Wu et al., "Multimerization of a chimeric anti-CD20 single-chain Fv-Fc fusion protein is mediated through variable domain exchange," Protein Eng., 14(12):1025-1033, Dec. 2001.
Wu et al., "Structure-based engineering of a monoclonal antibody for improved solubility," Protein Eng Des Sel., Aug. 2010;23(8):643-51, Epub Jun. 11, 2010.
Xiang et al., "Production of murine V-human Cr1 chimeric anti-TAG72 antibody using V region cDNA amplified by PCR," Mol Immunol., 27(8):809-817, Aug. 1990.
Zhang et al., "Immune complex/Ig negatively regulate TLR4-triggered inflammatory response in macrophages through Fc gamma RIIb-dependent PGE2 production," J Immunol., 182(1):554-62, Jan. 1, 2009.
Zhu et al., "Remodeling domain interfaces to enhance heterodimer formation," Protein Sci., 6(4):781-788, Apr. 1997.
Zimmers et al., "Induction of cachexia in mice by systemically administered myostatin," Science, 296(5572):1486-8, May 24, 2002.
USPTO Final Office Action in U.S. Appl. No. 12/295,075, dated Jul. 27, 2015, 32 pages.
Fish & Richardson P.C., Amendment in Reply to Action dated Jul. 27, 2015, in U.S. Appl. No. 12/295,075, filed Jan. 27, 2016, 26 pages.
Coloma et al., "Position effects of variable region carbohydrate on the affinity and in vivo behavior of an anti-(1-->6) dextran antibody," J Immunol., Feb. 15, 1999;162(4):2162-70.
Dufner et al., "Harnessing phage and ribosome display for antibody optimization," Trends Biotechnol., Nov. 2006;24(11):523-9. Epub Sep. 26, 2006.
Hird et al., "Tumour localisation with a radioactively labelled reshaped human monoclonal antibody," Br J Cancer, Nov. 1991;64(5):911-4.
Li et al., "Construction and characterization of a humanized anti-human CD3 monoclonal antibody 12F6 with effective immunoregulation functions," Immunology, Dec. 2005;116(4):487-98.
Marshall et al., "Rational design and engineering of therapeutic proteins," Drug Discov Today, Mar. 1, 2003;8(5):212-21.
Padlan, "X-ray crystallography of antibodies," Adv Protein Chem., 1996;49:57-133.
Pardridge et al., "Enhanced cellular uptake and in vivo biodistribution of a monoclonal antibody following cationization," J Pharm Sci., Aug. 1995;84(8):943-8.
Reimann et al., "A humanized form of a CD4-specific monoclonal antibody exhibits decreased antigenicity and prolonged plasma half-life in rhesus monkeys while retaining its unique biological and antiviral properties," AIDS Res Hum Retroviruses, Jul. 20, 1997;13(11):933-43.
Sarkar et al., "Rational cytokine design for increased lifetime and enhanced potency using pH-activated "histidine switching"," Nat Biotechnol., Sep. 2002;20(9):908-13. Epub Aug. 5, 2002.
Sharifi et al., "Improving monoclonal antibody pharmacokinetics via chemical modification," Q J Nucl Med., Dec. 1998;42(4):242-9.
Strohl, "Optimization of Fc-mediated effector functions of monoclonal antibodies," Curr Opin Biotechnol., Dec. 2009;20(6):685-91. doi: 10.1016/j.copbio.2009.10.011. Epub Nov. 4, 2009.
Tabrizi et al., "Elimination mechanisms of therapeutic monoclonal antibodies," Drug Discov Today, Jan. 2006;11(1-2):81-8.
Verhoeyen et al., "Construction of a reshaped HMFG1 antibody and comparison of its fine specificity with that of the parent mouse antibody," Immunology, Mar. 1993;78(3):364-70.
Verhoeyen et al., "Monoclonal Antibodies in Clinical Oncology," 1991, Edited by AA Epenetos, Chapter 5, pp. 37-43, Chapman and Hall.
U.S. Appl. No. 15/467,654, Nezu et al.
U.S. Appl. No. 14/921,590, filed Oct. 23, 2015, Hattori et al.
U.S. Appl. No. 15/467,654, filed Mar. 23, 2017, Nezu et al.
U.S. Appl. No. 15/490,936, filed Apr. 19, 2017, Igawa et al.
U.S. Appl. No. 15/495,026, filed Apr. 24, 2017, Igawa et al.
U.S. Appl. No. 15/562,186, filed Sep. 27, 2017, Igawa et al.
U.S. Appl. No. 15/614,842, filed Jun. 6, 2017, Igawa et al.
U.S. Appl. No. 15/617,008, filed Jun. 8, 2017, Igawa et al.
U.S. Appl. No. 15/701,630, filed Sep. 12, 2017, Hattori et al.
U.S. Appl. No. 15/725,692, filed Oct. 5, 2017, Igawa et al.
U.S. Appl. No. 15/782,256, filed Oct. 12, 2017, Igawa et al.
U.S. Appl. No. 15/688,004, filed Aug. 28, 2017, Ruike et al.
Akira et al., "Interleukin-6 in Biology & Medicine," Adv. Immunol., Dec. 1993; 54:1-78.
Annual Report 2012 (Integrated Edition Including CSR Report), Chugai Pharmaceutical Co., Ltd., Mar. 27, 2013, 154 pages.
Araki et al., "Clinical improvement in a patient with neuromyelitis optica following therapy with the anti-IL-6 receptor monoclonal antibody tocilizumab," Mod. Rheumatol., Jul. 2013;23(4):827-31. doi:10.1007/s10165-012-0715-9. Epub Jul. 11, 2012.
Aricha et al., "Blocking of IL-6 suppresses experimental autoimmune myasthenia gravis," J. Autoimmun., Mar. 2011;36(2):135-41. doi:10.1016/j.jaut.2010.12.001. Epub Dec 30, 2010.
Buque et al., "Trial Watch: Immunomodulatory monoclonal antibodies for oncological indications," Oncoimmunology, Mar. 2, 2015:4(4):e1008814. eCollection 2015.

(56) References Cited

OTHER PUBLICATIONS

Cooper et al., "Variable domain-identical antibodies exhibit IgG subclass-related differences in affinity and kinetic constants as determined by surface plasmon resonance," Mol. Immunol., Jun. 1994; 31(8):577-84.
De Felice et al., "Formation of amyloid aggregates from human lysozyme and its disease-associated variants using hydrostatic pressure," FASEB J., Jul. 18, 2004, 18(10):1099-101. (dol:10.1096/fj.03-1072fje; PMID 15155566).
Fukuzawa et al., "Long lasting neutralization of C5 by SKY59, a novel recycling antibody, is a potential therapy for complement-mediated diseases," Sci. Rep., Apr. 24, 2017; 7(1):1080. doi:10.1038/s41598-017-01087-7.
Gershoni et al., "Epitope Mapping," BioDrugs, May 2007;21(3):145-56.
Hattori, Introduction of ART-Ig and application to hemophilia A treatment, Chugai Seiyaku ni Okeru Dokuji no Kakushinteki Kotai Gijutsu. Dec. 2012; 18:42-57 (with English translation).
Hirano et al., "Complementary DNA for a novel human interleukin (BSF-2) that induces B lymphocytes to produce immunoglobulin," Nature, Nov. 1986, 324:73-76.
Hirata et al., "Characterization of IL-6 Receptor Expression by Monoclonal and Polyclonal Antibodies," J. Immunol., Nov. 1, 1989;143(9):2900-6.
Huang et al., "A Monoclonal Anti-Human IL-6 Receptor Antibody Inhibits the Proliferation of Human Myeloma Cells," Hybridoma., Oct. 1993:12(5):621-30.
Iwai et at, "Therapeutic Agents for Gastric Cancer," Igan Chiryoyaku, Yakkyoku, Jan. 2016:67(1)138-41 (with English translation).
Janeway et al., Immunobiology, 5th edition. Jun. 2001: Extract from Chapter 3, pp. 93-122.
Janeway et al., Immunobiology, 5th edition. Jun. 2001: Extract from Chapter 4, pp. 123-154.
Klinger et al., "Harnessing T cells to fight cancer with BiTE((R)) antibody constructs—past developments and future directions," Immunol. Rev., Mar. 2016 :270(1):193-208. doi:10.1111/imr.12393.
Krieckaert et al., "Immunogenicity of biologic therapies—we need tolerance," Nat. Rev. Rheumatol., Oct. 2010;6(10):558-9. doi:10.1038/nrrheum.2010.153.
Labrijn et al., "Controlled Fab-arm exchange for the generation of stable bispecific IgG1," Nat Protoc., Oct. 2014; 9(10):2450-63. doi:10.1038/nprot.2014.169. Epub Sep. 25, 2014.
Larkin et at, "Combined Nivolumab and Ipilimumab or Monotherapy in Untreated Melanoma," N. Engl. J. Med., Jul. 2, 2015:373(1):23-34. doi:10.1056/NEJMoa1504030. Epub May 31, 2015.
Lotz et al., "B Cell Stimulating Factor 2/Interleukin 6 is a Costimulant for Human Thymocytes and T Lymphocytes," J. Exp. Med., Mar. 1, 1988; 167(3):1253-1258.
Murata et al., "Anti-Digoxin Fab Variants Generated by Phage Display," Mol. Biotechnol., Jun. 2013:54(2):269-77. doi:10.1007/s12033-012-9564-1.
Nishimoto et al., "Humanized anti-interleukin-6 receptor antibody treatment of multicentric Castleman disease," Blood Oct. 15, 2005, 106:2627-32.
Novick et al., "Monoclonal Antibodies to the Soluble Human IL-6 Receptor Affinity Purification, ELISA, and Inhibition of Ligand Binding," Hybridoma., Feb. 1991;10(1):137-46.
Okabe, Proprietary Innovative Antibody Engineering Technologies in Chugai Pharmaceutical: Dec. 18, 2012, 78 pages.
Pejchal et al., "A Conformational Switch in Human Immunodeficiency Virus gp41 Revealed by the Structures of Overlapping Epitopes Recognized by Neutralizing Antibodies," J. Virol., Sep. 2009; 83(17):8451-62. doi:10.1128/JVI.00685-09. Epub Jun. 10, 2009.
Peters et al., "Engineering an improved IgG4 molecule with reduced disulfide bond heterogeneity and increased Fab domain thermal stability," J. Biol. Chem., Jul. 13, 2012; 287(29):24525-33. doi:10.1074/jbc.M112.369744. Epub May 18, 2012.

Raposo et al., "Epitope-specific antibody response is controlled by immunoglobulin Vh polymorphisms," J. Exp. Med., Mar. 10, 2014:211(3):405-11. doi:10.1084/jem.20130968. Epub Feb. 17, 2014.
Reichert, "Antibodies to watch in 2014," MAbs., Jul.-Aug. 2014;6(4):799-802. doi:10.4161fmabs.29282. Epub May 19, 2014.
Taga et al., "Interleukin-6 Triggers the Association of Its Receptor with a Possible Signal Transducer, gp130," Cell, Aug. 11, 1989; 58(3):573-581.
Taga et al., "Receptors for B Cell Stimulatory Factor 2," J. Exp. Med., Oct. 1, 1987; 166(4):967-981.
Tanzi et al, "Twenty years of the Alzheimer's disease amylold hypothesis: a genetic perspective," Cell, Feb. 2005, 120(4):545-55. (doi:10.1016/j.cell.2005.02.008; PMID 15734686).
Vidarsson et al., "IgG subclasses and allotypes: from structure to effector functions," Front Immunol., Oct. 20, 2014;5:520. doi:10.3389/fimmu.2014.00520. eCollection 2014.
Ward et al., "Binding activities of a repertoire of single immunoglobulin variable domains secreted from *Escherichia coli*," Nature, Oct. 1989;341:544-546.
Yamasaki et al., "Cloning and Express on of the Human Interleukin-6 (BSF-2/IFNb 2) receptor," Science, Aug. 12, 1988:241(4867):825-8.
Amann et al., "Therapeutic window of an EpCAM/CD3-specific BiTE antibody in mice is determined by a subpopulation of EpCAM-expressing lymphocytes that is absent in humans," Cancer Immunol Immunother. Jan. 2009;58(1):95•109. Epub Jul. 2, 2008.
Araujo et al., "Increased rheumatoid factor interference observed during immunogenicity assessment of an Fe-engineered therapeutic antibody," J Pharm Biomed Anal., Jul. 15, 2011;55(5):1041-9. doi: 10.1016/j.jpba.2011.03.008. Epub Mar. 11, 2011.
Borrok et at, "pH-dependent Binding Engineering Reveals an FcRn Affinity Threshold That Governs IgG Recycling," J Biol Chem. Feb. 13, 2015;290(7) :4282-90. doi: 10. 1074/ jbc. M114. 603712. Epub Dec. 23, 2014.
Brenner et al., "Errors in genome annotation," Trends in Genetics, Apr. 1999;15:132-133.
Campoli et at, "Immunotherapy of Malignant Disease with Tumor Antigen-Specific Monoclonal Antibodies," Clin Cancer Res. Jan. 1, 2010;16(1):11-20. Epub Dec. 22, 2009.
Chan et al., "Therapeutic antibodies for autoimmunity and inflammation," Nat Rev Immunol. May 2010;10(5):301-16. doi: 10.1038/nri2761.
Chen et al., "Enhancement and destruction of antibody function by somatic mutation: unequal occurrence is controlled by V gene combinatorial associations," EMBO J., Jun. 5, 1995;14(12):2784-94.
Choi et al., "Engineering of Immunoglobulin Fc Heterodimers Using Yeast Surface-Displayed Combinatorial Fc Library Screening," PLoS One, Dec. 16, 2015;10(12):e0145349. doi: 10.1371/journal.pone.0145349. eCollection 2015.
Colman et al., "Effects of amino acid sequence changes on antibody-antigen interactions," Res Immunol., Jan. 1994;145(1):33-6.
Diaz et al., "Effects of engineering charged amino acids in the CH3 domains on antibody heavy chain dimerization," Philippine Science Letters. 2011;4(1):48-55.
Ejima et al, "Effects of Acid Exposure on the Conformation, Stability, and Aggregation of Monoclonal Antibodies," Proteins. Mar. 1, 2007;66(4):954-62.
Gen Bank Accession No. AAG00910.2, "recombinant IgG2 heavy chain, partial [*Homo sapiens*]," May 14, 2001, 1 page.
Gunawardane et al., "Agonistic Human Antibodies Binding to Lecithin-Cholesterol Acyltransferase Modulate High Density Lipoprotein Metabolism," J Biol Chem. Feb. 5, 2016;291(6):2799-811. doi: 10.1074/ jbc.M115.672790. Epub Dec. 7, 2015.
Hess et al., "Cancer therapy with trifunctional antibodies: linking innate and adaptive immunity," Future Oncol. Jan. 2012;8(1):73•85. doi: 10.2217/ fon.11.138.
Hironiwa et al., "Calcium-dependent antigen binding as a novel modality for antibody recycling by endosomal antigen dissociation," MAbs., 2016;8(1):65-73. doi: 10.1080/19420862.2015.1110660. Epub Oct. 23, 2015.

(56) References Cited

OTHER PUBLICATIONS

Igawa et al., "pH-dependent antigen-binding antibodies as a novel therapeutic modality," Biochim Biophys Acta., Nov. 30, 2014;1844(11):1943-1950.

Iwabe et al., "Pathogenetic significance of increased levels • of interleukin-a in the peritoneal fluid of patients with endometriosis," Fertil Steril. May 1998:69(5):924-30.

Jones et al., "Growth factor receptor interplay and resistance in cancer," Endocr Relat Cancer. Dec. 2006;13 Suppl 1:S45•51.

Kabat et al., National Institute of Health, Publ'n No. 91-3242, Sequences of Proteins of Immunological Interest, vol. 1 p. 647-60 (5th ed. 1991).

Kontermann, "Dual targeting strategies with bispecific antibodies," MAbs. Mar.-Apr. 2012,4(2):182-97. doi: 10.4161/mabs.4.2.19000. Epub Mar. 1, 2012.

Kussie et al., "A single engineered amino acid substitution changes antibody fine specificity," J Immunol., Jan. 1, 1994;152(1):146-52.

Lacroix-Desmazes et al, "Dynamics of factor VIII interactions determine its immunologic fate in hemophilia A," Blood., Jul. 15, 2008;112(2):240-9. doi: 10.1182/blood-2008-02-124941. Epub May 9, 2008.

Lederman et al., "A single amino acid substitution in a common African allele of the CD4 molecule ablates binding of the monoclonal antibody, OKT4," Mol Immunol., Nov. 1991;28(11):1171-81.

Li et al., "beta-Endorphin omission analogs: dissociation of immunoreactivity from other biological activities," Proc Natl Acad Sci U.S.A. Jun. 1980;77(6):3211-4.

Maier et al., "Assessment of fully automated antibody homology modeling protocols in molecular operating environment," Proteins., Aug. 2014;82(8):1599-610. doi: 10.1002/prot.24576. Epub Apr. 23, 2014.

Mazda et al., "Regulation of Muscle Homeostasis and Metabolism by the TGF-β Superfamily Cytokine, Myostatin/growth Differentiation Factor 8 (GDF8)," Journal of Kyoto prefectural university of medicine. 2013;122(3):133-41.

Mezzanzanica et al., "Human Ovarian Carcinoma Lysis by Cytotoxic T Cells Targeted by Bispecific Monoclonal Antibodies: Analysis of the Antibody Components," Intl Cancer. Apr. 15, 1988;41(4):609-15.

Morrison, "Two heads are better than one," Nat Biotechnol., Nov. 2007;25(11):1233-4.

Nakano et al., Anti-glypican 3 antibodies cause ADCC against human hepatocellular carcinoma cells, Biochem Biophys Res Commun. Jan. 9, 2009;378(2):279-84. doi: 10.1016/ j.bbrc.2008.11.033. Epub Nov. 18, 2008.

Natsume et al., "Improving effector functions of antibodies for cancer treatment: Enhancing ADCC and CDC," Drug Des Devel Ther. Sep. 21, 2009;3:7-16.

Newman et al, "Modification of the Fc Region of a Primatized IgG Antibody to Human CD4 Retains Its Ability to Modulate CD4 Receptors but Does Not Deplete CD4 T Cells in Chimpanzees," Clin Immunol. Feb. 2001;98(2):164-74.

Radaev et al., "The Structure of a Human Type III Fcγ Receptor in Complex with Fc*," J Biol Chem. May 11, 2001;276(19):16469•77. Epub Jan. 31, 2001.

Riechelmann et al., "Adoptive therapy of head and neck squamous cell carcinoma with antibody coated immune cells: a pilot clinical trial," Cancer Immunol Immunother. Sep. 2007;56(9):1397-406. Epub Feb. 2, 2007.

Rothe et al., "Recombinant proteins in rheumatology—recent advances," N Biotechnol. Sep. 2011;28(5):502•10. doi: 10.1016/j.nbt.2011.03. 019. Epub Apr. 5, 2011.

Schlereth et al., "T-cell activation and B-cell depletion in chimpanzees treated with a bispecific anti-CD19/anti-CD3 single-chain antibody construct," Cancer Immunol Immunother. May 2006;55(5):503-14. Epub Jul. 20, 2005.

Sebastian et al., "Treatment of non-small cell lung cancer patients with the trifunctional monoclonal antibody catumaxomab (anti-EpCAM x anti-CD3): a phase I study," Cancer Immunol Immunother. Oct. 2007; 56{10}:1637•44. Epub Apr. 5, 2007.

Seimetz et al., "Development and approval of the trifunctional antibody catumaxomab (anti-EpCAM x anti-CD3) as a targeted cancer immunotherapy," Cancer Treat Rev.Oct. 2010;36(6):458•67. Epub Mar. 27, 2010.

Smith et al., "The challenges of genome sequence annotation or 'The devil is in the details'," Nature Biotechnology, Nov. 1997;15:1222-1223.

Staerz et al., "Hybrid antibodies can targetsites for attack by T cells," Nature. Apr. 18-24, 1985; 314(6012):628-31.

Unkeless et al., "Structure and Function of Human and Murine Receptors for IgG," Annu Rev Immunol. 1988;6:251•81.

Wozniak-Knopp et al., "Introducing antigen-binding sites in structural loops of immunoglobulin constant domains: Fc fragments with engineered HER2/neu-binding sites and antibody properties," Protein Eng Des Sel. Apr. 2010;23(4):289-97. doi: 10.1093/ protein/ gzq005. Epub Feb. 11, 2010.

Zeidler et al., "Simultaneous Activation of T Cells and Accessory Cells by a New Class of Intact Bispecific Antibody Results in Efficient Tumor Cell Killing1," J Immunol. Aug. 1, 1999;163(3):1246-52.

International Search Report for App. Ser. No. PCT/JP2016/003616, dated Nov. 25, 2016, 4 pages.

Smolen et al., "Interleukin-6: a new therapeutic target," *Arthritis Res Ther.*, 2006;8 Suppl 2:S5. Epub Jul. 28, 2006.

U.S. Appl. No. 12/295, 075, *Igawa et al.*, filed Apr. 20, 2009.
U.S. Appl. No. 14/741,786, *Igawa et al.*, filed Jun. 17, 2015.
U.S. Appl. No. 14/047,316, *Kuramochi et al.*, filed Oct. 7, 2013.
U.S. Appl. No. 14/974,350, filed Dec. 18, 2015.
U.S. Appl. No. 14/974,488.
U.S. Appl. No. 15/015,287.
U.S. Appl. No. 12/679,922, filed Oct. 1, 2010.
U.S. Appl. No. 10/575,905, filed Apr. 30, 2007.
U.S. Appl. No. 11/910,836, filed Jan. 12, 2009.
U.S. Appl. No. 13/434,643, filed Mar. 29, 2012.
U.S. Appl. No. 13/885,421, filed Aug. 30, 2013.
U.S. Appl. No. 14/019,117, filed Sep. 5, 2013.
U.S. Appl. No. 14//019,712, filed Sep. 6,2013.
U.S. Appl. No. 12/680,112, filed Jun. 23, 2013.
U.S. Appl. No. 13/959,489, filed Aug. 5, 2013.
U.S. Appl. No. 13/524,528, filed Jun. 15, 2012.
U.S. Appl. No. 14/520,423, filed Oct. 22, 2014.
U.S. Appl. No. 11/910,128, filed Oct. 7, 2008.
U.S. Appl. No. 12/680,082, filed Jun. 25, 2010.
U.S. Appl. No. 13/257,112, filed Nov. 22, 2011.
U.S. Appl. No. 13/257,145, filed Nov. 22, 2011.
U.S. Appl. No. 12/745,781, filed Sep. 13, 2010.
U.S. Appl. No. 14/340,883, filed Jul. 25, 2014.
U.S. Appl. No. 14/047,316, filed Oct. 7, 2013.
U.S. Appl. No. 12/809,138, filed Mar. 1, 2011.
U.S. Appl. No. 13/320,317, filed Feb. 1, 2012.
U.S. Appl. No. 13/497,269, filed Jun. 1, 2012.
U.S. Appl. No. 13/637,415, filed Feb. 4, 2013.
U.S. Appl. No. 13/582,073, filed Dec. 20, 2012.
U.S. Appl. No. 12/295,075, filed Apr. 20, 2009.
U.S. Appl. No. 13/518,861, filed Oct. 4, 2012.
U.S. Appl. No. 14/007,947, filed Sep. 26, 2013.
U.S. Appl. No. 14/347,034, filed Mar. 25, 2014.
U.S. Appl. No. 14/347,187, filed Jul. 25, 2014.
U.S. Appl. No. 16/061,454, *Takana et al.*, filed Jun. 12, 2018.
U.S. Appl. No. 13/497,269, *Kuramochi et al.*, filed Jun. 1, 2012.
U.S. Appl. No. 15/263,617, *Igawa et al.*, filed Sep. 13, 2016.
U.S. Appl. No. 10/575,905, *Hattori et al.*, filed Apr. 30, 2017 (abandoned).
U.S. Appl. No. 11/910,128, *Igawa et al.*, filed Oct. 7, 2018.
U.S. Appl. No. 15/963,221, Nezu et al., filed Apr. 26, 2018.
U.S. Appl. No. 61/313,102, Pons, filed Mar. 11, 2010.

(56) References Cited

OTHER PUBLICATIONS

Akbarzadeh-Sharbaf et al., "In silico design, construction and cloning of Trastuzumab humanized monoclonal antibody: A possible biosimilar for Herceptin," Advanced Biomedical Research 2012:1: 21. doi: 10. 4103/ 2277-9175. 98122. Epub Jul. 6, 2012.
Alignment of constant region sequences from WO 2009/125825 (document submitted in EP opposition and posted by EPO on Feb. 2, 2018); 1 page.
Alignment of the amino acid sequences of the Fc regions of antibodies exemplified in EP 2275443 (document submitted in EP opposition and posted by EPO on Feb. 2, 2018); 1 page.
Alignment of variable heavy and light chain amino acid sequences from WO 2009/125825 (document submitted in EP opposition and posted by EPO on Feb. 2, 2018); 2 pages.
Atherton et al., "Acid-base balance: maintenance of plasma pH," Anaesthesia & Intensive Care Medicine 2009:10(11):557-61 (abstract).
Breitbart et al., "Highly specific detection of myostatin prodomain by an immunoradiometric sandwich assay in serum of healthy individuals and patients," PloS One Nov. 15, 2013:8(11):e80454 doi 10.1371/journal.pone.0080454 eCollection 2013.
Claims as granted for EP 2275443 (document submitted in EP opposition); 6 pages.
Datta-Mannan et al., "Humanized IgG1 variants with differential binding properties to the neonatal Fc receptor: relationship to pharmacokinetics in mice and primates," Drug Metab Dispos. Jan. 2007, 35 (1):86-94. Epub Oct 18, 2006.
Davydov, "Omalizumab (Xolair) for treatment of asthma," Am Fam Physician Jan. 15, 2005:71(2):341-2.
Declaration of Nimish Gera, Ph.D., CV and Exhibits, Sep. 1, 2016 (submitted in the matter of EP 2275443, Opposition thereto by Alexion Pharmaceuticals, Inc.); 24 pages.
EMA product information: Annexes to file of the tocilizumab preparation RoActemra (WC500054890), published by EMA on Jan. 8, 2010.
EPO Register Extract EP 1915397 (document submitted in EP opposition and posted by EPO on Feb. 2, 2018); 4 pages.
Experimental data characterizing the binding of rituximab to its antigen CD20 and to human FcRn (document submitted in EP opposition and posted by EPO on Feb. 5, 2018); 6 pages.
Experimental information regarding off-rate of Xolair Fab for binding to human IgE at pH7.4 and.pH5.5 (document submitted in EP opposition and posted by EPO on Feb. 2, 2018); 3 pages.
Expert Declaration by Dr. Madhusudan Natarajan, submitted in EP opposition regarding EP 2552955 and posted by EPO on Feb. 5, 2018; 4 pages.
Geneseq Accession No. AEM45140, Feb. 22, 2007, "Light chain constant region of therapeutic human IgG antibody," 1 page.
Goebl et al., "Neonatal Fc receptor mediates internalization of Fc transfected human endothelial.cells," Molecular Biology of the Cell, Dec. 19, 2008(12):5490-5505.
Golay et al., "Mechanism of action of therapeutic monoclonal antibodies: Promises and pitfalls of in vitro and in vivo assays," Archives of Biochemistry and Biophysics 526: 146-153, Feb. 25, 2012.
Gurbaxani et al., "Analysis of a family of antibodies with different half-lives in mice fails to find a correlation between affinity for FcRn and serum half-life," Mol Immunol Mar. 2006, 43(9):1462-73. Epub Sep. 1, 2005.
Horiuchi et al., "Complement-targeted therapy: development of C5- and C5a-targeted inhibition," Inflammation and Regeneration, Jun. 3, 2016 36:11 doi: 10.1186/s41232-016-0013-6. eCollection.
Irani et al., "Molecular properties of human IgG subclasses and their implications for designing therapeutic monoclonal antibodies against infectious diseases," Molecular Immunology, Oct. 2015, 67 (2 Pt A):171-82. Doi:10.1016/ j. molimm 2015.03.255. Epub Apr. 18, 2015.
Kabat et al., "Identical V region amino acid sequences and segments of sequences in antibodies of different specificities," Journal of Immunology Sep. 1, 1991, 147(5):1709-19.

Kim et al., "Antibody light chain variable domains and their biophysically improved versions for human immunotherapy," Mabs Jan.-Feb. 2014: 6(1):219-35 doi: 10.4161/mabs 26844.
Kim et al., "Production of a polyclonal anti-myostatin antibody and the effects of in ovo administration of the antibody on posthatch broiler growth and muscle mass," Poult Sci. Jun. 2007, 86(6): 1196-205.
King et al., "Applications and Engineering of Monoclonal Antibodies," CRC Press Nov. 1998, pp. 68-71.
Kitazawa et al., "A bispecific antibody to factors IXa and X restores factor VIII hemostatic activity in a hemophilia a model," Nat Med. Oct. 18, 2012(10):1570-4. doi: 10.1038/nm.2942. Epub Sep. 30, 2012.
Li et al., "Framework selection can influence pharmacokinetics of a humanized therapeutic antibody through differences in molecule charge," Mabs Sep.-Oct. 2014:6(5):1255-64 doi:104161/mabs 29809 Epub Oct. 30, 2014.
Molina et al., "Trastuzumab (Herceptin), a humanized anti-HER2 receptor monoclonal antibody, inhibits basal and activated HER2 ectodomain cleavage in breast cancer cells," Cancer Res. Jun. 15, 2001;61(12):4744-9.
O'Donovan et al., "EGFR and HER-2 antagonists in breast cancer," Anticancer Res. May-Jun. 2007:27 (3A) :1285-94.
Official Action dated Oct. 13, 2016, issued for EP Application No. 11714860.1 and submitted as evidence during EP opposition; 3 pages.
Presta et al., "Humanization of an anti-vascular endothelial growth factor monoclonal antibody for the therapy of solid tumors and other disorders," Cancer Res. Oct. 15, 1997, 57 (20) :4593-9.
Product labelling information for Rituxan (Rituximab), dated Nov. 1997, 2 pages.
Raghavan et al., "Analysis of the pH dependence of the neonatal Fc receptor/Immunoglobulin G interaction using antibody and receptor variants," Biochemistry Nov. 14, 1995, 34(45):14649-57.
Ruggeri et al., "von Willebrand Factor and von Willebrand Disease," Blood, Oct. 1987; 70(4):895-904.
Stancovski et al., "Mechanistic aspects of the opposing effects of monoclonal antibodies to the ERBB2 receptor on tumor growth," Proc. Natl. Acad. Sci. USA, Oct. 1, 1991, 88:8691-8695.
Summary of information about antibodies in Examples of patent (document submitted in EP opposition and posted by EPO on Apr. 13, 2018); 3 pages.
Supplementary data provided by opponent for EP Application No. 11714860.1 (document submitted in EP opposition and posted by EPO on Feb. 20, 2018); 3 pages.
Technical data sheet: polyclonal anti-human C5, Quidel online catalogue, Jan. 1, 2010, pp. 1-1.
Vaccaro et al., "Divergent activities of an engineered antibody in murine and human systems.have implications for therapeutic antibodies," Proc Natl Acad Sci USA Dec. 5, 2006, 103(49):18709-14 Epub Nov. 20, 2006.
Waelbroeck et al., "The pH dependence of insulin binding," J Biol Chem Jul. 25, 1982, 257(14):8284-91.
Ward et al., "Evidence to support the cellular mechanism involved in serum IgG homeostasis in humans," Int Immunol Feb. 2003, 15(2):187-95.
Welch et al., "Adalimumab (Humira) for the treatment of rheumatoid arthritis" Am Fam Physician Dec. 15, 2008, 78(12):1406-1408.
Written Submissions by Opponent 1 (Alexion Pharmaceuticals, Inc.) in Opposition of EP 2006381 dated Apr. 13, 2018, 19 pages.
Written Submissions by Opponent 2 (Novo Nordisk A/S) in Opposition of EP 2006381 dated Apr. 13, 2018, 14 pages.
Written Submissions by Opponent 3 (name Unknown) in Opposition of EP 2006381 dated Apr. 13, 2018, 16 pages.
Wu et al., "Ultra-potent Antibodies Against Respiratory Syncytial Virus: Effects of Binding Kinetics and Binding Valence on Viral Neutralization," J Mol Biol. Jul. 1, 2005;350(1):126-44.
Yang et al., "Dataset of the binding kinetic rate constants of anti-PCSK9 antibodies obtained using the Biacore T100, Protean XPR36, Octet RED384, and Ibis MX96 biosensor platforms," Data Brief Jul. 27, 2016, 8:1173-83. doi : 10. 1016/ J. dib. 2016.07.044. eCollection Sep. 2016.

(56) References Cited

OTHER PUBLICATIONS

Yang et al., "Maximizing in vivo target clearance by design of pH-dependent target binding.antibodies with altered affinity to FcRn," MAbs Oct. 2017, 9(7):1105-1117. doi: 10. 1080/19420862. 2017. 1359455. Epub Aug. 8, 2017.
Yarilin et al., Fundamentals of Immunology M: Medicina, 1999, pp. 169-72, 354-8 (with English translation), 21 pages.
Yeung et al., "A therapeutic Anti-VEGF antibody with increased potency independent of pharmacokinetic half-life," Cancer Res Apr. 15, 2010, 70 (8):3269-77. doi: 10. 1158/ 0008-5472. CAN-09-4580. Epub Mar. 30, 2010.
Ying et al., "Large yellow croaker MSTN-1 prodomain prokaryotic expression, polyclonal antibody.preparation and antibody function identification," Chinese Journal of Cell Biology Oct. 2014, 36(10): 1344-1349 (in Chinese, with English abstract).
Giclas et al., "Preparation and characterization of monoclonal antibodies against the fifth component of rabbit complement (C5)," J. Immunol. Methods, Dec. 24, 1987, 105(2):201-9.
Rother et al., "Discovery and development of the complement inhibitor eculizumab for the treatment of paroxysmal nocturnal hemoglobinuria," Nature Biotechnol., Nov. 2007, 25(11):1256-64.
U.S. Appl. No. 15/963,345, *Ruike et al.*, filed Apr. 26, 2018.
Becker et al., "Prevention of postoperative abdominal adhesions by a sodium hyaluronate-based bioresorbable membrane: a prospective, randomized, double-blind multicenter study," J Am Coll Surg, Oct. 1996, 183(4): 297-306.
Besada, "Potential patient benefit of a subcutaneous formulation of a tocilizumab for the treatment of rheumatoid arthritis: a critical review," Patient Preference and Adherence, Aug. 1, 2014, 8:1051-9. doi: 10.2147/PPA. S34958. eCollection 2014.
Bulun, "Endometriosis," New Eng J Med, Jan. 2009, 360(3):268-279.
Donnez et al., "Current thinking on the pathogenesis of endometriosis," Gynecol Obstet Invest, 2002, 54(Suppl 1): 52-62.
Giudice et al., "Endometriosis," Lancet, Nov. 2004, 364(9447): 1789-1799.
Guo, "Recurrence of endometriosis and its control," Hum Reprod Update, Jul.-Aug. 2009 (Epub Mar. 2009), 15(4): 441-461.
Huizinga et al., "Sarilumab, a fully human monoclonal antibody against IL-6Rα in patients with rheumatoid arthritis and an inadequate response to methotrexate: efficacy and safety results from the randomised Saril-Ra-Mobility Part A trial," Ann Rheum Dis., Sep. 2014, 73(9):1626-34. doi: 10. 1136/annrheumdis-2013-204405. Epub Dec. 2, 2013.
Iwabe et al., "Pathogenetic significance of increased levels of interleukin-8 in the peritoneal fluid of patients with endometriosis," Fertil Steril, May 1998, 69(5):924-930.
Russo et al., "The CXCL8/IL-8 chemokine family and its receptors in inflammatory diseases," Expert Rev Clin Immunol, May 2014, 10(5):593-619.
Vercellini et al., "Postoperative oral contraceptive exposure and risk of endometrioma recurrence," Am J Obstet Gynecol, May 2008 (Epub Feb. 2008), 198(5): 504.
U.S. Appl. No. 16/028,140, *Igawa et al.*, filed Jul. 5, 2018.
U.S. Appl. No. 16/061,454, *Tanaka et al.*, filed Jun. 12, 2018.
U.S. Appl. No. 15/172,727, *Hattori et al.*, filed Jun. 3, 2016 (abandoned).
U.S. Appl. No. 15/050,145, *Igawa et al.*, filed Apr. 19, 2016.
U.S. Appl. No. 15/952,945, Igawa et al., filed Apr. 13, 2018.
[Anonymous] "Rabbit antibody to human pro-Myostatin (amino acids 79-92)", Meridian Life Science Inc, Nov. 13, 2015 (Nov. 13, 2015), XP055478289, Retrieved from the Internet: URL:https://meridianlifescience.com/biospecs/K24340R.pdf [retrieved on May 5, 2018].
[Anonymous] "Blog entry", Jun. 1, 2014 (Jun. 1, 2014), Retrieved from the Internet: URL:https://www.thundersplace.org/male-supplements/the-chemical-pe thread-7.htm192 [retrieved on May 23, 2018].
[Anonymous] "polyclonal human pro-Myostatin (aa 79-92) antibody", Immun Diagnostik Antibodies catalogue, Jun. 30, 2016 (Jun. 30, 2016), Retrieved from the Internet: URL:https://www.immundiagnostik.com/fileadmin/podf/AK3004.pclf [retrieved on May 24, 2018].
[Anonymous] "Mouse GDF-8/Myostatin Propeptide Antibody", R&D Catalogue AF 1539, Feb. 6, 2018 (Feb. 6, 2018), XP055478493, Retrieved from the Internet: URL:https://resources.rndsystems.com/podfs/datasheets/af1539.pdf [retrieved on MAY 25, 2018].
Alexion initiates simultaneous registration trials of ALXN1210 for patients with paroxysmal nocturnal hemoglobinuria(PNH) and atypical hemolytic uremic syndrome(aHUS), Press release, Alexion Pharmaceuticals, Inc. [online](retrieved on Jun. 6, 2018), retrieved from the Internet (URL: http://iralexion.com/releasedetail.cfm?releaseid=995788).
Beiboer et al., "Guided selection of a pan carcinoma specific antibody reveals similar binding characteristics yet structural divergence between the original murine antibody and its human equivalent," J Mol Biol, Feb. 25, 2000, 296(3):833-49.
Canfield et al., "The binding affinity of human IgG for its high affinity Fc receptor is determined by multiple amino acids in the CH2 domain and is modulated by the hinge region," J Exp Med, Jun. 1, 1991, 173(6):1483-91.
Chihara et al., "Interleukin 6 signaling promotes anti-aquaporin 4 autoantibody production from plasmablasts in neuromyelitis optica," Proc Natl Acad Sci USA, Mar. 1, 2011, 108(9):3701-3706.
European Medicines Agency, No. WC500054212, Jun. 22, 2016, pp. 1-41, XP002780707 Retrieved from the Internet:URL:http://www.ema.europa.eu/docs/en_GB/document_library/EPAR_-Scientific_Discussion/human/000791/WC500054212.pdf.
Feagan et al., "Ustekinumab as induction and maintenance therapy for Crohn's Disease," n. Engl J Med, Nov. 17, 2016, 375(20):1946-1960.
Han et al., "Targeting the myostatin signaling pathway to treat muscle wasting diseases,"Curr Opin Support Palliat Care, Dec. 2011, 5(4):334-41. doi:10.1097/SPC.0b013e32834b&lf9.
Harvey et al., Lippincott's Illustrated Reviews: Immunology Second Edition; Chapter 2, "Antigens and Receptors," pp. 11-23; Chapter 11, "Lymphocyte Effector Functions," pp. 141-157, 2008.
Hill et al., "The Myostatin propeptide and the follistatin-related gene are inhibitory binding proteins of myostatin in normal serum," J Biol Chem, Oct. 25, 2002, 277(43):40735-41. Epub Aug. 22, 2002.
Kawahata, Alnylam Pharmaceuticals, Mar. 22, 2016, XP055471916 Retrieved from the Internet: URL: http://www.alnylam.com/web/assets/ERA-EDTA_CC5_Ph-1_052216.pdf.
Kim et al., "Production of a monoclonal anti-myostatin antibody and the effects of in ovo administration of the antibody on posthatch broiler growth and muscle mass," Poult Sci, Jun. 2006, 85(6):1062-71.
Klimka et al., "Human anti-CD30 recombinant antibodies by guided phage antibody selection.using cell panning," Br J Cancer, Jul. 2000, 83(2):252-60.
Richter et al., "Hematopoietic cells as site of first-pass catabolism after subcutaneous dosing and contributors to systemic clearance of a monoclonal antibody in mice," Drug Metab Dispos, Nov. 2014, 42(11):1881-9. doi: 10.1124/dmd.114.059238. Epub Aug. 6, 2014.
Soliris(R)(eculizumab)injection, for intravenous use, BLA:125166, Jan. 13, 2017, Suppl-417, Label, Drugs@FDA[online](retrieved on Jun. 6, 2018), retrieved from the Internet URL:https://www.accessdata.fda.gov/scripts/cder/daf/index.cfm?event=overview.process&applno=125166.
Yada et al., Lippincott's Illustrated Reviews: Immunology Second Edition, Nov. 30, 2013, pp. 18, 19, 152, and 153.
Yarilin, Fundamentals of Immunology, M.:Medicina, 1999, pp. 169-174 (with English translation).
Zheng et al., Minipig as a potential translatable model for monoclonal antibody pharmacokinetics after intravenous and subcutaneous administration, mAbs, Mar.-Apr. 2012, 4(2):243-55. doi:10.4161/mabs.4.2.19387. Epub Mar. 1, 2012.
International Search Report for App. Ser. No. PCT/JP2015/006323, dated Jul. 12, 2018, 23 pages.
International Search Report for App. Ser. No. PCT/JP2017/028346, dated Oct. 31, 2017, 5 pages.

(56) References Cited

OTHER PUBLICATIONS

Jaeger, Clinical Immunology and Allergology, M: Medicina, 2$^{nd}$ edition, 1990, 2:484-5 (with English translation).
Popov et al., "The Stoichiometry and Affinity of the Interaction of Murine Fc Fragments with the MHC Class I-Related Receptor, FcRn," Mol Immunol, Apr. 1996, 33(6):521-30.
Roitt et al., Immunology, Moscow: Mir, 2000, 373-4 (with English translation).
Yarilin, Fundamentals of Immunology, M: Medicina, 1999, pp. 175 and 182 (with English translation of the Tables).
U.S. Appl. No. 15/533,609, Kakehi et al., filed Aug. 25, 2017.
Consolidated List of Document (cited in a decision of the EPO Opposition Division for EP 2 006 381, dated Jul. 25, 2018), 4 pages.
Adams et al., "Humanization of a recombinant monoclonal antibody to produce a therapeutic HER dimerization inhibitor, pertuzumab," Cancer Immunother., Jun. 2006, 55:717-727.
Chen et al., "Selection and analysis of an optimized anti-VEGF antibody: crystal structure of an affinity-matured Fab in complex with antigen," J Mol Biol., Nov. 5, 1999, 293(4):865-881.
Coloma et al., "Position effects of variable region carbohydrate on the affinity and in vivo behavior of an anti(1→6) dextran antibody," J Immunol., Feb. 15, 1999, 162(4):2162-2170.
Cruse et al., Atlas of Immunology, CRC Press LLC, 2004, "Chapter 3 Antigens and Immunogens," p. 109.
Dall'Acqua et al., "Antibody humanization by framework shuffling," Methods, May 2005, 36(1):43-60.
Dall'Acqua et al., "Properties of human IgG1s engineered for enhanced binding to the neonatal Fc receptor (FcRn)," J Biol Chem., Aug. 18, 2006, 281(33):23514-23524. Epub Jun. 21, 2006.
Ghetie et al., "Increasing the serum persistence of an IgG fragment by random mutagenesis,"Nat, Bioltechnol., Jul. 1997, 15(7):637-640.
He et al., "Humanization and pharmacokinetics of a monoclonal antibody with specificity for both E- and P-selection," J. Immunol., Jan. 1998, 160:1029-1035.
Hinton et al., "An engineered human IgG1 antibody with longer serum half-life," J. Immunol., Jan. 1, 2006, 176:346-356.
Hird et al., "Tumour localisation with a radioactively labelled reshaped human monoclonal antibody," Br J Cancer, Nov. 1991, 64(5):911-914.
Hong et al., "Enhanced cellular uptake and transport of polyclonal immunoglobulin G and fab after their cationization," J Drug Target., 2000 8(2):67-77.
Hotzel et al., "A strategy for risk mitigation of antibodies with fast clearance,"mAbs, Nov.-Dec. 2012, 4(6):753-60, doi: 10.4161/mabs. 22189.
Ito et al., "The His-probe method: effects of histidine residues introduced into the complementarity-determining regions of antibodies on antigen-antibody interactions at different pH values,"FEBS Lett., Aug. 31, 1992, 309:85-88.
Kobayashi et al., "The pharmacokinetic characteristics of glycolated humanized anti-Tac Fabs are determined by their isoelectric point," Cancer Res., Jan. 15, 1999, 59(2):422-430.
Li et al., "Construction and characterizations of a humanized anti-human CD3 monoclonal antibody 12F6 with effective immunoregulation functions," Immunology, Dec. 2005, 116(4):487-498.
Lobo et al., "Antibody pharmacokinetics and pharmacodynamics," J. Pharm. Sci., Nov. 2004, 93:2645-2668.
Marshall et al., "Rational design and engineering of therapeutics proteins," Drug Discov Today, Mar. 1, 2003, 8(5):212-221.
Martin et al., "Crystal structure at 2.8 A of an FcRn/heterodimeric Fc complex: mechanism of pH-dependent binding," Mol Cell., Apr. 2001, 7(4):867-877.
Onda et al., "Lowering the Isoelectric Point of the Fv Portion of Recombinant Immunotoxins Leads to Decreased Nonspecific Animal Toxicity without Affecting Antitumor Activity," Cancer Res., Jul. 2001, 61:5070-5077.

Pardridge et al., "Enhanced cellular uptake and in vivo biodistribution of a monoclonal antibody following cationization," J Pharm Sci., Aug. 1995, 84(8):943-948.
Pavlinkova et al., "Charge-modified single chain antibody constructs of monoclonal anitbody CC49: Generstion, characterization, pharmacokinetics, and biodistribution analysis," Nucl Med Biol., Jan. 1999, 26(1):27-34.
Pavlou et al., "The therapeutic antibodies market to 2008," Eur. J. Pharm. Biopharm., Apr. 2005, 59(3):389-396.
Poduslo et al., "Polyamine modification increases the permeability of proteins at the blood-nerve and blood-brain barriers," J. Neurochem., Apr. 1996, 66:1599-1609.
Reichert et al., "Monoclonal antibody successes in the clinic," Nat. Biotechnol., Sep. 2005, 23(9):1073-1078.
Reimann et al., "A humanized form of a CD4-specific monoclonal antibody exhibits decreased antigenicity and prolonged plasma half-life in rhesus monkeys while retaining its unique biological and antiviral properties," AIDS res Hum Retroviruses, Jul. 20, 1997, 13(11):933-943.
Roopernian et al., "FcRn: the neonatal Fc receptor comes of age," Nat Rev Immunol., Sep. 2007, 7(9):715-725. Epub Aug. 17, 2007.
Ryman et al., "Pharmacokinetics of Monoclonal Antibodies," CPT Pharmacometrics Syst Pharmacol. Sep. 2017, 6(9):576-588. doi: 10.1002/psp4.12224. Epub Jul. 29, 2017.
Sarkar et al., "Rational cytokine design for increased lifetime and enhanced potency using pH-activated"histidine switching"," Nat Biotechnol., Sep. 2002, 20(9):908-913. Epub Aug. 5, 2002.
Sequence alignments and modification scheme (document submitted during Oral Proceedings in EPO Opposition Division for EP 2 006 381 mentioned in minutes of the Oral Proceedings posted by EPO on Jul. 25, 2018): 3 pages.
Sharifi et al., "Improving monoclonal antibody pharmacokinetics via chemical modification," Q J Nucl Med., Dec. 1998, 42(4):242-249.
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., Mar. 2, 2001, 276(9):6591-6604. Epub Nov. 28, 2000.
Summary of information about antibodies in Examples of patent (document submitted in EP Opposition Division for EP 2 006 381 and posted by EPO on Apr. 13, 2018): 3 pages.
Tabrizi et al., "Elimination mechanisms of therapeutic monoclonal antibodies," Drug Discov Today, Jan. 2006, 11(1-2):81-88.
Van Den Abbeele et al., "Antigen-binding site protection during radiolabeling leads to a higher immunoreactive fraction," J Nucl Med, Jan. 1991, 32(1):116-1122.
Vaisitti et al., "Cationization of monoclonal antibodies: another step towards the 'magic bullet'?," J Biol Regul Homeost Agents., Jul.-Dec. 2005, 19(3-4):105-112.
Verhoeyen et al., "Construction of reshaped HMFG1 antibody and comparison of its fine specificity with that of the parent mouse antibody," Immunology, Mar. 1993, 78(3):364-370.
Verhoeyen et al., "Re-shaped human anti-PLAP antibodies," Monoclonal Antibodies in Clinical Oncology, Chapter 5, Chapman and Hall, 1991, pp. 34-43.
Wu et al., "Ultra-potent antibodies against respiratory syncytial virus: effects of binding kinetics and binding valence on viral neutralization," J Mol Biol. Jul. 1, 2005, 350(1):126-144.
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., May 2002, 301:467-477.
Yang et al., "CDR walking mutagenesis for the affinity maturation of a potent human anti-HIV-1 antibody into the picomolar range," J. Mol. Biol., Dec. 1, 1995, 254(3):392-403.
Zuckier et al., "Chimeric human-mouse IgG antibodies with shuffled constant region exons demonnstrate that multiple domains contribute to in vivo half-life," Cancer Res., Sep. 1998, 58:3905-3908.
U.S. Pat. No. 10,150,808, Kuramochi et al., filed Dec. 11, 2018.
U.S. Appl. No. 13/582,073 Kuramochi et al., filed Dec. 20, 2012.
U.S. Appl. No. 14/007,947, Igawa et al., filed Sep. 26, 2013.

(56) References Cited

OTHER PUBLICATIONS

U.S. Appl. No. 14/340,883, Kuramochi et al., filed Jul. 25, 2014.
U.S. Appl. No. 14/347,034, Igawa et al., filed Mar. 25, 2014.
U.S. Appl. No. 14/347,187, Igawa et al., filed Mar. 25, 2014.
U.S. Appl. No. 14/520,423, Igawa et al., filed Oct. 22, 2014.
U.S. Appl. No. 14/680,250, Igawa et al., filed Apr. 17, 2015.
U.S. Appl. No. 15/132,996, Igawa et al., filed Apr. 19, 2016.
U.S. Appl. No. 15/210,353, Igawa et al., filed Jul. 15, 2016.
U.S. Appl. No. 15/288,965, Igawa et al., filed Oct. 7, 2016.
U.S. Appl. No. 15/553,609, Kakehi et al., filed Aug 25, 2017
U.S. Appl. No. 15/617,008, Igawa et al., filed Jun. 8, 2017.
U.S. Appl. No. 15/688,004, Ruike et al., filed Aug. 28, 2017.
U.S. Appl. No. 15/701,630, Hattori et al., filed Sep. 12, 2017.
U.S. Appl. No. 15/963,345, Hattori et al., filed Apr. 26, 2018.
U.S. Appl. No. 16/226,798, Hattori et al., filed Dec. 20, 2018.
U.S. Appl. No. 10/575,905, Hattori et al., filed Apr. 30, 2007.
U.S. Appl. No. 11/910,836, Hattori et al., filed Jan. 12, 2009.
U.S. Appl. No. 13/434,643, Hattori et al., filed Mar. 29, 2012.
U.S. Appl. No. 16/019,752, Ruike et al., filed Jun. 22, 2018
U.S. Appl. No. 15/976,288, Igawa et al., filed May 10, 2018.
Barrabes et al., "Effect of sialic acid content on glycoprotein p/ analyzed by two-dimensional electrophoresis," Electrophoresis, Sep. 2010, 31(17):2903-2912. doi:10.1002/elps.200900764.
Cruse et al., Atlas of Immunology, CRC Press LLC, 2004, excerpt from Chapter 3, "Antigens and Immunogens," p. 109.
Decision of the EPO Opposition Division for EP 2 006 381, dated Jul. 25, 2018, 17 pages.
Sequence alignments and modification scheme (document filed during Oral Proceedings in EPO opposition for EP 2 006 381 and mentioned in minutes of the Oral Proceedings posted by EPO on Jul. 25, 2018); 3 pages.
Van Den Abbeele et al., "Antigen-Binding Site Protection During Radiolabeling Leads to a Higher Immunoreactive Fraction," Nucl Med, Jan. 1991, 32(1):116-22.
Davie, "A brief historical review of the waterfall/cascade of blood coagulation," J Biol Chem, Dec. 19, 2003, 278(51):50819-32. Epub Oct. 21, 2003.
Decision of the Opposition Division in EP 2 275 443, dated Apr. 26, 2018 (submitted on May 24, 2019, by the Patentee during EPO Opposition Procedure for EP 2 202 245), 29 pages.
Declaration of Taichi Kuramochi (submitted on May 24, 2019 by the Patentee during EPO Opposition Procedure for EP 2 202 245), 11 pages.
Granted claims of EP 2 275 443 (submitted on May 24, 2019 by the Patentee during EPO Opposition Procedure for EP 2 202 245), 1 page.
Supplemental Material to RAPOSO et al., "Epitope-specific antibody response is controlled by immunoglobulin $V_H$ polymorphisms," J Exp Med, Mar. 10, 2012, 211(3):405-11. doi:10.1084/jem. 20130968. Epub Feb. 17, 2013 (submitted on May 24, 2019 by the Patentee during EPO Opposition Procedure for EP 2 202 245), 4 pages.
U.S. Appl. No. 15/963,449, Ruike et al., filed Apr. 26, 2018.
U.S. Appl. No. 13/518,861, Igawa et al., filed Oct. 4, 2012.
U.S. Appl. No. 13/639,415, Igawa et al., filed Feb. 4, 2013.
U.S. Appl. No. 14/007,947, Igawa et al., filed Dec. 30, 2013.
U.S. Appl. No. 16/560,143, Kuramochi et al., filed Sep. 4, 2019.
U.S. Appl. No. 16/536,385, Hattori et al., filed Aug. 9, 2019.
Medesan et al., "Comparative studies of rat IgG to further delineate the Fc:FcRn interactions site," Eur J Immunol, Jul. 1998, 28(7):2092-2100.
U.S. Appl. No. 16/093,495, Saeki et al., filed Oct. 12, 2018.
U.S. Appl. No. 16/115,673, Igawa et al., filed Oct. 9, 2018.
Abe et al., "Novel Protein A Resin: Synthetic Polymer Matrix Design Impact on Antibody Binding Capacity," JSR Technical Review No. 119, 2012, p. 1-5 [online], [retrieved on Feb. 17, 2017], retrieved from the internet: <URL:http://www.jsr.co.jp/pdf/rd/tec119-1.pdf> (with English translation).
Antibodies from www.bioinf.org.uk: Dr. Andrew C.R. Martin's Group, downloaded Jul. 11, 2018, 9 pages.

Chaparro-Riggers et al., "Increasing Serum Half-life and Extending Cholestrol Lowering in Vivo by Engineering Antibody with pH-sensative Binding to PCSK9," J Biol Chem, Mar. 30, 2012, 287(14):11090-7. doi: 10.1074/jbc.M111.319764.Epub Jul. 31, 2012.
Choi et al., "Crystal structures of immunoglobulin Fc heterodimers reveal the molecular basis for heterodimer formation,"Mol Immunol, Jun. 2015, 65(2):377-83. doi: 10.1016/j.molimm.2015.02.017.Epub Mar. 2, 2015.
GE Healthcare Life Sciences, "Dynamic binding capacity study on MabSelect SuRe™ LX for capturing high-titer monoclonal antibodies," Application note 28-9875-25-AA, 2011, [online], [retrieved on Feb. 17, 2017], retrieved from the internet: , http://www.processdevelopmentforum.com/images/articles/28-9875-25_AA_AN_DBC_study_on_MabSelect_SuRe_LX_final.pdf>.
Geneseq Accession No. ARZ17615, Aug. 21, 2008, "Human antibody IgG2 heavy chain constant region SEQ ID No. 36," 1 page.
Goulet et al., "Kinetic mechanism of controlled Fab-arm exchange for the formation of bispecific immunoglobulin G1 antibodies," J Biol Chem, Jan. 12, 2018, 293(2):651-661. doi:10.10174/jbc.RA117. 000303. Epub Nov. 17, 2017.
Okiyama et al. "Therapeutic Side Effects of Interleukin-6 Blockade in a Murine Model of Polymyositis That Does Not Require Interleukin-17A, " Arthritis Rheum, Aug. 2009, 60(8):2505-12.
OriGene Technologies Inc., AP02123SU-N, Polyclonal Antibody to Myostatin (79-92)—Serum, Mar. 19, 2013, https://m1.acris-antibodies.com/pdf/AP02123SU-N.pdf.
Rispens et al., "Mechanisms of Immunoglobulin G4 Fab-arm Exchange, " J Am Chem Soc, Jul. 6, 2011, 133(26):10302-11. doi:10.1021/ ja203638y. Epub Jun. 15, 2011.
Sampei et al., "Non-antigen-contacting region of an asymmetric bispecific antibody to factors IXa/ significantly affects factor VIII-mimetic activity," mAbs, Jan./Feb. 2015, 7(1):120-8. doi: 10.4161/ 19420862.2015.989028.
U.S. Pat. No. 8,062,635, Hattori et al., filed Nov. 22, 2013.
U.S. Appl. No. 12/680,112, Igawa et al., filed Jun. 23, 2010.
U.S. Appl. No. 12/745,781, Kuramochi et al., filed Sep. 13, 2010.
U.S. Appl. No. 13/257,145, Igawa et al., filed Nov. 22, 2011.
U.S. Appl. No. 13/959,489, Igawa et al., filed Aug. 5, 2013.
U.S. Appl. No. 14/680,250, Igawa et al., filed Apr. 7, 2015.
U.S. Appl. No. 14/921,590, Hattori et al., filed Oct. 23, 2015.
U.S. Appl. No. 16/041,976, Igawa et al., filed Jul. 23, 2016.
U.S. Appl. No. 10/575,692, Hattori et al., filed Apr. 30, 2007 (abandoned).
U.S. Appl. No. 15/976,752, Igawa et al., filed May 10, 2018.
U.S. Appl. No. 16/264,735, Igawa et al., filed Feb. 2, 2019.
U.S. Appl. No. 15/172,727, Hattori et al., filed Jun. 3, 2016.
U.S. Appl. No. 15/875,847, Igawa et al., filed Jan. 19, 2018.
U.S. Appl. No. 16/155,673, Igawa et al., filed Oct. 9, 2018 (abandonded).
U.S. Appl. No. 16/448,088, Igawa et al., filed Jan. 21, 2019.
U.S. Appl. No. 15/402,580, Hattori et al., filed Jan. 10, 2017.
U.S. Appl. No. 10/385,122, Ruike et al., filed Aug. 20, 2019.
Actemra (tocilizumab), Highlights of Prescribing Information, as revised in Aug. 2017 (1 page).
Ando et al., "Tocilizumab, a Proposed Therapy for the Cachexia of Interleukin6-Expressing Lung Cancer,"PLOS One, Jul. 10, 2014, 9(7):e102436. doi: 10.1371/journal.pone.0102436. eCollection 2014.
Costa et al., "Efficacy of tocilizumab in a patient with refractory psoriatic arthritis," Clin. Rheumatol., Sep. 2014, 33(9):1355-1357.
Furuya et al., "Interleukin-6 as a Potential Therapeutic Target for Pulmonary Arterial Hypertension," Int. J. Rheumatol., Aug. 2010:720305:1-8. doi: 10.1155/2010/720305. Epub Aug. 2, 2010.
Hashizume et al., "Tocilizumab, a humanized anti-interleukin-6 receptor antibody, improved anemia in monkey arthritis by suppressing IL-6-induced hepcidin production," Rheumatol. Int., May 2010, 30(7):917-923. doi: 10.1007/s00296-009-1075-4. Epub Jul. 29, 2009.
Honda et al., "Marginal zone B cells exacerbate endotoxic shock via interleukin-6 secretion induced by Fcα/mR-coupled TLR4 signalling," Nat. Commun., May 5 2016, 7:11498. doi 10.1038/ ncomms11498.

(56) References Cited

OTHER PUBLICATIONS

Iijima et al., "Tocilizumab improves systemic rheumatoid vasculitis with necrotizing crescentic glomerulonephritis," Mod. Rheumatol., Jan. 2015, 25(1):138-142. doi: 0.3109/14397595.2013.874748. Epub Feb. 18, 2014.
Kishimoto, "Interleukin-6 and its Receptor in Autoimmunity," J. Autoimmun., Apr. 5, 1992 Suppl A:123-132.
Kondo et al., "A case of overlap syndrome successfully treated with tocilizumab: a hopeful treatment strategy for refractory dermatomyositis?," Rheumatology (Oxford), Oct. 2014, 53(10):1907-1908. doi: 10.1093/rheumatology.keu234. Epub May 23, 2014.
Mihara et al., "Anti-interleukin 6 receptor antibody inhibits murine AA-amyloidosis," J. Rheumatol., Jun. 2004, 31(6):1132-8.
Mori et al., "Novel models of cancer-related anemia in mice inoculated with IL-6-producing tumor cells," Biomed. Res. Feb. 2009, 30(1):47-51.
Motozawa et al., "Unique circumfrential peripheral keratitis in relasping polychondritis," Medicine (Baltimore), Oct. 2017, 96(41):e7951. doi: 10.1097/MD.0000000000007951.
Narazaki et al., "Therapeutic effect of tocilizumab on two patients with polymyositis," Rheumatology (Oxford), Jul. 2011, 50(7):1344-1346. doi: 10.1093/rheumatology/ker152. Epub Apr. 2011.
Serada et al., "IL-6 blockade inhibits the introduction of myelin antigen-specific Th17 cells and Th1 cells in experimental autoimmune encephalomyelitis," Proc. Natl. Acad. Sci. USA, Jul. 2008, 105(26):9041-9046. doi:10.1073/pnas.0802218105. Epub Jun. 24, 2008.
Shima et al., "Tocilizumab, a humanized anti-interleukin-6 receptor antibody, ameliorated clinical symptoms and MRI findings of a patient with ankylosing spondylitis," Mod. Rheumatol., Aug. 2011, 21(4):436-439. doi: 10.1007/s10165-011-0416-9. Epub Feb. 9, 2011.
Shimizu et al., "Successful treatment with tocilizumab for refractory scleritis associated with relapsing polychondritis," Scand. J. Rheumatol., Sep. 2017, 46(5):418-419. doi: 10.1080/03009742.2016.1275774. Epub Jan. 25, 2017.
Silpa-Archa et al., "Outcome of tocilizumab treatment in refractory ocular inflammatory diseases," Acta Opthalmol., Sep. 2016, 94(6):e400-406. doi:10.1111/aos.13015.Epub Mar. 24, 2016.
Suzuki et al., "Anti-murine IL-6 receptor antibody inhibits IL-6 effects in vivo," Immunol. Lett., Sep. 1991, 30(1):17-21.
Interleukin 6, Wikipedia, Feb. 22, 2019, XP055598802, (URL:https://protect-us.mimecast.com/s/6UxpCmZ28nsAp18JuGhTki?domain=en.wikipedia.org), retrieved on Jun. 24, 2019, 20 pages.
U.S. Pat. No. 9,670,269, *Igawa et al.*, filed Jun. 6, 2017.
U.S. Appl. No. 14/340,883, *Kuramochi et al.*, filed Jun. 25, 2014 (abandoned).
U.S. Appl. No. 15/064,063, *Igawa et al.*, filed Mar. 23, 2016.
Feige et al., "How antibodies fold," Trends Biochem Sci, Apr. 2010, 35(4):189-98. doi: 10.1016/j.tibs.2009.11.005. Epub Dec. 21, 2009.
Sondermann et al, "The 3.2-A crystal structure of the human IgG1 Fc fragment-FcγRIII complex," Nature, Jul. 20, 2000, 406(6793):267-273.
Yarilin, Fundamentals of Immunology, M.: Medicina, 1999, pp. 181-184.
Declaration of Dr. Anette Henriksen, signed on Apr. 17, 2019 (submitted by the Opponent during EPO opposition procedure for EP 2 006 381), 4 pages.
U.S. Appl. No. 15/230,904, *Igawa et al.*, filed Aug. 8, 2016.
U.S. Appl. No. 15/963,345, *Hattori et al.*, filed Apr. 26, 2017 (abandoned).
U.S. Appl. No. 16/266,798, Hattori et al., filed Dec. 20, 2018.
U.S. Appl. No. 14/340,883, *Kuramochi et al.*, filed Jun. 25, 2014.
U.S. Appl. No. 15/963,345, *Hattori et al.*, filed Apr. 26, 2017.
U.S. Appl. No. 16/266,798, *Hattori et al.*, filed Dec. 20, 2018 (abandoned).
U.S. Appl. No. 16/480,047, *Shinomaya et al.*, filed Jul. 23, 2019.
Devanaboyina et al., "The effect of pH dependence of antibody-antigen interactions on subcellular trafficking dynamics," mAbs, Nov. 1, 2013, 5(6):851-9.
Harvey et al., Lippincott's Illustrated Reviews: Immunology, Second Edition, Chapter 2, "Antigens and Receptors,"pp. 11-23 and Chapter 11, "Lymphocyte Effector Functions,"pp. 141-157 (2013).
Schroter et al., "A generic approach to engineer antibody pH-switches using combinatorial histidine scanning libraries and yeast display,"mAbs, Jan./Feb. 2015, 7(1):138-51. doi:10.4161/9420862. 2014.985993.
U.S. Appl. No. 14/962,293, *Igawa et al.*, filed Dec. 8, 2015.
U.S. Appl. No. 14/974,488, *Ruike et al.*, filed Dec. 18, 2015.
U.S. Appl. No. 15/015,287, *Igawa et al.*, filed Feb. 4, 2016.
U.S. Appl. No. 15/467,654, *Igawa et al.*, filed Mar. 23, 2017.
U.S. Appl. No. 11/910,128, *Igawa et al.*, filed Oct. 7, 2008.
U.S. Appl. No. 12/680,082, *Igawa et al.*, filed Jun. 25, 2010.
U.S. Appl. No. 16/065,192, Ruike et al., filed Jun. 22, 2018.
U.S. Appl. No. 16/448,088, Igawa et al., filed Jun. 21, 2019.
Yada et al., Lippincott's Illustrated Reviews: Immunology Second Edition, Nov. 30, 2013, Chapter 2, pp. 11-23 and Chapter 11, pp. 149-165 (in Japanese, with English equivalent).
Do et al., "A rapid method for determining dynamic binding capacity of resins for the purification of proteins," Protein Expr Purif, Aug. 2008, 60(2):147-150. doi: 10.1016/j.pep.2008.04.009. Epub May 3, 2008.
Pabst et al., "Engineering of novel *Staphylococcal* Protein A ligands to enable milder elution pH and high dynamic binding capacity," J Chromatogr A, Oct. 3, 2014, 1362:180-185. doi: 10.1016/j.chroma. 2014.08.046. Epub Aug. 19, 2014.
Pabst et al., "Evaluation of recent Protein A stationary phase innovations for capture of biotherapeutics,"J Chromatogr A, Jun. 15, 2018, 1554:45-60. doi: 10.1016/j.chroma.2018.03.060. Epub Apr. 7, 2018.
U.S. Appl. No. 15/725,692, *Hattori et al.*, filed Oct. 5, 2017.
U.S. Appl. No. 15/963,221, *Hattori et al.*, filed Apr. 26, 2018.
U.S. Appl. No. 15/963,455, *Ruike et al.*, filed Apr. 26, 2018.
U.S. Appl. No. 12/680,112, *Igawa et al.*, filed Jun. 23, 2010 (abandoned).
U.S. Appl. No. 12/745,781, *Kuramochi et al.*, filed Sep. 13, 2010 (abandoned).
U.S. Appl. No. 13/257,145, *Igawa et al.*, filed Nov. 22, 2011 (abandoned).
U.S. Appl. No. 13/518,861, *Igawa et al.*, filed Oct. 4, 2012 (abandoned).
U.S. Appl. No. 13/637,415, *Igawa et al.*, filed Feb. 4, 2013.
U.S. Appl. No. 13/959,489, *Igawa et al.*, filed Aug. 5, 2013 (abandoned).
U.S. Appl. No. 16/806,027, *Igawa et al.*, filed Mar. 2, 2020.
U.S. Appl. No. 14/340,883, *Kuramochi et al.*, filed Jul. 25, 2014 (abandoned).
U.S. Appl. No. 16/560,143, *Kuramochi et al.*, filed Jul. 25, 2014.
U.S. Appl. No. 14/347,034, *Igawa et al.*, filed Mar. 25, 2014 (abandoned).
U.S. Appl. No. 16/264,735, *Igawa et al.*, filed Feb. 1, 2019.
U.S. Appl. No. 16/838,415, *Igawa et al.*, filed Apr. 2, 2020.
U.S. Appl. No. 16/298,032, *Igawa et al.*, filed Mar. 11, 2019.
U.S. Appl. No. 14/921,590, *Hattori et al.*, filed Oct. 23, 2015 (abandoned).
U.S. Appl. No. 15/024,063, *Igawa et al.*, filed Mar. 23, 2016.
U.S. Appl. No. 15/050,145, *Igawa et al.*, filed Feb. 22, 2016.
U.S. Appl. No. 15/210,353, *Igawa et al.*, filed Jul. 14, 2016.
U.S. Appl. No. 15/210,360, *Igawa et al.*, filed Jul. 14, 2016.
U.S. Appl. No. 15/230,904, *Igawa et al.*, filed Aug. 8, 2016 (abandoned).
U.S. Appl. No. 15/263,617, *Igawa et al.*, filed Sep. 13, 2016 (abandoned).
U.S. Appl. No. 16/041,976, *Igawa et al.*, filed Jul. 23, 2018.
U.S. Appl. No. 15/288,965, *Igawa et al.*, filed Oct. 7, 2016 (abandoned).
U.S. Appl. No. 16/459,791, *Igawa et al.*, filed Jul. 2, 2019.
U.S. Appl. No. 15/402,580, *Hattori et al.*, filed Jan. 10, 2017 (abandoned).
U.S. Appl. No. 15/490,936, *Igawa et al.*, filed Apr. 19, 2017.
U.S. Appl. No. 15/495,026, *Igawa et al.*, filed Apr. 24, 2017.
U.S. Appl. No. 15/544,930, *Murata et al.*, filed Jul. 20, 2017.
U.S. Appl. No. 16/983,115, *Kakehi et al.*, filed Aug. 3, 2020.

(56) References Cited

OTHER PUBLICATIONS

U.S. Appl. No. 15/562,186, Igawa et al., filed Sep. 27, 2017.
U.S. Appl. No. 15/614,842, Igawa et al., filed Jun. 6, 2017.
U.S. Appl. No. 15/617,008, Igawa et al., filed Jun. 8, 2017 (abandoned).
U.S. Appl. No. 15/701,630, Hattori et al., filed Sep. 12, 2017 (abandoned).
U.S. Appl. No. 15/963,345, Hattori et al., filed Apr. 26, 2018 (abandoned).
U.S. Appl. No. 16/226,798, Hattori et al., filed Dec. 20, 2018 (abandoned).
U.S. Appl. No. 16/536,385, Hattori et al., filed Aug. 9, 2019 (abandoned).
U.S. Appl. No. 16/825,513, Hattori et al., filed Mar. 20, 2020.
U.S. Appl. No. 15/725,692, Igawa et al., filed Oct. 5, 2017.
U.S. Appl. No. 10/575,905, Hattori et al., filed Apr. 30, 2007 (abandoned).
U.S. Appl. No. 15/782,256, Igawa et al., filed Oct. 12, 2017.
U.S. Appl. No. 11/910,836, Hattori et al., filed Jan. 12, 2009 (abandoned).
U.S. Appl. No. 13/434,643, Hattori et al., filed Mar. 29, 2012 (abandoned).
U.S. Appl. No. 13/524,528, Igawa et al., filed Jun. 15, 2012 (abandoned).
U.S. Appl. No. 14/019,117, Igawa et al., filed Sep. 5, 2013 (abandoned).
U.S. Appl. No. 14/019,712, Igawa et al., filed Sep. 6, 2013 (abandoned).
U.S. Appl. No. 16/083,975, Kinoshita et al., filed Sep. 11, 2018.
U.S. Appl. No. 16/323,142, Kakiuchi et al., filed Feb. 4, 2019.
U.S. Appl. No. 16/514,467, Ruike et al., filed Jul. 19, 2019.
U.S. Appl. No. 16/480,047, Shinomiya et al., filed Jul. 23, 2019.
U.S. Appl. No. 16/928,129, Shinomiya et al., filed Jul. 14, 2020.
U.S. Appl. No. 16/889,066, Ruike et al., filed Jun. 1, 2020.
U.S. Appl. No. 16/697,310, Igawa et al., filed Nov. 27, 2019.
U.S. Appl. No. 16/496,089, Shima et al., filed Sep. 20, 2019.
U.S. Appl. No. 16/815,089, Igawa et al., filed Mar. 11, 2020.
Adlersberg et al., "The Immunoglobulin Hinge (Interdomain) Region," Ric Clin Lab, Jul.-Sep. 1976, 6(3): 191-205.
Aleshin et al., "Crystal Structure of C5b-6 Suggests Structural Basis for Priming Assembly of the Membrane Attack Complex," J Biol Chem, Jun. 1, 2012, 287(23):19642-19652. doi: 10.1074/jbc.M112.361121. Epub Apr. 12, 2012.
Alprolix® Intravenous, May 2019 revised ($9^{th}$ edition) (with English translation).
Altshuler et al., "Production of Recombinant Antibodies and Methods for Increasing Their Affinity," Progress of Biological Chemistry, 2010, 50:207 (with English translation).
Annotated amino acid sequence of the variable heavy (VH) and variable light (VL) domains of the monoclonal antibodies bevacizumab/Avastin, adalimumab/Humira, omalizumab/Xolair, and rituximab/Mabthera, dated Jul. 2019, 10 pages (submitted to the EPO with the written submissions to attend oral proceedings on Sep. 6, 2019 by Opponent 1 in EP 11714860.1).
Arici, "Local Cytokines and Endometrial Tissue: The Role of Interleukin-8 in the Pathogenesis of Endometriosis," Ann NY Acad Sci, Mar. 2002, 955:101-109; discussion 118, pp. 396-406.
Astermark et al., "A randomized comparison of bypassing agents in hemophilia complicated by an inhibitor: the FEIBA A NovoSeven Comparative (FENOC) Study," Blood, Jan. 15, 2007, 109(2):546-551. Epub Sep. 21, 2006.
Bork, "Powers and Pitfalls in Sequence Analysis: The 70% Hurdle," Genome Res, Apr. 2000, 10(4):398-400.
Buckler, vol. 4 "Molecular Medicine and Medicinal Chemistry," Section 2.4 "Library Selection," Antibody Drug Discovery, edited by Clive Wood, 2012, pp. 49-57.
Chattopadhyay et al., "Interleukin-31 and Oncostatin-M Mediate Distinct Signaling Reactions and Response Patterns in Lung Epithelial Cells," J Biol Chem, Feb. 2, 2007, 282(5):3014-3026. doi:10.1074/jbc.M609655200.

Chugai NMO Clinical Trial Webinar, Sakura Star Study, dated Dec. 12, 2014, downloaded on Sep. 5, 2019 from hhttps://s3.amazonaws.com/gicf-wp-uploads/wp-content/uploads/2016/05/16162202/12_12_14_Chugai_Webinar_PPT_Complete_Deck_FINAL.pdf, 18 pages.
Chugai Pharmaceutical, A phase I, multiple dose study of SA237, Study JapicCTI-No. 121786; submitted to Clinicaltrials.jp on Jan. 31, 2014; downloaded from clinicaltrials.jp archive on Sep. 5, 2019 as https://www.clincaltrials.jp/cti-user/trial/Show.jsp, 5 pages.
Chugai Pharmaceutical, A phase I, multiple dose study of SA237, Study JapicCTI-No. 121786; submitted to Clinicaltrials.jp on Mar. 19, 2012; downloaded from clinicaltrials.jp archive on Sep. 5, 2019 as https://www.clincaltrials.jp/cti-user/trial/Show.jsp, 5 pages.
Chugai Pharmaceutical, A phase I, multiple dose study of SA237, Study JapicCTI-No. 121786; submitted to Clinicaltrials.jp on Jun. 19, 2012; downloaded from clinicaltrials.jp archive on Sep. 5, 2019 as https://clincaltrials.jp/cti-user/trial/Show.jsp, 5 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 1; submitted to ClinicalTrials.gov on Jan. 6, 2014; downloaded from ClinicalTrials.gov archive on Sep. 4, 2019 as https://clincaltrials.gov/ct2/history/NCT02028884?V_1=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 2; submitted to ClinicalTrials.gov on Feb. 25, 2014; downloaded from ClinicalTrials.gov archive on Sep. 4, 2019 as https://clincaltrials.gov/ct2/history/NCT02028884?V_2=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 3; submitted to ClinicalTrials.gov on Sep. 4, 2015; downloaded from clinicalTrials.gov archive on Sep. 4, 2019 as https://clincaltrials.gov/ct2/history/NCT02028884?V_3=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 4; submitted to ClinicalTrials.gov on Dec. 8, 2015; downloaded from ClinicalTrials.gov archive on Sep. 4, 2019 as https://clincaltrials.gov/ct2/history/NCT02028884?V_4=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Spectrum Disorder (NMOSD), Study NCT02073279, version 1; submitted to ClinicalTrials.gov on Feb. 25, 2014; downloaded from ClinicalTrials.gov archive on Sep. 4, 2019 as https://clincaltrials.gov/ct2/history/NCT02073279?V_1=View#StudyPageTop, 6 pages.
Chugai Pharmaceutical, Efficacy and Safety Study of Satralizumab (SA237) as Monotherapy to Treat Participants With Neuromyelitis Optica (NMO) andNeuromyelitis Optica Spectrum Disorder (NMOSD), Study NCT02073279, version 10; submitted to ClinicalTrials.gov on Jul. 7, 2015; downloaded from ClinicalTrials.gov archive on Sep. 5, 2019 as https://clincaltrials.gov/ct2/history/NCT02073279?V_10=View#StudyPageTop, 9 pages.
Chugai Pharmaceutical, Efficacy and Safety Study of Satralizumab (SA237) as Monotherapy to Treat Participants With Neuromyelitis Optica (NMO) andNeuromyelitis Optica Spectrum Disorder (NMOSD), Study NCT02073279, version 11; submitted to ClinicalTrials.gov on Aug. 3, 2015; downloaded from ClinicalTrials.gov archive on Sep. 5, 2019 as https://clincaltrials.gov/ct2/history/NCT02073279?V_11=View#StudyPageTop, 10 pages.
Chugai Pharmaceutical, Efficacy and Safety Study of Satralizumab (SA237) as Monotherapy to Treat Participants With Neuromyelitis Optica (NMO) andNeuromyelitis Optica Spectrum Disorder (NMOSD), Study NCT02073279, version 12; submitted to ClinicalTrials.gov on Sep. 3, 2015; downloaded from ClinicalTrials.gov archive on Sep. 5, 2019 as https://clincaltrials.gov/ct2/history/NCT02073279?V_12=View#StudyPageTop, 10 pages.

(56) References Cited

OTHER PUBLICATIONS

Chugai Pharmaceutical, Efficacy and Safety Study of Satralizumab (SA237) as Monotherapy to Treat Participants With Neuromyelitis Optica (NMO) andNeuromyelitis Optica Spectrum Disorder (NMOSD), Study NCT02073279, version 13; submitted to ClinicalTrials.gov on Oct. 5, 2015; downloaded from ClinicalTrials.gov archive on Sep. 5, 2019 as https://clincaltrials.gov/ct2/history/NCT02073279?V_13=View#StudyPageTop, 10 pages.
Chugai Pharmaceutical, Efficacy and Safety Study of Satralizumab (SA237) as Monotherapy to Treat Participants With Neuromyelitis Optica (NMO) andNeuromyelitis Optica Spectrum Disorder (NMOSD), Study NCT02073279, version 14; submitted to ClinicalTrials.gov on Dec. 8, 2015; downloaded from ClinicalTrials.gov archive on Sep. 5, 2019 as https://clincaltrials.gov/ct2/history/NCT02073279?V_14=View#StudyPageTop, 10 pages.
Chugai Pharmaceutical, Efficacy and Safety Study of Satralizumab (SA237) as Monotherapy to Treat Participants With Neuromyelitis Optica (NMO) andNeuromyelitis Optica Spectrum Disorder (NMOSD), Study NCT02073279, version 2; submitted to ClinicalTrials.gov on Jul. 22, 2014; downloaded from ClinicalTrials.gov archive on Sep. 5, 2019 as https://clincaltrials.gov/ct2/history/NCT02073279?V_2=View#StudyPageTop, 6 pages.
Chugai Pharmaceutical, Efficacy and Safety Study of Satralizumab (SA237) as Monotherapy to Treat Participants With Neuromyelitis Optica (NMO) andNeuromyelitis Optica Spectrum Disorder (NMOSD), Study NCT02073279, version 3; submitted to ClinicalTrials.gov on Dec. 15, 2014; downloaded from ClinicalTrials.gov archive on Sep. 5, 2019 as https://clincaltrials.gov/ct2/history/NCT02073279?V_3=View#StudyPageTop, 6 pages.
Chugai Pharmaceutical, Efficacy and Safety Study of Satralizumab (SA237) as Monotherapy to Treat Participants With Neuromyelitis Optica (NMO) andNeuromyelitis Optica Spectrum Disorder (NMOSD), Study NCT02073279, version 4; submitted to ClinicalTrials.gov on Feb. 5, 2015; downloaded from ClinicalTrials.gov archive on Sep. 5, 2019 as https://clincaltrials.gov/ct2/history/NCT02073279?V_4=View#StudyPageTop, 6 pages.
Chugai Pharmaceutical, Efficacy and Safety Study of Satralizumab (SA237) as Monotherapy to Treat Participants With Neuromyelitis Optica (NMO) andNeuromyelitis Optica Spectrum Disorder (NMOSD), Study NCT02073279, version 5; submitted to ClinicalTrials.gov on Feb. 6, 2015; downloaded from ClinicalTrials.gov archive on Sep. 5, 2019 as https://clincaltrials.gov/ct2/history/NCT02073279?V_5=View#StudyPageTop, 6 pages.
Chugai Pharmaceutical, Efficacy and Safety Study of Satralizumab (SA237) as Monotherapy to Treat Participants With Neuromyelitis Optica (NMO) andNeuromyelitis Optica Spectrum Disorder (NMOSD), Study NCT02073279, version 6; submitted to ClinicalTrials.gov on Mar. 4, 2015; downloaded from ClinicalTrials.gov archive on Sep. 5, 2019 as https://clincaltrials.gov/ct2/history/NCT02073279?V_6=View#StudyPageTop, 9 pages.
Chugai Pharmaceutical, Efficacy and Safety Study of Satralizumab (SA237) as Monotherapy to Treat Participants With Neuromyelitis Optica (NMO) andNeuromyelitis Optica Spectrum Disorder (NMOSD), Study NCT02073279, version 7; submitted to ClinicalTrials.gov on Apr. 1, 2015; downloaded from ClinicalTrials.gov archive on Sep. 5, 2019 as https://clincaltrials.gov/ct2/history/NCT02073279?V_7=View#StudyPageTop, 9 pages.
Chugai Pharmaceutical, Efficacy and Safety Study of Satralizumab (SA237) as Monotherapy to Treat Participants With Neuromyelitis Optica (NMO) andNeuromyelitis Optica Spectrum Disorder (NMOSD), Study NCT02073279, version 8; submitted to ClinicalTrials.gov on May. 7, 2015; downloaded from ClinicalTrials.gov archive on Sep. 5, 2019 as https://clincaltrials.gov/ct2/history/NCT02073279?V_8=View#StudyPageTop, 9 pages.
Chugai Pharmaceutical, Efficacy and Safety Study of Satralizumab (SA237) as Monotherapy to Treat Participants With Neuromyelitis Optica (NMO) andNeuromyelitis Optica Spectrum Disorder (NMOSD), Study NCT02073279, version 9; submitted to ClinicalTrials.gov on Jun. 5, 2015; downloaded from ClinicalTrials.gov archive on Sep. 5, 2019 as https://clincaltrials.gov/ct2/history/NCT02073279?V_9=View#StudyPageTop, 9 pages.

Coico et al., Chapter 4 "Antibody Structure and Function," Immunology: Manual, M.: Publishing Center Academy, 2008, pp. 61-62 (with English translation).
Collins et al., "Implications of coagulation factor VIII and IX pharmaco-kinetics in the prophylactic treatment of haemophilia," Haemophilia, Jan. 20011, 17(1):2-10. doi: 10.1111/j.1365-2516.2010.02370.x. Epub Aug. 22, 2010.
Coppola et al., "Acquired Inhibitors of Coagulation Factors: Part I—Acquired Hemophilia A," Semin Thromb Hemost, Jul. 2012, 38(5):433-446. doi: 10.1055/s-0032-1315757. Epub Jun. 27, 2012.
D'Angelo et al., "Many Routes to an Antibody Heavy-Chain CDR3: Necessary, Yet Insufficient, for Specific Binding," Front Immunol, Mar. 8, 2018, 9:395. doi: 10.3389/fimmu.2018.00395.
Decision of the Opposition Division, dated Dec. 19, 2019, in EP 2 552 955, 18 pages (document submitted by Patentee (Chugai Seiyaku Kabushiki Kaisha) in the grounds of appeal on Apr. 28, 2020 in EP 2 552 955).
Edwards et al., "The Remarkable Flexibility of the Human Antibody Repertoire; Isolation of Over One Thousand Different Antibodies to a Single Protein, BLyS," J Mol Biol, Nov. 14 2003, 334(1):103-108.
Evidence for the publication date of Zalevsky et al., Nat Biotechnol, Feb. 2010, 28(2):157-9, 1 page (submitted to the EPO with the written submission to attend oral proceedings on Sep. 6, 2019 by Opponent 1 in EP 11714860.1).
Expert Declaration of J. Boucneau, dated Sep. 6, 2019, 13 pages (submitted to the EPO with the written submission to attend oral proceedings on Sep. 6, 2019 by Opponent 1 in EP 11714860.1).
F. Hoffman-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Germany; submitted to clinicaltrialsregister.eu on Dec. 20, 2013; downloaded from clinicaltrialsregister.eu archive on Sep. 5, 2019 ashttps://www.clincaltrialsregister.eu/ctr-search/trial/2013-003752-21/DE, 7 pages.
F. Hoffman-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Hungary; submitted to clinicaltrialsregister.eu on Feb. 25, 2015; downloaded from clinicaltrialsregister.eu archive on Sep. 5, 2019 ashttps://www.clincaltrialsregister.eu/ctr-search/trial/2013-003752-21/HU, 6 pages.
F. Hoffman-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Italy; submitted to clinicaltrialsregister.eu on Feb. 5, 2014; downloaded from clinicaltrialsregister.eu archive on Sep. 5, 2019 ashttps://www.clincaltrialsregister.eu/ctr-search/trial/2013-003752-21/IT, 5 pages.
F. Hoffman-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Poland; submitted to clinicaltrialsregister.eu on Oct. 15, 2013; downloaded from clinicaltrialsregister.eu archive on Sep. 5, 2019 ashttps://www.clincaltrialsregister.eu/ctr-search/trial/2013-003752-21/PL, 7 pages.
F. Hoffman-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Spain; submitted to clinicaltrialsregister.eu on Mar. 11, 2015; downloaded from clinicaltrialsregister.eu archive on Sep. 5, 2019 ashttps://www.clincaltrialsregister.eu/ctr-search/trial/2013-003752-21/ES, 7 pages.
F. Hoffman-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in the United Kingdom; submitted to clinicaltrialsregister.eu on Oct. 15, 2013; downloaded from clinicaltrialsregister.eu archive on Sep. 5, 2019 ashttps://www.clincaltrialsregister.eu/ctr-search/trial/2013-003752-21/GB, 6 pages.

(56) References Cited

OTHER PUBLICATIONS

F. Hoffman-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2015-005431-41 in Croatia; submitted to clinicaltrialsregister.eu on Dec. 15, 2016; downloaded from clinicaltrialsregister.eu archive on Sep. 5, 2019 ashttps://www.clincaltrialsregister.eu/ctr-search/trial/2013-003752-21/HR, 7 pages.
F. Hoffman-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2015-005431-41 in Poland; submitted to clinicaltrialsregister.eu on Oct. 15, 2013; downloaded from clinicaltrialsregister.eu archive on Sep. 5, 2019 ashttps://www.clincaltrialsregister.eu/ctr-search/trial/2013-003752-21/PL, 6 pages.
Feng et al., "Glypican-3 antibodies: A new therapeutic target for liver cancer," FEBS Lett, Jan. 21, 2014, 588(2):377-382. doi: 10.1016/j.febslet.2013.10.002. Epub Oct. 15, 2013.
Filmus et al., "Protein family review," Genome Biol, May 22, 2008, 9(5):224, 6 pages. doi:10.1186/gb-2008-9-5-224.
Franchini et al., "Acquired haemophilia A: A 2013 update," Thromb Haemost, Dec. 2013, 110(6):1114-1120. doi:10.1160/TH13-05-0363. Epub Sep. 5, 2013.
GenBank Accession No. AAA51925.1 (complement component C5 [Homo sapiens], Oct. 31, 1994, 3 pages.
Goel et al., "Plasticity within the Antigen-Combining Site May Manifest as Molecular Mimicry in the Humoral Immune Response ," J Immnunol, Dec. 15, 2004, 173(12):7358-7367.
Gonzalez et al., "BMP-1.Tolloid-like Metalloproteases Process Endorepellin, the Angiostatic C-terminal Fragment of Perlecan," J Biol Chem, Feb. 25, 2005, 280(8):7080-7087. Epub Dec, 9, 2004.
Guidelines for the Management of Hemophilia, World Federation of Hemophilia, 2005, 52 pages.
"Hemostatic Therapy Guideline for Inhibitor-negative Hemophilia Patients," Japanese Journal of Thrombosis and Hemostasis, 2013, 24(6):619-639 (with English translation).
"Hemostatic Therapy Guideline for Inhibitor-positive Hemophilia Patients," Japanese Journal of Thrombosis and Hemostasis, 2013, 24(6):640-658 (with English translation).
Igawa et al., "Engineered Monoclonal Antibody with Novel Antigen-Sweeping Activity In Vivo," PLoS One, May 7, 2013, 8(5):e63236. doi: 10.1371/journal.pone.0063236. Print 2013.
Igawa et al., "Sweeping antibody as a novel therapeutic antibody modality capable of eliminating soluble antigens from circulation," Immunol Rev. Mar. 2016, 270(1):132-151.
Ishii et al., "Molecular design of anitbody drugs," Journal of Pharmaceutical Science and Technology, Japan, 2014, 74(1)4-11 (with English translation).
Kanyavuz et al., "Breaking the law: unconventional strategies for antibody diversification," Nat Rev Immunol, Jun. 2019, 19(6):355-368. doi: 10.1038/s41577-019-0126-7.
Kipriyanov et al., "Generation of Recombinant Antibodies," Mol Biotechnol, Sep. 1999, 12(2):173-201.
Kruse-Jarres, "Inhibitors: our greatest challenge. Can we minimize the incidence?," Haemophilia, Jan. 2013, 10 Suppl 1:2-7. doi: 10.1111/hae.12049.
Labrijn et al., "Therapeutic IgG4 antibodies engage in Fab-arm exchange with endogenous human IgG4 in vivo," Nat Biotechnol, Aug. 2009, 27(8):767-771.
Lillicrap, "von Willebrand disease: advances in pathogenetic understanding, diagnosis, and therapy," Blood, Nov. 28, 2013, 122(23):3735-3740. doi: 10.1182/blood-2013-06-498303. Epub Sep. 24, 2013
Llyod et al., "Modelling the human immune response: performance of a $10^{11}$ human antibody repertoire against a broad panel of therapeutically relevant antigens," Protein Eng Des Sel, Mar. 2009, 22(3):159-168. doi: 10.1093/protein/gzn058. Epub Oct. 29, 2008.
Lund et al., "Multiple interactions of IgG with its core oligosaccharide can modulate recognition by complement and human Fc gamma receptor I and influence the synthesis of its oligosaccharide chains," The Journal of Immunology, Dec. 1, 1996, 157(11):4963-4969.
Marri et al., Chapter 4, Human Biochemistry, Moscow, Mir, 1993, 1:34 (with English translation).
Minami et al., "Bispecific Antibody ACE910 Improves Coagulation Function in Plasma of Patients with Factor XI Deficiency, " Japanese Journal of Thrombosis and Haemostasis, 2015, 26(2):188 0-024 (with English translation).
Miyata, "Factor IX Abnormality—Molecular Defects of Factor IX," Japanese Journal of Thrombosis and Hemostasis, 1991, 2(1):1-11 (with English translation).
Muramatsu, "Latent myosatin specific elimination by sweeping antibody® is a novel therapeutic approach to improve muscle strength," Neuromuscular Disorders, Oct. 1, 2019, 29(Supplement 1):S86.
Muto et al., "Anti-factor IXa/X bispecific antibody (ACE910): homostatic potency against ongoing bleeds in a hemophilia A model and the possibilty of routine supplementation," J Thromb Haemost, Feb. 2014, 12(2):206-213. doi: 10.1111/jth.12474.
Muto et al., "Anti-factor IXa/X bispecific antibody ACE910 prevents joint bleeds in a long-term primate model of acquired hemophilia A," Blood, Nov. 13, 2014, 124(20):3165-3171. doi: 10.1182/blood-2014-07-585737. Epub Oct. 1, 2014.
Nishimura etactor IX Fukuoka—Substitution of $ASN^{92}$ by His in the second epidermal growth factor-like domain results in defective interaction with factors VIIIa/X, Journal of Biological Chemistry, 1993, 268(32):24041-24046.
Nogami, "Bispecific Antibody that Substitutes for Factor VIII in the Treatment of Childhood Hemophilia A," The Japanese Journal of Pediatric Hematology/Oncology, 2016, 53:(2):69-74 (with English translation).
Ogiwara et al., "Effect of Emicizumab in improving coagulation ability in the presense of minor amount of Factor IX," Japanese Journal of Thrombosis and Hemostasis, 2017, 28(2):190 0-012.
Piche-Nicholas et al., "Changes in complementary-determining regions significantly alter IgG binding to the neonatal Fc receptor (FcRn) and pharmacokinetics," mAbs, 2018, 10(1):81-94. doi:10.1080/19420862.2017.1389355.
Pirruccello-Straub, "Blocking extracellular activation of myostatin as a strategy for treating muscle wasting," Scientific Reports, Feb. 2, 2018, vol. 8, Article No. 2292.
Proprietor's (Chugai Seiyaku Kabushiki Kaisha) Submission dated Sep. 5, 2016 in EP 11714860.1, 6 pages (submitted to the EPO with the written submission to attend oral proceedings on Sep. 6, 2019 by Opponent 1 in EP 11714860.1).
Proprietor's (Chugai Seiyaku Kabushiki Kaisha) Submission dated Sep. 19, 2016 in EP 11714860.1, 3 pages (submitted to the EPO with the written submission to attend oral proceedings on Sep. 6, 2019 by Opponent 1 in EP 11714860.1).
Proprietor's (Chugai Seiyaku Kabushiki Kaisha) Submission dated Feb. 20, 2017 in EP 2 275 443, 35 pages (submitted to the EPO with the written submission to attend oral proceedings on Sep. 6, 2019 by Opponent 1 in EP 11714860.1).
Rich et al., A global benchmark study using affinity-based biosensors, Anal Biochem, Mar. 15, 2009, 386(2):194-216. doi: 10.1016/j.ab.2008.11.021. Epub Nov. 27, 2008.
Shima et al., "Factor VIII-Mimetic Function of Humanized Bispecific Antibody in Hemophilia A," The New England Journal of Medicine, May 2016, 37(21):2044-2053. doi: 10.1056/NEJMoa1511769.
Shima, "The Forfront and Prospects of Hemophilia Treatment," The Journal of the Japan Pediatric Society, Mar. 1, 2017, 121(3):543-552 (with English translation).
Shirakawa et al,. "Glypican-3 is a useful diagnostic marker for a component of hepatocellular carcinoma in human liver cancer," Int J Oncol, Mar. 2009, 34(3):649-656.
Sigma product information for ACES buffer, 1 page (submitted to the EPO with the written submission to attend oral proceedings on Sep. 6, 2019 by Opponent 1 in EP 11714860.1).

(56) References Cited

OTHER PUBLICATIONS

Singer et al., "The Genetic Molecules," Genes & Genomes, 1998, 1:63-64 (with what are believed to be the corresponding pages from an English version of Genes & Genomes).

Table summarizing alleged lack of novelty over WO 2009/086320, dated Jul. 9, 2009, 4 pages (submitted to the EPO with the written submission to attend oral proceedings on Sep. 6, 2019 by Opponent 1 in EP 11714860.1).

Tarantino et al., "Safety of human plasma-derived clotting factor products and their role in haemostasis in patients with haemophilia: meeting report," Haemophilia, Sep. 2007, 13(5):663-669.

Tarantul et al., "Antibodies," Explanatory Biotechnological Dictionary, Moscow, 2009, p. 72 (with English translation).

Uchida et al., "A first-in-human phase 1 study of ACE910, a novel factor VIII-mimetic bispecific antibody, in healthy subjects," Blood, Mar. 2016, 127(13):1633-1641. doi: 10.1182/blood-2015-06-650226. Epub Dec. 1, 2015.

Wang et al., "Complement C5a, C5a receptor and their antagonist: research advances," J Int Pharm Res, 2010, 37(3):181-186 (with English Translation).

Watts et al., "Gene silencing by siRNAs and antisense oligonucleotides in the laboratory and the clinic," J Pathol, Jan. 2012, 226(2):365-379. doi: 10.1002/path.2993.

Wenig et al., "Structure of the *streptococcal endopeptidase* IdeS, a cysteine proteinase with strict specificity for IgG," Proc Nat Acad Sci USA, Dec. 23, 2003, 101(50):17371-17376.

Wolfman et al., "Activation of latent myosatin by the BMP-1/tolloid family of metalloproteinases," Proc Natl Acad Sci USA, Dec. 23, 2003, 100(26):15842-15846. Epub Dec. 11, 2003.

Yang et al., "Comparison of biosensor platforms in the evaluation of high affinity antibody-antigen binding kinetics," Anal Biochem, Sep. 1, 2016, 508:78-96. doi: 10.1016/j.ab.2016.06.024. Epub Jun. 27, 2016.

\* cited by examiner

| SAMPLE | pI |
|---|---|
| hB26-PF | 9.2 |
| hB26-p15 | 9.0 |
| BiAb | 8.7 |
| hB26-F123e4 | 8.7 |
| hA69-N97R | 8.9 |
| hA69-p18 | 8.5 |
| hA69-PF | 8.0 |
| ATF | 7.2 |

FIG. 5
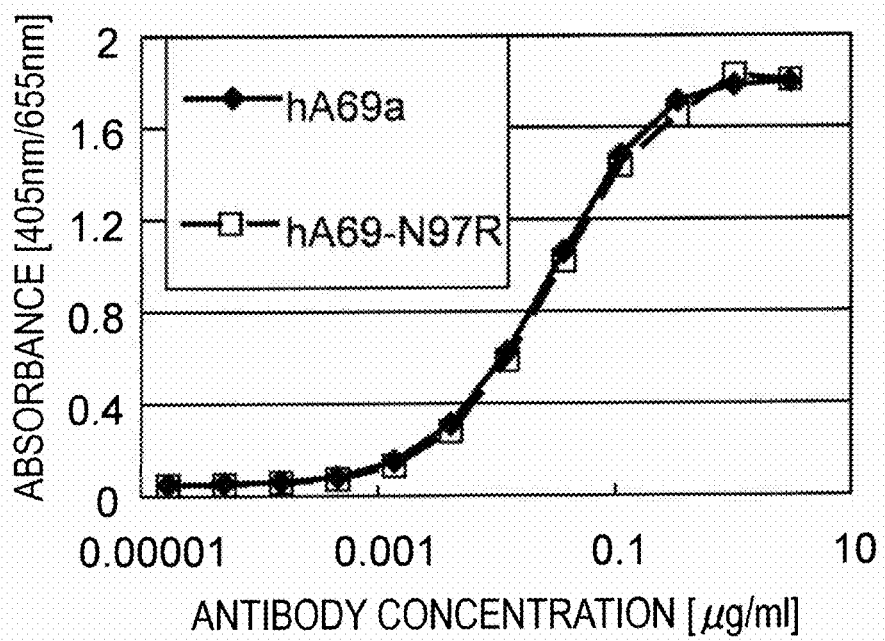
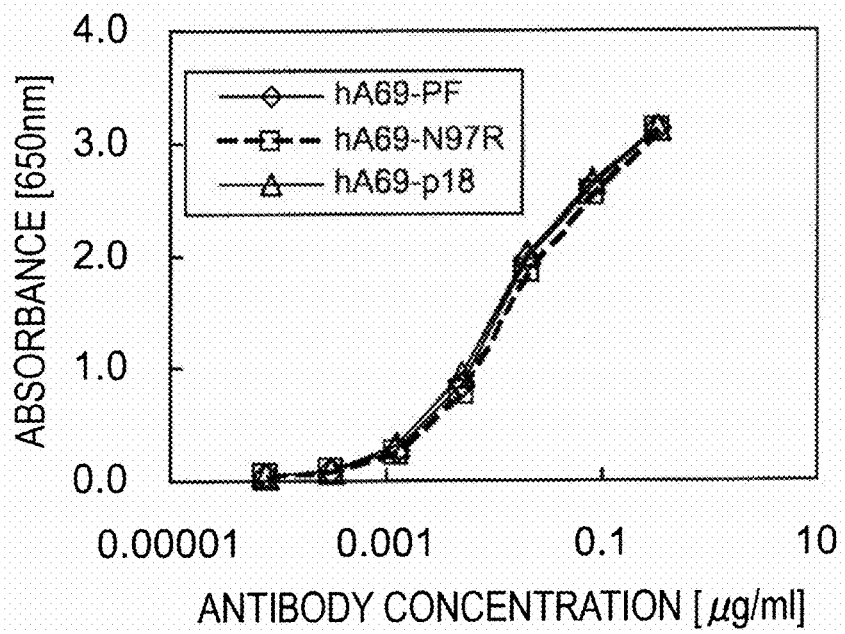

METHODS FOR CONTROLLING BLOOD PHARMACOKINETICS OF ANTIBODIES

CROSS-REFERENCE TO RELATED APPLICATIONS

This application is the National Stage of International Application Serial No. PCT/JP2007/057036, filed on Mar. 30, 2007, which claims the benefit of Japanese Application Serial No. 2006-097796, filed on Mar. 31, 2006. The contents of the foregoing applications are hereby incorporated by reference in their entirety.

TECHNICAL FIELD

The present invention relates to methods for modifying antibodies to control pharmacokinetics of the antibodies in blood, pharmaceutical compositions comprising as an active ingredient an antibody whose pharmacokinetics in blood is controlled, and methods for producing the same.

BACKGROUND ART

Since antibodies are highly stable in blood and have few adverse effects, they have drawn much attention as pharmaceuticals. There are a number of IgG type antibody pharmaceuticals available on the market and many such are currently under development (Non-patent Documents 1 and 2). Technologies for enhancing the effector function and such have been developed to produce second-generation antibody pharmaceuticals. For example, known are technologies for enhancing antibody-dependent cell-mediated cytotoxicity (ADCC) or complement-dependent cytotoxicity (CDC) through amino acid substitutions in the Fc domain of an IgG antibody (Non-patent Document 3). In addition to such amino acid substitutions that result in enhancement of the effector function, there are reports on other amino acid substitutions in the Fc domain, which prolong antibody half-life in blood (Non-patent Documents 4 and 5). Prolonging the antibody half-life in blood enables administration of antibody pharmaceuticals at reduced doses or at longer intervals and thereby results in providing low-cost, highly advantageous antibody pharmaceuticals. Specifically, the half-life in blood can be prolonged by modifying the Fc domain through amino acid substitutions that increase the affinity for the neonatal Fc receptor known as the IgG salvage receptor. Alternatively, the half-life in blood can be prolonged by shuffling the constant region CH1, CH2, and CH3 domains (Non-patent Document 6). However, the amino acid sequences of constant regions of an IgG antibody are conserved in humans, and therefore it is best to keep the number of artificial amino acid substitutions in the constant regions to a minimum from the viewpoint of antigenicity.

Reported techniques for substituting amino acids in IgG antibody variable regions include not only humanization (Non-patent Document 7) but also affinity maturation to enhance binding activity using amino acid substitutions in complementarity determining regions (CDRs) (Non-patent Document 8) and improvement of physicochemical stability through amino acid substitutions in frameworks (FRs) (Non-patent Document 9). Thus, unlike in constant regions, amino acid substitution in variable regions is a general technique for improving function and properties of an antibody. Since the CDR amino acid sequences of a humanized antibody are derived from a nonhuman animal, the risk of antigenicity need not be regarded as a problem. Alternatively, if the FR sequence is the same as that of a human antibody publicly disclosed in the Kabat Database (http://ftp.ebi.ac.uk/pub/databases/kabat/) or the IMGT Database (http://imgt.cines.fr/), the antigenicity risk is thought to be low. However, only the above-described amino acid substitutions in the constant region Fc are so far available as methods for improving the half-life of IgG antibodies in blood. There is no report on a method for improving the half-life of IgG antibody in blood using amino acid substitution in a variable region where the risk of antigenicity is lower. The reason is that it was considered that half-life of IgG in blood strongly depends on its binding to the neonatal Fc receptor, the salvage receptor, and antigen-dependent IgG elimination (Non-patent Document 10), and variable regions have no significant influence on this half-life in blood. Meanwhile, the isoelectric point (pI) of IgG is decreased when IgG is anionized through succination (Non-patent Document 11), or the pI of IgG is increased when the antibody is cationized through modification using a polyamine (Non-patent Document 12). However, in both cases, the half-life in blood is shortened rather than prolonged. Thus, improvement of the half-life in blood has not been achieved by changing the pI through modification.

Meanwhile, the half-life of minibodies (low molecular weight antibodies) such as Fab and scFv is shorter than that of IgG, which is a whole antibody. Therefore, the half-life of minibodies in blood can be prolonged by modification using a polymer such as polyethylene glycol to reduce its renal excretion (Non-patent Document 13). In addition to the modification with a polymer, a shift of the isoelectric point (pI) has also been reported to modify the pharmacokinetics of minibodies in blood. For example, Non-patent Document 14 described that modification of anti-Tac Fab with an organic acid decreased its pI, resulting in improvement of AUC (Area Under Curve). In contrast, Non-patent Documents 15 and 16 described that modification of anti-Tac dsFv with an organic acid decreased its pI, resulting in reduction of AUC. Non-patent Document 17 demonstrated that the half-life (t1/2) and AUC of anti-Tac-scFv toxin were reduced when its pI was decreased by modifying its variable regions through amino acid substitutions. Non-patent Document 18 describes that there was almost no change in the AUC of an scFv when its pI was decreased by adding amino acids to the C terminus. Thus, the AUC of a minibody may be increased or decreased when its pI is decreased by modification or amino acid substitution. Accordingly, the half-life of minibodies in blood cannot be exactly controlled as intended by shifting the pI.

[Non-patent Document 1] Monoclonal antibody successes in the clinic, Janice M Reichert, Clark J Rosensweig, Laura B Faden & Matthew C Dewitz, Nature Biotechnology 2005;23: 1073-1078

[Non-patent Document 2] Pavlou A K, Belsey M J., The therapeutic antibodies market to 2008, Eur J Pharm Biopharm. 2005 April;59(3):389-96.

[Non-patent Document 3] Kim S J, Park Y, Hong H J., Antibody engineering for the development of therapeutic antibodies, Mol Cells. Aug. 31, 2005;20(1):17-29. Review.

[Non-patent Document 4] Hinton P R, Xiong J M, Johlfs M G, Tang M T, Keller S, Tsurushita N., An engineered human IgG1 antibody with longer serum half-life, J Immunol. Jan. 1, 2006;176(1):346-56.

[Non-patent Document 5] Ghetie V, Popov S, Borvak J, Radu C, Matesoi D, Medesan C, Ober R J, Ward E S., Increasing the serum persistence of an IgG fragment by random mutagenesis, Nat Biotechnol. 1997 July; 15(7): 637-40.

[Non-patent Document 6] Zuckier L S, Chang C J, Scharff M D, Morrison S L., Chimeric human-mouse IgG antibodies with shuffled constant region exons demonstrate that multiple domains contribute to in vivo half-life, Cancer Res. Sep. 1, 1998;58(17):3905-8.

[Non-patent Document 7] Tsurushita N, Hinton P R, Kumar S., Design of humanized antibodies: from anti-Tac to Zenapax, Methods. 2005 May;36(1):69-83.

[Non-patent Document 8] Rajpal A, Beyaz N, Haber L, Cappuccilli G, Yee H, Bhatt R R, Takeuchi T, Lerner R A, Crea R., A general method for greatly improving the affinity of antibodies by using combinatorial libraries, Proc Natl Acad Sci USA. Jun. 14, 2005; 102(24):8466-71.

[Non-patent Document 9] Ewert S, Honegger A, Pluckthun A., Stability improvement of antibodies for extracellular and intracellular applications: CDR grafting to stable frameworks and structure-based framework engineering, Methods. 2004 October;34(2):184-99. Review

[Non-patent Document 10] Lobo E D, Hansen R J, Balthasar J P., Antibody pharmacokinetics and pharmacodynamics, J Pharm Sci. 2004 November;93(11):2645-68. Review.

[Non-patent Document 11] Yamasaki Y, Sumimoto K, Nishikawa M, Yamashita F, Yamaoka K, Hashida M, Takakura Y., harmacokinetic analysis of in vivo disposition of succinylated proteins targeted to liver nonparenchymal cells via scavenger receptors: importance of molecular size and negative charge density for in vivo recognition by receptors, Pharmacol Exp Ther. 2002 May;301(2):467-77.

[Non-patent Document 12] Poduslo J F, Curran G L., olyamine modification increases the permeability of proteins at the blood-nerve and blood-brain barriers, Neurochem. 1996 April;66(4): 1599-609.

[Non-patent Document 13] Yang K, Basu A, Wang M, Chintala R, Hsieh M C, Liu S, Hua J, Zhang Z, Zhou J, Li M, Phyu H, Petti G, Mendez M, Janjua H, Peng P, Longley C, Borowski V, Mehlig M, Filpula D., Tailoring structure-function and pharmacokinetic properties of single-chain Fv proteins by site-specific PEGylation, Protein Eng. 2003 October;16(10):761-70.

[Non-patent Document 14] Kobayashi H, Le N, Kim I S, Kim M K, Pie J E, Drumm D, Paik D S, Waldmann T A, Paik C H, Carrasquillo J A., The pharmacokinetic characteristics of glycolated humanized anti-Tac Fabs are determined by their isoelectric points, Cancer Res. Jan. 15, 1999;59(2):422-30.

[Non-patent Document 15] Kim I, Kobayashi H, Yoo T M, Kim M K, Le N, Han E S, Wang Q C, Pastan I, Carrasquillo J A, Paik C H., Lowering of pI by acylation improves the renal uptake of 99mTc-labeled anti-Tac dsFv: effect of different acylating reagents, Nucl Med Biol. 2002 November;29(8):795-801

[Non-patent Document 16] Kim I S, Yoo T M, Kobayashi H, Kim M K, Le N, Wang Q C, Pastan I, Carrasquillo J A, Paik C H., Chemical modification to reduce renal uptake of disulfide-bonded variable region fragment of anti-Tac monoclonal antibody labeled with 99mTc, Bioconjug Chem. 1999 May-June;10(3):447-53.

[Non-patent Document 17] Onda M, Nagata S, Tsutsumi Y, Vincent J J, Wang Q, Kreitman R J, Lee B, Pastan I., Lowering the isoelectric point of the Fv portion of recombinant immunotoxins leads to decreased nonspecific animal toxicity without affecting antitumor activity, Cancer Res. Jul. 1, 2001;61(13):5070-7.

[Non-patent Document 18] Pavlinkova G, Beresford G, Booth B J, Batra S K, Colcher D., Charge-modified single chain antibody constructs of monoclonal antibody CC49: generation, characterization, pharmacokinetics, and biodistribution analysis, Nucl Med Biol. 1999 January;26(1): 27-34.

[Non-patent Document 19] Deen W M, Lazzara M J, Myers B D., Structural determinants of glomerular permeability, Am J Physiol Renal Physiol. 2001 October;281(4):F579-96.

[Non-patent Document 20] Schaeffer R C Jr, Gratrix M L, Mucha D R, Carbajal J M., The rat glomerular filtration barrier does not show negative charge selectivity, Microcirculation. 2002 October;9(5):329-42.

[Non-patent Document 21] Goode N P, Shires M, Davison A M., The glomerular basement membrane charge-selectivity barrier: an oversimplified concept?, Nephrol Dial Transplant. 1996 September;11(9):1714-6.

[Non-patent Document 22] Comper W D, Glasgow E F., Charge selectivity in kidney ultrafiltration, Kidney Int. 1995 May;47(5):1242-51.

[Non-patent Document 23] Ghetie V, Ward E S. FcRn: the MHC class I-related receptor that is more than an IgG transporter. Immunol Today. 1997 December;18(12):592-8.

[Non-patent Document 24] He X Y, Xu Z, Melrose J, Mullowney A, Vasquez M, Queen C, Vexler V, Klingbeil C, Co M S, Berg E L. Humanization and pharmacokinetics of a monoclonal antibody with specificity for both E- and P-selectin. J Immunol. Jan. 15, 1998;160(2):1029-35.

[Non-patent Document 25] Gobburu J V, Tenhoor C, Rogge M C, Frazier D E Jr, Thomas D, Benjamin C, Hess D M, Jusko W J. Pharmacokinetics/dynamics of 5c8, a monoclonal antibody to CD154 (CD40 ligand) suppression of an immune response in monkeys. J Pharmacol Exp Ther. 1998 August;286(2):925-30.

[Non-patent Document 26] Kashmiri S V, Shu L, Padlan E A, Milenic D E, Schlom J, Hand P H., Generation, characterization, and in vivo studies of humanized anti-carcinoma antibody CC49, Hybridoma. 1995 October; 14(5):461-73.

[Non-patent Document 27] Graves S S, Goshorn S C, Stone D M, Axworthy D B, Reno J M, Bottino B, Searle S, Henry A, Pedersen J, Rees A R, Libby R T., Molecular modeling and preclinical evaluation of the humanized NR-LU-13 antibody, Clin Cancer Res. 1999 April;5(4): 899-908.

[Non-patent Document 28] Couto J R, Blank E W, Peterson J A, Ceriani R L., Anti-BA46 monoclonal antibody Mc3: humanization using a novel positional consensus and in vivo and in vitro characterization, Cancer Res. Apr. 15, 1995;55(8):1717-22.

[Non-patent Document 29] Adams C W, Allison D E, Flagella K, Presta L, Clarke J, Dybdal N, McKeever K, Sliwkowski M X. Humanization of a recombinant monoclonal antibody to produce a therapeutic HER dimerization inhibitor, pertuzumab, Cancer Immunol Immunother. Sep. 3, 2005;1-11

[Non-patent Document 30] Binz H K, Amstutz P, Pluckthun A., Engineering novel binding proteins from nonimmunoglobulin domains, Nat Biotechnol. 2005 October;23 (10):1257-68.

DISCLOSURE OF THE INVENTION

[Problems to be Solved by the Invention]

The present invention was achieved in view of the above circumstances. An objective of the present invention is to provide methods for controlling the blood half-life of polypeptides comprising an FcRn-binding domain, such as IgG antibodies, by modifying the polypeptides through substitution of amino acid residues exposed on their surface; pharmaceutical compositions that comprise polypeptides comprising an FcRn-binding domain, whose half-life in blood is controlled by amino acid substitutions; and methods for producing the pharmaceutical compositions.

[Means for Solving the Problems]

The present inventors conducted dedicated studies on methods for controlling the blood half-life of polypeptides comprising an FcRn-binding domain through amino acid substitutions. As a result, the present inventors developed methods for controlling the half-life of IgG antibodies by controlling the surface charge through modification of residues exposed on the surface in the variable regions of the IgG antibodies, polypeptides comprising an FcRn-binding domain. Specifically, the present inventors discovered modification sites in variable regions to control the surface charge and the half-life of IgG antibodies in blood without influencing antibody structure and function. Furthermore, the present inventors confirmed that antibodies whose half-life in blood is controlled by the present invention actually retain their activity.

Regardless of the type of target antigen, the methods of the present invention are widely applicable to polypeptides comprising an FcRn-binding domain, such as IgGs, which are recycled via the FcRn salvage pathway, and whose major metabolic pathway is not renal excretion.

The present invention relates to methods for controlling the blood half-life of polypeptides comprising an FcRn-binding domain, such as IgG antibodies, by modifying the polypeptides through substitution of amino acid residues exposed on their surface; pharmaceutical compositions that comprise polypeptides comprising an FcRn-binding domain, whose half-life in blood is controlled by amino acid substitutions; and methods for producing the pharmaceutical compositions.

More specifically, the present invention relates to the following:

[1] a method for producing a polypeptide comprising an FcRn-binding domain, whose pharmacokinetics in blood is controlled, wherein the method comprises:
(a) modifying a nucleic acid encoding a polypeptide comprising an FcRn-binding domain to change the charge of at least one amino acid residue that can be exposed on the surface of the polypeptide,
(b) culturing a host cell to express the nucleic acid, and
(c) collecting the polypeptide comprising an FcRn-binding domain from the host cell culture;

[2] the method of [1], wherein the amino acid residue that can be exposed on the surface of the polypeptide comprising an FcRn-binding domain is located in a domain other than the FcRn-binding domain within the polypeptide;

[3] the method of [2], wherein the FcRn-binding domain comprises an Fc or Fc-like domain;

[4] the method of [1], wherein the polypeptide comprising an FcRn-binding domain is an IgG antibody;

[5] the method of [4], wherein the amino acid residue whose charge is changed in step (a) is an amino acid residue in a heavy chain or light chain variable region of the IgG antibody;

[6] the method of [1], wherein the control of pharmacokinetics in blood is the control of any one of the following parameters: half-life in blood, mean residence time in blood, or blood clearance;

[7] the method of [1], wherein the change of charge of the amino acid residue in step (a) is achieved by an amino acid substitution;

[8] a polypeptide comprising an FcRn-binding domain, which is produced by the method of [1];

[9] a method for controlling blood pharmacokinetics of a polypeptide comprising an FcRn-binding domain, which comprises changing the charge of at least one amino acid residue that can be exposed on the surface of the polypeptide;

[10] the method of [9], wherein the amino acid residue that can be exposed on the surface of the polypeptide comprising an FcRn-binding domain is located in a domain other than the FcRn-binding domain within the polypeptide;

[11] the method of [10], wherein the FcRn-binding domain comprises an Fc or Fc-like domain;

[12] the method of [9], wherein the polypeptide comprising an FcRn-binding domain is an IgG antibody;

[13] the method of [12], wherein the amino acid residue whose charge is changed is an amino acid residue in a heavy chain or light chain variable region of the IgG antibody;

[14] the method of [9], wherein the control of pharmacokinetics in blood is the control of any one of the following parameters: half-life in blood, mean residence time in blood, or blood clearance;

[15] the method of [9], wherein the change of charge of the amino acid residue is achieved by an amino acid substitution;

[16] a polypeptide comprising an FcRn-binding domain, whose pharmacokinetics in blood is controlled by the method of [9];

[17] a humanized antibody comprising complementarity determining regions (CDRs) of a nonhuman animal, human-derived framework regions (FRs), and human constant regions, wherein at least one amino acid residue that can be exposed on the surface in the CDRs or FRs has a charge different from that of the corresponding amino acid residue in CDRs or FRs of the wild type, and wherein its pharmacokinetics in blood is controlled as compared to a chimeric antibody whose variable regions are derived from an antibody of the nonhuman animal and whose constant regions are the same;

[18] the humanized antibody of [17], wherein the human constant regions comprise a wild-type human Fc domain;

[19] a composition comprising the humanized antibody of [17] or [18] and a pharmaceutically acceptable carrier;

[20] a nucleic acid encoding a polypeptide constituting the humanized antibody of [17] or 18;

[21] a host cell comprising the nucleic acid of [20];

[22] a method for producing the humanized antibody of [17] or [18], which comprises culturing the host cell of [21] and collecting a polypeptide from the cell culture;

[23] an IgG antibody, in which the charge of at least one amino acid residue selected from the amino acid residues at positions 10, 12, 23, 39, 43, and 105 according to the Kabat's numbering system in a heavy chain variable region is changed, and whose pharmacokinetics in blood is controlled as compared to before the modification of the amino acid residue;

[24] the IgG antibody of [23], wherein the modified amino acid residue is selected from the amino acid residues of group (a) or (b) below:
(a) glutamic acid (E) and aspartic acid (D), and
(b) lysine (K), arginine (R), and histidine (H);

[25] a composition comprising the IgG antibody of [23] or [24] and a pharmaceutically acceptable carrier;
[26] a nucleic acid encoding a polypeptide constituting the IgG antibody of [23] or [24];
[27] a host cell comprising the nucleic acid of [26]; and
[28] a method for producing the antibody of [23] or [24], which comprises culturing the host cell of [27] and collecting a polypeptide from the cell culture.

BRIEF DESCRIPTION OF THE DRAWINGS

FIG. 5 shows results of analyzing humanized A69 antibodies (hA69a and hA69-N97R; hA69-N97R, hA69-p 18, and hA69-PF) with unmodified or modified variable regions for their binding activity to the antigen Factor IXa. The results demonstrate that the modified antibodies with shifted isoelectric points have a binding activity comparable to that of unmodified antibodies.

BEST MODE FOR CARRYING OUT THE INVENTION

Figure 1:
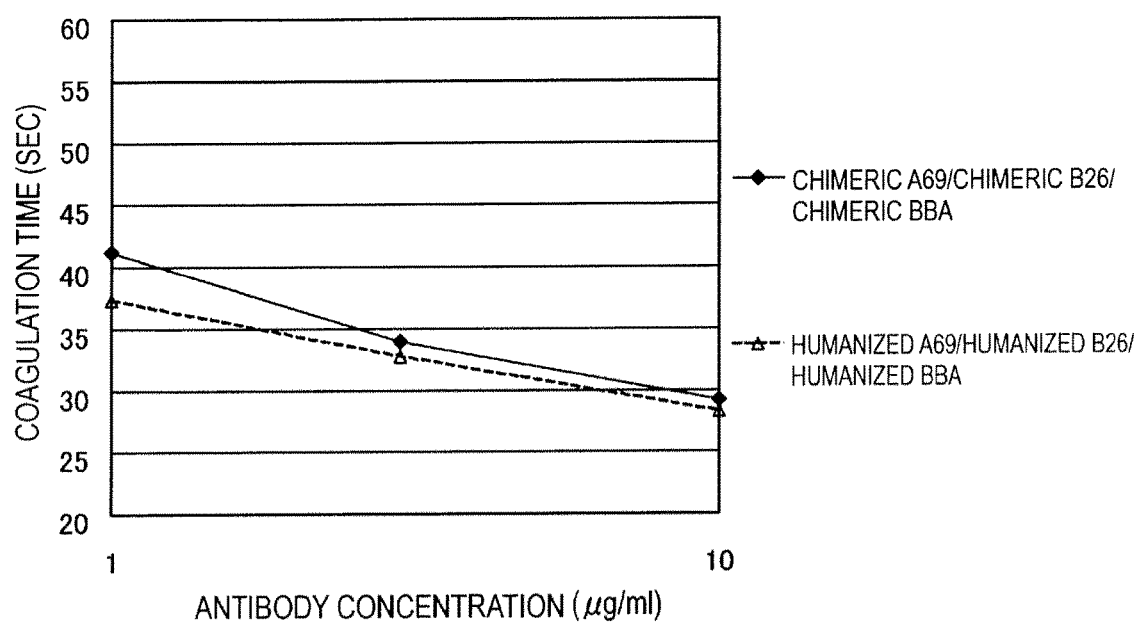
FIG. 1 is a graph showing the assessment of coagulation activity for a humanized bispecific antibody (humanized A69 (hA69a), humanized B26 (hB26-F123e4), and humanized BBA (hAL-F123j4)). The assessment result demonstrates that the coagulation activities are equivalent to or greater than those of chimeric bispecific antibodies.

The present invention provides methods for controlling pharmacokinetics of polypeptides comprising an FcRn-binding domain in blood. In a preferred embodiment, the methods of the present invention comprise changing the charge of at least one amino acid residue that can be exposed on the surface of such polypeptides. Specifically, pharmacokinetics of these polypeptides in blood can be controlled by shifting their isoelectric point (pI) by changing the charge of their amino acid residues.

As described above, blood pharmacokinetics of minibodies such as scFvs and Fabs cannot necessarily be controlled by shifting pI. Renal excretion is known to be the major metabolic pathway of such minibodies. However, some of Non-patent Documents 19 to 22 describe that renal filtration efficiency in renal excretion is lower if protein charge is more negative, while others report that protein charge has no influence on renal filtration efficiency. In addition, some of Non-patent Documents 14 to 18 report that the half-life of a minibody in blood can be prolonged by decreasing its pI, while others report that it can be shortened by decreasing its pI. Proteins filtered through the kidney are reabsorbed by the proximal tubule. This reabsorption can become more suppressed when the charge of a protein is more negative. This suggests that the half-life of a minibody cannot be exactly controlled as intended by shifting the pI.

On the other hand, the major metabolic pathway of IgG antibodies is not renal excretion because their molecular weight is quite high. IgG antibodies with Fe are known to be recycled via the FcRn salvage pathway expressed in the endothelial cells of blood vessels and such, and thereby have a long half-life. IgG is assumed to be metabolized primarily in endothelial cells (Non-patent Document 23). Accordingly, it has been speculated that free IgG molecules are metabolized while IgG molecules non-specifically incorporated into endothelial cells are recycled via binding to FcRn. IgGs with decreased FeRn-binding activity have a shorter half-life in blood, while their half-life in blood can be prolonged by increasing their FcRn-binding activity (Non-patent Document 23). Accordingly, previous methods for controlling pharmacokinetics of IgGs in blood have been conducted by altering FcRn-binding activity through Fe modification. In contrast, Example 8 herein demonstrates that when IgGs share the same Fe domain, the IgG half-life correlates to pI showing a high correlation coefficient regardless of the type of target antigen, and that the half-life in blood of two types of antibodies against different antigens can actually be controlled by modifying the pIs of their variable regions without modifying Fe. The rate of nonspecific antibody uptake by endothelial cells is assumed to depend on the physicochemical Coulomb interaction between an IgG and a negatively charged cell surface. Therefore, it is thought that a decrease (an increase) in the pI of IgG reduces (enhances) the Coulomb interaction, and this is followed by a reduction (an increase) in nonspecific uptake by endothelial cells, leading to a decrease (an increase) in metabolism in these cells, and as a result, pharmacokinetics in blood can be controlled. Since the Coulomb interaction between negatively-charged cell surface of the endothelial cells is a physicochemical interaction, the interaction is assumed not to depend on the target antigen. Thus, the methods of the present invention for controlling pharmacokinetics in blood are widely applicable to polypeptides such as arbitrary IgGs comprising an FcRn-binding domain which are recycled via the FcRn salvage pathway and whose major metabolic pathway is not renal excretion, regardless of the type of antigen.

Thus, the polypeptides of the present invention comprising an FcRn-binding domain are not limited to IgG antibodies, but may be any protein that can bind (has binding activity or affinity) to an Fe receptor (FcRn). Thus, polypeptides of the present invention comprising an FcRn-binding domain are not particularly limited; however, they are preferably proteins comprising an antibody Fc domain or Fc-like domain. The polypeptides of the present invention comprising an FcRn-binding domain include, for example, IgG antibodies. Furthermore, the polypeptides of the present invention comprising an FcRn-binding domain include modified forms of antibodies (proteins) as long as they can bind to FcRn. The most preferred examples of polypeptides of the present invention comprising an FcRn-binding domain are IgG antibodies.

When an IgG antibody is used as a polypeptide comprising an FcRn-binding domain in the present invention, it may be of any IgG subtype or a bispecific IgG antibody. Bispecific antibodies are antibodies specific to two different epitopes, and include antibodies that recognize different antigens and those that recognize different epitopes on a single antigen. On the other hand, when the antibody is a minibody such as scFv or Fab, whose major metabolic pathway is renal excretion, its pharmacokinetics in blood cannot be controlled by shifting pI, as described above. The present invention is applicable to any type of antibody, as long as it is an Fc-binding protein whose major metabolic pathway is not renal excretion, for example, scFv-Fc, dAb-Fc, and Fc fusion proteins. Since renal excretion is not the major metabolic pathway of these molecules, their pharmacokinetics in blood can be controlled by shifting the pI using the methods of the present invention. Antibody molecules to which the present invention is applicable may be antibody-like molecules. Antibody-like molecules refer to molecules that exert their functions by binding to target molecules (Non-patent Document 30), and include, for example, DARPins, Affibodies, and Avimers.

Herein, the phrase "pharmacokinetics in blood is controlled" indicates that pharmacokinetics in blood is shifted in a desired direction when compared between before and after modification of a polypeptide comprising an FcRn-binding domain. Specifically, when the purpose is to prolong the half-life in blood, the control of pharmacokinetics in blood means prolongation of the half-life in blood. Alternatively, when the purpose is to reduce the half-life in blood, the control of pharmacokinetics in blood refers to reduction of the half-life in blood.

In the present invention, whether the blood pharmacokinetics of a polypeptide comprising an FcRn-binding domain is shifted in a desired direction, or whether the blood pharmacokinetics can be exactly controlled as intended, can be assessed by conducting appropriate kinetic tests, for example, tests using mice, rats, rabbits, dogs, monkeys or such. More specifically, as used herein, "control of pharmacokinetics in blood" includes the control of any parameter such as half-life in blood, mean residence time in blood, or blood clearance (Pharmacokinetics: Enshu niyoru Rikai (Understanding through Exercises), Nanzando). For example, the control of pharmacokinetics in blood can be assessed by appropriate noncompartmental analysis using in vivo kinetics analysis software, WinNonlin (Pharsight), according to the attached instruction manual.

Herein, the phrase "amino acids that can be exposed on the surface" generally means amino acids which constitute a polypeptide comprising an FcRn-binding domain and which are present on the polypeptide surface. The side chains of an amino acid that is present on the polypeptide surface can contact solvent molecules (typically, water molecules). However, not the whole side chain has to be in contact with solvent molecules. When even a portion of the side chains contacts solvent molecules, the amino acid is judged to be present on the polypeptide surface. Those skilled in art can prepare homology models for polypeptides and antibodies through homology modeling using commercially available software, and so on, and they can also select appropriate residues as surface amino acids using the models.

In the present invention, "amino acids that can be exposed on the surface" are not particularly limited; however, they are preferably outside an FcRn-binding domain of a polypeptide comprising such a domain. An FcRn-binding domain includes, for example, Fc and Fc-like domains.

When a polypeptide of the present invention comprising an FcRn-binding domain is an IgG, amino acid residues whose charges are to be changed according to the present invention are preferably present within the heavy or light chain variable regions of the IgG antibody. Specifically, the variable regions include complementarity determining regions (CDRs) and framework regions (FRs).

Those skilled in art can select appropriate surface amino acids in antibody variable regions using homology models prepared by homology modeling or the like. Such surface amino acids include, for example, amino acids at H1, H3, H5, H8, H10, H12, H13, H15, H16, H19, H23, H25, H26, H39, H42, H43, H44, H46, H68, H71, H72, H73, H75, H76, H81, H82b, H83, H85, H86, H105, H108, H110, and H112 in an H chain FR region, but are not limited thereto in the present invention.

Likewise, those skilled in the art can also select surface amino acids in an H chain CDR region using homology models. For example, the amino acid at H97 is exposed on the surface in almost all antibodies. Surface amino acids in an L chain FR region include, for example, the amino acids at L1, L3, L7, L8, L9, L11, L12, L16, L17, L18, L20, L22, L38, L39, L41, L42, L43, L45, L46, L49, L57, L60, L63, L65, L66, L68, L69, L70, L74, L76, L77, L79, L80, L81, L85, L100, L103, L105, L106, L107, and L108, but are not limited thereto in the present invention. Likewise, those skilled in art can also select surface amino acids in an L chain CDR region using homology models.

In the methods of the present invention, "modification" of an amino acid residue specifically refers to substitution of the original amino acid residue with a different amino acid residue, deletion of the original amino acid residue, addition of another amino acid residue, and so on. The modification preferably means substitution of the original amino acid residue with a different amino acid residue. Specifically, as used herein, "modification of the charge of an amino acid residue" preferably includes amino acid substitutions.

When a polypeptide of the present invention comprising an FcRn-binding domain is an IgG antibody, the above-described "changing the charge of an amino acid residue" includes, for example, changing the charge of at least one amino acid residue selected from the group consisting of amino acid residues at positions 10, 12, 23, 39, 43, and 105 according to the Kabat's numbering system in a heavy chain of the IgG antibody. Of the amino acid residues at the positions indicated above, amino acid residues other than the amino acid residues whose charges have been modified need not be modified as long as the pharmacokinetics in blood have been controlled as intended. The amino acids can be modified to have a charge of the same type as that of modified amino acid residues or not to have any charge.

Amino acids are known to include charged amino acids. Generally known amino acids with a positive charge (positively-charged amino acids) include lysine (K), arginine (R), and histidine (H). Known amino acids with a negative charge (negatively-charged amino acids) include aspartic acid (D) and glutamic acid (E). Amino acids other than these are known as uncharged amino acids.

Preferably, the above-described "modified amino acid residues" are appropriately selected from amino acid residues of either group (a) or (b) indicated below; however, the modified amino acids are not particularly limited thereto.
(a) glutamic acid (E) and aspartic acid (D)
(b) lysine (K), arginine (R), and histidine (H)

When an original (unmodified) amino acid residue already has a charge, modification of the amino acid into an uncharged amino acid is also a preferred embodiment of the present invention. Specifically, the modification in the present invention includes:
(1) substitution of a charged amino acid with an uncharged amino acid;
(2) substitution of a charged amino acid with an amino acid carrying a charge opposite from the original amino acid; and
(3) substitution of an uncharged amino acid with a charged amino acid.

In the methods of the present invention, preferably, amino acid residues in polypeptides comprising an FcRn-binding domain are modified to shift the isoelectric point (pI). When the number of amino acid residues to be introduced through the modification is two or more, a few of them may be uncharged amino residues.

The number of amino acid residues to be modified in the methods of the present invention is not particularly limited. However, when an antibody variable region is modified for instance, only a minimum number of amino acid residues required to achieve the blood pharmacokinetics controlled as intended are preferably modified so as not to reduce the antigen-binding activity and not to increase the antigenicity.

The amino acid sequence after modification is preferably a human sequence so as not to increase the antigenicity; however, the present invention is not limited thereto. Furthermore, mutations may be introduced at sites other than those where modifications have been made for shifting the isoelectric point, so that the respective FRs (FR1, FR2, FR3, and FR4) after modification are human sequences. Such a method for substituting each FR with a human sequence has been reported in a non-patent document (Ono K et al., Mol Immunol. 1999 April; 36(6): 387-395). Alternatively, to shift the isoelectric point, each FR may be modified into another human FR with a different isoelectric point (for example, FR3 may be substituted by another human FR with a lower isoelectric point). Such a humanization method has been reported in a non-patent document (Dall'Acqua W F, Methods. 2005 May; 36(1): 43-60).

Even when pharmacokinetics in blood cannot be controlled as intended by modifying only a small number of surface charges, a desired polypeptide comprising an FcRn-binding domain, whose pharmacokinetics in blood is controlled, can be obtained by repeating surface charge modifications and assessment of pharmacokinetics in blood.

In rhesus monkeys, Non-patent Document 24 reports on a comparison of blood pharmacokinetics between chimeric EP5C7.g4, a chimeric antibody (IgG4), and HuEP5C7.g4, a humanized antibody (IgG4), both of which are derived from an anti-E, P-Selectin antibody, which found that the pharmacokinetics were comparable to each other. Non-patent Document 25 describes a comparison of blood pharmacokinetics in cynomolgus monkeys between ch5d8, a chimeric antibody, and Hu5c8, a humanized antibody, both of which are derived from an anti-CD 154 antibody, which found the pharmacokinetics to be comparable to each other. Non-patent Document 26 demonstrates that blood pharmacokinetics in mice of cCC49, a chimeric antibody, was comparable to that of HuCC49, a humanized antibody. Furthermore, Non-patent Documents 27 and 28 reports that pharmacokinetics and distribution in blood of mouse antibodies were comparable to those of humanized antibodies when assessed using mice. Since both mouse Fcs and human Fcs are reactive to mouse FcRn, the above findings suggest that pharmacokinetics and distribution in blood of chimeric antibodies are comparable to those of the humanized antibodies described above. As shown by these examples, pharmacokinetics of chimeric antibodies in blood are comparable to that of humanized antibodies. Specifically, when an antibody is humanized by a known method such as that described in Non-patent Document 7, its pharmacokinetics in blood is comparable to that of a chimeric antibody. Thus, humanized antibodies whose pharmacokinetics in blood is controlled cannot be produced by known methods.

Humanized antibodies whose pharmacokinetics in blood is controlled (specifically, the half-life in blood is prolonged or pharmacokinetics in blood is reduced) as compared to chimeric antibodies can be produced by shifting their pIs through modification of surface amino acids at the time of humanization of chimeric antibodies, using the methods discovered by the present invention. The modification of surface amino acids to control pharmacokinetics in blood may be made at the time of humanization or after humanization.

Non-patent Document 29 describes that pharmacokinetics in blood of three types of humanized antibodies, trastuzumab, bevacizumab, and pertuzumab, obtained through humanization using the same FR sequence of a human antibody, was nearly the same. Specifically, pharmacokinetics in blood is nearly the same when humanization is performed using the same FR sequence. The blood concentration can be controlled only when the pIs of antibodies are shifted by modifying surface amino acids using the methods discovered by the present invention, in addition to the above-described humanization process.

Furthermore, human antibodies whose pharmacokinetics in blood is controlled (specifically, the half-life in blood is prolonged or pharmacokinetics in blood is reduced) as compared to the original human antibodies can be produced by shifting the pIs of human antibodies prepared from human antibody libraries or mice producing human antibodies and such, through modification of surface amino acids.

The "antibodies" of the present invention include antibodies obtained by further introducing amino acid substitutions, deletions, additions and/or insertions and such into the amino acid sequences of antibodies that have been already modified to change the charges of their amino acid residues as described above. The antibodies of the present invention also include antibodies obtained by further changing the charge of the amino acid residues in antibodies whose amino acid sequences have been already modified by amino acid substitutions, deletions, additions and/or insertions, chimerization, humanization or such.

Amino acid modifications such as amino acid substitutions, deletions, additions and/or insertions, and chimerization and humanization, can be achieved by methods known to those skilled in the art. Likewise, the amino acid sequences of antibody constant and variable regions that are used to produce antibodies of the present invention as recombinant antibodies may also be modified by amino acid substitutions, deletions, additions and/or insertions, or chimerization, humanization or such.

The antibodies of the present invention may be antibodies derived from any animal such as a mouse, human, rat, rabbit, goat, or camel. Furthermore, the antibodies may be modified antibodies, for example, chimeric antibodies and in particular, humanized antibodies that comprise amino acid substitutions in their sequence. The antibodies also include antibody modification products linked to various molecules.

"Chimeric antibodies" are antibodies prepared by combining sequences derived from different animals. Chimeric antibodies include, for example, antibodies comprising heavy and light chain variable (V) regions from a mouse antibody and heavy and light chain constant (C) regions from a human antibody. Chimeric antibodies can be prepared by known methods, for example, by the following procedure: a DNA encoding an antibody V region is ligated with a DNA encoding a human antibody C region; the resulting ligation product is inserted into an expression vector; and the construct can be introduced into a host to produce a chimeric antibody.

"Humanized antibodies" are also referred to as reshaped human antibodies, and can be obtained by substituting the complementarity determining regions (CDRs) of a human antibody for the CDRs of an antibody derived from a nonhuman mammal, for example, a mouse. Methods for identifying CDRs are known (Kabat et al., Sequence of Proteins of Immunological Interest (1987), National Institute of Health, Bethesda, Md.; Chothia et al., Nature (1989) 342: 877). General genetic recombination techniques for the above procedure are also known (see European Patent Application Publication No. EP 125023, and WO 96/02576). For example, the CDRs of a mouse antibody are determined by known methods, and a DNA is prepared so that it encodes an antibody in which the CDRs are linked to the framework regions (FRs) of a human antibody. A humanized antibody can then be produced by a system using a conventional expression vector. Such DNAs can be synthesized by PCR using as primers several oligonucleotides designed to comprise portions that overlap the ends of both the CDR and FR regions (see the method described in WO 98/13388). Human antibody FRs linked via CDRs are selected such that the CDRs can form a suitable antigen binding site. If required, amino acids in the FRs of an antibody variable region may be modified so that the CDRs of a reshaped human antibody can form a suitable antigen binding site (Sato, K. et al., Cancer Res. (1993) 53: 851-856). Modifiable amino acid residues in the FRs include portions that directly bind to an antigen via noncovalent bonds (Amit et al., Science (1986) 233: 747-53), portions that have an impact or effect on the CDR structure (Chothia et al., J. Mol. Biol. (1987) 196: 901-17), and portions involved in the interaction between VH and VL (EP 239400).

When the antibodies of the present invention are chimeric antibodies or humanized antibodies, the C regions of these antibodies are preferably derived from human antibodies. For example, Cγ1, Cγ2, Cγ3, and Cγ4 can be used for the H chains, and Cκ and Cλ can be used for the L chains. Meanwhile, the human antibody C regions may be modified as required to improve antibody or production stability. A chimeric antibody of the present invention preferably comprises a variable region of an antibody derived from a nonhuman mammal and a constant region derived from a human antibody. A humanized antibody of the present invention preferably comprises CDRs of an antibody derived from a nonhuman mammal and FRs and C regions derived from a human antibody. Constant regions of human antibodies comprise amino acid sequences specific to each antibody isotype, for example, IgG (IgG1, IgG2, IgG3, and IgG4), IgM, IgA, IgD, and IgE. The constant regions used to prepare the humanized antibodies of the present invention may be the constant regions of antibodies of any isotype. A constant region of a human IgG is preferably used, but the constant regions are not limited thereto. FRs derived from a human antibody, which are used to prepare humanized antibodies, are not particularly limited, and thus may be derived from an antibody of any isotype.

The variable and constant regions of chimeric or humanized antibodies of the present invention may be modified by deletions, substitutions, insertions, and/or additions, as long as the antibodies exhibit the same binding specificity as that of the original antibodies.

Chimeric and humanized antibodies using human-derived sequences are expected to be useful when administered to humans for therapeutic purposes or such, since their antigenicity in the human body has been reduced.

Known sequences can be used as genes encoding the H chain or L chain of antibodies before introduction of mutations by methods of the present invention (herein, they may be simply referred to as "antibodies of the present invention"), or the genes can be obtained by methods known to those skilled in the art. For example, they may be obtained from an antibody library, or by cloning genes encoding the antibodies from hybridomas producing monoclonal antibodies.

Regarding antibody libraries, many antibody libraries are already well known, and since methods for producing antibody libraries are known, those skilled in the art can appropriately obtain antibody libraries. For example, with regard to antibody phage libraries, one can refer to the literature such as Clackson et al., Nature 1991, 352: 624-8; Marks et al., J. Mol. Biol. 1991, 222: 581-97; Waterhouses et al., Nucleic Acids Res. 1993, 21: 2265-6; Griffiths et al., EMBO J. 1994, 13: 3245-60; Vaughan et al., Nature Biotechnology 1996, 14: 309-14; and Japanese Patent Kohyo Publication No. H10-504970 (unexamined Japanese national phase publication corresponding to a non-Japanese international publication). In addition, known methods such as methods that use eukaryotic cells as libraries (WO95/15393) and ribosome display methods, may be used. Furthermore, techniques to obtain human antibodies by panning using human antibody libraries are also known. For example, variable regions of human antibodies can be expressed on the surface of phages as single chain antibodies (scFvs) using phage display methods, and phages that bind to antigens can be selected. Genetic analysis of the selected phages can determine the DNA sequences encoding the variable regions of human antibodies that bind to the antigens. Once the DNA sequences of scFvs that bind to the antigens are revealed, suitable expression vectors can be produced based on these sequences to obtain human antibodies. These methods are already well known, and one can refer to WO92/01047, WO92/20791, WO93/06213, WO93/11236, WO93/19172, WO95/01438, and WO95/15388.

As for methods for obtaining genes encoding antibodies from hybridomas, known techniques may be used, involving the use of desired antigens or cells expressing the desired antigens as sensitizing antigens, using these to perform immunizations according to conventional immunization methods, fusing the immune cells thus obtained with known parent cells by ordinary cell fusion methods, screening monoclonal antibody producing cells (hybridomas) by ordinary screening methods, synthesizing cDNAs of antibody variable regions (V regions) from mRNAs of the obtained hybridomas using a reverse transcriptase, and linking them to DNAs encoding the desired antibody constant regions (C regions).

More specifically, without being particularly limited to the following examples, sensitizing antigens for obtaining the above-mentioned antibody genes encoding the H chains and L chains include both complete antigens with immunogenicity and incomplete antigens comprising haptens and such that do not show immunogenicity. For example, full-length proteins and partial peptides of proteins of interest can be used. In addition, it is known that substances composed of polysaccharides, nucleic acids, lipids and such may become antigens. Thus, there are no particular limitations on antigens of the antibodies of the present invention. Antigens can be prepared by methods known to those skilled in the art, and they can be prepared, for example, by the methods using baculoviruses (for example, see WO98/46777). Hybridomas can be produced, for example, by the method of Milstein et al. (G. Kohler and C. Milstein, Methods Enzymol. 1981, 73: 3-46). When the immunogenicity of an antigen is low, it can be linked to a macromolecule that has immunogenicity, such as albumin, and then used for immunization. Furthermore, by linking antigens to other molecules if necessary, they can be converted into soluble antigens. When transmembrane molecules such as receptors are used as antigens, portions of the extracellular regions of the receptors can be used as fragments, or cells expressing transmembrane molecules on their cell surface may be used as immunogens.

Antibody-producing cells can be obtained by immunizing animals using the suitable sensitizing antigens described above. Alternatively, antibody-producing cells can be prepared by in vitro immunization of lymphocytes that can produce antibodies. Various mammals can be used as the animals for immunization, where rodents, lagomorphas, and primates are generally used. Examples of such animals include mice, rats, and hamsters for rodents, rabbits for lagomorphas, and monkeys including cynomolgus monkeys, rhesus monkeys, hamadryas, and chimpanzees for primates. In addition, transgenic animals carrying human antibody gene repertoires are also known, and human antibodies can be obtained by using these animals (see WO96/34096; Mendez et al., Nat. Genet. 1997, 15: 146-56). Instead of using such transgenic animals, for example, desired human antibodies having binding activity to desired antigens can be obtained by sensitizing in vitro human lymphocytes with the desired antigens or cells expressing the desired antigens, and then fusing the sensitized lymphocytes with human myeloma cells such as U266 (see Japanese Patent Application Kokoku Publication No. H1-59878 (examined, approved Japanese patent application published for opposition)). Furthermore, desired human antibodies can be obtained by immunizing transgenic animals carrying a complete repertoire of human antibody genes, with desired antigens (see WO93/12227, WO92/03918, WO94/02602, WO96/34096, and WO96/33735).

Animal immunization can be carried out by appropriately diluting and suspending a sensitizing antigen in Phosphate-Buffered Saline (PBS), physiological saline or such, and forming an emulsion by mixing an adjuvant if necessary, followed by an intraperitoneal or subcutaneous injection into animals. After that, the sensitizing antigen mixed with Freund's incomplete adjuvant is preferably administered several times every four to 21 days. Antibody production can be confirmed by measuring the target antibody titer in animal sera using conventional methods.

Antibody-producing cells obtained from lymphocytes or animals immunized with a desired antigen can be fused with myeloma cells using conventional fusing agents (for example, polyethylene glycol) to generate hybridomas (Goding, Monoclonal Antibodies: Principles and Practice, Academic Press, 1986, 59-103). When required, hybridoma cells can be cultured and grown, and the binding specificity of the antibodies produced from these hybridomas can be measured using known analysis methods such as immunoprecipitation, radioimmunoassay (RIA), and enzyme-linked immunosorbent assay (ELISA). Thereafter, hybridomas that produce antibodies in which specificity, affinity, or activity of interest has been determined can be subcloned by methods such as limiting dilution.

Next, genes encoding the selected antibodies can be cloned from hybridomas or antibody-producing cells (sensitized lymphocytes and such) using probes that can specifically bind to the antibodies (for example, oligonucleotides complementary to sequences encoding the antibody constant regions). Cloning from mRNAs using RT-PCR is also possible. Immunoglobulins are classified into five different classes, IgA, IgD, IgE, IgG, and IgM. These classes are further divided into several subclasses (isotypes) (for example, IgG-1, IgG-2, IgG-3, and IgG-4; and IgA-1 and IgA-2). H chains and L chains used in the present invention to produce antibodies are not particularly limited and may derive from antibodies belonging to any of these classes or subclasses; however, IgGs are particularly preferred.

Herein, it is possible to modify H-chain-encoding genes and L-chain-encoding genes using genetic engineering techniques. Genetically modified antibodies such as chimeric antibodies and humanized antibodies that have been artificially modified to decrease heterologous antigenicity against humans, and such, can be appropriately produced if necessary for antibodies such as mouse antibodies, rat antibodies, rabbit antibodies, hamster antibodies, sheep antibodies, and camel antibodies. Chimeric antibodies are antibodies composed of H chain and L chain variable regions of a nonhuman mammal antibody such as mouse antibody, and the H chain and L chain constant regions of a human antibody. They can be obtained by linking DNAs encoding variable regions of a mouse antibody to DNAs encoding the constant regions of a human antibody, incorporating them into an expression vector, and introducing the vector into a host for production of the antibodies. A humanized antibody, which is also called a reshaped human antibody, can be obtained as follows: A DNA sequence designed to link the complementarity determining regions (CDRs) of an antibody of a nonhuman mammal such as a mouse is synthesized by PCR from a number of oligonucleotides produced so that they have overlapping portions at the ends of the sequence. The obtained DNA can be linked to a DNA encoding a human antibody constant region. The linked DNA can be incorporated into an expression vector, and the vector can be introduced into a host to produce the antibody (see EP239400 and WO96/02576). Human antibody FRs that are linked via the CDRs are selected so that the CDRs form a favorable antigen-binding site. If necessary, amino acids in the framework regions of antibody variable regions may be substituted such that the CDRs of a reshaped human antibody form an appropriate antigen-binding site (K. Sato et al., Cancer Res. 1993, 53: 851-856).

In addition to the humanization described above, antibodies may be modified to improve their biological properties, for example, binding activity to an antigen. Modifications in the present invention can be carried out using methods such as site-directed mutagenesis (see, for example, Kunkel (1985) Proc. Natl. Acad. Sci. USA 82: 488), PCR mutagenesis, and cassette mutagenesis. In general, mutant antibodies whose biological properties have been improved show amino acid sequence homology and/or similarity of 70% or higher, more preferably 80% or higher, and even more preferably 90% or higher (for example, 95% or higher, 97%, 98%, 99% and so on), when compared to the amino acid sequences of the original antibody variable regions. Herein, sequence homology and/or similarity is defined as the ratio of amino acid residues that are homologous (same residue) or similar (amino acid residues classified into the same group based on the general properties of amino acid side chains) to the original antibody residues, after the sequence homology value has been maximized by sequence alignment and gap introduction, if necessary. Generally, naturally-occurring amino acid residues are classified into groups based on the characteristics of their side chains: (1) hydrophobic: alanine, isoleucine, valine, methionine, and leucine; (2) neutral hydrophilic: asparagine, glutamine, cysteine, threonine, and serine; (3) acidic: aspartic acid and glutamic acid; (4) basic: arginine, histidine, and lysine; (5) residues that affect the orientation of the chain: glycine and proline; and (6) aromatic: tyrosine, tryptophan, and phenylalanine.

Ordinarily, a total of six complementarity determining regions (CDRs; hypervariable regions) present in the H chain and L chain variable regions interact to form the antigen binding site(s) of an antibody. Even one of these variable regions is known to have the ability to recognize and bind to the antigen, although the affinity will be lower than when all binding sites are included. Therefore, antibody genes of the present invention encoding H chains and L chains only have to encode fragment portions having each of the antigen binding sites of H chains and L chains, and polypeptides encoded by these genes only have to maintain binding activity to the desired antigens.

Heavy chain variable regions are ordinarily composed of three CDR regions and four FR regions as described above. In a preferred embodiment of the present invention, amino acid residues subjected to "modification" can be appropriately selected from among amino acid residues positioned in the CDR regions or FR regions. Generally, modification of the amino acid residues in the CDR regions can decrease the binding activity to antigens. Therefore, in the present invention, amino acid residues subjected to "modification" are not particularly limited but are preferred to be appropriately selected from among amino acid residues positioned in the FR regions. Even amino acid residues in the CDRs may be selected, as long as modifications of these residues have been confirmed not to reduce the binding activity.

Furthermore, sequences that can be used as variable region FRs of the antibodies of organisms such as humans or mice, can be appropriately obtained by those skilled in the art using public databases.

The present invention also relates to polypeptides comprising an FcRn-binding domain whose pharmacokinetics in blood is controlled by a method of the present invention.

In a preferred embodiment, the present invention provides humanized antibodies whose pharmacokinetics in blood is controlled by a method of the present invention. For example, the human antibodies are humanized antibodies comprising complementarity determining regions (CDRs) derived from a nonhuman animal, framework regions (FRs) derived from a human, and human constant regions, with at least one amino acid residue in the CDRs or FRs, which can be exposed on antibody surface, has a charge different from that of the corresponding amino acid residue in the wild-type CDRs or FRs, and whose variable regions are derived from an antibody of the nonhuman animal and pharmacokinetics in blood is controlled as compared to corresponding chimeric antibodies having the same constant regions.

The above-described "human constant region" preferably refers to a region comprising a wild-type human Fc domain; however, it may be a modified Fc.

The present invention also relates to methods for producing polypeptides comprising an FcRn-binding domain, whose pharmacokinetics in blood is controlled by using the methods of the present invention. Specifically, the present invention provides methods for producing polypeptides comprising an FcRn-binding domain, whose pharmacokinetics in blood is controlled. The present invention also includes polypeptides comprising an FcRn-binding domain, which are produced by the methods of the present invention.

In a preferred embodiment, the production methods of the present invention are methods for producing polypeptides comprising an FcRn-binding domain, whose pharmacokinetics in blood is controlled, and which comprise:
(a) modifying the nucleic acids encoding polypeptides comprising an FcRn-binding domain to change the charge of at least one amino acid residue that can be exposed on the surface of the polypeptides;
(b) culturing host cells to express the nucleic acids; and
(c) collecting the polypeptides comprising an FcRn-binding domain from the host cell cultures.

The phrase "modifying nucleic acids" in the above-mentioned methods of the present invention refers to modifying nucleic acids so that they correspond to amino acid residues introduced by the "modifications" of the present invention. More specifically, it refers to modifying the nucleic acids encoding the original (pre-modified) amino acid residues to the nucleic acids encoding the amino acid residues that are to be introduced by the modification. Ordinarily, it means performing a gene manipulation or a mutation treatment that would result in at least one nucleotide insertion, deletion, or substitution to an original nucleic acid so that codons encoding amino acid residues of interest is formed. More specifically, codons encoding the original amino acid residues are substituted with codons encoding the amino acid residues that are to be introduced by the modification. Such nucleic acid modifications can be suitably performed by those skilled in the art using known techniques such as site-directed mutagenesis and PCR mutagenesis.

Furthermore, nucleic acids of the present invention are usually carried by (inserted into) suitable vectors and then introduced into host cells. These vectors are not particularly limited so long as the inserted nucleic acids are stably maintained. For example, when using *E. coli* as the host, the cloning vector is preferably pBluescript vector (Stratagene) and such, but various commercially available vectors may be used. Expression vectors are particularly useful as vectors for producing the polypeptides of the present invention. Expression vectors are not particularly limited so long as they can express polypeptides in test tubes, *E. coli*, cultured cells, or individual organisms. For example, preferred vectors include pBEST vector (Promega) for expression in test tubes, pET vector (Invitrogen) for *E. coli*, pME18S-FL3 vector (GenBank Accession No. AB009864) for cultured cells, and pME18S vector (Mol. Cell Biol. 8: 466-472 (1998)) for individual organisms. Insertion of a DNA of the present invention into vectors can be performed by standard methods such as ligase reactions using restriction enzyme sites (Current protocols in Molecular Biology edit. Ausubel et al. (1987) Publish. John Wiley & Sons. Section 11.4-11.11).

The above-mentioned host cells are not particularly limited, and various host cells can be used, depending on the purpose. Cells used for expressing the polypeptides include bacterial cells (for example, *Streptococcus, Staphylococcus, E. coli, Streptomyces*, and *Bacillus subtilis*), fungal cells (for example, yeast and *Aspergillus*), insect cells (for example, *Drosophila* S2 and *Spodoptera* SF9), animal cells (for example, CHO, COS, HeLa, C127, 3T3, BHK, HEK293, and Bowes melanoma cell), and plant cells. Vectors can be introduced into host cells using known methods such as the calcium phosphate precipitation method, electroporation method (Current protocols in Molecular Biology edit. Ausubel et al. (1987) Publish. John Wiley & Sons. Section 9.1-9.9), lipofection method, and microinjection method.

For secreting host cell-expressed polypeptides into the lumen of the endoplasmic reticulum, periplasmic space, or extracellular environment, suitable secretion signals can be incorporated into the polypeptides of interest. These signals may be intrinsic or foreign to the polypeptides of interest.

When the polypeptides of the present invention are secreted into the culture media, the polypeptides produced by the above-mentioned methods can be harvested by collecting the media. When the polypeptides of the present invention are produced inside cells, first, the cells are lysed, and then these polypeptides are collected.

The polypeptides of the present invention can be collected and purified from recombinant cell cultures by using known methods, including ammonium sulfate or ethanol precipitation, acidic extraction, anion or cation exchange chromatography, phosphocellulose chromatography, hydrophobic interaction chromatography, affinity chromatography, hydroxyapatite chromatography, and lectin chromatography.

The present invention relates to compositions (pharmaceutical agents) which comprise polypeptides (for example, IgG antibodies) comprising an FcRn-binding domain, whose pharmacokinetics in blood is controlled by the methods of the present invention, and pharmaceutically acceptable carriers.

In the present invention, pharmaceutical compositions usually refer to pharmaceutical agents for treating or preventing, or testing and diagnosing diseases.

The pharmaceutical compositions of the present invention can be formulated by methods known to those skilled in the art. For example, such pharmaceutical compositions can be used parenterally, as injections which are sterile solutions or suspensions including the compositions along with water or another pharmaceutically acceptable liquid. For example, such compositions may be formulated as unit doses that meet the requirements for the preparation of pharmaceuticals by appropriately combining the compositions with pharmaceutically acceptable carriers or media, specifically with sterile water, physiological saline, a vegetable oil, emulsifier, suspension, surfactant, stabilizer, flavoring agent, excipient, vehicle, preservative, binder or such. In such preparations, the amount of active ingredient is adjusted such that an appropriate dose that falls within a pre-determined range can be obtained.

Sterile compositions for injection can be formulated using vehicles such as distilled water for injection, according to standard protocols for formulation.

Aqueous solutions for injection include, for example, physiological saline and isotonic solutions containing dextrose or other adjuvants (for example, D-sorbitol, D-mannose, D-mannitol, and sodium chloride). Appropriate solubilizers, for example, alcohols (ethanol and such), polyalcohols (propylene glycol, polyethylene glycol, and such), nonionic surfactants (polysorbate 80™, HCO-50, and such), may be used in combination.

Oils include sesame and soybean oils. Benzyl benzoate and/or benzyl alcohol can be used in combination as solubilizers. Buffers (for example, phosphate buffer and sodium acetate buffer), soothing agents (for example, procaine hydrochloride), stabilizers (for example, benzyl alcohol and phenol), and/or antioxidants can also be combined. Prepared injections are generally filled into appropriate ampules.

The pharmaceutical compositions of the present invention are preferably administered parenterally. For example, the compositions may be injections, transnasal compositions, transpulmonary compositions or transdermal compositions. For example, such compositions can be administered systemically or locally by intravenous injection, intramuscular injection, intraperitoneal injection, subcutaneous injection or such.

The administration methods can be appropriately selected considering the patient's age and symptoms. The dose of a pharmaceutical composition comprising an antibody or a polynucleotide encoding an antibody may be, for example, from 0.0001 to 1000 mg/kg for each administration. Alternatively, the dose may be, for example, from 0.001 to 100,000 mg per patient. However, the doses in the present invention are not limited to the ranges described above. The doses and administration methods vary depending on a patient's weight, age, symptoms and such. Those skilled in the art can select appropriate doses and administration methods considering the factors described above.

The present invention also provides nucleic acids encoding polypeptides that comprise polypeptides (for example, humanized antibodies) comprising an FcRn-binding domain, whose pharmacokinetics in blood is controlled by the methods of the present invention. Furthermore, vectors carrying these nucleic acids are encompassed by the present invention.

The present invention also provides host cells carrying the above described nucleic acids. The host cells are not particularly limited and include, for example, *E. coli* and various animal cells. The host cells may be used, for example, as a production system to produce and express the antibodies or the polypeptides of the present invention. In vitro and in vivo production systems are available for polypeptide production systems. Production systems that use eukaryotic cells or prokaryotic cells are examples of in vitro production systems.

Eukaryotic cells that can be used as a host cell include, for example, animal cells, plant cells, and fungal cells. Animal cells include mammalian cells such as CHO (J. Exp. Med. (1995) 108: 945), COS, HEK293, 3T3, myeloma, BHK (baby hamster kidney), HeLa, and Vero; amphibian cells such as *Xenopus laevis* oocytes (Valle, et al. (1981) Nature 291: 338-340); and insect cells such as Sf9, Sf21, and Tn5. In the expression of the antibodies of the present invention, CHO-DG44, CHO-DX11B, COS7 cells, HEK293 cells, and BHK cells can be suitably used. Among animal cells, CHO cells are particularly preferable for large-scale expression. Vectors can be introduced into a host cell by, for example, calcium phosphate methods, DEAE-dextran methods, methods using cationic liposome DOTAP (Boehringer-Mannheim), electroporation methods, or lipofection methods.

Plant cells include, for example, *Nicotiana tabacum*-derived cells and duckweed (*Lemna minor*) known as a protein production system. Calluses can be cultured from these cells to produce the antibodies of the present invention. Known protein production systems are those using fungal cells including yeast cells, for example, cells of genus *Saccharomyces* (such as *Saccharomyces cerevisiae* and *Saccharomyces pombe*); and cells of filamentous fungi, for example, genus *Aspergillus* (such as *Aspergillus niger*). These cells can be used as a host to produce the antibodies of the present invention.

Bacterial cells can be used in prokaryotic production systems. Examples of bacterial cells include *Bacillus subtilis* as well as *E. coli* described above. Such cells can be used to produce the antibodies of the present invention.

When producing an antibody using a host cell of the present invention, the polynucleotide encoding an antibody of the present invention may be expressed by culturing the host cell transformed with an expression vector containing the polynucleotide. The culture can be performed using known methods. For example, when using animal cells as a host, DMEM, MEM, RPMI 1640, or IMDM may be used as the culture medium, and may be used with or without serum supplements such as FBS or fetal calf serum (FCS). The preferred pH is about 6 to 8 during the culture. The culture is carried out typically at a temperature of about 30 to 40° C. for about 15 to 200 hours. Medium is exchanged, aerated, or agitated, as necessary.

On the other hand, production systems using animals or plants may be used as systems for producing polypeptides in vivo. For example, a polynucleotide of interest is introduced into an animal or plant and the polypeptide is produced in the body of the animal or plant and then collected. The "hosts" of the present invention include such animals and plants.

Animals to be used for production systems include mammals and insects. Mammals such as goats, pigs, sheep, mice, and cattle may be used (Vicki Glaser SPECTRUM Biotechnology Applications (1993)). Alternatively, the mammals may be transgenic animals.

For example, a polynucleotide encoding an antibody of the present invention may be prepared as a fusion gene with a gene encoding a polypeptide specifically produced in milk, such as the goat β-casein gene. Polynucleotide fragments containing the fusion gene are injected into goat embryos, which are then transplanted into female goats. The desired antibody can be obtained from milk produced by the transgenic goats born from the goats that received the embryos, or from their offspring. Appropriate hormones may be administered to the transgenic goats to increase the volume of milk containing the antibody produced by the goats (Ebert et al., Bio/Technology 12: 699-702 (1994)).

Insects such as silkworms, may also be used for producing the antibodies of the present invention. Baculoviruses carrying a polynucleotide encoding an antibody of interest can be used to infect silkworms, and the antibody of interest can be obtained from the body fluids of the silkworms (Susumu et al., Nature 315: 592-594 (1985)).

Plants used for producing the antibodies of the present invention include, for example, tobacco. When tobacco is used, a polynucleotide encoding an antibody of interest is inserted into a plant expression vector, for example, pMON 530, and then the vector is introduced into a bacterium such as *Agrobacterium tumefaciens*. The bacteria are then used to infect tobacco such as *Nicotiana tabacum*, and the desired antibody can be obtained from the leaves (Ma et al., Eur. J. Immunol. 24: 131-138 (1994)). Alternatively, duckweed (*Lemna minor*) is infected with similar bacteria and then cloned. The desired antibody can be obtained from the cloned duckweed cells (Cox K M et al. Nat. Biotechnol. 2006 December; 24(12): 1591-1597).

The resulting antibody may be isolated from the inside or outside (such as the medium and milk) of host cells, and purified as a substantially pure and homogenous antibody. Methods for isolating and purifying antibodies are not limited to any specific method and any standard method for isolating and purifying polypeptides may be used. Antibodies can be isolated and purified, by appropriately selecting or combining, for example, chromatographic columns, filtration, ultrafiltration, salting out, solvent precipitation, solvent extraction, distillation, immunoprecipitation, SDS-polyacrylamide gel electrophoresis, isoelectric focusing, dialysis, recrystallization, and others.

Chromatographies include, for example, affinity chromatographies, ion exchange chromatographies, hydrophobic chromatographies, gel filtrations, reverse-phase chromatographies, and adsorption chromatographies (Strategies for Protein Purification and Characterization: A Laboratory Course Manual. Ed Daniel R. Marshak et al., Cold Spring Harbor Laboratory Press, 1996). These chromatographies can be carried out using liquid phase chromatographies such as HPLC and FPLC. Examples of affinity chromatography columns include protein A columns and protein G columns. Examples of the proteins A columns include Hyper D, POROS, and Sepharose F. F. (Pharmacia).

An antibody can be modified freely and peptide portions can be deleted from it by treating the antibody with an appropriate protein modifying enzyme before or after antibody purification, as necessary. Such protein modifying enzymes include, for example, trypsins, chymotrypsins, lysyl endopeptidases, protein kinases, and glucosidases.

The above-described methods for producing polypeptides of the present invention comprising an FcRn-binding domain, whose pharmacokinetics in blood is controlled, which comprise culturing host cells of the present invention and collecting the polypeptides from the cell cultures, are also preferred embodiments of the present invention.

All prior art documents cited herein are incorporated herein by reference.

EXAMPLES

Herein below, the present invention is specifically described with reference to Examples, but it is not to be construed as being limited thereto.

Example 1

Humanization of Bispecific Antibody

A bispecific antibody consisting of the combination of the anti-Factor IXa antibody A69-VH, anti-Factor X antibody B26-VH, and hybrid L chain (BBA), which was found to be most effective in shortening blood coagulation time in Japanese Patent Application No. 2005-112514, was humanized as described below.

1-1. Homology Search of Humanized Antibodies

Using a database constructed by obtaining amino acid sequence data of human antibodies from the publicly-disclosed Kabat Database (ftp://ftp.ebi.ac.uk/pub/databases/kabat/) and IMGT Database (http://imgt.cines.fr/), homology search was carried out separately for the mouse A69-H chain variable region (amino acid sequence; SEQ ID NO: 15), mouse B26-H chain variable region (amino acid sequence; SEQ ID NO: 16), and mouse BBA-L chain variable region (amino acid sequence; SEQ ID NO: 17). The results confirmed that they have high homologies to the human antibody sequences shown below, and thus it was decided that they would be used as the framework regions (hereinafter abbreviated as FRs) of humanized antibodies.

(1) A69-H chain variable region: KABATID-000064 (Kabat Database) (Kipps et al., J. Clin. Invest. 1991; 87:2087-2096)

(2) B26-H chain variable region: EMBL Accession No. AB063872 (IMGT Database) (Unpublished data)

(3) BBA-L chain variable region: KABATID-024300 (Kabat Database) (Welschof et al., J. Immunol. Method 1995; 179:203-214)

Humanized antibodies in which complementarity determining regions (hereinafter abbreviated as CDRs) of each mouse antibody were grafted into the FRs of the human antibodies (1)-(3) were prepared.

Also, the web homology search site publicly disclosed by NCBI (http://www.ncbi.nlm.nih.gov/BLAST/) was used to search secretory signal sequences of human antibodies that are highly homologous to the human antibodies of (4)-(6). The following secretory signal sequences obtained by the search were used.

(4) A69-H chain variable region: GenBank Accession No. AF062257
(5) B26-H chain variable region: GenBank Accession No. AAC 18248
(6) BBA-L chain variable region: GenBank Accession No. AAA59100

1-2. Construction of Humanized Antibody Gene Expression Vector

Twelve synthetic oligoDNAs of about 50 bases were prepared from a nucleotide sequence encoding the amino acid sequence from a secretory signal sequence to an antibody variable region, such that about 20 bases of their 3'-end anneal with each other. The synthetic oligoDNAs were designed so that the 5'-terminal nucleotides encode a human sequence, the 3'-terminal nucleotides encode a mouse sequence, or all nucleotides encode human sequences. Furthermore, a primer annealing to the 5'-end of an antibody variable region gene and having the XhoI cleavage sequence, and a primer annealing to the 3'-end of an antibody variable region gene, having the SfiI cleavage sequence and also encoding the 5'-end sequence of an intron sequence were prepared.

1 µl each of the synthetic oligoDNAs prepared at 2.5 µM were mixed, and 1× TaKaRa Ex Taq Buffer, 0.4 mM dNTPs, and 0.5 units TaKaRa Ex Taq (all from Takara) were added to prepare 48 µl of a reaction solution. After heating this at 94° C. for 5 minutes, 2 cycles of reacting at 94° C. for 2 minutes, 55° C. for 2 minutes, and 72° C. for 2 minutes were performed to assemble and elongate each of the synthetic oligoDNAs. Next, 1 µl (10 µM each) of primers annealing to the 5'-end and to the 3'-end of the antibody gene were added, and the antibody variable region genes were amplified by 35 cycles of reacting at 94° C. for 30 seconds, 55° C. for 30 seconds, and 72° C. for 1 min and then reacting at 72° C. for 5 minutes. After PCR, the whole amount of the reaction solution was subjected to 1% agarose gel electrophoresis. Amplified fragments having the size of interest (approximately 400 bp) were purified using the QIAquick Gel Extraction Kit (QIAGEN) according to the method described in the instruction manual, and were eluted with 30 µl of sterile water. These fragments were cloned using the pGEM-T Easy Vector System (Promega) according to the method described in the instruction manual. The nucleotide sequence of each of the DNA fragments was determined using the BigDye Terminator Cycle Sequencing Kit (Applied Biosystems) and ABI PRISM 3730xL DNA Sequencer or ABI PRISM 3700 DNA Sequencer (Applied Biosystems) according to the method described in the instruction manual.

The H-chain variable region fragment-inserted plasmid and the L-chain variable region fragment-inserted plasmid, each of which was confirmed to have a correct humanized antibody variable region gene sequence, were digested with XhoI and SfiI, and EcoRI respectively. Next, the reaction solution was subjected to 1% agarose gel electrophoresis. DNA fragments having the size of interest (approximately 400 bp) were purified using QIAquick Gel Extraction Kit (QIAGEN) according to the method described in the instruction manual, and eluted with 30 µl of sterile water. Then, expression vectors for animal cells were prepared as follows. To preferentially express IgG4 whose H chains are of a heterologous combination, a CH3 portion amino acid-substituted IgG4 was used by referring to the knobs-into-holes technique of IgG1 (Merchant A M et al., Nature Biotechnology, Vol. 16, p. 677-681 (1998)). Furthermore, to promote H chain dimer formation, amino acid substitution (-ppcpScp-→-ppcpPcp-) was also introduced to the hinge. Humanized A69 H chain expression vector was prepared by inserting a humanized A69 H chain variable region antibody gene fragment into an expression vector prepared by inserting Y349C and T366W-substituted constant region gene to pCAGGS comprising a chicken β-actin promoter (Niwa et al., Gene Vol. 108, p. 193-199 (1991)). In addition, humanized B26 H chain expression vector was prepared by inserting a humanized B26 H chain variable region antibody gene fragment into an expression vector prepared by inserting E356C, T366S, L368A, and Y407V-substituted constant region gene to pCAGGS. The plasmid (pCAG-gκDNA) prepared by inserting a wild type antibody L chain constant region into pCAGGS was digested with EcoRI to prepare an expression vector inserted with a humanized BBA L chain variable region antibody gene fragment. Ligation reaction was performed using Rapid DNA Ligation Kit (Roche Diagnostics), and DH5α strain *E. coli* (TOYOBO) was transformed.

1-3. Expression of the Humanized Bispecific Antibody

The humanized bispecific antibody was expressed according to the following method. Human fetal renal carcinoma cell-derived HEK293H strain (Invitrogen) was suspended in DMEM medium (Invitrogen) containing 10% Fetal Bovine Serum (Invitrogen), and 10 ml of this was seeded at a cell density of 5-6×$10^5$ cells/ml in each dish used for adhesive cells (10-cm diameter, CORNING) and cultured for one day in a $CO_2$ incubator (37° C., 5% $CO_2$). Then, the medium was removed by suction, and 6.9 ml of CHO-S-SFM-II medium (Invitrogen) containing 1% Fetal Bovine Serum (Invitrogen) was added. The plasmid DNA mixture solution prepared in Example 1-2 (total of 13.8 µg) was mixed with 20.7 µl of 1 µg/ml Polyethylenimine (Polysciences Inc.) and 690 µl of CHO-S-SFMII medium, left to stand at room temperature for 10 minutes, then the cells were added to the cells in each dish and incubated in a $CO_2$ incubator (37° C., 5% $CO_2$) for 4-5 hours. Thereafter, 6.9 ml of CHO-S-SFM-II medium (Invitrogen) containing 1% Fetal Bovine Serum (Invitrogen) was added and then the cells were incubated in a $CO_2$ incubator for 3 days. The culture supernatant was recovered, then cells were removed by centrifugation (at approximately 2000 g for 5 minutes at room temperature), and the solution was sterilized by passing it through a 0.22 µm filter MILLEX®-GV (Millipore). The sample was stored at 4° C. until use.

1-4. Purification of the Humanized Bispecific Antibody

100 µl of rProtein A Sepharose™ Fast Flow (Amersham Biosciences) was added to the culture supernatant obtained according to the method described in Example 1-2, and the solution was mixed by inversion at 4° C. for 4 hours or more. The solution was transferred to a 0.22 µm filter cup, Ultrafree®-MC (Millipore), and after washing 3 times with 500 µl of TBS containing 0.01% Tween®, 20, the rProtein A Sepharose™ resin was suspended in 100 µl of 50 mM sodium acetate solution containing 0.01% Tween® 20 at pH 3.3 and left to stand for 2 minutes. Then, the antibody was eluted, and the eluate was immediately neutralized by adding 6.7 µl of 1.5 M Tris-HCl, pH 7.8.

1-5. Quantification of Humanized Bispecific Antibody Concentration

The antibody concentration was determined using the following two types of methods.

Goat anti-human IgG (Biosource International) was adjusted to 1 µg/ml with a coating buffer, and immobilized to a Nunc-Immuno plate (Nunc). After blocking with a diluent buffer (D.B.), a sample of the culture supernatant suitably diluted with D.B. was added. Furthermore, as a standard for calculating the antibody concentration, human IgG4 (humanized anti-TF antibody, see WO 99/51743) diluted with D.B. in a three-fold dilution series up to eleven stages starting from 2000 ng/ml was added similarly. After three washes, a goat anti-human IgG, alkaline phosphatase (Biosource International) was reacted. After five washes, the color was developed using Sigma 104® phosphatase substrate (Sigma-Aldrich) as a substrate, and the absorbance at 405 nm was measured on an absorbance reader Model 3550 (Bio-Rad Laboratories) with a reference wavelength of 655 nm. Using the Microplate Manager III (Bio-Rad Laboratories) software, human IgG concentration in the culture supernatant was calculated from the standard curve.

Furthermore, the antibody concentration was quantified using Sensor Chip CM5 (BIACORE) to which Protein A had been immobilized, with Biacore 1000 or Biacore Q (BIACORE). More specifically, Protein A-immobilized sensor chip was prepared according to the manufacturer's protocol by reacting an activated sensor chip with a Protein A solution (SIGMA) diluted to 50 µg/ml with 10 mM aqueous sodium acetate solution (pH 4.0, BIACORE) at 5 µl/min for 30 minutes, and then performing a blocking operation. This sensor chip was used to measure the concentration of the culture supernatant and the purified product using BIAcore 1000 (BIACORE). HBS-EP Buffer (BIACORE) was used for the immobilization of the sensor chip and for the measurements of concentration. As a standard for concentration measurements, humanized IgG4 antibody (humanized anti-tissue factor antibody, see WO 99/51743) diluted with HBS-EP Buffer in a two-fold dilution series up to six stages beginning at 4000 ng/ml was used.

1-6. Assessment of Blood Coagulation Activity of Humanized Bispecific Antibody

To elucidate whether a bispecific antibody corrects the coagulation ability of hemophilia A blood, effects of the bispecific antibody on activated partial thromboplastin time (APTT) were examined using Factor VIII-deficient plasma. A mixed solution comprising 50 µl of an antibody solution at various concentrations, 50 µl of Factor VIII-deficient plasma (Biomerieux), and 50 µl of APTT reagent (Dade Behring) was heated at 37° C. for 3 minutes. Coagulation reaction was initiated by adding 50 µl of 20 mM $CaCl_2$ (Dade Behring) to this mixed solution. The time required for coagulation was measured with CR-A (Amelung)-connected KC10A (Amelung).

Using a calibration curve provided by defining the coagulation time of Factor VIII-deficient plasma as 0% and that of normal plasma as 100%, Factor VIII-like activity (%) of a bispecific antibody was calculated from the coagulation time measured when the bispecific antibody was added.

1-7. Preparation of Humanized Bispecific Antibody Retaining Blood Coagulation Activity For humanized bispecific antibodies which had reduced blood coagulation ability in the above-described blood coagulation activity assessment, amino acids of their human antibody FRs were modified to increase their activities. Specifically, mutations were introduced to the humanized antibody variable region using a QuikChange Site-Directed Mutagenesis Kit (Stratagene) according to the method described in the instruction manual. The H-chain variable region fragment-inserted plasmid and L-chain variable region fragment-inserted plasmid were confirmed to have the humanized antibody variable region gene sequences of interest and were digested with XhoI and SfiI, and EcoRI respectively. The reaction solution was subjected to 1% agarose gel electrophoresis. DNA fragments having the size of interest (approximately 400 bp) were purified using a QIAquick Gel Extraction Kit (QIAGEN) according to the method described in the instruction manual, and eluted with 30 µl of sterile water. Then, expression vectors for animal cells were prepared according to the method described in Example 1-2. A humanized bispecific antibody was prepared according to the method described in Examples 1-3, 1-4, and 1-5 and blood coagulation activity was evaluated according to the method described in Example 1-6.

By repeated amino acid modifications of the FR sequences and assessment of blood coagulation ability, a humanized bispecific antibody (humanized A69 (hA69a)/humanized B26 (hB26-F123e4)/humanized BBA (hAL-F123j4)) having the same level of activity as the chimeric bispecific antibody (A69/B26/BBA) was obtained (FIG. 1). Each of the antibody variable region sequences is indicated in the following SEQ ID NOs.

(1) humanized A69 antibody VH (hA69a) SEQ ID NO: 1 (nucleotide sequence), SEQ ID NO: 2 (amino acid sequence)
(2) humanized B26 antibody VH (hB26-F123e4) SEQ ID NO: 3 (nucleotide sequence), SEQ ID NO: 4 (amino acid sequence)
(3) humanized BBA antibody VL (hAL-F123j4) SEQ ID NO: 5 (nucleotide sequence), SEQ ID NO: 6 (amino acid sequence)

Example 2

Figure 2:
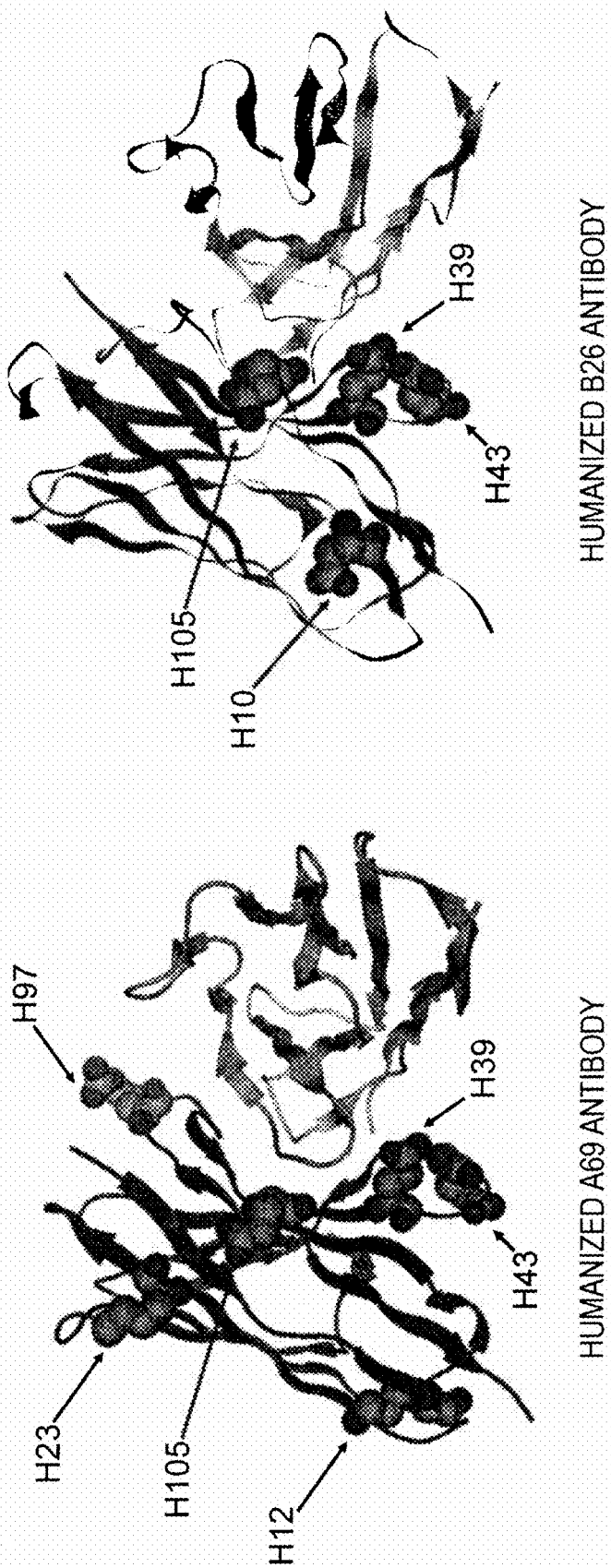
FIG. 2 is a diagram showing antibody modeling for the combinations of humanized A69-H chain variable region (hA69a) and humanized BBA (hAL-F123j4), and humanized hB26-H chain variable region (hB26-F123e4) and humanized BBA (hAL-F123j4). The side chains of amino acids that can change the surface charge are shown emphasized. The numbering was done according to the Kabat database numbering system (Kabat E A et al., (1991) Sequences of Proteins of Immunological Interest. NIH).

Selection of Amino Acid Modification Sites in Variable Regions to Isolate a Bispecific Antibody Antibody Fv region models for humanized A69 and B26 antibodies were prepared by homology modeling using MOE software (Chemical Computing Group Inc.) to confirm amino acid residues exposed on the surface of variable regions of these antibodies. The models are shown in FIG. 2. A detailed analysis of the models suggested that among surface-exposed amino acids in the FR sequences other than CDRs, those at H10, H12, H23, H39, H43, and H105 (according to the Kabat's numbering; Kabat E A et al. 1991. Sequences of Proteins of Immunological Interest. NIH) were candidate amino acids that could be modified to shift the isoelectric point without reduction of activity. The amino acid at H97 was selected as a surface-exposed amino acid in CDRs.

Example 3

Modification of Variable Region Amino Acid Sequences of Humanized A69 Antibody and Modified Form Thereof, and Humanized B26 Antibody Amino acids of the H chain variable regions of humanized A69 and B26 antibodies were modified to shift the isoelectric points of the antibodies. Specifically, mutations were introduced into the H chain variable regions of humanized A69 antibody (hA69a; nucleotide SEQ ID NO: 1) and humanized B26 antibody (hB26-F123e4; nucleotide SEQ ID NO: 3) prepared using a QuikChange Site-Directed Mutagenesis Kit (Stratagene) according to the method described in the attached instruction manual. H chain variable region fragment-inserted plasmids which had been confirmed to have the sequence of humanized antibody variable region gene of interest were digested with XhoI and SfiI, and then the reaction mixtures were subjected to electrophoresis using 1% agarose gel. DNA fragments having the size of interest (about 400 bp) were purified using a QIAquick Gel Extraction Kit (QIAGEN) according to the method described in the attached instruction manual, and then eluted using 30 µl of sterile water. The DNA fragments were inserted into an expression plasmid carrying the wild type constant region by the method described in Example 1-2 to construct H chain expression vectors. Modified amino acid residues in the respective antibodies and their SEQ IDs are shown in Table 1. (hA69-N97R, hA69-p18), and humanized B26 antibody (hB26-F123e4) and its modified form (hB26-p15) were prepared. A humanized A69 antibody (hA69a) and its modified forms (hA69-N97R, hA69-p18) were expressed using a combination of H chain expression vectors (variable region is hA69-N97R, hA69-p18) and an an L chain expression vector (variable region is hAL-F123j4; SEQ ID NO: 6) according to Example 1-3. Meanwhile, a humanized B26 antibody (hB26-F123e4) and its modified form (hB26-p15) were expressed using a combination of H chain expression vectors (variable region is hB26-F123e4, hB26-p15) and an L chain expression vector (variable region is B26-VL; the amino acid sequence is described in WO2005/035756 (SEQ ID NO: 18)) according to Example 1-3. The antibodies were purified from culture supernatants by the method described in Example 1-4.

TABLE 1

| Humanized A69-H chain variable region | | |
|---|---|---|
| Name | Modification site | Amino acid SEQ ID NO: |
| hA69a | — | 2 |
| hA69-p18 | Q43E, Q105E | 7 |
| HA69-N97R | N97R | 9 |

| Humanized B26-H chain variable region | | |
|---|---|---|
| Name | Modification site | Amino acid SEQ ID NO: |
| hB26-F123e4 | — | 4 |
| hB26-p15 | Q39K, Q43K, Q105R | 10 |

Example 4

Establishment of a Cell Line that Expresses a Bispecific Antibody Derived from Humanized A69 or B26 Antibodies To prepare a humanized bispecific antibody, an antibody-expressing cell line was established by the procedure described below.

An H-chain constant region was amplified by PCR using a wild-type human IgG4 H-chain constant region gene as a template and using a 5'-end primer designed so that the nucleotide sequence encoding two amino acids (Ala-Ser) in the N-terminal side of the H-chain constant region will be an NheI recognition sequence (GCTAGC) and a primer that anneals to the 3'-end and that carries a NotI recognizing site. Then, the amplified fragments were ligated to pBluescriptKS+ vector (TOYOBO) digested with NheI and Not I (both from Takara) to prepare pBCH4 (comprising an IgG4 constant region gene). PCR was performed using primers which are complementary to the 5'-end nucleotide sequence of the H-chain variable regions of the humanized A69-H chain antibody (hA69-PFL: SEQ ID NO: 11) and humanized B26-H chain antibody (hB26-PF: SEQ ID NO: 12) and which have a Kozak sequence (CCACC) and an EcoRI recognition sequence, and a primer on the 3'-end nucleotide sequence having an NheI recognition sequence. The obtained PCR products were digested with EcoRI and NheI (both from Takara) and inserted into pBCH4 also digested with EcoRI and NheI, and then the variable regions and the constant regions were linked. The prepared vector for humanized A69-H chain antibody was digested with EcoRI and NotI (both Takara), and then cloned into the animal cell expression vector pCXND3 digested with EcoRI and NotI. The procedure for the construction of the vector pCXND3 is described below.

DHFR-ΔE-rVH-PM1-f (see WO92/19759) was cleaved at the EcoRI and SmaI restriction sites to separate the vector backbone form the antibody H chain gene. Only the vector backbone was recovered, and then an EcoRI-NotI-BamHI adaptor (Takara) was cloned into it. The resulting vector was named pCHOI. The DHFR gene expression region derived from pCHOI was cloned into pCXN (Niwa et al., Gene 108: 193-200 (1991)) at the HindIII restriction site. The resulting vector was named pCXND3. In addition, the prepared vector for humanized B26-H chain antibody was digested with EcoRI and NotI (both Takara), and then cloned into the animal cell expression vector pCXZD1 digested with EcoRI and NotI. pCXZD1 vector is an expression vector obtained from pCXND3 by substituting the Zeocin resistance gene for the neomycin resistance gene. Furthermore, an L-chain expression vector was prepared by inserting the L chain variable region of the humanized BBA-L chain antibody (hAL-s8; SEQ ID NO: 8) into a plasmid (pCAG-gκDNA) having an inserted L chain constant region according to Example 1-2. The prepared three types of expression vectors were linearized with restriction enzymes and then introduced into CHO-DG44 cells to establish an antibody-expressing cell line.

A stable expression cell line was prepared by the procedure described below. Genes were introduced by electroporation using GenePulserXcell (Bio-Rad). Each antibody expression vector was combined with 0.75 ml of CHO cells suspended in PBS ($1 \times 10^7$ cells/ml). The mixtures were cooled on ice for ten minutes, transferred into cuvettes, and pulsed at 1.5 kV and 25 µFD. After a ten-minute restoration period at room temperature, the electroporated cells were suspended in 40 ml of CHO-S-SFMII medium (Invitrogen) containing 1× HT supplement (Invitrogen). The suspension was diluted 10 times with the same medium and aliquoted into 96-well culture plates at 100 µl/well. After 24 hours of culture in a $CO_2$ incubator (5% $CO_2$), Geneticin and Zeocin (both Invitrogen) were added at 0.5 mg/ml and 0.6 mg/ml, respectively. The cells were cultured for two weeks. Expansion cultures were sequentially performed for colonies of drug-resistant transformants. An established high expression cell line was used for large scale culture to obtain the culture supernatant.

Example 5

Separation and Purification of Humanized Antibody Homodimers and a Humanized Bispecific Antibody Using the method described below, the bispecific antibody was purified from the culture supernatants obtained in Example 4. The culture supernatants were loaded onto an rProtein A Sepharose Fast Flow column (Amersham Biosciences; 50 mm I.D.×9.9 cm H.=194.3 ml resin) equilibrated with an equilibration buffer (20 mmol/l sodium phosphate buffer, 150 mol/l NaCl, pH 7.0). After washing with wash buffer 1 (20 mmol/l sodium phosphate buffer, 150 mol/l NaCl, pH 7.0) and wash buffer 2 (50 mmol/l sodium acetate buffer, pH 6.0), the column was eluted with 50 mmol/l acetic acid. Immediately after elution, pH was adjusted to 6.3 by adding 1.5 mol/l Tris-HCl (pH 7.8).

The resulting purified solution was loaded onto an SP TOYOPEARL 650M column (Tosoh; 26 mm I.D.×22.3 cm H.=118.3 ml resin) equilibrated with Solvent A (10 mmol/l sodium phosphate buffer, pH 6.3). The antibodies were separated based on their surface charges using the solutions and gradients indicated below.

---

Solvent A: 20 mmol/l sodium acetate buffer (pH 6.0)
Solvent B: 20 mmol/l sodium acetate buffer, 1 mol/l NaCl (pH 6.0)
Flow rate: 10 ml/min (113 cm/h); 5.3 ml/min (60 cm/h) only at the time of elution

| Gradient: | 0 → 15% B | stepwise | 3 column volumes (CV) |
|---|---|---|---|
| | 15 → 35% B | gradient | 6 CV |
| | 35 → 50% B | gradient | 10 CV |
| | 50 → 100% B | gradient | 3 CV |
| | 100% B | stepwise | 4 CV |

---

Two types of homodimers (hA69-PF and hB26-PF) and a single type of heterodimer, the bispecific antibody BiAb, were obtained by collecting eluted fractions of the detected three peaks separately.

Example 6

Analysis of Prepared Antibodies by Isoelectric Focusing

ATF is a previously obtained monoclonal antibody against human tissue factor, and is a humanized antibody comprising the constant region of human IgG4. The origin of ATF is described in detail in WO99/051743. The amino acid sequences of its H chain and L chain variable regions are shown in SEQ ID Nos: 13 and 14, respectively. hA69-PF, BiAb, and hB26-PF prepared in Example 5; hA69-N97R, hA69-p18, hB26-e, and hB26-p15 prepared in Example 3; and ATF were analyzed by isoelectric focusing to assess changes in the surface charge due to the following: differences in the amino acid sequences of their variable regions and amino acid modifications.

ATF, hA69-PF, BiAb, hB26-PF, and the humanized A69 antibody hA69-N97R and a modified form thereof, hA69-p18, as well as the humanized B26 antibody hB26-F123e4 and a modified form thereof, hB26-p15, were subjected to isoelectric focusing, as described below. Using Phastsystem Cassette (Amersham Bioscience), Phast-Gel Dry IEF gel (Amersham Bioscience) was allowed to swell for about 30 minutes in the swelling solution indicated below.

---

| Milli-Q water | 1.5 ml |
|---|---|
| Pharmalyte 5-8 for IEF (Amersham Bioscience) | 50 µl |
| Pharmalyte 8-10.5 for IEF (Amersham Bioscience) | 50 µl |

---

Electrophoresis was carried out in PhastSystem (Amersham Bioscience) using the swollen gel according to the program indicated below. The samples were loaded onto the gel in Step 2. The pI marker used is a calibration kit for pI (Amersham Bioscience).

| Step 1: | 2000 V | 2.5 mA | 3.5 W | 15° C. | 75 Vh |
|---|---|---|---|---|---|
| Step 2: | 200 V | 2.5 mA | 3.5 W | 15° C. | 15 Vh |
| Step 3: | 2000 V | 2.5 mA | 3.5 W | 15° C. | 410 Vh |

Figure 3:
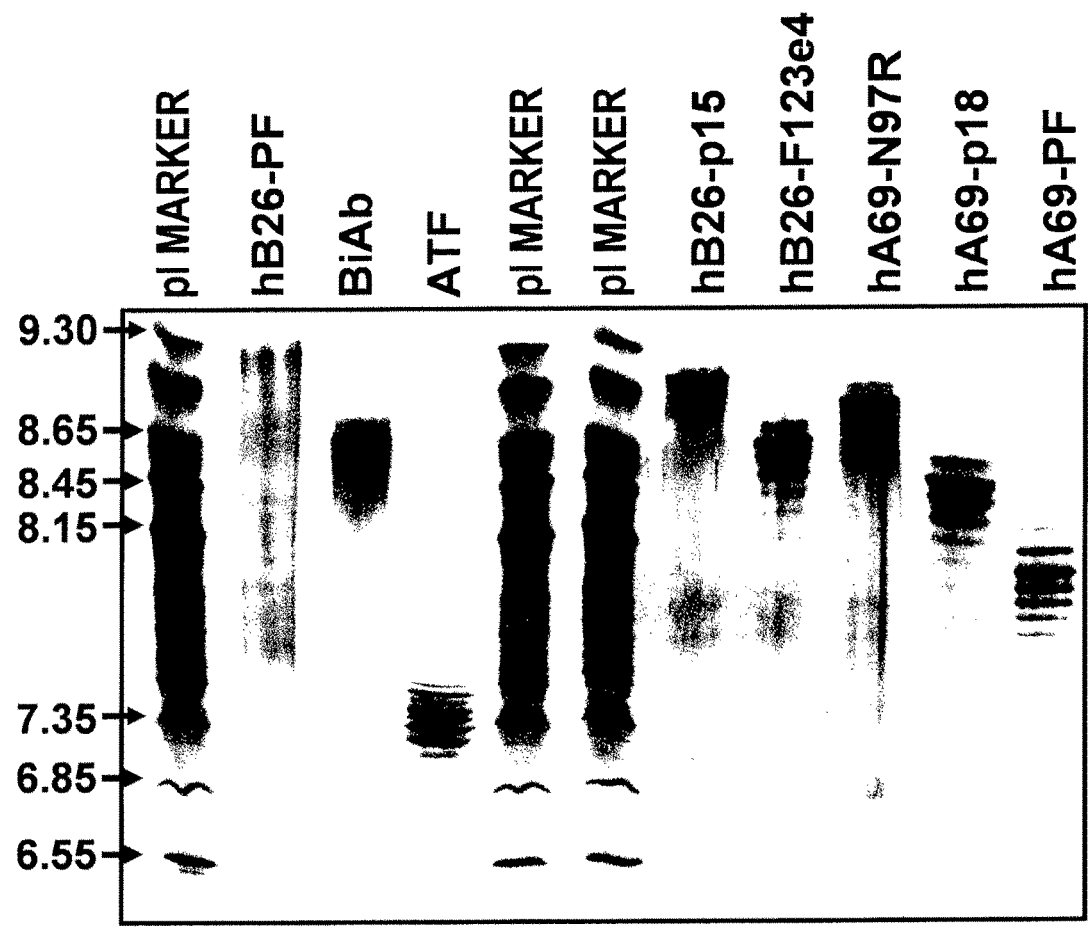
FIG. 3 is a photograph showing a result of isoelectric focusing analysis of ATF, hA69-PF, BiAb, hB26-PF, hA69-N97R, hA69-p18, hB26-F123e4, and hB26-p15.
Figure 4:
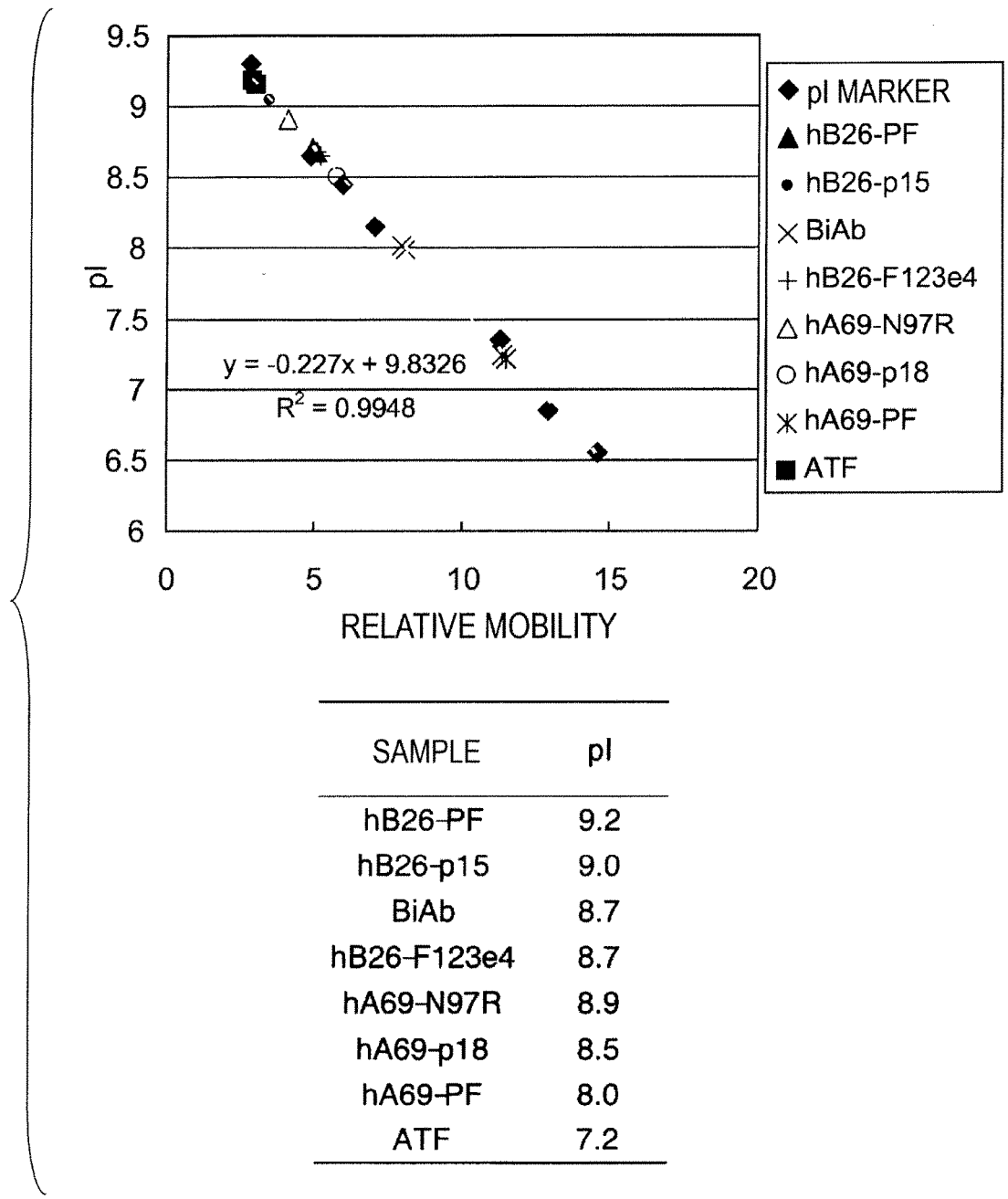
FIG. 4 shows a calibration curve of a pI marker and the pI of each sample determined from the curve, which were obtained from the isoelectric focusing analysis of ATF, hA69-PF, BiAb, hB26-PF, hA69-N97R, hA69-p18, hB26-F123e4, and hB26-p15. The diagrams demonstrate that the surface charge varies depending on the amino acid sequences of variable regions and differences in the surface charge resulting from amino acid modifications shift the pI.

After electrophoresis, the gel was fixed with 20% TCA, and then silver-stained using a silver staining kit protein (Amersham Bioscience) according to the protocol attached to the kit. After staining, the pIs of the samples were calculated from the known pIs of the pI marker. The analysis result of isoelectric focusing is shown in FIG. 3. The calibration curve of pI vs mobility prepared using the pI marker and pIs calculated from the curve are shown in FIG. 4. The pIs were calculated based on the mobility of major bands since each sample exhibited antibody-derived charge heterogeneity.

The result showed that the surface charges were changed due to differences in the amino acid sequences of the variable regions and that the pIs were shifted due to the change in surface charge through amino acid modifications. The pIs were as follows: about 9.2 for hB26-PF, about 8.7 for BiAb, about 8.0 for hA69-PF, about 7.2 for ATF, about 8.9 for hA69-N97R, about 8.5 for hA69-p18, about 8.7 for hB26-F123e4, and about 9.0 for hB26-p15. hA69-N97R, hA69-p18, and hA69-PF were obtained by modifying the same humanized antibody variable region. A pI shift of about 0.9 could be achieved in hA69-PF compared with hA69-N97R, and a pI shift of about 0.3 could be achieved in hB26-p15 compared with hB26-F123e4. The examination described above demonstrates that pI can be shifted depending on the amino acid sequence of a variable region as well as by modifying a surface amino acid at H10, H12, H23, H39, H43, H97, or H105 in a selected variable region to change its charge.

Example 7

Assessment of Humanized Antibodies A69 and B26 and Modified Forms Thereof for Their Binding Activity The functions of the humanized A69 antibody and its modified form were assessed by assaying their binding activities to the antigen Factor IXa, as described below. Humanized A69 antibody (hA69a) and its modified form, hA69-N97R, were assessed by the following procedure. Factor IXaβ (Enzyme Research Laboratories) diluted to 1 µg/ml with a coating buffer (100 mM sodium bicarbonate (pH 9.6), 0.02% sodium azide) was aliquoted (100 µl/well) into a Nunc-Immuno plate (a Nunc-Immuno™ 96 MicroWell™ MaxiSorp™ plate (Nalge Nunc International)), and then the plate was incubated overnight at 4° C. After washing three times with PBS(−) containing Tween® 20, the plate was blocked with a diluent buffer (50 mM Tris-HCl (pH 8.1), 1% bovine serum albumin, 1 mM MgCl$_2$, 0.15 M NaCl, 0.05% Tween® 20, 0.02% sodium azide) at room temperature for two hours. After removal of the buffer, the purified antibodies diluted with the diluent buffer were added to the plate at 100 µl/well. Then, the plate was incubated at room temperature for one hour. After the plate was washed three times, alkaline phosphatase-labeled goat anti-mouse IgG (BIOSOURCE) diluted to 1/4000 with the diluent buffer was added at 100 µl/well. Then, the plate was incubated at room temperature for one hour. After washing the plate five times, a chromogenic substrate (Sigma) was added at 100 µl/well. The plate was then incubated at room temperature for 30 minutes. Absorbance at 405 nm (reference at 655 nm) was measured using the Model 3550 Microplate Reader (Bio-Rad Laboratories).

The modified antibodies (hA69-N97R, hA69-p18, and hA69-PF) used in Example 8 were assessed by the following procedure. After Factor IXa (Enzyme Research Laboratories) diluted to 1 μg/ml with a coating buffer (0.05 M carbonate-bicarbonate buffer, pH 9.6) was aliquoted (100 μl/well) into a Nunc-Immuno plate (a Nunc-Immuno™ 96 MicroWell™ MaxiSorp™ plate (Nalge Nunc International)), the plate was incubated at 4° C. overnight or for a longer period. After washing three times with PBS containing 0.05% Tween® 20, a diluent buffer (Tris buffered saline containing Tween 20 (pH 8.0) (Sigma), 1% bovine serum albumin, 0.02% sodium azide) was added to the plate at 200 μl/well. Then, the plate was blocked at room temperature for two hours. After removal of the buffer, the purified antibodies diluted with the diluent buffer were added at 100 μl/well. The plate was then incubated overnight at 4° C. After washing the plate three times, alkaline phosphatase-labeled mouse anti-human IgG4 (Southern Biotechnology)) diluted to 1/500 with the diluent buffer was added at 100 μl/well. The plate was incubated at room temperature for two hours. After washing the plate five times, the BluePhos Microwell Phosphatase Substrates System (Kirkegaard & Perry Laboratories) was added as a substrate at 100 μl/well. The plate was then incubated at room temperature for about 30 minutes. Absorbance at 650 nm was measured using the Vmax Microplate Reader (Molecular Devices). As shown in FIG. 5, the results demonstrate that the antibodies in which the variable region had been modified to change the surface charge showed a binding activity comparable to that of the original antibodies before modification.

Figure 6:
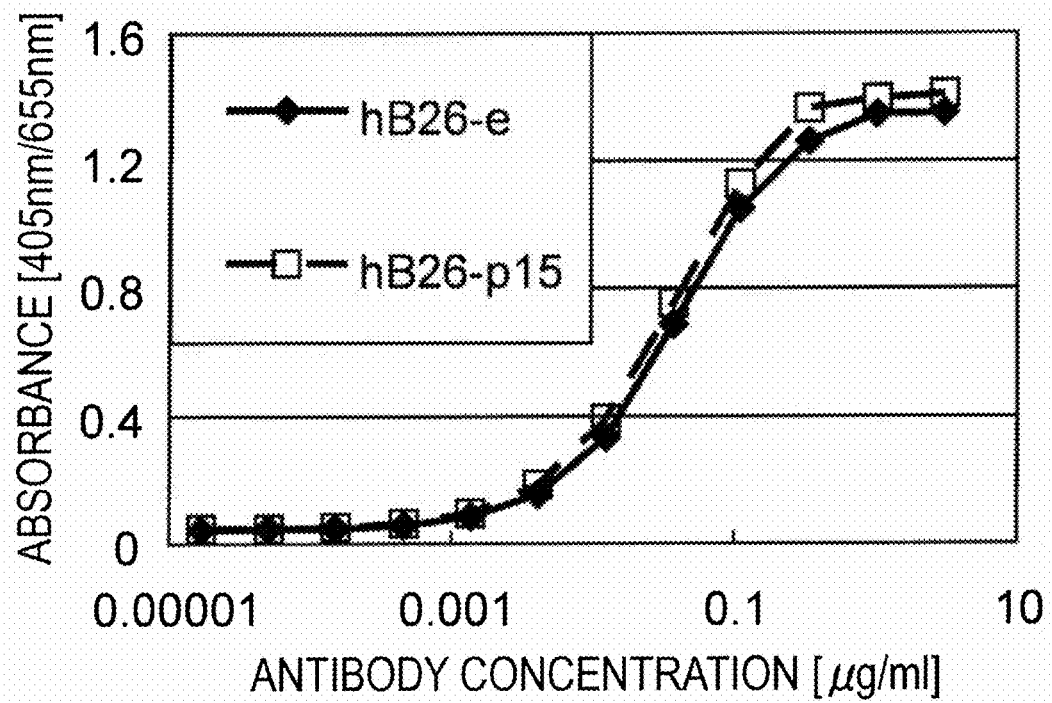
FIG. 6 is a graph showing a result of analyzing humanized B26 antibodies (hB26-F123e4 and hB26-p15) with unmodified or modified variable regions, respectively, for their binding activity to the antigen Factor X. The results demonstrate that the modified antibody with shifted isoelectric point has a binding activity comparable to that of the unmodified antibody.

Furthermore, the functions of the humanized B26 antibody hB26-F123e4 and its modified form, hB26-p15, were assessed by assaying their binding activities to the antigen Factor X. Factor X (Enzyme Research Laboratories) diluted to 1 μg/ml with a coating buffer (100 mM sodium bicarbonate (pH 9.6), 0.02% sodium azide) was aliquoted (100 μl/well) into a Nunc-Immuno plate (a Nunc-Immuno™ 96 MicroWell™ MaxiSorp™ plate), and then the plate was incubated overnight at 4° C. After washing three times with PBS(-) containing Tween® 20, the plate was blocked with a diluent buffer (50 mM Tris-HCl (pH 8.1), 1% bovine serum albumin, 1 mM $MgCl_2$, 0.15 M NaCl, 0.05% Tween® 20, 0.02% sodium azide) at room temperature for two hours. After removal of the buffer, the purified antibodies diluted with the diluent buffer were added at 100 μl/well to the plate. The plate was incubated at room temperature for one hour. After the plate was washed three times, alkaline phosphatase-labeled goat anti-mouse IgG (BIOSOURCE) diluted to 1/4000 with the diluent buffer was added at 100 μl/well. The plate was then incubated at room temperature for one hour. After washing the plate five times, a chromogenic substrate (Sigma) was added at 100 μl/well. The plate was then incubated at room temperature for 30 minutes. Absorbance at 405 nm (reference at 655 nm) was measured using the Model 3550 Microplate Reader (Bio-Rad Laboratories). As shown in FIG. 6, the results demonstrated that the antibody in which the variable region had been modified to change the surface charge showed binding activity comparable to that of the original antibody before modification.

The findings described above demonstrate that the modifications of variable regions performed in the Examples have no influence on the antigen binding activity of the antibodies.

Example 8

Assessment of the Prepared Antibodies for Pharmacokinetics 8-1. Test of Pharmacokinetics Using Mice ATF was obtained as a monoclonal antibody against human tissue factor, and is a humanized antibody comprising the constant regions of human IgG4. The origin of ATF is described in detail in WO99/051743. The amino acid sequences of its H chain and L chain variable regions are shown in SEQ ID NOs: 13 and 14, respectively. hA69-PF, BiAb, and hB26-PF prepared in Example 5, hA69-N97R, hA69-p18, hB26-e, and hB26-p15 prepared in Example 3, and ATF were assessed for the in vivo kinetics in mice (C57BL/6J; Charles River Japan, Inc.). ATF, hA69-PF, BiAb, and hB26-PF were intravenously administered once at 5 mg/kg to mice (C57BL/6J; Charles River Japan, Inc.). The blood was collected before administration and 15 minutes, two hours, eight hours, and one, two, four, seven, 11, 14, 21, and 28 days after administration. The collected blood was immediately centrifuged at 4° C. and 15,000 rpm for 15 minutes to obtain plasma. The separated plasma was stored in a freezer at -20° C. or below until use. Likewise, hA69-N97R, hA69-p18, hB26-F123e4, and hB26-p15 were intravenously administered once at 1 mg/kg to mice (C57BL/6J; Charles River Japan, Inc.). The blood was collected before administration and 15 minutes, two hours, eight hours, and one, two, five, seven, nine, 14, 21, and 28 days after administration. The collected blood was immediately centrifuged at 4° C. and 15,000 rpm for 15 minutes to obtain plasma. The separated plasma was stored in a freezer at -20° C. or below until use.

8-2. Measurement of Plasma Concentration by ELISA

Figure 7:
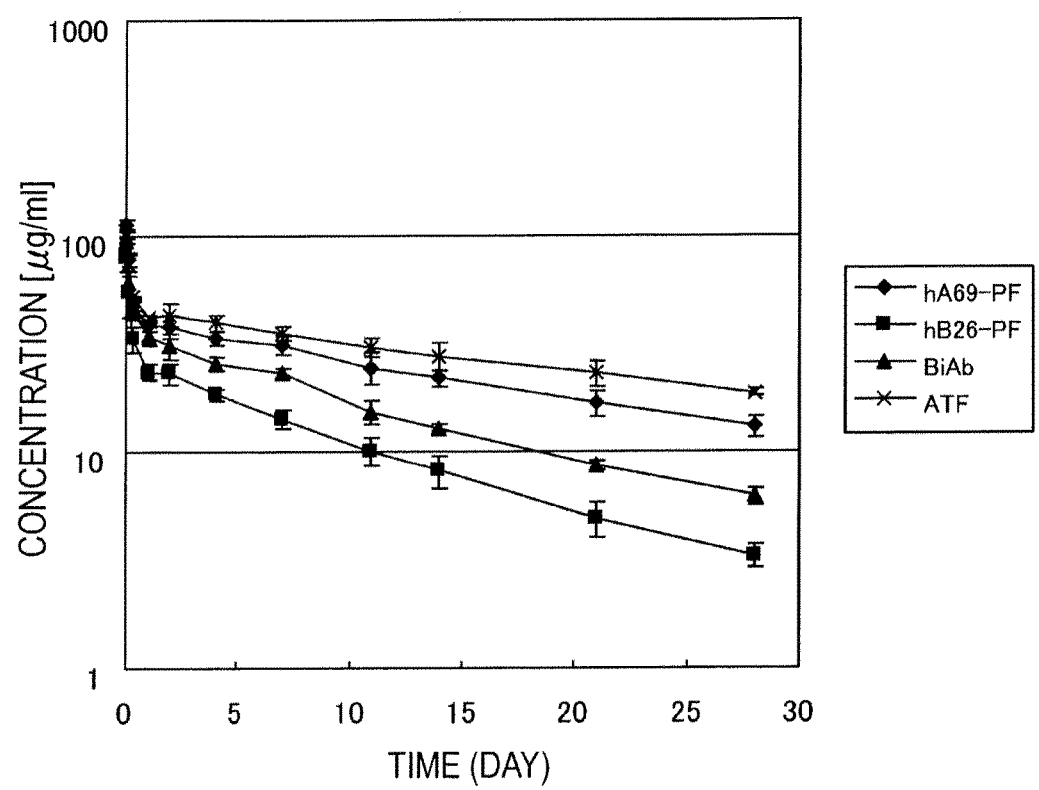
FIG. 7 is a graph showing time courses of plasma concentrations of ATF, hA69-PF, BiAb, and hB26-PF.

Plasma concentrations in mice were determined by ELISA. Calibration curve samples of 6.4, 3.2, 1.6, 0.8, 0.4, 0.2, and 0.1 μg/ml plasma concentrations were prepared. The standard curve samples and mouse plasma samples to be tested were aliquoted into immunoplates (Nunc-Immuno MaxiSorp plates (Nalge nunc International) immobilized with an anti-human IgG (γ-chain specific) F(ab')2 (Sigma). The samples were left to stand at room temperature for one hour, and then reacted with Goat Anti-Human IgG-BIOT (Southern Biotechnology Associates) and Streptavidin-alkaline phosphatase conjugate (Roche Diagnostics) in succession. The color development was carried out using BluePhos Microwell Phosphatase Substrates System (Kirkegaard & Perry Laboratories) as a substrate. The absorbance at 650 nm was measured using a microplate reader. The plasma concentrations in mice were calculated from the absorbance on the calibration curve using the analysis software SOFTmax PRO (Molecular Devices). The time courses of plasma concentrations of ATF, hA69-PF, BiAb, and hB26-PF are shown in FIG. 7.

8-3. Method for Calculating Pharmacokinetic Data

The obtained data on the time courses of plasma concentrations were evaluated by a model-independent analysis using the pharmacokinetic analysis software WinNonlin (Pharsight) to calculate pharmacokinetic parameters (clearance (CL), half-life (T1/2)). T1/2 was calculated from plasma concentrations at the last three points or in the terminal phase automatically selected by WinNonlin. The determined pharmacokinetic parameters are shown in Table 2.

TABLE 2

|  | hA69-N97R | hA69-p18 | hA69-PF | ATF |
|---|---|---|---|---|
| pI | 8.9 | 8.5 | 8.0 | 7.2 |
| CL mL/h/kg | 0.412 | 0.300 | 0.204 | 0.136 |
| T½ day | 12.6 | 15.0 | 18.7 | 26.1 |

|  | hB26-F123e4 | hB26-p15 | hB26-PF | BiAb |
|---|---|---|---|---|
| pI | 8.7 | 9.0 | 9.2 | 8.7 |
| CL mL/h/kg | 0.346 | 0.450 | 0.600 | 0.362 |
| T½ day | 13.4 | 11.9 | 10.8 | 13.6 |

Figure 8:
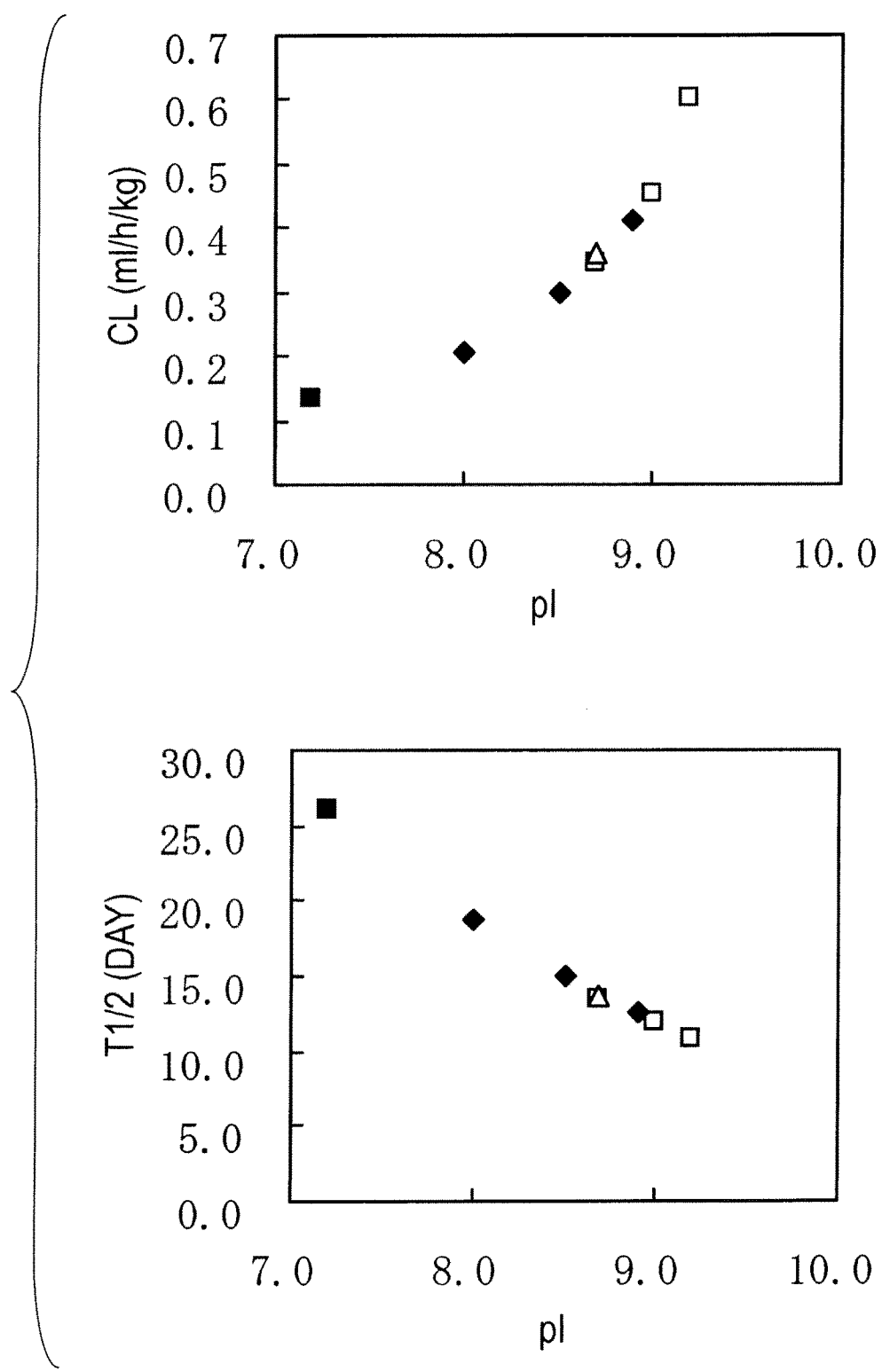
FIG. 8 shows the correlation between pI and pharmacokinetic parameters, clearance (CL) and half-life (T1/2), for ATF, hA69-PF, BiAb, hB26-PF, hA69-N97R, hA69-p18, hB26-F123e4, and hB26-p15.

Furthermore, plots of antibody clearance (CL) and half-life (T1/2) relative to pI are shown in FIG. 8. While the respective antibodies used share the same constant region sequences, each of clearance (CL) and half-life (T1/2) is strongly correlated with pI. This shows that, as pI is lower, clearance is lower and half-life in blood is more prolonged. Thus, half-life in blood can be controlled by pI values even when antibodies share the same constant region sequences. Accordingly, it is suggested that the half-life in blood can be prolonged by decreasing pI or can be reduced by increasing pI. In this Example, it is demonstrated that the half-life in blood could be actually prolonged by decreasing pI through modification of surface amino acids (the modification sites are shown in Table 3) in the variable regions of hA69-N97R. Half-life in blood can be reduced by increasing pI through modification of surface amino acids (the modification sites are shown in Table 4) in the variable regions of hB26-F123e4. These findings suggest that pharmacokinetics of IgGs in blood can be controlled by changing charges of surface amino acids (for example, at positions H10, H12, H23, H39, H43, H97, and H105) in their variable regions through modifications.

TABLE 3

| Name | H1 | H12 | H23 | H27 | H43 | H97 | H105 | L99 |
|---|---|---|---|---|---|---|---|---|
| hA69-N97R | Pyr(Q) | K | K | G | Q | R | Q | G |
| hA69-p18 | Pyr(Q) | K | K | G | E | N | E | G |
| hA69-PF | E | V | T | Y | E | L | E | Q |
|  |  | * | * |  | * | * | * |  |

TABLE 4

| Name | H1 | H9 | H10 | H28 | H37 | H39 | H43 | H105 | L99 |
|---|---|---|---|---|---|---|---|---|---|
| hB26-F123e4 | Pyr(Q) | P | D | M | A | Q | Q | Q | G |
| hB26-p15 | Pyr(Q) | P | D | M | A | K | K | R | G |
| hB26-PF | E | A | Q | T | V | Q | K | R | Q |
|  |  |  | * |  |  | * | * | * |  |

In Tables 3 and 4 above, Pyr(Q) represents an N-terminal glutamine residue which is assumed to be pyroglutamylated. Since the N-terminal amino group is protected, there is no significant charge difference between Pyr(Q) and E. Furthermore, sites of amino acid substitution which results in a pI shift are indicated by an asterisk.

The present invention discovered that the half-life in blood of an IgG could be prolonged or reduced by decreasing or increasing the pI of IgG through substitution of surface amino acids in the variable regions, respectively.

According to a non-patent document (Nat Biotechnol. 1997; 15: 637-640) on blood pharmacokinetics in mice, the half-life in blood (T1/2) could be prolonged by about 1.5 times by increasing the affinity for FcRn through modification of amino acids in the Fc in the constant region. Also in the present invention, by decreasing pI through modification of surface amino acids in variable regions, the half-life in blood (T1/2) could be prolonged by about 1.5 times in the comparison between hA69-N97R and hA69-PF sharing the same constant region sequences. Furthermore, when hA69-N97R is compared with hA69-PF and ATF, T1/2 of ATF with the lowest pI is longer by about 2.1 times than that of hA69-N97R. Thus, the half-life of hA69-N97R in blood can be further prolonged by decreasing its pI through additional modification of surface amino acids in the variable regions of hA69-N97R. When the antibodies used in this Example are compared to each other, the half-life in blood is different by about 2.4 times between hB26-PF with the highest pI and ATF with the lowest pI. Accordingly, the control of pharmacokinetics in blood through amino acid modifications in variable regions is expected to be more effective as compared to previous control techniques. Furthermore, the number of amino acid substitutions artificially introduced into constant regions is desired to be smaller from the viewpoint of anti. Thus, the present invention, in which half-life in blood is controlled by modifying surface amino acids in variable regions, is expected to be useful in developing pharmaceuticals.

INDUSTRIAL APPLICABILITY

In a preferred embodiment of the methods of the present invention, amino acid substitutions are performed in variable regions, and thus the risk of antigenicity is low as compared to conventional methods that modify constant regions. Furthermore, the methods of the present invention can be more effective in prolonging the half-life in blood as compared to the conventional methods that modify constant regions. In addition, the half-life in blood of polypeptides comprising an FcRn-binding domain, such as IgG antibodies, can be controlled by controlling the surface charge in variable regions without changing structure or function (activity). Polypeptides comprising an FcRn-binding domain, which retain the original activity and whose half-life in blood is controlled, can be obtained by using the methods of the present invention.

The invention claimed is:

1. A method for producing a nucleic acid, the method comprising:
   (a) providing a nucleotide sequence encoding a first antibody heavy chain of a first IgG antibody, the first heavy chain comprising an Fc domain;
   (b) producing a nucleic acid encoding a second antibody heavy chain,
   wherein the second heavy chain is identical to the first heavy chain except at one or more amino acid positions in the first heavy chain selected from the group consisting of heavy chain framework region positions H1, H8, H10, H12, H13, H15, H16, H19, H23, H26, H39, H42, H43, H46, H68, H72, H76, H81, H83, H85, and H86 (numbered according to the Kabat numbering system), wherein the amino acid residue at at least one of the one or more positions in the second heavy chain is a different amino acid residue of a different charge than the amino acid residue at the corresponding position in the first heavy chain, and
   wherein a second IgG antibody comprising two copies of the second heavy chain binds to the same antigen as the first IgG antibody and has altered pharmacokinetics in blood compared to the first IgG antibody; and
   (c) determining that the second IgG antibody has a pI shift compared to the first IgG antibody,
   wherein either
   (i) the pI of the second IgG antibody is decreased compared to the pI of the first IgG antibody, and the second IgG antibody has a prolonged half-life in blood, a prolonged mean residence time in blood, or a decreased blood clearance compared to the first IgG antibody; or
   (ii) the pI of the second IgG antibody is increased compared to the pI of the first IgG antibody.

2. The method of claim 1, wherein the altered pharmacokinetics in blood comprises a change in any one or more of the following parameters: half-life in blood, mean residence time in blood, or blood clearance.

3. The method of claim 1, further comprising:
   expressing the nucleic acid, thereby producing the second heavy chain.

4. A nucleic acid produced by the method of claim 1.

5. The method of claim 1, wherein the second IgG antibody is a humanized IgG antibody or a chimeric IgG antibody.

6. The method of claim 1, wherein the one or more amino acid positions are selected from the group consisting of heavy chain framework region positions H10, H12, H23, H39, and H43, numbered according to the Kabat numbering system.

7. The method of claim 6, wherein each different amino acid residue is selected from the group consisting of glutamic acid, aspartic acid, lysine, arginine, and histidine.

8. The method of claim 1, wherein the pI shift is a decrease in pI of at least 0.3, and the altered pharmacokinetics in blood comprises increased half-life in blood or decreased clearance from blood.

9. The method of claim 1, wherein the pI shift is an increase in pI of at least 0.3, and the altered pharmacokinetics in blood comprises decreased half-life in blood or increased clearance from blood.

10. The method of claim 1, wherein the one or more positions are at least two positions.

11. The method of claim 1, wherein the antigen-binding activity of the second IgG antibody is not reduced compared to the antigen-binding activity of the first IgG antibody.

12. A method for producing a nucleic acid, the method comprising:
   producing a desired nucleic acid encoding a desired antibody heavy chain, the desired heavy chain having been previously designed by a method comprising:
   (a) providing a nucleotide sequence encoding a first heavy chain of a first IgG antibody, the first heavy chain comprising an Fc domain;
   (b) selecting one or more amino acid positions in the first heavy chain from the group consisting of heavy chain framework region positions H1, H8, H10, H12, H13, H15, H16, H19, H23, H26, H39, H42, H43, H46, H68, H72, H76, H81, H83, H85, and H86 (numbered according to the Kabat numbering system);
   (c) designing the desired heavy chain to comprise an amino acid sequence that differs from the sequence of the first heavy chain in that the amino acid residue at at least one of the one or more amino acid positions selected in (b) is substituted with a different amino acid residue of a different charge;
   wherein a second IgG antibody comprising two copies of the desired heavy chain binds to the same antigen as the first IgG antibody and has altered pharmacokinetics in blood compared to the first IgG antibody; and
   (d) determining that the second IgG antibody has a pI shift compared to the first IgG antibody,
   wherein either
   (i) the pI of the second IgG antibody is decreased compared to the pI of the first IgG antibody, and the second IgG antibody has a prolonged half-life in blood, a prolonged mean residence time in blood, or a decreased blood clearance compared to the first IgG antibody; or
   (ii) the pI of the second IgG antibody is increased compared to the pI of the first IgG antibody.

13. A method for producing a nucleic acid, the method comprising:
   (a) providing a nucleotide sequence encoding a first heavy chain of a first IgG antibody that is not human or humanized, the heavy chain comprising an Fc domain;
   (b) producing a nucleic acid encoding a second antibody heavy chain, the second heavy chain differing from the first heavy chain in that (i) the second heavy chain is humanized, and (ii) the second heavy chain has a different amino acid residue of a different charge than in the first heavy chain at one or more amino acid positions selected from the group consisting of heavy chain framework region positions H1, H8, H10, H12, H13, H15, H16, H19, H23, H26, H39, H42, H43, H46, H68, H72, H76, H81, H83, H85, and H86 (numbered according to the Kabat numbering system),
   wherein a second IgG antibody comprising two copies of the second heavy chain binds to the same antigen as the first IgG antibody and has altered pharmacokinetics in blood compared to the first IgG antibody; and
   (c) determining that the second IgG antibody has a pI shift compared to the first IgG antibody,
   wherein either
   (1) the pI of the second IgG antibody is decreased compared to the pI of the first IgG antibody, and the second IgG antibody has a prolonged half-life in blood, a prolonged mean residence time in blood, or a decreased blood clearance compared to the first IgG antibody; or
   (2) the pI of the second IgG antibody is increased compared to the pI of the first IgG antibody.

14. The method of claim 13, wherein the antigen-binding activity of the second IgG antibody is not reduced compared to the antigen-binding activity of the first IgG antibody.

15. The method of claim 13, wherein the pI shift is a decrease in pI of at least 0.3, and the altered pharmacokinetics in blood comprises increased half-life in blood or decreased clearance from blood.

16. The method of claim 13, wherein the pI shift is an increase in pI of at least 0.3, and the altered pharmacokinetics in blood comprises decreased half-life in blood or increased clearance from blood.

17. The method of claim 13, wherein the one or more positions are at least two positions.

18. A method for producing a nucleic acid, the method comprising:
producing a desired nucleic acid encoding a desired antibody heavy chain, the desired heavy chain having been previously designed by a method comprising:
(a) providing a nucleotide sequence encoding a first heavy chain of a first IgG antibody that is not human or humanized, the first heavy chain comprising an Fc domain;
(b) selecting one or more amino acid positions in the first heavy chain from the group consisting of heavy chain framework region positions H1, H8, H10, H12, H13, H15, H16, H19, H23, H26, H39, H42, H43, H46, H68, H72, H76, H81, H83, H85, and H86 (numbered according to the Kabat numbering system);
(c) designing the desired heavy chain to be humanized and to comprise an amino acid sequence that differs from the sequence of the first heavy chain not only in the sites changed as a result of the humanization, but also in that the amino acid residue at at least one of the one or more amino acid positions selected in (b) is substituted with a different amino acid residue of a different charge,
wherein a second IgG antibody comprising two copies of the desired heavy chain binds to the same antigen as the first IgG antibody, and has altered pharmacokinetics in blood compared to the first IgG antibody; and
(d) determining that the second IgG antibody has a pI shift compared to the first IgG antibody,
wherein either
(i) the pI of the second IgG antibody is decreased compared to the pI of the first IgG antibody, and the second IgG antibody has a prolonged half-life in blood, a prolonged mean residence time in blood, or a decreased blood clearance compared to the first IgG antibody; or
(ii) the pI of the second IgG antibody is increased compared to the pI of the first IgG antibody.

19. A method for producing a nucleic acid, the method comprising:
(a) providing a nucleotide sequence encoding a first light chain of a first IgG antibody, wherein the first IgG antibody comprises the first light chain and a heavy chain comprising an Fc domain;
(b) producing a nucleic acid encoding a second antibody light chain,
wherein the second light chain is identical to the first light chain, except at one or more amino acid positions selected from the group consisting of light chain framework region positions L1, L7, L8, L9, L11, L12, L16, L17, L18, L20, L38, L39, L41, L45, L46, L57, L60, L63, L65, L68, L69, L70, L74, L76, L77, L79, L80, L81, and L85 (numbered according to the Kabat numbering system),
wherein the amino acid residue at at least one of the one or more positions in the second light chain is a different amino acid residue of a different charge than the amino acid residue at the corresponding position in the first light chain, and
wherein two copies of the second light chain, when associated with two copies of the heavy chain of the first IgG antibody, form a second IgG antibody that binds to the same antigen as the first IgG antibody and has altered pharmacokinetics in blood compared to the first IgG antibody; and
(c) determining that the second IgG antibody has a pI shift compared to the first IgG antibody,
wherein either
(i) the pI of the second IgG antibody is decreased compared to the pI of the first IgG antibody, and the second IgG antibody has a prolonged half-life in blood, a prolonged mean residence time in blood, or a decreased blood clearance compared to the first IgG antibody; or
(ii) the pI of the second IgG antibody is increased compared to the pI of the first IgG antibody.

20. The method of claim 19, wherein the pI shift is a decrease in pI of at least 0.3, and the altered pharmacokinetics in blood comprises increased half-life in blood or decreased clearance from blood.

21. The method of claim 19, wherein the pI shift is an increase in pI of at least 0.3, and the altered pharmacokinetics in blood comprises decreased half-life in blood or increased clearance from blood.

22. The method of claim 19, wherein the one or more positions are at least two positions.

23. The method of claim 19, wherein the antigen-binding activity of the second IgG antibody is not reduced compared to the antigen-binding activity of the first IgG antibody.

24. A method for producing a nucleic acid, the method comprising:
producing a desired nucleic acid encoding a desired antibody light chain, the desired light chain having been previously designed by a method comprising:
(a) providing a nucleotide sequence encoding a first light chain of a first IgG antibody;
(b) selecting one or more amino acid positions in the first light chain from the group consisting of light chain framework region positions L1, L7, L8, L9, L11, L12, L16, L17, L18, L20, L38, L39, L41, L45, L46, L57, L60, L63, L65, L68, L69, L70, L74, L76, L77, L79, L80, L81, and L85 (numbered according to the Kabat numbering system);
(c) designing the desired light chain to comprise an amino acid sequence that differs from the sequence of the first light chain in that the amino acid residue at at least one of the one or more amino acid positions selected in (b) is substituted with a different amino acid residue of a different charge,
wherein the first IgG antibody comprises the first light chain and a heavy chain comprising an Fc domain, and
wherein two copies of the desired light chain, when associated with two copies of the heavy chain of the first IgG antibody, form a second IgG antibody that binds to the same antigen as the first IgG antibody and has altered pharmacokinetics in blood compared to the first IgG antibody; and
(d) determining that the second IgG antibody has a pI shift compared to the first IgG antibody,
wherein either
(i) the pI of the second IgG antibody is decreased compared to the pI of the first IgG antibody, and the second IgG antibody has a prolonged half-life in blood, a prolonged mean residence time in blood, or a decreased blood clearance compared to the first IgG antibody; or (ii) the pI of the second IgG antibody is increased compared to the pI of the first IgG antibody.

25. A method for producing a nucleic acid, the method comprising:
    (a) providing a nucleotide sequence encoding a first light chain of a first IgG antibody;
    (b) producing a nucleic acid encoding a second antibody light chain, the second light chain differing from the first light chain in that (i) the second light chain is humanized, and (ii) the second light chain has a different amino acid residue of a different charge than in the first light chain at one or more amino acid positions selected from the group consisting of light chain framework region positions L1, L7, L8, L9, L11, L12, L16, L17, L18, L20, L38, L39, L41, L45, L46, L57, L60, L63, L65, L68, L69, L70, L74, L76, L77, L79, L80, L81, and L85 (numbered according to the Kabat numbering system),
    wherein a second IgG antibody comprising two copies of the second light chain binds to the same antigen as the first IgG antibody and has altered pharmacokinetics in blood compared to the first IgG antibody; and
    (c) determining that the second IgG antibody has a pI shift compared to the first IgG antibody,
    wherein either
    (1) the pI of the second IgG antibody is decreased compared to the pI of the first IgG antibody, and the second IgG antibody has a prolonged half-life in blood, a prolonged mean residence time in blood, or a decreased blood clearance compared to the first IgG antibody; or
    (2) the pI of the second IgG antibody is increased compared to the pI of the first IgG antibody.

26. A method for producing a nucleic acid, the method comprising:
    producing a desired nucleic acid encoding a desired antibody light chain, the desired light chain having been previously designed by a method comprising:
    (a) providing a nucleotide sequence encoding a first light chain of a first IgG antibody that is not human or humanized;
    (b) selecting one or more amino acid positions in the first light chain from the group consisting of light chain framework region positions L1, L7, L8, L9, L11, L12, L16, L17, L18, L20, L38, L39, L41, L45, L46, L57, L60, L63, L65, L68, L69, L70, L74, L76, L77, L79, L80, L81, and L85 (numbered according to the Kabat numbering system);
    (c) designing the desired light chain to be humanized and to comprise an amino acid sequence that differs from the sequence of the first light chain not only in the sites changed as a result of the humanization, but also in that the amino acid residue at at least one of the one or more amino acid positions selected in (b) is substituted with a different amino acid residue of a different charge,
    wherein a second IgG antibody comprising two copies of the desired light chain binds to the same antigen as the first IgG antibody and has altered pharmacokinetics in blood compared to the first IgG antibody; and
    (d) determining that the second IgG antibody has a pI shift compared to the first IgG antibody,
    wherein either
    (i) the pI of the second IgG antibody is decreased compared to the pI of the first IgG antibody, and the second IgG antibody has a prolonged half-life in blood, a prolonged mean residence time in blood, or a decreased blood clearance compared to the first IgG antibody; or
    (ii) the pI of the second IgG antibody is increased compared to the pI of the first IgG antibody.

27. The method of claim 1, wherein the first IgG antibody is a humanized IgG antibody or a chimeric IgG antibody.

28. The method of claim 12, wherein the first IgG antibody is a humanized IgG antibody or a chimeric IgG antibody.

29. The method of claim 13, wherein the first IgG antibody is a chimeric IgG antibody.

30. The method of claim 18, wherein the first IgG antibody is a chimeric IgG antibody.

31. The method of claim 19, wherein the first IgG antibody is a humanized IgG antibody or a chimeric IgG antibody.

32. The method of claim 24, wherein the first IgG antibody is a humanized IgG antibody or a chimeric IgG antibody.

33. The method of claim 25, wherein the first IgG antibody is a chimeric IgG antibody.

34. The method of claim 26, wherein the first IgG antibody is a chimeric IgG antibody.

35. The method of claim 12, wherein the one or more amino acid positions are selected from the group consisting of heavy chain framework region positions H10, H12, H23, H39, and H43, numbered according to the Kabat numbering system.

36. The method of claim 13, wherein the one or more amino acid positions are selected from the group consisting of heavy chain framework region positions H10, H12, H23, H39, and H43, numbered according to the Kabat numbering system.

37. The method of claim 18, wherein the one or more amino acid positions are selected from the group consisting of heavy chain framework region positions H10, H12, H23, H39, and H43, numbered according to the Kabat numbering system.

38. The method of claim 12, wherein the one or more positions are at least two positions.

39. The method of claim 18, wherein the one or more positions are at least two positions.

40. The method of claim 24, wherein the one or more positions are at least two positions.

41. The method of claim 25, wherein the one or more positions are at least two positions.

42. The method of claim 26, wherein the one or more positions are at least two positions.

43. A method for producing an IgG antibody, the method comprising:
    (i) carrying out the method of claim 1;
    (ii) culturing a cell comprising the nucleic acid and a second nucleic acid encoding an antibody light chain, thereby producing an IgG antibody product comprising the second heavy chain and the encoded light chain; and
    (iii) recovering the IgG antibody product.

44. A method for producing an IgG antibody, the method comprising:
    (i) carrying out the method of claim 12;
    (ii) culturing a cell comprising the desired nucleic acid and a second nucleic acid encoding an antibody light chain, thereby producing an IgG antibody product comprising the desired heavy chain and the encoded light chain; and
    (iii) recovering the IgG antibody product.

45. A method for producing an IgG antibody, the method comprising:
  (i) carrying out the method of claim 13;
  (ii) culturing a cell comprising the nucleic acid and a second nucleic acid encoding an antibody light chain, thereby producing an IgG antibody product comprising the second heavy chain and the encoded light chain; and
  (iii) recovering the IgG antibody product.

46. A method for producing an IgG antibody, the method comprising:
  (i) carrying out the method of claim 18;
  (ii) culturing a cell comprising the desired nucleic acid and a second nucleic acid encoding an antibody light chain, thereby producing an IgG antibody product comprising the desired heavy chain and the encoded light chain; and
  (iii) recovering the IgG antibody product.

47. A method for producing an IgG antibody, the method comprising:
  (i) carrying out the method of claim 19;
  (ii) culturing a cell comprising the nucleic acid and a second nucleic acid encoding an antibody heavy chain, thereby producing an IgG antibody product comprising the second light chain and the encoded heavy chain; and
  (iii) recovering the IgG antibody product.

48. A method for producing an IgG antibody, the method comprising:
  (i) carrying out the method of claim 24;
  (ii) culturing a cell comprising the desired nucleic acid and a second nucleic acid encoding an antibody heavy chain, thereby producing an IgG antibody product comprising the desired light chain and the encoded heavy chain; and
  (iii) recovering the IgG antibody product.

49. A method for producing an IgG antibody, the method comprising:
  (i) carrying out the method of claim 25;
  (ii) culturing a cell comprising the nucleic acid and a second nucleic acid encoding an antibody heavy chain, thereby producing an IgG antibody product comprising the second light chain and the encoded heavy chain; and
  (iii) recovering the IgG antibody product.

50. A method for producing an IgG antibody, the method comprising:
  (i) carrying out the method of claim 26;
  (ii) culturing a cell comprising the desired nucleic acid and a second nucleic acid encoding an antibody heavy chain, thereby producing an IgG antibody product comprising the desired light chain and the encoded heavy chain; and
  (iii) recovering the IgG antibody product.

* * * * *

SEQUENCE LISTING

<160> NUMBER OF SEQ ID NOS: 18

<210> SEQ ID NO 1
<211> LENGTH: 354
<212> TYPE: DNA
<213> ORGANISM: Artificial Sequence
<220> FEATURE:
<223> OTHER INFORMATION: An artificially synthesized nucleotide sequence

```
<400> SEQUENCE: 1
caggtccagc ttgtgcagtc tggggctgag gtgaagaagc ctgggtcctc agtgaaggtt      60
tcctgcaagg cctctggagg caccttcagt gactactata tgcactgggt gcgccaggcc    120
cccggacaag gcttgagtg gatgggatac attaatccta gcagtggtta tactaagtac     180
aatcggaagt tcagggacag agtcaccatt accgcggaca atccacgag cacagcctac     240 atggagctga gcagcctgag atctgaagac acggctgtgt attactgtgc gagagggggt    300
aacggttact accttgacta ctgggggccag ggcaccacgg tcaccgtctc ctca         354
```

<210> SEQ ID NO 2
<211> LENGTH: 118
<212> TYPE: PRT
<213> ORGANISM: Artificial Sequence
<220> FEATURE:
<223> OTHER INFORMATION: An artificially synthesized peptide sequence

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met His Trp Val Arg Gln Ala Pro Gly Gln Gly Leu Glu Trp Met
        35                  40                  45

Gly Tyr Ile Asn Pro Ser Ser Gly Tyr Thr Lys Tyr Asn Arg Lys Phe
    50                  55                  60

Arg Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Gly Tyr Tyr Leu Asp Tyr Trp Gly Gln Gly Thr
            100                 105                 110

Thr Val Thr Val Ser Ser
        115

<210> SEQ ID NO 3
<211> LENGTH: 357
<212> TYPE: DNA
<213> ORGANISM: Artificial Sequence
<220> FEATURE:
<223> OTHER INFORMATION: An artificially synthesized nucleotide sequence

```
<400> SEQUENCE: 3
caggtgcagc tggtgcagtc tggacctgac gtgaagaagc cggggggcctc agtgaaggtc     60 tcctgcaagg cctctggcta catgttttcc gacaacaaca tggactgggc gcgacaggcc    120
cctggacaag gcttgagtg gatgggagat attaatacta aaagtggtgg ttctatctac     180
aaccagaagt tcaagggcag agtcatcatg accatagaca atccacggg cacagcctac    240 atggaattga ggagcctgag atcagacgac acggccatat attactgtgc gaggaggagg    300
agctacggct actactttga ctactggggc agggaaccc tggtcaccgt ctcctca       357
```

<210> SEQ ID NO 4
<211> LENGTH: 119
<212> TYPE: PRT
<213> ORGANISM: Artificial Sequence
<220> FEATURE:
<223> OTHER INFORMATION: An artificially synthesized peptide sequence -continued

<400> SEQUENCE: 4

```
Gln Val Gln Leu Val Gln Ser Gly Pro Asp Val Lys Lys Pro Gly Ala
1               5                   10                  15
Ser Val Lys Val Ser Cys Lys Ala Ser Gly Tyr Met Phe Ser Asp Asn
            20                  25                  30
Asn Met Asp Trp Ala Arg Gln Ala Pro Gly Gln Gly Leu Glu Trp Met
        35                  40                  45
Gly Asp Ile Asn Thr Lys Ser Gly Ser Ile Tyr Asn Gln Lys Phe
    50                  55                  60
Lys Gly Arg Val Ile Met Thr Ile Asp Lys Ser Thr Gly Thr Ala Tyr
65                  70                  75                  80
Met Glu Leu Arg Ser Leu Arg Ser Asp Asp Thr Ala Ile Tyr Tyr Cys
                85                  90                  95
Ala Arg Arg Arg Ser Tyr Gly Tyr Tyr Phe Asp Tyr Trp Gly Gln Gly
            100                 105                 110
Thr Leu Val Thr Val Ser Ser
        115
```

<210> SEQ ID NO 5
<211> LENGTH: 318
<212> TYPE: DNA
<213> ORGANISM: Artificial Sequence
<220> FEATURE:
<223> OTHER INFORMATION: An artificially synthesized nucleotide sequence

<400> SEQUENCE: 5

```
gacatcgtga tgacccagtc tccatcctcc ctgtctgcat ctgtaggaga cagagtcacc      60
atcacttgca aggccagtca gaatgtgggg actgctgtag cctggtatca gcagaaacca     120
gggaaagccc ctaagctcct gatctattcg catcctacc ggtacagtgg ggtcccatca     180
aggttcagtg gcagtcgata tgggacagat ttcactctca ccatctcaag cttgcaacct     240
gaagatttag caacttacta ctgtcagcaa tatagcaact atatcacgtt cggcggaggg     300
accaaggtgg agatcaaa                                                    318
```

<210> SEQ ID NO 6
<211> LENGTH: 106
<212> TYPE: PRT
<213> ORGANISM: Artificial Sequence
<220> FEATURE:
<223> OTHER INFORMATION: An artificially synthesized peptide sequence

<400> SEQUENCE: 6

```
Asp Ile Val Met Thr Gln Ser Pro Ser Ser Leu Ser Ala Ser Val Gly
1               5                   10                  15
Asp Arg Val Thr Ile Thr Cys Lys Ala Ser Gln Asn Val Gly Thr Ala
            20                  25                  30
Val Ala Trp Tyr Gln Gln Lys Pro Gly Lys Ala Pro Lys Leu Leu Ile
        35                  40                  45
Tyr Ser Ala Ser Tyr Arg Tyr Ser Gly Val Pro Ser Arg Phe Ser Gly
    50                  55                  60
Ser Arg Tyr Gly Thr Asp Phe Thr Leu Thr Ile Ser Ser Leu Gln Pro
65                  70                  75                  80
Glu Asp Leu Ala Thr Tyr Tyr Cys Gln Gln Tyr Ser Asn Tyr Ile Thr
                85                  90                  95
Phe Gly Gly Gly Thr Lys Val Glu Ile Lys
            100                 105
```

```
<210> SEQ ID NO 7
<211> LENGTH: 118
<212> TYPE: PRT
<213> ORGANISM: Artificial Sequence
<220> FEATURE:
<223> OTHER INFORMATION: An artificially synthesized peptide sequence

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met His Trp Val Arg Gln Ala Pro Gly Glu Gly Leu Glu Trp Met
        35                  40                  45

Gly Tyr Ile Asn Pro Ser Ser Gly Tyr Thr Lys Tyr Asn Arg Lys Phe
    50                  55                  60

Arg Asp Arg Val Thr Ile Thr Ala Asp Lys Ser Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Gly Tyr Tyr Leu Asp Tyr Trp Gly Glu Gly Thr
            100                 105                 110

Thr Val Thr Val Ser Ser
        115

<210> SEQ ID NO 8
<211> LENGTH: 106
<212> TYPE: PRT
<213> ORGANISM: Artificial Sequence
<220> FEATURE:
<223> OTHER INFORMATION: An artificially synthesized peptide sequence

<400> SEQUENCE: 8

Asp Ile Val Met Thr Gln Ser Pro Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Leu Ala Thr Tyr Tyr Cys Gln Gln Tyr Ser Asn Tyr Ile Thr
                85                  90                  95

Phe Gly Gln Gly Thr Lys Val Glu Ile Lys
            100                 105

<210> SEQ ID NO 9
<211> LENGTH: 118
<212> TYPE: PRT
<213> ORGANISM: Artificial Sequence
<220> FEATURE:
<223> OTHER INFORMATION: An artificially synthesized peptide sequence

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30
```

```
Tyr Met His Trp Val Arg Gln Ala Pro Gly Gln Gly Leu Glu Trp Met
        35                  40                  45

Gly Tyr Ile Asn Pro Ser Ser Gly Tyr Thr Lys Tyr Asn Arg Lys Phe
 50                  55                  60

Arg Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Arg Gly Tyr Tyr Leu Asp Tyr Trp Gly Gln Gly Thr
                100                 105                 110

Thr Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: An artificially synthesized peptide sequence

<400> SEQUENCE: 10

Gln Val Gln Leu Val Gln Ser Gly Pro Asp Val Lys Lys Pro Gly Ala
 1               5                  10                  15

Ser Val Lys Val Ser Cys Lys Ala Ser Gly Tyr Met Phe Ser Asp Asn
                 20                  25                  30

Asn Met Asp Trp Ala Arg Lys Ala Pro Gly Lys Gly Leu Glu Trp Met
        35                  40                  45

Gly Asp Ile Asn Thr Lys Ser Gly Gly Ser Ile Tyr Asn Gln Lys Phe
 50                  55                  60

Lys Gly Arg Val Ile Met Thr Ile Asp Lys Ser Thr Gly Thr Ala Tyr
 65                  70                  75                  80

Met Glu Leu Arg Ser Leu Arg Ser Asp Asp Thr Ala Ile Tyr Tyr Cys
                 85                  90                  95

Ala Arg Arg Arg Ser Tyr Gly Tyr Tyr Phe Asp Tyr Trp Gly Arg Gly
                100                 105                 110

Thr Leu Val Thr Val Ser Ser
        115

<210> SEQ ID NO 11
<211> LENGTH: 118
<212> TYPE: PRT
<213> ORGANISM: Artificial Sequence
<220> FEATURE:
<223> OTHER INFORMATION: An artificially synthesized peptide sequence

<400> SEQUENCE: 11

Glu Val Gln Leu Val Gln Ser Gly Ala Glu Val Lys Pro Gly Ser
 1               5                  10                  15

Ser Val Lys Val Ser Cys Thr Ala Ser Gly Tyr Thr Phe Ser Asp Tyr
                 20                  25                  30

Tyr Met His Trp Val Arg Gln Ala Pro Gly Glu Gly Leu Glu Trp Met
        35                  40                  45

Gly Tyr Ile Asn Pro Ser Ser Gly Tyr Thr Lys Tyr Asn Arg Lys Phe
 50                  55                  60

Arg Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

Ala Arg Gly Gly Leu Gly Tyr Tyr Leu Asp Tyr Trp Gly Glu Gly Thr
            100                 105                 110

Thr Val Thr Val Ser Ser
        115

<210> SEQ ID NO 12
<211> LENGTH: 119
<212> TYPE: PRT
<213> ORGANISM: Artificial Sequence
<220> FEATURE:
<223> OTHER INFORMATION: An artificially synthesized peptide sequence

<400> SEQUENCE: 12

Glu Val Gln Leu Val Gln Ser Gly Ala Gln Val Lys Lys Pro Gly Ala
1               5                   10                  15

Ser Val Lys Val Ser Cys Lys Ala Ser Gly Tyr Thr Phe Ser Asp Asn
            20                  25                  30

Asn Met Asp Trp Val Arg Gln Ala Pro Gly Lys Gly Leu Glu Trp Met
        35                  40                  45

Gly Asp Ile Asn Thr Lys Ser Gly Ser Ile Tyr Asn Gln Lys Phe
    50                  55                  60

Lys Gly Arg Val Ile Met Thr Ile Asp Lys Ser Thr Gly Thr Ala Tyr
65                  70                  75                  80

Met Glu Leu Arg Ser Leu Arg Ser Asp Asp Thr Ala Ile Tyr Tyr Cys
                85                  90                  95

Ala Arg Arg Arg Ser Tyr Gly Tyr Tyr Phe Asp Tyr Trp Gly Arg Gly
            100                 105                 110

Thr Leu Val Thr Val Ser Ser
        115

<210> SEQ ID NO 13
<211> LENGTH: 463
<212> TYPE: PRT
<213> ORGANISM: Homo sapiens

<400> SEQUENCE: 13

Met Asp Trp Thr Trp Arg Phe Leu Phe Val Val Ala Ala Ala Thr Gly
1               5                   10                  15

Val Gln Ser Gln Val Gln Leu Leu Glu Ser Gly Ala Val Leu Ala Arg
            20                  25                  30

Pro Gly Thr Ser Val Lys Ile Ser Cys Lys Ala Ser Gly Phe Asn Ile
        35                  40                  45

Lys Asp Tyr Tyr Met His Trp Val Lys Gln Arg Pro Gly Gln Gly Leu
    50                  55                  60

Glu Trp Ile Gly Gly Asn Asp Pro Ala Asn Gly His Ser Met Tyr Asp
65                  70                  75                  80

Pro Lys Phe Gln Gly Arg Val Thr Ile Thr Ala Asp Thr Ser Thr Ser
                85                  90                  95

Thr Val Phe Met Glu Leu Ser Ser Leu Arg Ser Glu Asp Thr Ala Val
            100                 105                 110

Tyr Tyr Cys Ala Arg Asp Ser Gly Tyr Ala Met Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

-continued

```
Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Gln Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
        435                 440                 445

His Asn His Tyr Thr Gln Lys Ser Leu Ser Leu Ser Leu Gly Lys
450                 455                 460

<210> SEQ ID NO 14
<211> LENGTH: 236
<212> TYPE: PRT
<213> ORGANISM: Homo sapiens

<400> SEQUENCE: 14

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Ile Lys Ser Phe Leu Ser Trp Tyr Gln Gln Lys Pro Glu Lys
50                  55                  60

Ala Pro Lys Ser Leu Ile Tyr Tyr Ala Thr Ser Leu Ala Asp Gly Val
65                  70                  75                  80
```

```
Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Thr Tyr Tyr Cys Leu Gln
            100                 105                 110

His Gly Glu Ser Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 15
<211> LENGTH: 119
<212> TYPE: PRT
<213> ORGANISM: Mus musculus

<400> SEQUENCE: 15

Met Glu Val Gln Leu Gln Gln Ser Gly Ala Glu Leu Val Lys Pro Gly
1               5                   10                  15

Ala Ser Val Lys Leu Ser Cys Thr Ala Ser Gly Phe Asn Ile Lys Asp
            20                  25                  30

Tyr Tyr Met His Trp Ile Lys Gln Arg Pro Gly Gln Gly Leu Glu Trp
        35                  40                  45

Leu Gly Tyr Ile Asn Pro Ser Ser Gly Tyr Thr Lys Tyr Asn Arg Lys
    50                  55                  60

Phe Arg Asp Lys Ala Thr Leu Thr Ala Asp Lys Ser Ser Ser Thr Ala
65                  70                  75                  80

Tyr Met Gln Leu Thr Ser Leu Thr Tyr Glu Asp Ser Ala Val Tyr Tyr
                85                  90                  95

Cys Ala Arg Gly Gly Asn Gly Tyr Tyr Leu Asp Tyr Trp Gly Gln Gly
            100                 105                 110

Thr Thr Leu Thr Val Ser Ser
        115

<210> SEQ ID NO 16
<211> LENGTH: 120
<212> TYPE: PRT
<213> ORGANISM: Mus musculus

<400> SEQUENCE: 16

Met Gln Val Gln Leu Gln Gln Ser Gly Pro Glu Leu Val Lys Pro Gly
1               5                   10                  15

Ala Ser Val Lys Ile Ser Cys Lys Ala Ser Gly Tyr Thr Phe Thr Asp
            20                  25                  30

Asn Asn Met Asp Trp Val Lys Gln Ser His Gly Lys Gly Leu Glu Trp
        35                  40                  45
```

```
Ile Gly Asp Ile Asn Thr Lys Ser Gly Gly Ser Ile Tyr Asn Gln Lys
 50                  55                  60

Phe Lys Gly Lys Ala Thr Leu Thr Ile Asp Lys Ser Ser Ser Thr Ala
 65                  70                  75                  80

Tyr Met Glu Leu Arg Ser Leu Thr Ser Glu Asp Thr Ala Val Tyr Tyr
                 85                  90                  95

Cys Ala Arg Arg Arg Ser Tyr Gly Tyr Tyr Phe Asp Tyr Trp Gly Gln
                100                 105                 110

Gly Thr Thr Leu Thr Val Ser Ser
                115                 120

<210> SEQ ID NO 17
<211> LENGTH: 107
<212> TYPE: PRT
<213> ORGANISM: Homo sapiens

<400> SEQUENCE: 17

Asp Ile Val Met Thr Gln Ser His Lys Phe Met Ser Thr Ser Val Gly
 1               5                  10                  15

Asp Arg Val Ser Ile Thr Cys Lys Ala Ser Gln Asn Val Gly Thr Ala
                 20                  25                  30

Val Ala Trp Tyr Gln Gln Lys Pro Gly Gln Ser Pro Lys Leu Leu Ile
             35                  40                  45

Tyr Ser Ala Ser Tyr Arg Tyr Ser Gly Val Pro Asp Arg Phe Thr Gly
 50                  55                  60

Ser Arg Tyr Gly Thr Asp Phe Thr Leu Thr Ile Ser Asn Val Gln Ser
 65                  70                  75                  80

Glu Asp Leu Ala Asp Tyr Leu Cys Gln Gln Tyr Ser Asn Tyr Ile Thr
                 85                  90                  95

Phe Gly Gly Gly Thr Lys Leu Glu Leu Lys Arg
                100                 105

<210> SEQ ID NO 18
<211> LENGTH: 108
<212> TYPE: PRT
<213> ORGANISM: Mus musculus

<400> SEQUENCE: 18

Asp Ile Val Leu Thr Gln Ser Gln Lys Phe Met Ser Thr Ser Val Gly
 1               5                  10                  15

Asp Arg Val Ser Ile Thr Cys Lys Ala Ser Gln Asn Val Gly Thr Ala
                 20                  25                  30

Val Ala Trp Tyr Gln Gln Lys Pro Gly Gln Ser Pro Lys Ala Leu Ile
             35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Leu
                 85                  90                  95

Thr Phe Gly Ala Gly Thr Lys Leu Glu Ile Lys Arg
                100                 105
```